(12) United States Patent
Hongu et al.

(10) Patent No.: US 7,759,373 B2
(45) Date of Patent: Jul. 20, 2010

(54) LARGE CONDUCTANCE CALCIUM-ACTIVATED K CHANNEL OPENER

(75) Inventors: Mitsuya Hongu, Saitama (JP); Toshihiro Hosaka, Tokyo (JP); Toshihiko Kashiwagi, Saitama (JP); Rikako Kono, Saitama (JP); Hiroyuki Kobayashi, Saitama (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 1185 days.

(21) Appl. No.: 10/474,850

(22) PCT Filed: Apr. 15, 2002

(86) PCT No.: PCT/JP02/03723

§ 371 (c)(1),
(2), (4) Date: Feb. 10, 2004

(87) PCT Pub. No.: WO02/083111

PCT Pub. Date: Oct. 24, 2002

(65) Prior Publication Data

US 2004/0127527 A1    Jul. 1, 2004

(30) Foreign Application Priority Data

Apr. 16, 2001 (JP) ............................. 2001-116436
Aug. 20, 2001 (JP) ............................. 2001-249671

(51) Int. Cl.
*A01N 43/78* (2006.01)
*A61K 31/425* (2006.01)
*C07D 277/04* (2006.01)
*C07D 277/06* (2006.01)

(52) U.S. Cl. ..................................... 514/365; 548/146

(58) Field of Classification Search ................ 548/146; 514/365
See application file for complete search history.

(56) References Cited

U.S. PATENT DOCUMENTS

| | | |
|---|---|---|
| 3,476,766 A | 11/1969 | Brown |
| 3,546,342 A | 12/1970 | Brown et al. |
| 3,574,228 A | 4/1971 | Brown et al. |
| 3,575,991 A | 4/1971 | Santilli et al. |
| 3,579,529 A | 5/1971 | Brown et al. |
| 4,127,663 A | 11/1978 | Cavalla |
| 4,356,185 A | 10/1982 | Cavalla |
| 4,486,436 A | 12/1984 | Sunshine et al. |
| 5,332,833 A | 7/1994 | Sekiya et al. |
| 5,519,033 A | 5/1996 | Rosen et al. |
| 5,773,388 A | 6/1998 | Satow et al. |
| 5,869,509 A | 2/1999 | Gribkoff et al. |
| 5,994,378 A | 11/1999 | Nishimura et al. |
| 5,998,459 A | 12/1999 | Nakamura et al. |
| 6,034,113 A | 3/2000 | Ding et al. |
| 6,159,998 A | 12/2000 | Jeon et al. |
| 6,177,452 B1 | 1/2001 | Momose et al. |
| 6,248,897 B1 | 6/2001 | Ando et al. |

FOREIGN PATENT DOCUMENTS

| | | |
|---|---|---|
| DE | 31 28 453 A | 2/1983 |
| DE | 31 28 492 A | 2/1983 |
| EP | 0 092 239 A | 10/1983 |
| EP | 0 489 660 A | 6/1992 |
| EP | 0 842 923 A | 5/1998 |
| FR | 2 096 994 A | 3/1972 |
| GB | 1 147 626 A | 4/1969 |
| GB | 1 380 507 A | 1/1975 |
| GB | 1 574 583 A | 9/1980 |
| HU | 185038 B | 2/1989 |
| JP | EP 0 120 270 A2 | 10/1984 |
| JP | 60188371 A | 9/1985 |
| JP | 61167685 | 7/1986 |
| JP | 5-246980 A | 9/1993 |
| JP | 07291936 A | 11/1995 |
| WO | WO 87 03807 A | 7/1987 |
| WO | WO-95/04725 A1 | 2/1995 |
| WO | WO-99/01128 A1 | 1/1999 |
| WO | WO 99/32464 | 7/1999 |

OTHER PUBLICATIONS

Fox, A.J. et al. "Activation of Large Conductance Potassium Channel Inhibits the Afferent and Efferent Function of Airway Sensory Nerves in the Guinea Pig", Feb. 1997, vol. 99, No. 3, pp. 513-519.*

(Continued)

*Primary Examiner*—Sreeni Padmanabhan
*Assistant Examiner*—Kendra D Carter
(74) *Attorney, Agent, or Firm*—Birch, Stewart, Kolasch & Birch, LLP

(57) ABSTRACT

A large conductance calcium-activated K channel opener comprising as an active ingredient a nitrogen-containing 5-membered heterocyclic compound represented by the following formula (I):

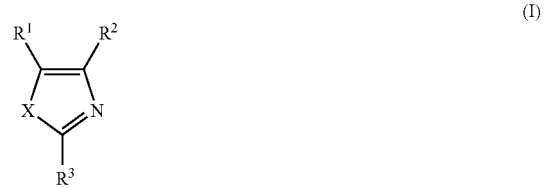

(I)

wherein X represents N—$R^4$, O or S, $R^1$ and $R^2$ each independently represent hydrogen, halogen, carboxyl, amino, lower alkyl, lower alkoxycarbonyl, lower alkenyl, cyclo-lower alkyl, carbamoyl, aryl, heterocyclic or heterocyclic-substituted carbonyl group, $R^3$ represents aryl, heterocyclic or lower alkyl group, and $R^4$ represents hydrogen or lower alkyl group,
or a pharmaceutically acceptable salt thereof.

4 Claims, No Drawings

OTHER PUBLICATIONS

Benassayag E. et al. "500 cases of pollakiuria and cystalgia treated with an anti-inflammatory agent", Therapie; Nov.-Dec. 1970; vol. 25(6); citation. Paper has been ordered.*

Patent Abstracts of Japan: vol. 016, No. 369 (C-0972), (Aug. 10, 1992).

Patent Abstracts of Japan: vol. 010, No. 373 (C-391), (Dec. 12, 1986).

Patent Abstracts of Japan: vol. 1996, No. 03, (Mar. 29, 1996).

Patent Abstracts of Japan: vol. 016, No. 016 (C-0910), (Feb. 17, 1992).

Miyachi H et al.: Bioorganic & Medicinal Chemistry, vol. 7, No. 6, (Jun. 1999) pp. 1151-1161, XP002210545.

Kaiser C et al.: Journal of Medicinal Chemistry, Chemical Society, vol. 35, No. 23, (1992), pp. 4415-4424, XP002926460.

*J. Med. Chem.*, vol. 33, (1990), pp. 492-504.

Data Submitted By Applicant on Nov. 21, 2008 (Appendix A: Rhythmic Bladder Contraction in Female Rat; and Appendix B: Protocol of the rat RC model with results).

Patent Abstracts of Japan, publication No. 07-002808, publication date Jan. 6, 1995.

Patent Abstracts of Japan, publication No. 04-117371, publication date Apr. 17, 1992.

Patent Abstracts of Japan, publication No. 61-167676, publication date Jul. 29, 1986.

Patent Abstracts of Japan, publication No. 59-036614, publication date Feb. 28, 1984.

Patent Abstracts of Japan, publication No. 59-172488, publication date Sep. 29, 1984.

Patent Abstracts of Japan, publication No. 58-150591, publication date Sep. 7, 1983.

Patent Abstracts of Japan, publication No. 60-034951, publication date Feb. 22, 1985.

Patent Abstracts of Japan, publication No. 63-054369, publication date Aug. 3, 1988.

Patent Abstracts of Japan, Publication No. 2000-351773, publication date Dec. 19, 2000.

Patent Abstracts of Japan, publication No. 07-291936, publication date Jul. 11, 1995.

Romine, J. et al., 4,5-Diphenyltriazol-3-ones: Openers of Large-Conductance $Ca^{2+}$—Activated Potassium (Maxi-K) Channels, *J. Med. Chem.* 2002, vol. 45, pp. 2942-2952.

*J. Org. Chem.* 1990, vol. 55, pp. 386-388.

*Journal of The Chemical Society*, 1945, Part II, pp. 455-460.

*Chem. Pharm. Bull.*, 1986, vol. 34 (11), pp. 4516-4522.

*Chem. Pharm. Bull.*, 1983, vol. 31 (12), pp. 4417-4424.

*J. Med. Chem.*, 1988, vol. 31, pp. 1197-1204.

*Chem. Pharm. Bull.*, 1986, vol. 40, No. 12, pp. 3206-3213.

*J. Med. Chem.* 1986, vol. 29, pp. 333-341.

* cited by examiner

LARGE CONDUCTANCE CALCIUM-ACTIVATED K CHANNEL OPENER

This application is the national phase under 35 U.S.C. §371 of PCT International Application No. PCT/JP02/03723 which has an International filing date of Apr. 15, 2002, which designated the United States of America.

FIELD OF THE INVENTION

This invention relates to an excellent large conductance calcium-activated K channel opener containing a nitrogen-containing 5-membered heterocyclic compound as an active ingredient, which is useful for treatment of disorders or diseases such as pollakiuria, urinary incontinence, cerebral infarction, subarachnoid hemorrhage, and the like.

BACKGROUND OF THE INVENTION

Potassium is the most abundant intracelluar cation, and is very important in maintaining physiological homeostasis. Potassium channels are present in almost all vertebrate cells, and the potassium influx through these channels is indispensable for maintaining hyperpolarized resting membrane potential.

Large conductance calcium activated potassium channels (also BK channels or maxi-K channels) are expressed especially in neurons and smooth muscle cells. Because both of the increase of intracellular calcium concentration and membrane depolarization can activate maxi-K channels, maxi-K channels have been thought to play a pivotal role in regulating voltage-dependent calcium influx. Increase in the intra-cellular calcium concentration mediates many processes such as release of neurotransmitters, contraction of smooth muscles, cell growth and death, and the like. Actually, the opening of maxi-K channels causes strong membrane hyperpolarization, and inhibits these calcium-induced responses thereby. Accordingly, by inhibiting various depolarization-mediated physiological responses, a substance having an activity of opening maxi-K channels is expected to have potential for the treatment of diseases such as cerebral infarction, subarachnoid hemorrhage, pollakiuria, urinary incontinence, and the like.

There have been various reports on a large conductance calcium-activated potassium channel opener, and examples of such channel opener are as follows; a pyrrole derivative disclosed in International Publication WO96/40634, a furan derivative disclosed in Japanese Provisional Patent Publication No. 2000-351773, and a nitrogen-containing 5-membered derivative in which the nitrogen atom is substituted by phenyl group or benzyl group disclosed in International Publication WO98/04135.

Also, a compound having a similar structure to the nitrogen-containing 5-membered heterocyclic compound which is an active ingredient of the present invention has been disclosed. For example, oxazole derivatives have been reported in Japanese Provisional Patent Publications No. 36614/1984, No. 152382/1984 and No. 172488/1984, but their uses are limited only to antihypolipidemic agent. Also, in Japanese Provisional Patent Publications No. 150591/1983, No. 34951/1985 and No. 54369/1988, imidazole derivatives have been reported but their uses are limited only to a cardiotonic, an antithrombosis, an antipyretic analgesic or an anti-inflammation agent.

SUMMARY OF THE INVENTION

An object of the present invention is to provide an excellent large conductance calcium-activated K channel opener containing a nitrogen-containing 5-membered heterocyclic compound as an active ingredient.

The present inventors have studied intensively to solve the problems, and as a result, they have found that a certain kind of a nitrogen-containing 5-membered heterocyclic compound has an excellent large conductance calcium-activated K channel opening activity, whereby they have accomplished the present invention.

That is, the present invention relates to a large conductance calcium-activated K channel opener comprising a nitrogen-containing 5-membered heterocyclic compound represented by the following formula (I):

wherein X represents N—$R^4$, O or S, $R^1$ and $R^2$ are different from each other and each independently represents hydrogen atom, a halogen atom, carboxyl group, a substituted or unsubstituted amino group, a substituted or unsubstituted lower alkyl group, a lower alkoxycarbonyl group, a substituted or unsubstituted lower alkenyl group, a cyclo-lower alkyl group, a substituted or unsubstituted carbamoyl group, a substituted or unsubstituted aryl group, a substituted or unsubstituted heterocyclic group or a substituted or unsubstituted heterocyclic group-substituted carbonyl group, $R^3$ represents a substituted or unsubstituted aryl group, a substituted or unsubstituted heterocyclic group or a substituted or unsubstituted lower alkyl group, and $R^4$ represents hydrogen atom or a substituted or unsubstituted lower alkyl group, or a pharmaceutically acceptable salt thereof as an active ingredient.

BEST MODE FOR CARRYING OUT THE INVENTION

In the nitrogen-containing 5-membered heterocyclic compound (I) which is an active ingredient of the present invention, the aryl group is a monocyclic, dicyclic or tricyclic 6- to 14-membered aromatic hydrocarbon cyclic group, and specific examples of the aryl group may include a phenyl group, a naphthyl group and the like. Of these, a phenyl group or a naphthyl group is preferred.

The heterocyclic group or the heterocyclic group portion of the heterocyclic group-substituted carbonyl group is a monocyclic, dicyclic or tricyclic 6- to 14-membered aromatic hydrocarbon cyclic group, containing 1 to 4 heteroatoms selected from nitrogen atom, oxygen atom and sulfur atom, which may be partially or wholly saturated.

As the monocyclic heterocyclic group, a 5- to 7-membered heterocyclic group, containing 1 to 4 hetero atoms selected from nitrogen atom, oxygen atom and sulfur atom, which may be partially or wholly saturated is preferred, and specific examples of the monocyclic heterocyclic group may include furyl group, thienyl group, thiazolyl group, thiazolidinyl group, isoxazolyl group, pyrrolidinyl group, pyrrolyl group, pyridyl group, pyrazinyl group, pyrimidinyl group, tetrazolyl group, and the like.

As the dicyclic heterocyclic group, a dicyclic heterocyclic group in which two of the above-mentioned monocyclic heterocyclic groups are fused or a dicyclic heterocyclic group in which the above monocyclic heterocyclic group and a benzene ring are fused is preferred, and specific examples of the dicyclic heterocyclic group may include indolyl group, quinolyl group, tetrahydroquinolyl group, isoquinolyl group, quinoxalyl group, benzofuryl group, dihydrobenzofuryl group, benzothienyl group, benzodioxanyl group, trihydro-cyclo-pentathienyl group, benzothianyl group, benzothiazolyl group, imidazopyridyl group, indolyl group, indolinyl group, chromanyl group, thiophenopyridyl group, furanopyridyl group, and the like.

As the tricyclic heterocyclic group, a tricyclic heterocyclic group in which the above-mentioned monocyclic heterocyclic group and the above-mentioned dicyclic heterocyclic group are fused or a tricyclic heterocyclic group in which the above-mentioned monocyclic heterocyclic group and two benzene rings are fused is preferred, and specific examples of the tricyclic heterocyclic group may include carbazolyl group, carbolinyl group and the like.

Of these heterocyclic groups, more specifically preferred are furyl group, thienyl group, thiazolyl group, isoxazolyl group, pyrrolidinyl group, pyrrolyl group, pyridyl group, pyrazinyl group, pyrimidinyl group, tetrazolyl group, indolyl group, quinolyl group, isoquinolyl group, benzofuryl group, benzothienyl group, dihydrobenzofuryl group, thiophenopyridyl group and benzodioxanyl group.

As a substituent for the amino group of $R^1$ or $R^2$, there may be mentioned, for example, a group selected from formyl group, a lower alkyl group, a lower alkanoyl group, a lower alkylsulfonyl group and a lower alkoxycarbonyl group.

As a substituent for the lower alkyl group, there may be mentioned, for example, a group selected from a halogen atom, hydroxyl group, cyano group, carboxyl group, carbamoyl group, amino group, aminosulfonyl group, a halogenosulfonyl group, amidinothio group, a mono- or di-lower alkylamino group, a lower alkanoylamino group, a lower alkylsulfonylamino group, hydroxyamino group, a mono- or di-lower alkylcarbamoyl group, trifluoromethyl group, a lower alkoxy group, a lower alkylthio group, a lower alkylsulfinyl group, a lower alkylsulfonyl group, a lower alkylsulfonylamino group, a lower alkoxycarbamoyl group, a lower alkylsulfonylcarbamoyl group, sulfamoyl group, a mono- or di-lower alkylsulfamoyl group, a lower alkoxycarbonyl group, a heterocyclic group, a heterocyclic group-substituted carbamoyl group, a heterocyclic group-substituted lower alkylcarbamoyl group and a heterocyclic group-substituted sulfonylcarbamoyl group.

As a substituent for the lower alkenyl group, there may be mentioned, for example, carboxyl group or a lower alkoxycarbonyl group.

As a substituent for the carbamoyl group, there may be mentioned, for example, a group selected from a lower alkyl group, a lower alkoxy group and a lower alkylsulfonyl group.

As a substituent for the aryl group, there may be mentioned, for example, a group selected from nitro group, amino group, hydroxyl group, carbamoyl group, cyano group, carboxyl group, trifluoromethyl group, a lower alkoxycarbonyl group, a halogen atom, a lower alkyl group, a hydroxy-lower alkyl group, a lower alkoxy group, a lower alkoxy-lower alkoxy group, a mono- or di-lower alkylamino group, a mono- or di-lower alkanoylamino group, a lower alkylthio group, a lower alkylsulfonyl group, a lower alkylsulfinyl group, sulfamoyl group, a mono- or di-lower alkylsulfamoyl group, a lower alkylsulfonylamino group and a phenyl-lower alkoxy group.

As a substituent for the heterocyclic group, there may be mentioned, for example, a group selected from nitro group, amino group, hydroxyl group, formyl group, carbamoyl group, cyano group, carboxyl group, a lower alkoxycarbonyl group, a halogen atom, a lower alkyl group, a hydroxy-lower alkyl group, a lower alkoxy group, a mono- or di-lower alkylamino group, a mono- or di-lower alkanoylamino group, a lower alkylthio group, a lower alkylsulfonyl group, a lower alkylsulfinyl group, sulfamoyl group and a mono- or di-lower alkylsulfamoyl group.

As a substituent on the heterocyclic group for the heterocyclic group-substituted carbonyl group, there may be mentioned, for example, a group selected from nitro group, hydroxyl group, carbamoyl group, cyano group, carboxyl group, a lower alkoxycarbonyl group, a halogen atom, a lower alkyl group, a hydroxy-lower alkyl group, a lower alkoxy group, a lower alkanoyl group, a mono- or di-lower alkylamino group, a mono- or di-lower alkanoylamino group, a lower alkylthio group, a lower alkylsulfonyl group, a lower alkylsulfinyl group, sulfamoyl group and a mono- or di-lower alkylsulfamoyl group.

The above-mentioned amino group, lower alkyl group, carbamoyl group, aryl group, heterocyclic group and heterocyclic group-substituted carbonyl group may be substituted by the same or different 1 to 3 above-mentioned substituents.

As a substituent for the aryl group of $R^3$, there may be mentioned, for example, a group selected from cyano group, nitro group, amino group, a halogen atom, trifluoromethyl group, carboxyl group, hydroxyl group, carbamoyl group, a mono- or di-lower alkylamino group, a mono- or di-lower alkylamino-lower alkyl group, a mono- or di-lower alkylcarbamoyl group, a lower alkyl group, a hydroxy-lower alkyl group, a lower alkoxy group, a lower alkoxycarbonyl group, a lower alkanoyl group, a lower alkanoyloxy group, a lower alkanoyloxy-lower alkyl group, sulfo group, a lower alkylthio group, a lower alkylthio-lower alkyl group, a lower alkylsulfonyl group, a lower alkylsulfamoyl group and a lower alkylsulfinyl group.

As a substituent for the heterocyclic group, there may be mentioned, for example, a group selected from oxo group, cyano group, nitro group, amino group, a halogen atom, carboxyl group, hydroxyl group, formyl group, carbamoyl group, a mono- or di-lower alkylamino-group, a N-lower alkyl-N-cyclo-lower alkylamino group, a mono- or di-lower alkylamino-lower alkyl group, a mono- or di-lower alkylcarbamoyl group, a lower alkyl group, a hydroxy-lower alkyl group, a lower alkoxy group, a lower alkoxy-lower alkyl group, a lower alkoxycarbonyl group, a lower alkanoyl group, sulfo group, a lower alkylthio group, a lower alkylsulfonyl group, a lower alkylsulfamoyl group, a lower alkylsulfinyl group and a heterocyclic group.

As a substituent for the alkyl group, there may be mentioned, for example, a group selected from hydroxyl group, cyano group, carboxyl group, carbamoyl group, amino group, a mono- or di-lower alkylamino group, a lower alkanoylamino group, a lower alkylsulfonylamino group, hydroxyamino group, a mono- or di-lower alkylcarbamoyl group, trifluoromethyl group, a halogen atom, a lower alkoxy group, a lower alkylthio group, a lower alkylsulfinyl group, a lower alkylsulfonyl group, sulfamoyl group, a mono- or di-lower alkylsulfamoyl group, a lower alkoxycarbonyl group and a heterocyclic group.

The above-mentioned aryl group, heterocyclic group and lower alkyl group may be substituted by the same or different above-mentioned 1 to 3 substituents.

As a substituent for the lower alkyl group of $R^4$, there may be mentioned a mono- or di-lower alkylamino group. The lower alkyl group may be substituted by the same or different above-mentioned 1 to 2 substituents.

Of the compounds (I) which are active ingredients of the present invention, preferred compounds may be compounds wherein X is N—$R^4$, O or S; $R^1$ or $R^2$ is independently hydrogen atom, a lower alkyl group, a lower alkyl group substituted by a heterocyclic group, a di-lower alkylamino group, a carboxy-lower alkyl group, a halogeno-lower alkyl group, a lower alkoxy-lower alkyl group, a lower alkylsulfinyl-lower alkyl group, a lower alkyl-sulfonyl-lower alkyl group, a lower alkylthio-lower alkyl group, a trifluoromethyl-lower alkyl group, a cyclo-lower alkyl group, an aryl group, a trifluoromethylaryl group, a cyanoaryl group, a halogenoaryl group, a dihalogenoaryl group, a lower alkylaryl group, a lower alkoxyaryl group, a mono- or di-lower alkylaminoaryl group, a heterocyclic group, a lower alkyl-heterocyclic group, a haogeno-heterocyclic group, or a heterocyclic group substituted by a halogen atom and a lower alkyl group; $R^3$ is an aryl group, a halogenoaryl group, a hydroxyaryl group, a cyanoaryl group, a nitroaryl group, a lower alkylaryl group, a lower alkoxyaryl group, a lower alkylthio-aryl group, a heterocyclic group, a lower alkoxycarbonyl-heterocyclic group, a cyano-heterocyclic group, a halogeno-heterocyclic group, a lower alkyl-heterocyclic group, a di-lower alkyl-heterocyclic group, a heterocyclic group substituted by a di-lower alkylamino group, a heterocyclic group substituted by a halogen atom and a lower alkyl group, or a heterocyclic group substituted by a halogen atom and a hydroxy-lower alkyl group; and $R^4$ is hydrogen atom.

In another preferred embodiment of the present invention, X is N—$R^4$, O or S; $R^1$ or $R^2$ is independently hydrogen atom, a lower alkyl group, a lower alkyl group substituted by a heterocyclic group, a lower alkylamino group, a di-lower alkylamino group, a cyano-lower alkyl group, a hydroxy-lower alkyl group, a carboxy-lower alkyl group, a halogeno-lower alkyl group, a lower alkoxy-lower alkyl group, a lower alkylsulfinyl-lower alkyl group, a lower alkylthio-lower alkyl group, a cyclo-lower alkyl group, an aryl group, a trifluoromethylaryl group, a hydroxyaryl group, a halogenoaryl group, a dihalogenoaryl group, a lower alkylaryl group, a di-lower alkoxyaryl group, a di-lower alkylamnoaryl group, a lower alkylsulfonylaminoaryl group, an aryl group substituted by hydroxyl group and a lower alkoxy group, an aryl group substituted by hydroxy group and a halogen atom, an aryl group substituted by a halogen atom and a di-lower alkoxy group, a heterocyclic group, a halogeno-heterocyclic group, a lower alkyl-heterocyclic group, a hydroxy-lower alkyl-heterocyclic group, a heterocyclic group substituted by a halogen atom and a lower alkyl group, a heterocyclic group substituted by a lower alkyl group and a hydroxy-lower alkyl group, or a heterocyclic group-substituted carbonyl group; $R^3$ is a halogenoaryl group, a hydroxyaryl group, a cyanoaryl group, a lower alkylaryl group, a lower alkoxyaryl group, a lower alkylthioaryl group, an aryl group substituted by a hydroxyl group and a lower alkoxy group, a heterocyclic group, a cyano-heterocyclic group, a halogen-heterocyclic group, a lower alkyl-heterocyclic group, a di-lower alkyl-heterocyclic group, a hydroxy-lower alkyl-heterocyclic group, a di-lower aralkylamino-heterocyclic group, a heterocyclic group substituted by a halogen atom and a sulfo group, a heterocyclic group substituted by a halogen atom and a sulfamoyl group, or a heterocyclic group substituted by a halogen atom and a lower alkyl group; and $R^4$ is hydrogen atom or a lower alkyl group.

Of these, particularly preferred compounds are compounds wherein X is O or S; $R^1$ or $R^2$ is independently a carboxy-lower alkyl group, a lower alkyl group substituted by a heterocyclic group, an aryl group, a halogenoaryl group, a di-halogenoaryl group, a di-lower alkoxyaryl group, a lower alkylthioaryl group, a heterocyclic group, a halogeno-heterocyclic group, or a lower alkyl-heterocyclic group; and $R^3$ is a halogenoaryl group, a lower alkylaryl group, a di-lower alkylaminoaryl group, a lower alkylthioaryl group, a lower alkoxyaryl group, a heterocyclic group, a halogeno-heterocyclic group, a lower alkyl-hetero-cyclic group, a lower alkoxy-heterocyclic group, a lower alkylthio-heterocyclic group, or a di-lower alkylamino-heterocyclic group.

Among the nitrogen-containing 5-membered heterocyclic compounds (I), more preferred compounds in view of pharmaceutical effects are compounds wherein $R^1$ is (1) a lower alkyl group which may be substituted by carboxyl group, a lower alkoxycarbonyl group or a heterocyclic group, (2) an aryl group which may be substituted by one or two halogen atoms, or (3) a heterocyclic group which may be substituted by a halogen atom, $R^2$ is (1) a lower alkyl group which may be substituted by carboxyl group, a lower alkoxycarbonyl group or a heterocyclic group, (2) a heterocyclic group which may be substituted by a halogen atom, or (3) an aryl group which may be substituted by one or two halogen atoms; $R^3$ is (1) a heterocyclic group which may be substituted by one or two groups selected from amino group, a halogen atom, a lower alkyl group, a lower alkoxy group, a mono- or di-lower alkylamino group and a lower alkylthio group, or (2) an aryl group which may be substituted by amino group, a halogen atom, a lower alkyl group, a lower alkylthio group, a lower alkoxy group or a mono- or di-lower alkylamino group; and $R^4$ is hydrogen atom or a lower alkyl group.

Of these, more preferred compounds are compounds wherein $R^1$ is (1) a carboxyl-lower alkyl group, (2) a lower alkoxy-carbonyl-lower alkyl group, (3) a lower alkyl group substituted by a tetrazolyl group, (4) a phenyl group which may be substituted by one or two halogen atoms, or (5) a thienyl group which may be substituted by a halogen atom; $R^2$ is (1) a carboxyl-lower alkyl group, (2) a lower alkoxycarbonyl-lower alkyl group, (3) a lower alkyl group substituted by a tetrazolyl group, (4) a thienyl group which may be substituted by a halogen atom, or (5) a phenyl group which may be substituted by one or two halogen atoms; and $R^3$ is (1) a benzothienyl group which may be substituted by a halogen atom, (2) a phenyl group which may be substituted by a halogen atom, a lower alkylthio group, a lower alkoxy group or a di-lower alkylamino group, (3) a pyridyl group which may be substituted by a lower alkyl group, a lower alkoxy group or a di-lower alkylamino group, (4) a pyrimidinyl group which may be substituted by a di-lower alkylamino group or a lower alkylthio group, (5) a thienyl group which may be substituted by one or two lower alkyl groups, (6) thieno-[3,2-b]pyridyl group, (7) benzofuryl group, (8) dihydro-benzofuryl group or (9) an indolyl group which may be substituted by a lower alkyl group.

Of these, particularly preferred compounds are compounds wherein X is O or S; $R^1$ is (1) a carboxyl-lower alkyl group, (2) a lower alkoxycarbonyl-lower alkyl group, (3) a phenyl group which may be substituted by one or two halogen atoms, or (4) a thienyl group which may be substituted by a halogen atom; R² is (1) a carboxyl-lower alkyl group, (2) a lower alkoxycarbonyl-lower alkyl group, (3) a thienyl group which may be substituted by a halogen atom, or (4) a phenyl group which may be substituted by one or two halogen atoms; and R³ is (1) a benzothienyl group which may be substituted by a halogen atom, (2) a phenyl group which may be substituted by a halogen atom, a lower alkylthio group, a lower alkoxy group or a di-lower alkylamino group, (3) a pyridyl group which may be substituted by a lower alkoxy group or a di-lower alkylamino group, (4) a pyrimidinyl group which may be substituted by a di-lower alkylamino group, (5) a thienyl group which may be substituted by two lower alkyl groups, (6) thieno[3,2-b]pyridyl group, or (7) an indolyl group which may be substituted by a lower alkyl group.

The most preferred compound in view of pharmaceutical effects is the compound selected from the group consisting of:
4-(5-chlorothiophen-2-yl)-2-(2-benzo[b]thienyl)thiazol-5-yl acetic acid,
5-(4-chlorophenyl)-2-(2-N,N-dimethylaminopyrimidin-5-yl)-oxazol-4-yl acetic acid,
4-(5-chlorothiophen-2-yl)-2-(4-methoxyphenyl)thiazol-5-yl acetic acid,
5-(5-chlorothiophen-2-yl)-2-(4,5-dimethylthiophen-2-yl)-oxazol-4-yl acetic acid,
4-(5-chlorothiophen-2-yl)-2-(2-N,N-dimethylaminopyrimidin-5-yl)thiazol-5-yl acetic acid,
4-(5-chlorothiophen-2-yl)-2-(2-N,N-dimethylaminopyridin-5-yl)thiazol-5-yl acetic acid,
5-(4-chlorophenyl)-2-(4-fluorophenyl)oxazol-4-yl acetic acid,
5-(4-chlorophenyl)-2-(2-benzo[b]thienyl)oxazol-4-yl acetic acid,
4-(5-chlorothiophen-2-yl)-2-(2-benzo[b]thienyl)oxazol-5-yl acetic acid,
5-(5-chlorothiophen-2-yl)-2-(2-N,N-dimethylaminopyrimidin-5-yl)oxazol-4-yl acetic acid,
4-(4-chlorophenyl)-2-(2-N,N-dimethylaminopyrimidin-5-yl)-thiazol-5-yl acetic acid,
5-(5-chlorothiophen-2-yl)-2-(2-benzo[b]thienyl)oxazol-4-yl acetic acid,
4-(4-chlorophenyl)-2-(4-methoxyphenyl)thiazol-5-yl acetic acid,
5-(5-chlorothiophen-2-yl)-2-(4-fluorophenyl)oxazol-4-yl acetic acid,
5-(5-chlorothiophen-2-yl)-2-(6-fluorobenzo[b]thiophene-2-yl)oxazol-4-yl acetic acid,
5-(3-thienyl)-2-(2-benzo[b]thienyl)oxazol-4-yl acetic acid,
5-(5-chlorothiophen-2-yl)-2-(2-thieno[3,2-b]pyridyl)-oxazol-4-yl acetic acid,
5-(3-fluoro-4-chlorophenyl)-2-(2-benzo[b]thienyl)oxazol-4-yl acetic acid,
5-(5-chlorothiophen-2-yl)-2-(2-benzo[b]thienyl)thiazol-4-yl acetic acid,
5-(5-chlorothiophen-2-yl)-2-(4-methylthiophenyl)oxazol-4-yl acetic acid,
4-(5-chlorothiophen-2-yl)-2-(4-fluorophenyl)oxazol-5-yl acetic acid,
5-(5-chlorothiophen-2-yl)-2-(4-chlorophenyl)oxazol-4-yl acetic acid,
4-(3-fluoro-4-chlorophenyl)-2-(4-methoxyphenyl)thiazol-5-yl acetic acid,
4-(5-chlorothiophen-2-yl)-2-(4,5-dimethylthiophen-2-yl)-thiazol-5-yl acetic acid,
4-(3-fluoro-4-chlorophenyl)-2-(4-fluorophenyl)thiazol-5-yl acetic acid,
4-(4-chlorophenyl)-2-(2-N,N-dimethylaminopyridin-5-yl)-thiazol-5-yl acetic acid,
4-(5-chlorothiophen-2-yl)-2-(4-N,N-dimethylaminophenyl)-thiazol-5-yl acetic acid,
5-(5-chlorothiophen-2-yl)-2-(N-methylindol-2-yl)oxazol-4-yl acetic acid,
5-(5-chlorothiophen-2-yl)-2-(4,5-dimethylthiophen-2-yl)-thiazol-4-yl acetic acid;
a lower alkyl ester of these compounds; and
a pharmaceutically acceptable salt of these compounds.

In still another preferred embodiment of the present invention, X is O, one of R¹ and R² is a thienyl group substituted by a chlorine atom, and the other is a carboxyl-lower alkyl group, a lower alkoxycarbonyl-lower alkyl group or a lower alkyl group substituted by a tetrazolyl group; and R³ is a substituted or unsubstituted aryl group or a substituted or unsubstituted heterocyclic group.

Of these, more preferred compounds are compounds wherein R³ is (1) an aryl group which may be substituted by one or two substituents selected from a halogen atom, a di-lower alkylamino group, a lower alkylthio group and a lower alkoxy group, or (2) a heterocyclic group which may be substituted by one or two substituents selected from a halogen atom, a lower alkyl group, a lower alkoxy group, a lower alkylthio group and a mono- or di-lower alkylamino group.

Of these, particularly preferred compounds are compounds wherein one of R¹ and R² is a thienyl group substituted by a chlorine atom, and the other is a carboxyl-lower alkyl group or a lower alkoxycarbonyl-lower alkyl group; the aryl group is phenyl group; and the heterocyclic group is a thienyl group, a pyridyl group, a pyrimidinyl group, a benzothienyl group, a benzofuryl group, a dihydrobenzofuryl group, an indolyl group or a thieno[3,2-b]pyridyl group.

Of these, further preferred compounds are compounds wherein R³ is a phenyl group which is substituted by a halogen atom or a lower alkylthio group; a thienyl group which is substituted by one or two lower alkyl groups; a pyrimidinyl group which is substituted by a di-lower alkylamino group; a benzothienyl group which may be substituted by a halogen atom; an indolyl group which may be substituted by a lower alkyl group; or a thieno[3,2-b]pyridyl group.

In still another preferred embodiment of the present invention, X is S, one of R¹ and R² is a thienyl group substituted by a chlorine atom, and the other is a carboxyl-lower alkyl group, a lower alkoxycarbonyl-lower alkyl group or a lower alkyl group substituted by a tetrazolyl group, and R³ is a substituted or unsubstituted heterocyclic group, where said heterocyclic group is selected from a pyridyl group, a pyrimidinyl group, a benzothienyl group, an indolyl group and a thieno[3,2-b]-pyridyl group.

In a more preferred embodiment, R³ is a heterocyclic group which may be substituted by one or two substituents selected from a halogen atom, a lower alkoxy group, a lower alkyl group, a lower alkylthio group and a mono- or di-lower alkylamino group, where said heterocyclic group is selected from a pyridyl group, a pyrimidinyl group, a benzothienyl group, and a thieno[3,2-b]pyridyl group.

In a further preferred embodiment, one of R¹ and R² is a thienyl group substituted by a chlorine atom, and the other is a carboxyl-lower alkyl group or a lower alkoxycarbonyl-lower alkyl group; R³ is a pyridyl group which may be substituted by a di-lower alkylamino group; a pyrimidinyl group which may be substituted by a mono- or di-lower alkylamino group; or a benzothienyl group which may be substituted by a halogen atom.

In the compound (I), an optical isomer based on an asymmetric carbon may be present depending on a kind of a substituent(s). Either of the optical isomer or a mixture thereof may be used as the active ingredient of the present invention.

The active ingredient (I) of the present invention can be used in the free form or in the form of a pharmaceutically acceptable salt. Examples of pharmaceutically acceptable salts of the compound (I) include inorganic acid salts such as hydrochloride, sulfate, phosphate or hydrobromide, and organic acid salts such as acetate, fumarate, oxalate, citrate, methanesulfonate, benzenesulfonate, tosylate or maleate. In addition, in case of a compound with substituents such as a carboxyl group, salts with a base (for example, alkali metal salts such as a sodium salt and a potassium salt or alkaline earth metal salts such as a calcium salt) can be mentioned.

The compound (I) or pharmaceutically acceptable salts thereof includes its internal salts, addition products, solvates and hydrates.

The active ingredient (I) of the present invention or pharmaceutically acceptable salts thereof can be administered orally or parenterally and used as common pharmaceutical preparations such as tablets, granules, capsules, powders, injection solution and inhalants.

As a pharmaceutically acceptable carrier for a preparation of oral administration, there may be mentioned a material commonly used, for example, a binder (such as syrup, Gum Arabic, gelatin, sorbit, tragacanth and polyvinyl pyrrolidone), an excipient (such as lactose, sugar, corn starch, potassium phosphate, sorbit and glycine), a lubricant (such as magnesium stearate, talc, polyethylene glycol and silica), a disintegrator (such as potato starch) and a humectant (such as lauryl sodium sulfate).

On the other hand, when the active ingredient of the present invention is administered non-orally, it may be formulated into the form of an injection or a drip infusion by using distilled water for injection, physiological saline, an aqueous glucose solution and the like, or a suppository.

A dose of the compound (I) or a pharmaceutically acceptable salt thereof may vary depending on an administration method, an age, weight, conditions or a kind or degree of disease of a patient, and may be generally about 0.1 to 50 mg/kg per day, more preferably about 0.3 to 30 mg/kg per day.

The compound (I) or a pharmaceutically acceptable salt thereof has an excellent large conductance calcium-activated K channel opening activity and hyperpolarizes a membrane electric potential of cells, so that it may be used for a prophylactic, relief and/or treatment agent of, for example, hypertension, asthma, premature birth, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, male-pattern baldness, erectile dysfunction, diabetes, diabetic peripheral nerve disorder, other diabetic complication, sterility, urolithiasis and pain accompanied thereby, pollakiuria, urinary incontinence, nocturnal enuresis, and the like.

In the present specification, as the lower alkyl group, a hydroxy lower alkyl group, a lower alkoxy group, a lower alkylthio group, a lower alkylsulfinyl group, a lower alkoxysulfonyl group, a lower alkylsulfamoyl group, a lower alkylcarbamoyl group, a lower alkylamino group, or a lower alkylsulfonylamino group, there may be mentioned those which are straight or branched and having 1 to 6 carbon atoms, particularly those which are straight or branched and having 1 to 4 carbon atoms.

As a lower alkenyl group, a lower alkanoyl group, a lower alkanoyloxy group, a lower alkanoylamino group or a lower alkoxycarbonyl group, there may be mentioned those which are a straight or branched and having 2 to 7 carbon atoms, particularly those which are a straight or branched and having 2 to 5 carbon atoms.

As a cyclo-lower alkyl group, there may be mentioned those having 3 to 6 carbon atoms.

As a halogen atom, there may be mentioned fluorine atom, chlorine atom, bromine atom or iodine atom.

The nitrogen-containing 5-membered heterocyclic compound (I) which is an active ingredient of the present invention can be prepared by the following Method A, Method B, Method C or Method D, but the preparation methods are not limited to these methods.

(Method A)

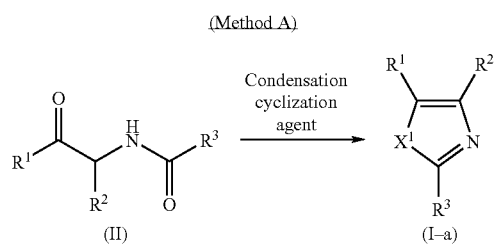

wherein $X^1$ represents NH, O or S, and other symbols have the same meanings as defined above.

Among the nitrogen-containing 5-membered heterocyclic compound (I), a compound (I-a) can be prepared by reacting the compound represented by the formula (II) or a salt thereof with a condensation reagent.

As the condensation reagent, there may be suitably used, when $X^1$ is NH, for example, ammonia or an ammonium salt (such as ammonium acetate, ammonium formate, ammonium carbonate, ammonium benzoate and ammonium picolate), when $X^1$ is O, for example, phosphorus oxychloride, thionyl chloride, acetyl chloride, triphenylphosphine-iodine, triphenylphosphine-phosgene, sulfuric acid, polyphosphoric acid, p-toluene-sulfonic acid, etc., and when $X^1$ is S, for example, phosphorus pentasulfide, Lawesson's reagent (2,4-bis(4-methoxyphenyl)-1,3-dithia-2,4-diphosphetan-2,4-disulfide), and the like.

The present reaction can be carried out in a suitable solvent or in the absence of a solvent. As the solvent, it is not particularly limited so long as it does not disturb the reaction, and there may be used, for example, acetic acid, dimethylformamide, benzene, toluene, tetrahydrofuran, chloroform, methylene chloride, acetonitrile or a mixed solvent of the above-mentioned solvents. The present reaction proceeds suitably at 15 to 150° C., particularly at room temperature to 120° C.

(Method B)

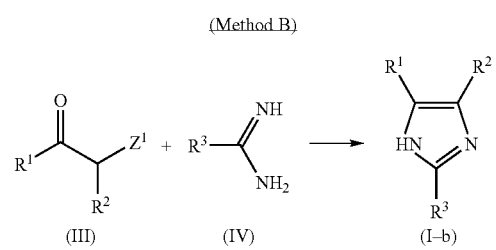

wherein $Z^1$ represents a reactive residue, and other symbols have the same meanings as defined above.

Also, among the compound (I), a compound (I-b) can be prepared by reacting a compound represented by the formula (III) or a salt thereof with a compound represented by the formula (IV) or a salt thereof in the presence of a base. As the base, there may be suitably used, for example, an alkali metal carbonate, an alkali metal hydride, an alkali metal alkoxide, an alkali metal hydroxide, and the like.

The present reaction can be carried out in a suitable solvent or in the absence of a solvent. As the solvent, it is not particularly limited so long as it does not disturb the reaction, and there may be used, for example, acetonitrile, methanol, ethanol, chloroform, methylene chloride, dimethylformamide, acetone, tetrahydrofuran or a mixed solvent of the above-mentioned solvents. The present reaction proceeds suitably at 30 to 150° C., particularly at 60 to 120° C.

(Method C)

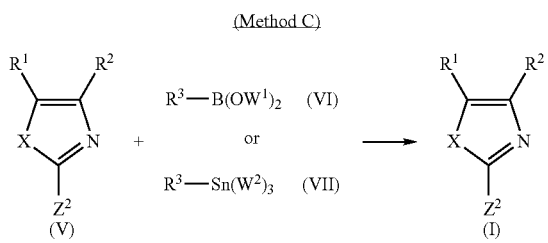

wherein $Z^2$ represents a reactive residue, $W^1$ represents hydrogen atom or a lower alkyl group, $W^2$ represents a lower alkyl group, and other symbols have the same meanings as defined above.

The compound (I) can be also prepared by reacting a compound represented by the formula (V) with a compound represented by the formula (VI) or a compound represented by the formula (VII) in the presence of a palladium catalyst. As the palladium catalyst, there may be suitably used a zero-valent or divalent palladium catalyst, for example, tetrakis (triphenylphosphine) palladium (0), bis (triphenylphosphine) palladium (II) chloride, palladium (II) acetate, etc.

When Method C is carried out by using the compound (VI), it is preferably carried out in the presence of a base. As the base, there may be suitably used, for example, an inorganic base such as an alkali metal carbonate, an alkali metal hydroxide, an alkali metal phosphate, an alkali metal fluoride, and the like, or an organic base such as triethylamine, and the like.

The present reaction can be carried out in a suitable solvent or in the absence of a solvent. As the solvent, it is not particularly limited so long as it does not disturb the reaction, and there may be used, for example, dimethoxyethane, tetra-hydrofuran, dimethylformamide, methanol, ethanol, toluene, benzene, chloroform or a mixed solvent of the above-mentioned solvents. The present reaction proceeds suitably at 60 to 150° C., particularly at 80 to 120° C.

(Method D)

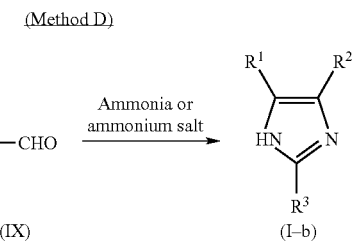

wherein the symbols have the same meanings as defined above.

Also, among the compound (I), a compound (I-b) can be prepared by reacting a compound represented by the formula (VIII) or a salt thereof with a compound represented by the formula (IX) and a salt thereof in the presence of ammonia or an ammonium salt.

As the ammonium salt, there may be suitably used, for example, ammonium acetate, ammonium formate, ammonium carbonate, ammonium benzoate, ammonium picolate, and the like.

The present reaction can be carried out in a suitable solvent or in the absence of a solvent. As the solvent, it is not particularly limited so long as it does not disturb the reaction, and there may be used, for example, acetic acid, methanol, ethanol, dimethoxyethane, tetrahydrofuran, dimethylformamide or a mixed solvent of the above-mentioned solvents. The present reaction proceeds suitably at 0 to 150° C., particularly at 30 to 120° C.

In the above-mentioned Methods A to D, the compounds (II), (III), (IV), (V), (VIII) or (IX) may be used as a salt of an inorganic acid such as hydrochloride, sulfate, etc., or a salt of an inorganic base such as an alkali metal salt, an alkaline earth metal salt, etc.

As the reactive residue of $Z^1$ and $Z^2$, a halogen atom is suitably used.

The nitrogen-containing 5-membered heterocyclic compound (I) can be prepared by converting objective compounds obtained from one of the above methods into other objective compounds. Such conversion reactions may be suitably used depending on a substituent(s) in a compound, and it can be carried out, for example, by a conventional method as mentioned in the following Methods (a) to (v).

Method (a):

A compound (I) wherein $R^1$ or $R^2$ is a halogen atom can be prepared by reacting a compound (I) where corresponding $R^1$ or $R^2$ is a hydrogen atom with a halogenating agent. As the halogenating agent, there may be suitably used bromine, chlorine, iodine, [bis(trifluoroacetoxy)iodo]benzene, N-bromosuccinic imide and the like. This reaction proceeds suitably at 0° C. to 30° C.

Method (b):

A compound (I) wherein $R^1$ or $R^2$ is a substituted or unsubstituted aryl group, or a substituted or unsubstituted heterocyclic group can be prepared by reaction of a compound (I) where corresponding $R^1$ or $R^2$ is a halogen atom with a (tri-lower alkyl)(a substituted or unsubstituted aryl)tin compound, or (tri-lower alkyl)(a substituted or unsubstituted hetero-cyclic)tin compound in the presence of a catalyst. As the catalyst, there may be suitably used a zero-valent or divalent palladium catalyst such as bis(triphenylphosphine)palladium (II) chloride, palladium (II) acetate, tetrakis(triphenyl-phosphine) palladium (0), etc. Also this reaction proceeds more suitably in the presence of a zinc salt such as zinc chloride, zinc bromide, zinc iodide, etc. This reaction proceeds suitably at 50° C. to 120° C.

Also, this reaction may be carried out by using a corresponding boric acid or its ester in place of the tin compound, in the presence of a base. As the palladium catalyst and the base, those as mentioned in the above Method C are suitably used. This reaction proceeds suitably at 60° C. to 120° C.

Method (c):

A compound (I) wherein $R^1$ or $R^2$ is a substituted or unsubstituted heterocyclic group-substituted carbonyl group can be prepared by reacting a compound (I) where corresponding $R^1$ or $R^2$ is a substituted carbamoyl group with a substituted or unsubstituted heterocyclyl lithium. This reaction proceeds suitably at −78° C. to 30° C. The substituted or unsubstituted heterocyclyl lithium can be prepared by lithiation of a corresponding halogeno-heterocyclic compound with n-butyl lithium, etc.

Method (d):

A compound (I) where X is N—$R^4$ and $R^4$ is a substituted or unsubstituted alkyl group can be prepared by reaction of a compound (I) where corresponding X is N—$R^4$ and $R^4$ is hydrogen atom with a substituted or unsubstituted lower alkyl halide (such as a lower alkyl iodide, a lower alkyl chloride and a lower alkyl bromide) or a lower alkyl sulfonate (such as a lower alkyl trifluoromethanesulfonate and a lower alkyl methanesulfonate) in the presence of a base. As the base, there may be suitably used an alkali metal hydride, an alkali metal carbonate, an alkali metal alkoxide, an alkali metal hydroxide, and the like. This reaction proceeds suitably at 30° C. to 80° C.

Method (e):

A compound (I) where $R^1$ or $R^2$ is a formylamino group or an N-lower alkyl-N-formylamino group can be prepared by reacting a compound (I) where corresponding $R^1$ or $R^2$ is an amino group or an N-lower alkylamino group with a formic acid lower alkyl ester (such as methyl ester and ethyl ester). This reaction proceeds suitably at 60° C. to 100° C.

Method (f):

A compound (I) where $R^1$ or $R^2$ is an N-methylamino group, an N-lower alkyl-N-methylamino group or an N-ethylamino group can be prepared by reacting a compound (I) where corresponding $R^1$ or $R^2$ is a formylamino group, an N-lower alkyl-N-formylamino group or an N-acetylamino group with a reducing agent. As the reducing agent, there may be suitably used a borane complex (such as borane-dimethylsulfide complex), lithium aluminum hydride, and the like. This reaction proceeds suitably at 0° C. to 60° C.

Method (g):

A compound (I) where $R^1$ or $R^2$ is a lower alkoxycarbonylamino group can be prepared by reacting a compound (I) where corresponding $R^1$ or $R^2$ is an amino group with a lower alkoxycarbonyl halide in the presence of a base. As the base, there may be suitably used pyridine, triethylamine, an alkali metal carbonate, an alkali metal lower alkoxide, an alkali metal hydride and the like. This reaction proceeds suitably at 0° C. to 30° C.

Method (h):

A compound (I) where $R^1$ or $R^2$ is a hydroxy-lower alkyl group can be prepared by reacting a compound (I) where corresponding $R^1$ or $R^2$ is a hydrogen atom with formaldehyde or a lower alkyl aldehyde in the presence of a base. As the base, there may be suitably used an alkali metal carbonate, an alkali metal lower alkoxide, triethylamine, and the like. This reaction proceeds suitably at 60° C. to 120° C.

Method (i)

A compound (I) where $R^1$ or $R^2$ is a halogeno-lower alkyl group can be prepared by reacting a compound (I) where corresponding $R^1$ or $R^2$ is a hydroxy-lower alkyl group with a halogenating agent. As the halogenating agent, there may be suitably used thionyl chloride, thionyl bromide and the like. This reaction proceeds suitably at 0° C. to 50° C.

Method (j):

A compound (I) where $R^1$ or $R^2$ is a lower alkoxy-lower alkyl group can be prepared by reacting a compound (I) where corresponding $R^1$ or $R^2$ is a halogeno-lower alkyl group with a lower alkanol. As the lower alkanol, there may be suitably used methanol, ethanol and the like. This reaction proceeds suitably at 30° C. to 80° C.

Method (k):

A compound (I) where $R^1$ or $R^2$ is a lower alkylthio-lower alkyl group can be prepared by reacting a compound (I) where corresponding $R^1$ or $R^2$ is a halogeno-lower alkyl group with a lower alkyl sulfide salt. As the lower alkyl sulfide salt, there may be suitably used an alkali metal lower alkyl sulfide such as sodium methyl sulfide and the like. This reaction is preferably carried out in the presence of a base. As the base, there may be suitably used triethylamine, pyridine, an alkali metal carbonate, an alkali metal alkoxide and the like. This reaction proceeds suitably at 0° C. to 60° C.

Method (l):

A compound (I) where $R^1$ or $R^2$ is a lower alkylsulfinyl-lower alkyl group or a lower alkylsulfonyl-lower alkyl group can be prepared by reacting a compound (I) where corresponding $R^1$ or $R^2$ is a lower alkylthio-lower alkyl group with an oxidizing agent. As the oxidizing agent, there may be suitably used metachloroperbenzoic acid, aqueous hydrogen peroxide solution and the like. This reaction proceeds suitably at −20° C. to 30° C.

Method (m):

A compound (I) where $R^1$ or $R^2$ is a carboxy-lower alkyl group or a carboxy-lower alkenyl group can be prepared by hydrolysis of a compound (I) where corresponding $R^1$ or $R^2$ is a lower alkoxycarbonyl-lower alkyl or a cyano-lower alkyl group or a lower alkoxycarbonyl-lower alkenyl or a cyano-lower alkeny group with a base or an acid. As the base, an alkali metal hydroxide and the like may be suitably used. As the acid, hydrochloric acid or boron tribromide and the like may be suitably used. This reaction proceeds suitably at 0° C. to 80° C.

Method (n):

A compound (I) where $R^3$ is a heterocyclic group substituted by a sulfo group can be prepared by reaction of a compound (I) where corresponding $R^3$ is a heterocyclic group (which may be substituted onto the other position of the heterocyclic ring than that to which the sulfo group is to be bonded) with halogenosulfonic acid (such as chlorosulfonic acid), and then, treating with a basic aqueous solution (such as aqueous ammonia) This reaction proceeds suitably at 0° C. to 50° C.

Method (o):

A compound (I) where $R^3$ is a heterocyclic group substituted by sulfamoyl group can be prepared by treating a compound (I) where corresponding $R^3$ is a heterocyclic group substituted by chlorosulfonyl group with ammonia. This reaction proceeds suitably at 0° C. to 60° C.

Method (p):

A compound (I) where $R^1$, $R^2$ or $R^3$ is a heterocyclic group substituted by a hydroxy-lower alkyl group or $R^1$ or $R^2$ is a hydroxy-lower alkyl group can be prepared by reacting a compound (I) where corresponding $R^1$, $R^2$ or $R^3$ is a heterocyclic group substituted by a lower alkoxycarbonyl-lower alkyl group or corresponding $R^1$ or $R^2$ is a lower alkoxycarbonyl-lower alkyl group with a reducing agent. As the reducing agent, there may be suitably used lithium aluminum hydride, lithium borohydride, a borane complex (such as borane.dimethylsulfide complex) and the like. This reaction proceeds suitably at 0° C. to 60° C.

Method (q):

A compound (I) where $R^1$ or $R^2$ is a substituted or unsubstituted carbamoyl group can be prepared by reaction of a compound (I) where corresponding $R^1$ or $R^2$ is a carboxyl group with a corresponding substituted or unsubstituted amine in the presence of a condensing agent. As the condensing agent, there may be suitably used 3-ethyl-1-(3-dimethylaminopropyl)-carbodiimide hydrochloride, diethylcyanophosphate and the like. This reaction proceeds suitably at 0° C. to 50° C.

Method (r):

A compound (I) where $R^3$ is a pyridyl group substituted with a mono- or di-lower alkylamino group or $R^3$ is a pyrazinyl group substituted with a mono- or di lower alkylamino group can be prepared by reacting a compound (I) where corresponding $R^3$ is a halogenopyridyl group or a halogenopyrazinyl group with a corresponding mono- or di-lower alkylamine. This reaction proceeds suitably at 30° C. to 120° C.

Method (s):

A compound (I) where $R^3$ is a pyrimidinyl group substituted with a mono- or di-lower alkylamino group can be prepared by reacting a compound (I) where corresponding $R^3$ is a pyrimidinyl group substituted with a lower alkylthio group with a oxidizing agent, followed by reacting the resulting compound with corresponding mono- or di-lower alkylamine. Examples of the oxidizing agent may be m-chloroperbenzoic acid, hydrogen peroxide, and the like. This reaction proceeds suitably at 0° C. to 30° C.

Method (t):

A compound (I) where $R^1$ or $R^2$ is a substituted or unsubstituted carbamoyl-lower alkyl group can be prepared by reacting a compound (I) where corresponding $R^1$ or $R^2$ is a carboxy-lower alkyl group with a corresponding amine in the presence of a condensing agent. Examples of the condensing agent may be 3-ethyl-1-(3-dimethylaminopropyl)carbodiimide hydrochloride, diethyl cyanophosphonate, and the like. This reaction proceeds suitably at 0° C. to 50° C.

Method (u):

A compound (I) where $R^1$ or $R^2$ is a cyano-lower alkyl group can be prepared by reacting a compound (I) where corresponding $R^1$ or $R^2$ is a carbamoyl-lower alkyl group with a dehydrating agent. Examples of the dehydrating agent may be phosphorus oxychloride, acetic anhydride, thionyl chloride and the like. This reaction proceeds suitably at 50° C. to 100° C.

Method (v):

A compound (I) where $R^1$ or $R^2$ is a tetrazolyl-lower alkyl group can be prepared by reacting a compound (I) where corresponding $R^1$ or $R^2$ is a cyano-lower alkyl group with an azide compound.

Examples of the azide compound may be sodium azide, a trialkyltin azide, a trialkylsilyl azide, and the like. This reaction proceeds suitably at 80° C. to 120° C.

The reactions mentioned in the above Methods (a) to (v) can be carried out in an inert solvent to the reaction or in the absence of a solvent, which is not specifically limited, and the solvent may be mentioned, for example, methylene chloride, chloroform, tetrahydrofuran, methanol, ethanol, isopropanol, dimethylformamide, dimethylsulfoxide, water, ethyl acetate, dimethoxyethane, toluene, benzene, and the like, or a mixed solvent of the above solvents.

Also, among the compounds (I), known compounds are included and these known compounds have been reported in,
for example, Japanese Provisional Patent Publications No. 5832/1972, No. 29771/1973, 172488/1984, 34951/1985, No. 188371/1985 and No. 167676/1986, U.S. Pat. No. 3,470,195, U.S. Pat. No. 3,476,766, U.S. Pat. No. 3,546,342, U.S. Pat. No. 3,574,228 and U.S. Pat. No. 3,905,961, International Publications No. WO95/04724 and No. WO99/01128, Chem. Pharm. Bull., 34(8), 3111-3120 (1986), Chem. Pharm. Bull., 36(11), 4435-4440 (1988), Chem. Pharm. Bull., 40(12), 3206-3213 (1992), Angew. Chem., 85(13), 584-585 (1973), J. Heterocyclic Chem., 22(2), 569-574 (1985), J. Med. Chem., 29(3), 333-341 (1986), J. Med. Chem., 31(6), 1197-1204 (1988) and the like. However, there is no description in these references that these compounds have large conductance calcium-activated K channel opening activity.

Incidentally, the starting compound (II) or (III) of the present invention can be prepared, for example, according to the method described in J. Med. Chem., 29, 333-341 (1986), Chem. Pharm. Bull., 34(8), 3111-3120 (1986) or Japanese Provisional Patent Publication No. 167676/1986.

The compound (II) can be prepared specifically by the conventional method as mentioned below.

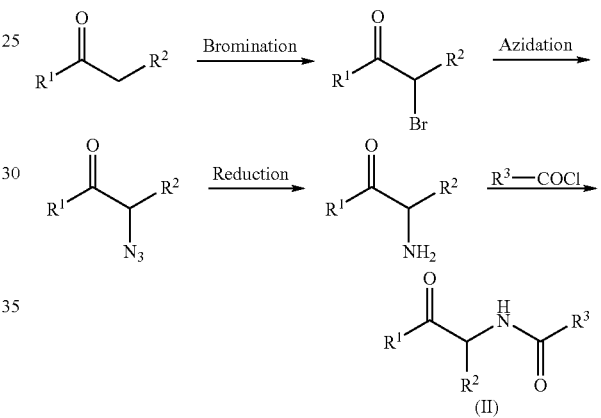

wherein the symbols have the same meanings as defined above.

Also, among the compounds (V), a compound (V-a) wherein $R^2$ is a halogen atom can be prepared specifically by the conventional method as mentioned below.

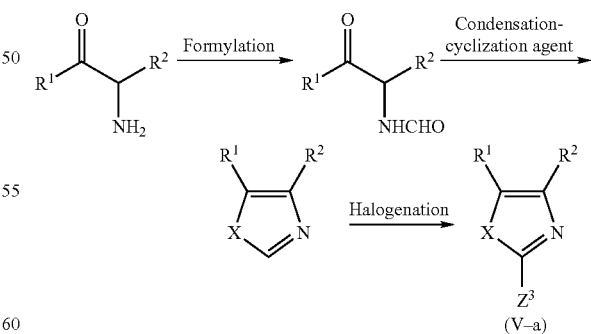

wherein $Z^3$ represents a halogen atom, and the other symbols have the same meaning as defined above.

The active ingredients of the present invention can be exemplified by the following Preparation examples but they are not limited thereto.

PREPARATION EXAMPLE

Preparation Example 1

A crude product of 2-(6-methylnicotinoylamino)-1-(3-pyridyl)-1-butanone (425 mg) was dissolved in acetic acid (5 ml), and ammonium acetate (2.30 g) was added to the solution. The resulting mixture was stirred under reflux for one hour. After cooling, 28% of aqueous ammonia was added to the reaction mixture and the mixture was extracted with ethyl acetate. The organic layer was washed with brine, dried over anhydrous sodium sulfate and the solvent was removed under reduced pressure. To the residue was added hydrogen chloride-methanol solution, and the solvent was again removed under reduced pressure. The resulting residue was triturated with acetone to obtain 5-ethyl-2-(2-methyl-pyridin-5-yl)-4-(3-pyridyl)imidazole trihydrochloride (369 mg) as pale yellowish crystalline powder.

Melting point: 270 to 273° C. (decomposed)
MS·APCI (m/z): 265 (MH+)

Preparation Examples 2 to 42

The following compounds shown in Table 1 were prepared in a manner similar to Preparation example 1 by using corresponding starting materials.

TABLE 1

| Preparation example No. | Chemical structure | Salt | Physical constant, etc. |
|---|---|---|---|
| 2 | 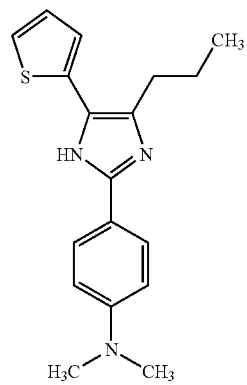 | 2HCl | Crystal Melting point: 170-172° C. MS · APCI(m/z): 312(M + H)+ |
| 3 | 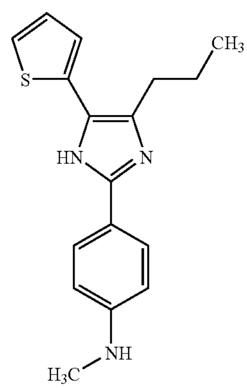 | 2HCl | Crystal Melting point: 175-180° C. MS · APCI(m/z): 298(M + H)+ |
| 4 | 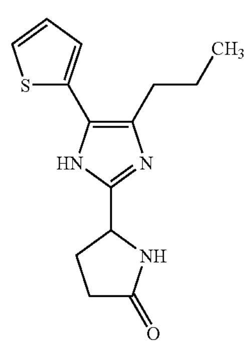 | 1HCl | Crystal Melting point: 234-237° C. MS · APCI(m/z): 276(M + H)+ |

TABLE 1-continued

| Preparation example No. | Chemical structure | Salt | Physical constant, etc. |
| --- | --- | --- | --- |
| 5 | 5-(thiophen-2-yl)-4-propyl-2-(pyridin-2-yl)-1H-imidazole | 1HCl | Powder<br>MS · APCI(m/z): 270(M + H)+ |
| 6 | 5-(thiophen-2-yl)-4-propyl-2-(pyridin-4-yl)-1H-imidazole | 2HCl | Crystal<br>Melting point: 275-280° C.<br>MS · APCI(m/z): 270(M + H)+ |
| 7 | 5-(thiophen-2-yl)-4-propyl-2-(5-methylpyridin-3-yl)-1H-imidazole | 2HCl | Crystal<br>Melting point: 183-185° C.<br>MS · APCI(m/z): 284(M + H)+ |
| 8 | 5-(thiophen-2-yl)-4-propyl-2-(4-cyanophenyl)-1H-imidazole | 1HCl | Crystal<br>Melting point: 251-254° C.<br>MS · APCI(m/z): 294(M + H)+ |

TABLE 1-continued

| Preparation example No. | Chemical structure | Salt | Physical constant, etc. |
|---|---|---|---|
| 9 | 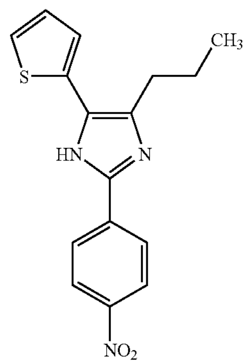 | 1HCl | Crystal<br>Melting point:<br>278-281° C.<br>MS · APCI(m/z):<br>314(M + H)+ |
| 10 | 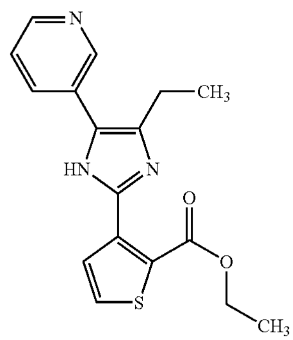 | Free material | Crystal<br>Melting point:<br>127-129° C.<br>MS · APCI(m/z):<br>328(M + H)+ |
| 11 | 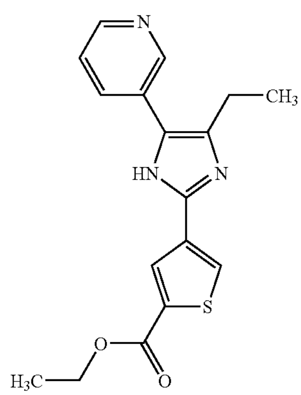 | Free material | Crystal<br>Melting point:<br>187-189° C.<br>MS · APCI(m/z):<br>328(M + H)+ |
| 12 | 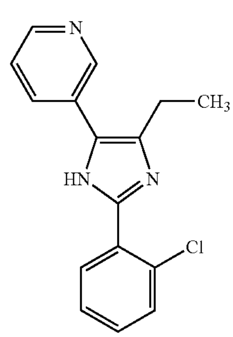 | 2HCl | Crystal<br>Melting point:<br>221-223° C.<br>MS · APCI(m/z):<br>284/286(M + H)+ |

TABLE 1-continued

| Preparation example No. | Chemical structure | Salt | Physical constant, etc. |
|---|---|---|---|
| 13 | (pyridin-3-yl at C5, ethyl at C4, 3-chlorophenyl at C2 of 1H-imidazole) | 2HCl | Crystal<br>Melting point: 223-224° C.<br>MS·APCI(m/z): 284/286(M + H)+ |
| 14 | (pyridin-3-yl at C5, ethyl at C4, 5-chlorothiophen-2-yl at C2 of 1H-imidazole) | 2HCl | Powder<br>MS·APCI(m/z): 290(M + H)+ |
| 15 | (pyridin-3-yl at C5, ethyl at C4, 3-methylfuran-2-yl at C2 of 1H-imidazole) | 2HCl | Powder<br>MS·APCI(m/z): 254(M + H)+ |
| 16 | (pyridin-3-yl at C5, ethyl at C4, 5-cyanothiophen-2-yl at C2 of 1H-imidazole) | 2HCl | Powder<br>MS·APCI(m/z): 281(M + H)+ |

TABLE 1-continued

| Preparation example No. | Chemical structure | Salt | Physical constant, etc. |
| --- | --- | --- | --- |
| 17 | [structure: 4-methyl-5-(pyridin-3-yl)-2-(2-nitrophenyl)-1H-imidazole] | 2HCl | Solid<br>MS·APCI(m/z):<br>295(M + H)+ |
| 18 | [structure: 2-(4-methyl-5-(pyridin-3-yl)-1H-imidazol-2-yl)benzamide] | 2HCl | Crystal<br>Melting point:<br>250-253° C.<br>MS·APCI(m/z):<br>293(M + H)+ |
| 19 | [structure: 2-(5-bromothiophen-2-yl)-4-methyl-5-(pyridin-3-yl)-1H-imidazole] | 2HCl | Crystal<br>Melting point:<br>214-216° C.<br>MS·APCI(m/z):<br>334/336(M + H)+ |
| 20 | [structure: 4-methyl-5-(pyridin-3-yl)-2-(thiophen-2-yl)-1H-imidazole] | 2HCl | Crystal<br>Melting point:<br>215-217° C.<br>MS·APCI(m/z):<br>256(M + H)+ |

TABLE 1-continued

| Preparation example No. | Chemical structure | Salt | Physical constant, etc. |
|---|---|---|---|
| 21 | (3-pyridyl, 5-ethyl, 2-(2-methoxycarbonylphenyl)-1H-imidazole) | Free material | Powder MS·APCI(m/z): 308(M + H)+ |
| 22 | (3-pyridyl, 2-(4-fluorophenyl)-1H-imidazole) | 2HCl | Crystal Melting point: 192-195° C. EI·MS(m/z): 239(M+) |
| 23 | (3-pyridyl, 2-(4-cyanophenyl)-1H-imidazole) | 2HCl | Crystal Melting point: 325-328° C. MS·APCI(m/z): 247(M + H)+ |
| 24 | (3-pyridyl, 2-(5-chlorothiophen-3-yl)-1H-imidazole) | 2HCl | Powder MS·APCI(m/z): 262(M + H)+ |

TABLE 1-continued

| Preparation example No. | Chemical structure | Salt | Physical constant, etc. |
|---|---|---|---|
| 25 | 3-pyridyl-1H-imidazol-2-yl-(5-chlorothien-2-yl) | 2HCl | Powder<br>MS · APCI(m/z):<br>262/264(M + H)+ |
| 26 | 3-pyridyl-1H-imidazol-2-yl-(6-methylpyridin-3-yl) | 3HCl | Crystal<br>Melting point:<br>269-273° C.<br>MS · APCI(m/z):<br>237(M + H)+ |
| 27 | 4-phenyl-5-methyl-1H-imidazol-2-yl-(4-cyanophenyl) | 1HCl | Crystal<br>Melting point:<br>285-288° C.<br>MS · APCI(m/z):<br>274(M + H)+ |
| 28 | 4-phenyl-5-methyl-1H-imidazol-2-yl-(6-methylpyridin-3-yl) | 2HCl | Crystal<br>Melting point:<br>248-251° C.<br>MS · APCI(m/z):<br>264(M + H)+ |

TABLE 1-continued

| Preparation example No. | Chemical structure | Salt | Physical constant, etc. |
| --- | --- | --- | --- |
| 29 | 5-phenyl-4-propyl-2-(3-chlorophenyl)-1H-imidazole | 1HCl | Crystal<br>Melting point: 202-204° C.<br>MS · APCI(m/z): 297(M + H)+ |
| 30 | 5-phenyl-4-propyl-2-(3-fluorophenyl)-1H-imidazole | 1HCl | Crystal<br>Melting point: 192-193° C.<br>MS · APCI(m/z): 281(M + H)+ |
| 31 | 5-phenyl-4-propyl-2-(4-cyanophenyl)-1H-imidazole | 1HCl | Crystal<br>Melting point: 258-260° C.<br>MS · APCI(m/z): 288(M + H)+ |
| 32 | 5-phenyl-4-propyl-2-(naphthalen-2-yl)-1H-imidazole | 1HCl | Crystal<br>Melting point: 189-190° C.<br>MS · APCI(m/z): 313(M + H)+ |

TABLE 1-continued

| Preparation example No. | Chemical structure | Salt | Physical constant, etc. |
| --- | --- | --- | --- |
| 33 | 2-(3-thienyl)-4-propyl-5-phenyl-1H-imidazole | 1HCl | Crystal<br>Melting point: 215-217° C.<br>MS·APCI(m/z): 269(M + H)+ |
| 34 | 2-(5-chloro-3-thienyl)-4-propyl-5-phenyl-1H-imidazole | 1HCl | Crystal<br>Melting point: 194-196° C.<br>MS·APCI(m/z): 303/305(M + H)+ |
| 35 | 2-(2-pyrrolyl)-4-propyl-5-phenyl-1H-imidazole | 1HCl | Crystal<br>Melting point: 220-222° C.<br>MS·APCI(m/z): 252(M + H)+ |
| 36 | 2-(1-naphthyl)-4-propyl-5-phenyl-1H-imidazole | 1HCl | Foam<br>MS·APCI(m/z): 313(M + H)+ |

TABLE 1-continued
| Preparation example No. | Chemical structure | Salt | Physical constant, etc. |
|---|---|---|---|
| 37 | 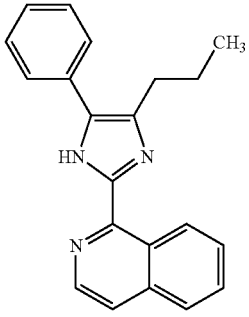 | 1HCl | Powder<br>MS · APCI(m/z):<br>314(M + H)+ |
| 38 | 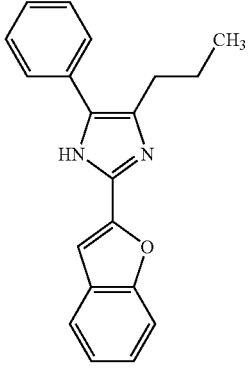 | 1HCl | Crystal<br>Melting point:<br>185-188° C.<br>MS · APCI(m/z):<br>303(M + H)+ |
| 39 | 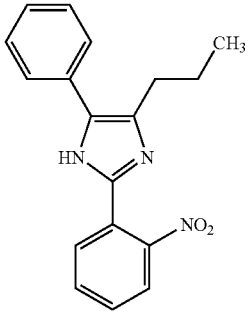 | 1HCl | Crystal<br>Melting point:<br>233-236° C.<br>MS · APCI(m/z):<br>308(M + H)+ |
| 40 | 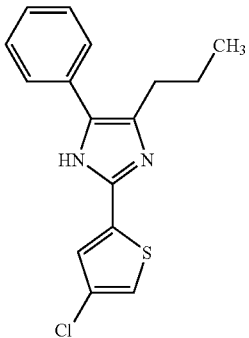 | 1HCl | Crystal<br>Melting point:<br>188-190° C.<br>MS · APCI(m/z):<br>303(M + H)+ |

TABLE 1-continued

| Preparation example No. | Chemical structure | Salt | Physical constant, etc. |
|---|---|---|---|
| 41 | 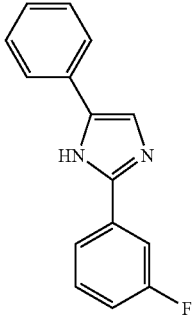 | 1HCl | Crystal<br>Melting point:<br>250-255° C.<br>MS · APCI(m/z):<br>239(M + H)+ |
| 42 | 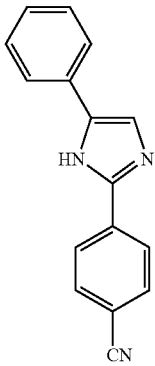 | 1HCl | Crystal<br>Melting point:<br>>300° C.<br>MS · APCI(m/z):<br>246(M + H)+ |

Preparation Example 43

4-Cyano-2-(4-fluorobenzoylamino)-1-(3-pyridyl)-1-butanone (500 mg) was dissolved in acetic acid (3 ml), and ammonium acetate (2.99 g) was added to the solution and the resulting mixture was refluxed overnight. After cooling, 28% of aqueous ammonia was added to the reaction mixture and the mixture was extracted with ethyl acetate. The organic layer was washed with brine, dried over anhydrous sodium sulfate and the solvent was removed under reduced pressure. The resulting residue was purified by silica gel flush column chromatography (solvent: hexane:ethyl acetate=1:2) and treated with hydrogen chloride-ethanol to obtain 5-(2-cyanoethyl)-2-(4-fluorophenyl)-4-(3-pyridyl)-imidazole dihydrochloride (172 mg) as colorless powder.

MS•APCI (m/z): 293 (MH+)

Preparation Examples 44 to 62

The following compounds shown in Table 2 were prepared in a manner similar to Preparation example 43 by using corresponding starting materials.

TABLE 2

| Preparation example No. | Chemical structure | Salt | Physical constant, etc. |
|---|---|---|---|
| 44 | 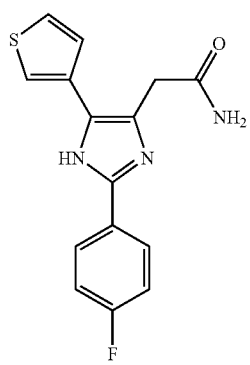 | Free material | Crystal<br>Melting point:<br>200-202° C.<br>(Decomposed)<br>EI · MS(m/z):<br>301(M+) |

TABLE 2-continued
| Preparation example No. | Chemical structure | Salt | Physical constant, etc. |
|---|---|---|---|
| 45 | 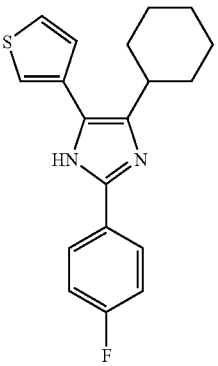 | Free material | Crystal<br>Melting point: 171-173° C.<br>EI · MS(m/z): 326(M+) |
| 46 | 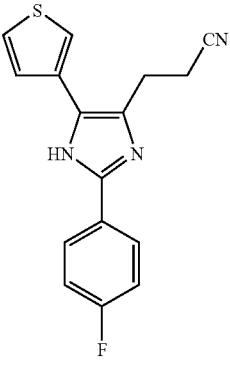 | 1HCl | Powder<br>MS · APCI(m/z): 298(M + H)+ |
| 47 | 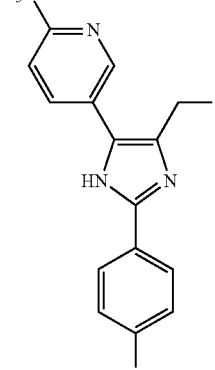 | 2HCl | Crystal<br>Melting point: 260-262° C.<br>MS · APCI(m/z): 282(M + H)+ |
| 48 | 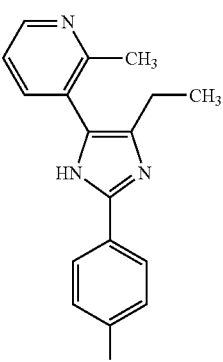 | 2HCl | Powder<br>MS · APCI(m/z): 282(M + H)+ |

TABLE 2-continued

| Preparation example No. | Chemical structure | Salt | Physical constant, etc. |
|---|---|---|---|
| 49 | 2-pyrazinyl-4-methyl-2-(4-fluorophenyl)-1H-imidazole | 1HCl | Crystal<br>Melting point: 241-243° C.<br>MS·APCI(m/z): 269(M + H)+ |
| 50 | 2-pyrimidinyl-4-methyl-2-(4-fluorophenyl)-1H-imidazole | 1HCl | Crystal<br>Melting point: 190-192° C.<br>MS·APCI(m/z): 269(M + H)+ |
| 51 | 2-thiazolyl-4-methyl-2-(4-fluorophenyl)-1H-imidazole | 1HCl | Crystal<br>Melting point: 215-218° C.<br>MS·APCI(m/z): 274(M + H)+ |

TABLE 2-continued
| Preparation example No. | Chemical structure | Salt | Physical constant, etc. |
|---|---|---|---|
| 52 | 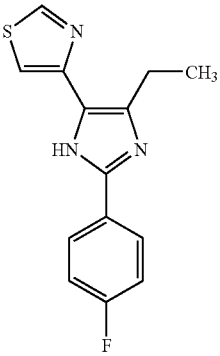 | 1HCl | Crystal<br>Melting point: 267-269° C.<br>MS · APCI(m/z): 274(M + H)+ |
| 53 | 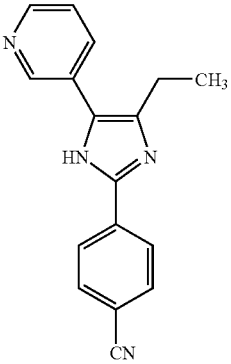 | 2HCl | Powder<br>MS · APCI(m/z): 275(M + H)+ |
| 54 | 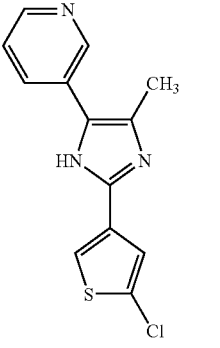 | 2HCl | Crystal<br>Melting point: 198-201° C. |
| 55 | 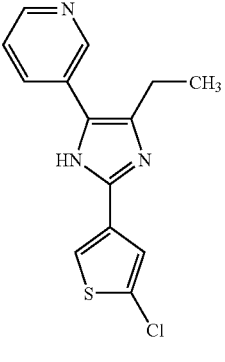 | 2HCl | Crystal<br>Melting point: 205-207° C.<br>MS · APCI(m/z): 290(M + H)+ |

TABLE 2-continued

| Preparation example No. | Chemical structure | Salt | Physical constant, etc. |
| --- | --- | --- | --- |
| 56 | 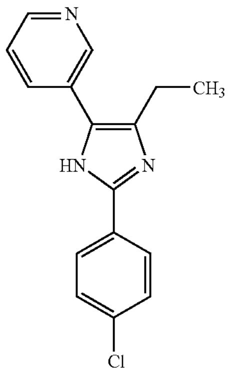 | 2HCl | Powder<br>MS·APCI(m/z):<br>284(M + H)+ |
| 57 | 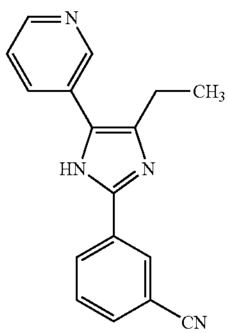 | 2HCl | Powder<br>MS·APCI(m/z):<br>275(M + H)+ |
| 58 | 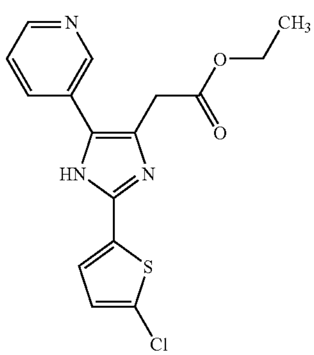 | 2HCl | Powder<br>MS·APCI(m/z):<br>348(M + H)+ |
| 59 | 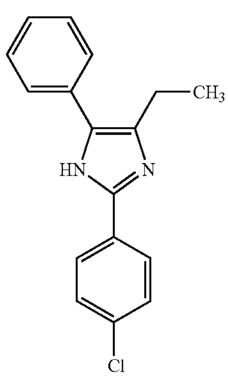 | Free material | Crystal<br>Melting point:<br>174-176° C.<br>EI·MS(m/z):<br>282/284(M+) |

TABLE 2-continued

| Preparation example No. | Chemical structure | Salt | Physical constant, etc. |
|---|---|---|---|
| 60 | 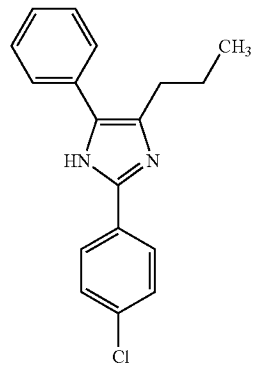 | Free material | Crystal Melting point: 147-149° C. EI · MS(m/z): 297/299(M+) |
| 61 | 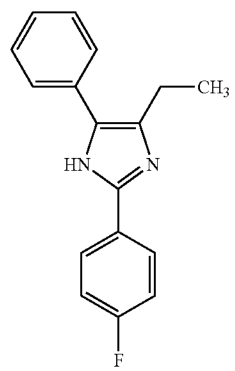 | Free material | Crystal Melting point: 169-170° C. EI · MS(m/z): 266(M+) |
| 62 | 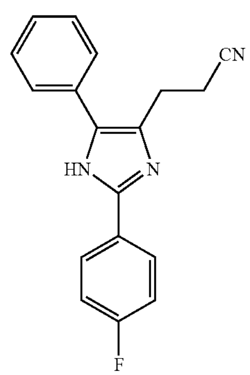 | Free material | Crystal Melting point: 176-178° C. EI · MS(m/z): 291(M+) |

Preparation Example 63

Under ice-cooling, phosphorus oxychloride (0.24 ml) was added dropwise to a solution of 2-(5-chlorothiophen-2-yl) amino-1-(3-pyridyl)-1-butanone (610 mg) in N, N-dimethylformamide (7 ml), and the resulting mixture was stirred at room temperature overnight and further at 60° C. overnight. After cooling, the reaction mixture was poured into ice water, neutralized by a saturated aqueous sodium hydrogen carbonate solution and extracted with ethyl acetate. The organic layer was washed with water and brine, and then, dried over anhydrous magnesium sulfate and the solvent was removed under reduced pressure. The resulting residue was purified by silica gel column chromatography (solvent: chloroform:ethyl acetate=2:1) and treated with hydrogen chloride-ethanol solution to obtain 2-(5-chlorothiophen-2-yl)-4-ethyl-5-(3-pyridyl)oxazole hydrochloride (466 mg) as pale yellowish powder.

Melting point: 201 to 204° C.

MS·APCI (m/z): 291/293 (MH+)

Preparation Examples 64 and 65

The following compounds shown in Table 3 were prepared in a manner similar to Preparation example 63 by using corresponding starting materials.

TABLE 3

| Preparation example No. | Chemical structure | Salt | Physical constant, etc. |
|---|---|---|---|
| 64 | (pyridine-oxazole-phenyl-Cl with ethyl ester) | 1HCl | Powder MS · APCI(m/z): 343(M + H)+ |
| 65 | (pyridine-oxazole-thiophene-Cl with ethyl ester) | Free material | Powder MS · APCI(m/z): 349(M + H)+ |

Preparation Example 66

A mixture of 2-bromo-2'-methoxy-acetophenone (514 mg), 4-fluorobenzamidine hydrochloride (392 mg) and potassium carbonate (930 mg) in acetonitrile (5 ml) was refluxed for 2 hours. After cooling, to the reaction mixture were added chloroform and water, the organic layer was collected and dried over anhydrous sodium sulfate, and the solvent was removed under reduced pressure. The resulting residue was recrystallized from methanol to obtain 2-(4-fluorophenyl)-4-(2-methoxyphenyl)imidazole (1.54 g) as pale yellowish crystal. This compound was treated with hydrogen chloride-ethanol solution to be converted into a hydrochloride salt form.
  Melting point: 165 to 167° C. (free material)
  Melting point: 245 to 248° C. (hydrochloride)
  MS•APCI (m/z): 269 (MH+) (hydrochloride)

Preparation Example 67

A mixture of 5-ethyl-2-iodo-4-(3-pyridyl)-imidazole (150 mg) 3-hydroxymethylthiophene-2-boric acid (105 mg) and tetrakis(triphenylphosphine)palladium (0) (58 mg) in an aqueous 2M sodium carbonate solution (1 ml) and dimethoxyethane (3 ml) was stirred under argon atmosphere at 100° C. for 2.5 hours. After cooling, to the reaction mixture were added water and ethyl acetate. The organic layer was collected, and after washing with brine, it was dried over anhydrous sodium sulfate and the solvent was removed under reduced pressure. The resulting residue was purified by NH silica gel flush column chromatography (solvent: ethyl acetate) and treated with hydrogen chloride-dioxane solution to obtain 5-ethyl-2-(3-hydroxymethylthiphen-2-yl)-4-(3-pyridyl)imidazole dihydrochloride (110 mg) as colorless powder.
  MS•APCI (m/z): 286 (MH+)

Preparation Example 68

The following compounds shown in Table 4 were prepared in a manner similar to Preparation example 67 by using corresponding starting materials.

TABLE 4

| Preparation example No. | Chemical structure | Salt | Physical constant, etc. |
|---|---|---|---|
| 68 | (pyridine-imidazole-thiazole with CH₃) | 2HCl | Powder MS · APCI(m/z): 257(M + H) |

Preparation Example 69

A mixture of ethyl 2,3-diketovalerate (8.00 g), 4-fluorobenzaldehyde (11.30 g) and ammonium acetate (35.00 g) in acetic acid (120 ml) was stirred under argon atmosphere at 70 to 80° C. for 40 minutes. After cooling, water was added to the reaction mixture and the reaction mixture was extracted with a mixed solution of ethyl acetate-diethyl ether. The organic layer was washed successively with a saturated aqueous sodium hydrogen carbonate solution and brine, dried over anhydrous sodium sulfate and the solvent was removed under reduced pressure. The resulting residue was purified by silica gel flush column chromatography (solvent: hexane:ethyl acetate=3:1) and recrystallized from ethyl acetate-diethyl ether to obtain ethyl 5-ethyl-2-(4-fluorophenyl)imidazol-4-carboxylate (5.16 g) as colorless crystal.
Melting point: 197 to 198° C.
MS•APCI (m/z): 263 (MH+)

Preparation Example 70

A mixture of ethyl 5-ethyl-2-(4-fluorophenyl)imidazol-4-carboxylate (2.81 g), 4N aqueous sodium hydroxide solution (14 ml), ethanol (35 ml) and tetrahydrofuran (15 ml) was stirred at room temperature overnight, followed by refluxing for 3 hours. 4N aqueous sodium hydroxide solution (28 ml) was added to the mixture and the mixture was refluxed overnight. After cooling, the reaction mixture was concentrated under reduced pressure and neutralized by 10% hydrochloric acid, and precipitated solid was collected by filtration. The solid was dissolved in tetrahydrofuran, dried over anhydrous sodium sulfate and the solvent was removed under reduced pressure. The resulting residue was triturated with diethyl ether to obtain first crop of 5-ethyl-2-(4-fluorophenyl)imidazol-4-carboxylic acid (1.06 g) as colorless powder. Moreover, the filtrate was purified by HP-20 resin (trade name, available from Nippon Rensui K.K.) (solvent: water→methanol) to give second crop of 5-ethyl-2-(4-fluorophenyl)imidazol-4-carboxylic acid (1.60 g).
ESI•MS (m/z): 233 (M-H)

Preparation Example 71

A mixture of 5-ethyl-2-(4-fluorophenyl)imidazol-4-carboxylic acid (600 mg), N,O-dimethylhydroxylamine hydrochloride (325 mg), 3-ethyl-1-(3-dimethylaminopropyl)carbodiimide hydrochloride (540 mg), 1-hydroxybenzotriazole (381 mg) and triethylamine (0.54 ml) in N,N-dimethylformamide (9 ml) was stirred at room temperature overnight. Water was added to the reaction mixture, and the reaction mixture was extracted with ethyl acetate. The organic layer was washed with water and brine and dried over anhydrous sodium sulfate, and the solvent was removed under reduced pressure. The resulting residue was purified by silica gel flush column chromatography (solvent: hexane:ethyl acetate=2:1) to obtain 5-ethyl-2-(4-fluorophenyl)-4-(N-methoxy-N-methylcarbamoyl)imidazole (656 mg) as colorless powder.
MS•APCI (m/z): 278 (MH+)

Preparation Example 72

To a solution of 2-bromopyridine (855 mg) in tetrahydrofuran (16 ml) was added dropwise 1.6M n-butyl lithium (3.38 ml, hexane solution) under argon gas atmosphere at −78° C., and after stirring the mixture at the same temperature for 30 minutes, a solution of 5-ethyl-2-(4-fluorophenyl)-4-(N-methoxy-N-methylcarbamoyl)imidazole (300 mg) in tetrahydrofuran (4 ml) was added dropwise to the mixture. After the reaction mixture was stirred under ice-acetone cooling for 30 minutes, a saturated aqueous ammonium chloride solution was added to the mixture and the mixture was extracted with ethyl acetate. The organic layer was washed with water and brine, dried over anhydrous sodium sulfate, and the solvent was removed under reduced pressure. The resulting residue was triturated with diethyl ether-hexane to obtain 5-ethyl-2-(4-fluorophenyl)-imidazol-4-yl-(2-pyridyl) ketone (324 mg). 132 mg of the product was treated with hydrogen chloride-dioxane solution to obtain the dihydrochloride salt (73 mg) as colorless solid.
MS•APCI (m/z): 296 (MH+)

Preparation Example 73

The following compounds shown in Table 5 were prepared in a manner similar to Preparation example 72 by using corresponding starting materials.

TABLE 5

| Preparation example No. | Chemical structure | Salt | Physical constant, etc. |
| --- | --- | --- | --- |
| 73 | (structure) | 2HCl | Solid<br>MS · APCI(m/z): 296(M + H)+ |

Preparation Example 74

In acetonitrile (80 ml) were dissolved 2,2-dichlorobutanal (16.2 g) and 4-fluorobenzaldehyde (14.9 g). To the solution was added dropwise 28% aqueous ammonia (135 ml) under ice-cooling, and the resulting mixture was stirred at room temperature for 4 days. Water was added to the reaction mixture and the mixture was extracted with chloroform. The organic layer was washed with brine, dried over anhydrous sodium sulfate and the solvent was removed under reduced pressure. The resulting residue was crystallized from methanol-diethyl ether to obtain 4-ethyl-2-(4-fluorophenyl)imidazole (9.36 g).

MS•APCI (m/z): 191 (MH+)

Preparation Examples 75 and 76

The following compounds shown in Table 6 were prepared in a manner similar to Preparation example 74 by using corresponding starting materials.

TABLE 6

| Preparation example No. | Chemical structure | Salt | Physical constant, etc. |
|---|---|---|---|
| 75 | [structure] | 2HCl | Solid<br>MS · APCI(m/z):<br>188(M + H)+ |
| 76 | [structure] | Free material | Crystal<br>Melting point:<br>168-170° C.<br>MS · APCI(m/z):<br>205(M + H)+ |

Preparation Example 77

To a suspension of 4-ethyl-2-(4-fluorophenyl)imidazole (4.90 g) in chloroform (100 ml) was added bromine (4.53 g), and the mixture was stirred at room temperature for 3 hours. To the reaction mixture was added a saturated aqueous sodium hydrogen carbonate solution, and the organic layer was collected. The organic layer was washed with water and brine, dried over anhydrous sodium sulfate, and the solvent was removed under reduced pressure. The resulting residue was crystallized from chloroform to obtain 5-bromo-4-ethyl-2-(4-fluorophenyl)-imidazole (5.16 g) as colorless crystal. 53 mg of the product was treated with 4N hydrogen chloride-dioxane solution to obtain 5-bromo-4-ethyl-2-(4-fluorophenyl)imidazole (60 mg) as colorless crystal.

Melting point: 192 to 193° C. (Free material)
MS•APCI (m/z): 269/271 (MH+) (Free material)
Melting point: 219 to 221° C. (decomposed) (Hydrochloride)
MS•APCI (m/z): 269/271 (MH+) (Hydrochloride)

Preparation Examples 78 and 79

The following compounds shown in Table 7 were prepared in a manner similar to Preparation example 77 by using corresponding starting materials.

TABLE 7

| Preparation example No. | Chemical structure | Salt | Physical constant, etc. |
|---|---|---|---|
| 78 | [structure] | 2HCl | Solid<br>MS · APCI(m/z):<br>264/266(M + H)+ |
| 79 | [structure] | 1HCl | Crystal<br>Melting point:<br>178-180° C.<br>MS · APCI(m/z):<br>283/285(M + H)+ |

Preparation Example 80

A mixture of 5-bromo-4-ethyl-2-(4-fluorophenyl)imidazole (100 mg), tributyl(3-pyridyl)tin (206 mg), zinc chloride (53 mg) and bis(triphenylphosphine)palladium (II) dichloride (26 mg) in N,N-dimethylformamide (3 ml) was refluxed under argon atmosphere for 5 hours. After cooling, a 10% aqueous potassium fluoride solution was added to the reaction mixture and the mixture was extracted with ethyl acetate. The organic layer was washed with brine, dried over anhydrous sodium sulfate, and the solvent was removed under reduced pressure. The resulting residue was purified by silica gel column chromatography (solvent: hexane:ethyl acetate=1:4), and recrystallized from ethyl acetate-hexane and treated with hydrogen chloride-methanol solution to obtain 5-ethyl-2-(4-fluorophenyl)-4-(3-pyridyl)imidazole dihydrochloride (48 mg) as colorless powder.

MS•APCI (m/z): 268 (MH+)

Preparation Examples 81 to 101

The following compounds shown in Table 8 were prepared in a manner similar to Preparation example 80 by using corresponding starting materials.

TABLE 8

| Preparation example No. | Chemical structure | Salt | Physical constant, etc. |
|---|---|---|---|
| 81 | (structure) | 2HCl | Solid<br>MS·APCI(m/z):<br>270(M + H)+ |
| 82 | (structure) | 2HCl | Solid<br>MS·APCI(m/z):<br>300(M + H)+ |
| 83 | (structure) | 2HCl | Crystal<br>Melting point:<br>247-251° C.<br>MS·APCI(m/z):<br>271(M + H)+ |
| 84 | (structure) | 1HCl | Crystal<br>Melting point:<br>200-203° C.<br>(Decomposed)<br>MS·APCI(m/z):<br>297(M + H)+ |

TABLE 8-continued

| Preparation example No. | Chemical structure | Salt | Physical constant, etc. |
|---|---|---|---|
| 85 | 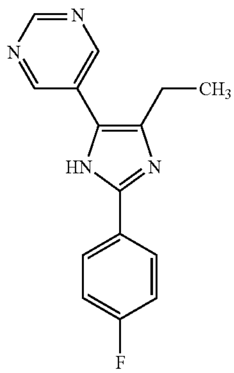 | 1HCl | Crystal<br>Melting point: 287-289° C.<br>MS · APCI(m/z): 269(M + H)+ |
| 86 | 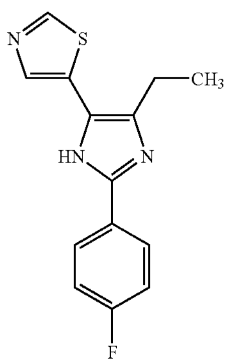 | 1HCl | Crystal<br>Melting point: 254-256° C.<br>MS · APCI(m/z): 274(M + H)+ |
| 87 | 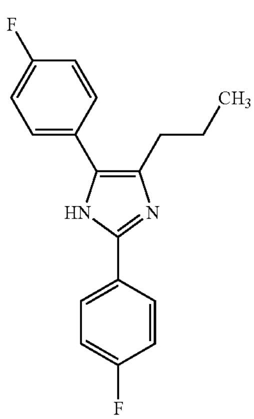 | 1HCl | Crystal<br>Melting point: 233-235° C.<br>MS · APCI(m/z): 299(M + H)+ |
| 88 | 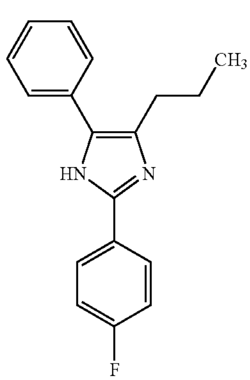 | 1HCl | Crystal<br>Melting point: 224-226° C.<br>MS · APCI(m/z): 281(M + H)+ |

TABLE 8-continued

| Preparation example No. | Chemical structure | Salt | Physical constant, etc. |
|---|---|---|---|
| 89 | H₃CS-C₆H₄-[imidazole with propyl]-C₆H₄-F | 1HCl | Crystal<br>Melting point: 174-176° C.<br>MS·APCI(m/z): 327(M + H)+ |
| 90 | (CH₃)₂N-C₆H₄-[imidazole with propyl]-C₆H₄-F | 2HCl | Powder<br>MS·APCI(m/z): 324(M + H)+ |
| 91 | O₂N-C₆H₄-[imidazole with propyl]-C₆H₄-F | 1HCl | Crystal<br>Melting point: 220-222° C.<br>MS·APCI(m/z): 326(M + H)+ |

TABLE 8-continued
| Preparation example No. | Chemical structure | Salt | Physical constant, etc. |
|---|---|---|---|
| 92 | 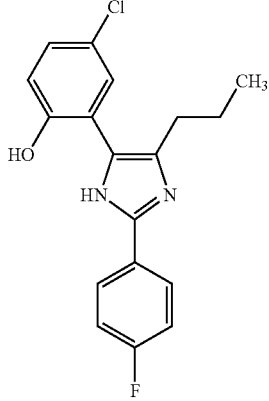 | 1HCl | Crystal<br>Melting point: 262-264° C.<br>MS·APCI(m/z): 331(M + H)+ |
| 93 | 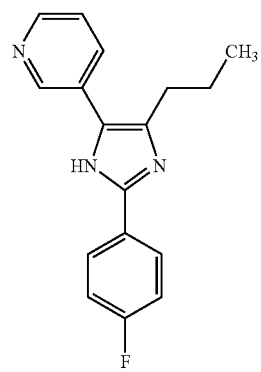 | 2HCl | Powder<br>MS·APCI(m/z): 282(M + H)+ |
| 94 | 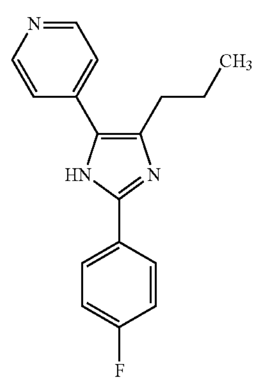 | 2HCl | Powder<br>MS·APCI(m/z): 282(M + H)+ |
| 95 | 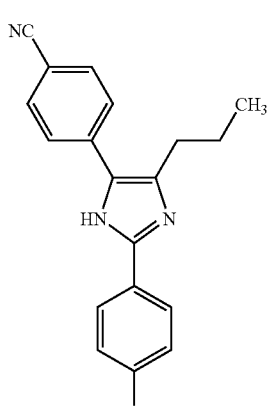 | Free material | Crystal<br>Melting point: 240-242° C.<br>MS·APCI(m/z): 306(M + H)+ |

TABLE 8-continued

| Preparation example No. | Chemical structure | Salt | Physical constant, etc. |
|---|---|---|---|
| 96 | 4-(3-methoxyphenyl)-5-propyl-2-(4-fluorophenyl)-1H-imidazole | 1HCl | Crystal<br>Melting point: 120-122° C.<br>MS · APCI(m/z): 311(M + H)+ |
| 97 | 4-(2-pyridyl)-5-propyl-2-(4-fluorophenyl)-1H-imidazole | 2HCl | Powder<br>MS · APCI(m/z): 282(M + H)+ |
| 98 | 4-(6-acetamido-3-pyridyl)-5-propyl-2-(4-fluorophenyl)-1H-imidazole | 2HCl | Powder<br>MS · APCI(m/z): 339(M + H)+ |

TABLE 8-continued

| Preparation example No. | Chemical structure | Salt | Physical constant, etc. |
|---|---|---|---|
| 99 | (3-fluorophenyl and 4-fluorophenyl substituted imidazole with propyl) | 1HCl | Crystal<br>Melting point: 228-230° C.<br>MS·APCI(m/z): 299(M + H)+ |
| 100 | (acetamido-pyrimidine imidazole with propyl and 4-fluorophenyl) | 2HCl | Powder<br>MS·APCI(m/z): 340(M + H)+ |
| 101 | (benzamide-phenyl imidazole with propyl and 4-fluorophenyl) | 1HCl | Crystal<br>Melting point: 186-189° C.<br>MS·APCI(m/z): 324(M + H)+ |

Preparation Example 102

To a solution of 5-ethyl-2-(4-fluorophenyl)-4-(3-pyridyl)-imidazole (481 mg) in N,N-dimethylformamide (7 ml) was added sodium hydride (79 mg, 60% mineral oil) under ice-acetone cooling, and the mixture was stirred for 15 minutes. To the mixture was added methyl iodide (307 mg) and the mixture was stirred at room temperature for one hour. To the reaction mixture was added a saturated aqueous ammonium chloride solution, and the mixture was extracted with ethyl acetate. The organic layer was washed with brine, dried over anhydrous sodium sulfate, and the solvent was removed under reduced pressure. The resulting residue was purified by silica gel flush column chromatography (solvent: chloroform:methanol=95:5), and treated with hydrogen chloride-methanol solution to obtain 5-ethyl-2-(4-fluoro-phenyl)-1-methyl-4-(3-pyridyl)imidazole dihydrochloride (285 mg).

MS•APCI (m/z): 282 (MH+)

Preparation Examples 103 and 104

The following compounds shown in Table 9 were prepared in a manner similar to Preparation example 102 by using corresponding starting materials.

TABLE 9

| Preparation example No. | Chemical structure | Salt | Physical constant, etc. |
|---|---|---|---|
| 103 | 4-phenyl-5-methyl-1-(2-dimethylaminoethyl)-2-(4-fluorophenyl)imidazole | 2HCl | Powder<br>MS·APCI (m/z):<br>338 (M + H) + |
| 104 | 4-(pyridin-3-yl)-5-methyl-1-ethyl-2-(4-fluorophenyl)imidazole | 2HCl | Powder<br>MS·APCI (m/z):<br>296 (M + H) + |

Preparation Example 105

A mixture of 5-amino-2-(4-fluorophenyl)-4-phenylimidazole (1.00 g) and ethyl formate (10 ml) was refluxed for 15 hours. After cooling, the reaction mixture was concentrated under reduced pressure and crystallized from diethyl ether to obtain 5-formylamino-2-(4-fluorophenyl)-4-phenylimidazole (1.17 g) as colorless crystal.
Melting point: 245 to 247° C.
MS•APCI (m/z): 282 (MH+)

Preparation Example 106

A mixture of 5-methylamino-2-(4-fluorophenyl)-4-phenyl-imidazole (560 mg) methyl formate (20 ml) was refluxed overnight. After cooling, the reaction mixture was concentrated under reduced pressure and crystallized from diethyl ether-hexane to obtain 5-formylmethylamino-2-(4-fluorophenyl)-4-phenyl-imidazole (480 mg) as colorless crystal.
Melting point: 256 to 258° C.
MS•APCI (m/z): 296 (MH+)

Preparation Example 107

To a solution of 5-formylamino-2-(4-fluorophenyl)-4-phenylimidazole (1.06 g) in tetrahydrofuran (15 ml) was added dropwise 10M borane.dimethylsulfide complex (1.90 ml), and the mixture was stirred under argon atmosphere at room temperature for 2.5 hours. To the reaction mixture was slowly added 10% hydrochloric acid, and the mixture was refluxed for one hour. After cooling, the mixture was neutralized by adding a saturated aqueous sodium hydrogen carbonate solution, and extracted with ethyl acetate. The organic layer was washed with water and brine, dried over anhydrous sodium sulfate and the solvent was removed under reduced pressure. The resulting residue was purified by silica gel flush column chromatography (solvent: hexane:ethyl acetate=5:1) to obtain 5-methylamino-2-(4-fluorophenyl)-4-phenylimidazole (702 mg) as colorless powder. 88 mg of the product was treated with hydrogen chloride-methanol solution to obtain the hydrochloride salt (84 mg) as colorless powder.
Melting point: 253 to 255° C.
MS•APCI (m/z): 268 (MH+)

Preparation Example 108

To a solution of 5-formylmethylamino-2-(4-fluorophenyl)-4-phenylimidazole (200 mg) in tetrahydrofuran (5 ml) was added dropwise 10M borane.dimethylsulfide complex (0.34 ml), and the mixture was stirred under argon atmosphere at room temperature for overnight. To the reaction mixture was slowly added 10% hydrochloric acid, and the mixture was refluxed for one hour. After cooling, the mixture was neutralized by adding a saturated aqueous sodium hydrogen carbonate solution, and extracted with ethyl acetate. The organic layer was washed with water and brine, dried over anhydrous sodium sulfate and the solvent was removed under reduced pressure. The resulting residue was purified by silica gel flush column chromatography (solvent: hexane:ethyl acetate=5:1), and then, treated with hydrogen chloride-methanol solution to obtain 5-dimethylamino-2-(4-fluorophenyl)-4-phenylimidazole hydrochloride (174 mg) as colorless powder.
MS•APCI (m/z): 282 (MH+)

Preparation Example 109

To a solution of 5-amino-2-(4-fluorophenyl)-4-phenylimidazole (63 mg) and pyridine (40 mg) in methylene chloride (5 ml) was added methyl chlorocarbonate (28 mg) under ice-cooling and the mixture was stirred at room temperature overnight. To the reaction mixture was added diethyl ether, and the solvent was removed under reduced pressure. The resulting residue was triturated with diethyl ether and the powder was collected by filtration. The powder was treated with hydrogen chloride-methanol solution to obtain 5-methoxycarbonylamino-2-(4-fluorophenyl)-4-phenylimidazole hydrochloride (67 mg) as colorless powder.

MS•APCI (m/z): 312 (MH+)

Preparation Example 110

To a solution of 5-acetylamino-2-(4-fluorophenyl)-4-phenyl-imidazole (142 mg) in tetrahydrofuran (7 ml) was added 10M borane.tetrahydrofuran complex (12 ml, tetrahydrofuran solution), and the mixture was stirred under argon atmosphere at room temperature for 2 days. To the reaction mixture was slowly added 10% hydrochloric acid, and the mixture was stirred at 60° C. for 10 minutes. After cooling, the mixture was neutralized by adding a saturated aqueous sodium hydrogen carbonate solution, and extracted with ethyl acetate. The organic layer was washed with water and brine, dried over anhydrous sodium sulfate and the solvent was removed under reduced pressure. The resulting residue was purified by silica gel flush column chromatography (solvent: hexane:ethyl acetate=1:2), and then, treated with hydrogen chloride-methanol solution to obtain 5-ethylamino-2-(4-fluorophenyl)-4-phenyl-imidazole hydrochloride (89 mg) as colorless powder.

MS•APCI (m/z): 282 (MH+)

Preparation Example 111

A mixture of 5-ethylamino-2-(4-fluorophenyl)-4-phenyl-imidazole (145 mg) in ethyl formate (8 ml) was refluxed for 8 hours. After cooling, the mixture was concentrated under reduced pressure, and crystallized from diethyl ether to obtain 5-formylethylamino-2-(4-fluorophenyl)-4-phenylimidazole (136 mg) as colorless crystal.

Melting point: 201 to 202° C.
MS•APCI (m/z): 310 (MH+)

Preparation Example 112

A mixture of 2-(5-chlorothiophen-2-yl)-4-(3-pyridyl) imidazole (1.07 g), 35% formalin aqueous solution (35 ml), potassium carbonate (1.70 g), isopropanol (30 ml) and N,N-dimethyl-formamide (10 ml) was stirred at 90° C. for 2 hours. After cooling, water was added to the mixture and precipitated solid was collected by filtration. The solid was dissolved in methanol and, after removing insolubles by filtration, the solvent was removed under reduced pressure. The resulting residue was triturated with ethyl acetate to obtain 2-(5-chlorothiophen-2-yl)-5-hydroxymethyl-4-(3-pyridyl)imidazole (519 mg) as colorless powder.

MS•APCI (m/z): 292/294 (MH+)

Preparation Examples 113 and 118

The following compounds shown in Table 10 were prepared in a manner similar to Preparation example 112 by using corresponding starting materials.

TABLE 10

| Preparation example No. | Chemical structure | Salt | Physical constant, etc. |
|---|---|---|---|
| 113 | 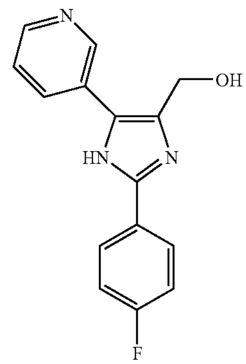 | Free material | Crystal Melting point: 225-228° C. MS · APCI (m/z): 270 (M + H) + |
| 114 | 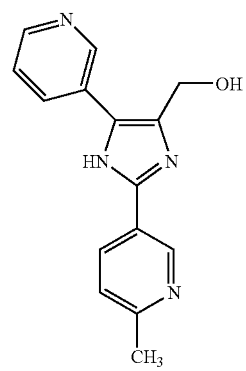 | 3HCl | Crystal Melting point: 266-269° C. MS · APCI (m/z): 267 (M + H) + |
| 115 | 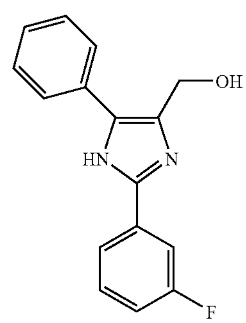 | Free material | Crystal Melting point: 232-234° C. MS · APCI (m/z): 269 (M + H) + |
| 116 | 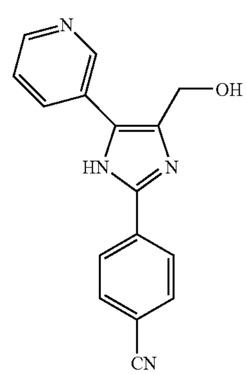 | Free material | Powder MS · APCI (m/z): 277 (M + H) + |

TABLE 10-continued

| Preparation example No. | Chemical structure | Salt | Physical constant, etc. |
|---|---|---|---|
| 117 | (4-fluorophenyl / phenyl / imidazole / CH2OH) | Free material | Crystal Melting point: 240-243° C. MS · APCI (m/z): 269 (M + H) + |
| 118 | (4-cyanophenyl / phenyl / imidazole / CH2OH) | Free material | Powder MS · APCI (m/z): 276 (M + H) + |

Preparation Example 119

To a solution of 2-(5-chlorothiophen-2-yl)-5-hydroxy-methyl-4-(3-pyridyl) imidazole (200 mg) in methylene chloride (5 ml) was added thionyl chloride (5 ml), and the mixture was refluxed for one hour. After cooling, the reaction mixture was concentrated under reduced pressure to obtain a crude product of 2-(5-chlorothiophen-2-yl)-5-chloromethyl-4-(3-pyridyl)-imidazole dihydrochloride (260 mg) as yellowish powder.

Preparation Example 120

In methanol (10 ml) was dissolved a crude product of 2-(5-chlorothiophen-2-yl)-5-chloromethyl-4-(3-pyridyl)-imidazole dihydrochloride (260 mg) and the mixture was refluxed for 2 hours. After cooling, a saturated aqueous sodium hydrogen carbonate solution was added to the reaction mixture, and the mixture was extracted with a mixed solution of ethyl acetate-tetrahydrofuran. The organic layer was washed with brine, dried over anhydrous magnesium sulfate and the solvent was removed under reduced pressure. The resulting residue was purified by silica gel column chromatography (solvent: chloroform:methanol=40:1), and then, treated with hydrogen chloride-dioxane solution to obtain 2-(5-chlorothiophen-2-yl)-5-methoxymethyl-4-(3-pyridyl) imidazole dihydrochloride (63 mg) as pale yellowish powder.

Melting point: 245 to 248° C. (decomposed)

MS·APCI (m/z): 306/308 (MH+)

Preparation Examples 121 to 128

The following compounds shown in Table 11 were prepared in a manner similar to Preparation example 112 or 120 by using corresponding starting materials.

TABLE 11

| Preparation example No. | Chemical structure | Salt | Physical property, etc. |
|---|---|---|---|
| 121 | (phenyl / 4-fluorophenyl / imidazole / CH2OCH3) | 1HCl | Crystal Melting point: 204-207° C. MS · APCI (m/z): 283 (M + H) + |
| 122 | (thiophen-3-yl / 4-fluorophenyl / imidazole / CH2OCH3) | 1HCl | Powder MS · APCI (m/z): 289 (M + H) + |
| 123 | (phenyl / 3-fluorophenyl / imidazole / CH2OCH3) | 1HCl | Crystal Melting point: 185-188° C. MS · APCI (m/z): 283 (M + H) + |

TABLE 11-continued

| Preparation example No. | Chemical structure | Salt | Physical property, etc. |
|---|---|---|---|
| 124 | 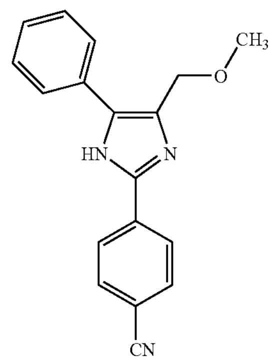 | 1HCl | Powder MS · APCI (m/z): 290 (M + H) + |
| 125 | 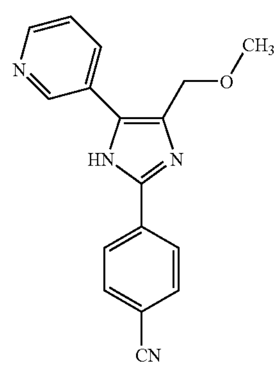 | 2HCl | Powder MS · APCI (m/z): 291 (M + H) + |
| 126 | 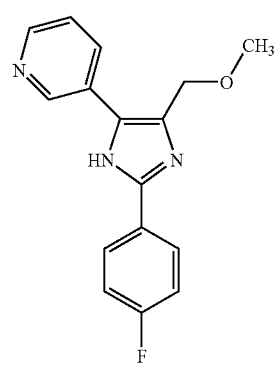 | 2HCl | Powder MS · APCI (m/z): 284 (M + H) + |
| 127 | 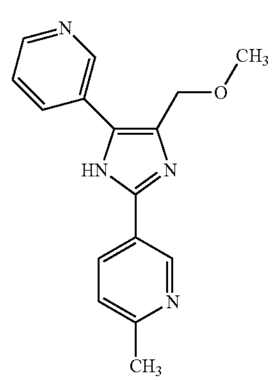 | 3HCl | Crystal Melting point: 251-255° C. MS · APCI (m/z): 281 (M + H) + |
| 128 | 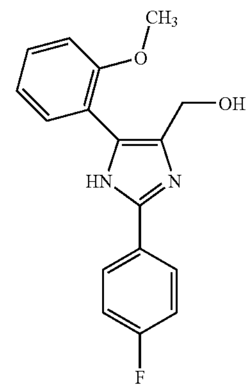 | 1HCl | Powder MS · APCI (m/z): 299 (M + H) + |

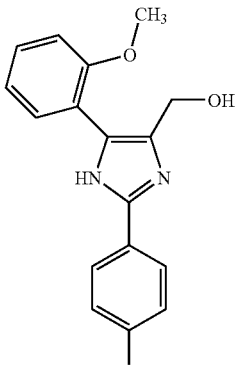

Preparation Example 129

To a solution of 2-(3-fluorophenyl)-5-hydroxymethyl-4-(3-pyridyl)imidazole (389 mg) in methylene chloride (10 ml) was added thionyl chloride (10 ml), and the mixture was refluxed for one hour. After cooling, the reaction mixture was concentrated under reduced pressure to obtain a crude product of 2-(3-fluorophenyl)-5-chloromethyl-4-(3-pyridyl)imidazole dihydrochloride (508 mg) as colorless powder.

Preparation Example 130

To a suspension of a crude product of 2-(3-fluorophenyl)-5-chloromethyl-4-(3-pyridyl)imidazole dihydrochloride (268 mg) in tetrahydrofuran (10 ml) were added 15% aqueous sodium methyl sulfide solution (0.95 ml) and triethylamine (206 mg), and the mixture was stirred at room temperature for 1.5 hours. Water was added to the reaction mixture, and the reaction mixture was extracted with ethyl acetate. The organic layer was washed with brine and dried over anhydrous sodium sulfate, and the solvent was removed under reduced pressure. The resulting residue was purified by silica gel column chromatography (solvent: chloroform:methanol=19:1) to obtain 2-(3-fluorophenyl)-5-methylthiomethyl-4-(3-pyridyl)imidazole (198 mg) as colorless powder.

MS•APCI (m/z): 300 (MH+)

Preparation Examples 131 to 134

The following compounds shown in Table 12 were prepared in a manner similar to Preparation example 130 by using corresponding starting materials.

TABLE 12

| Preparation example No. | Chemical structure | Salt | Physical property, etc. |
|---|---|---|---|
| 131 | 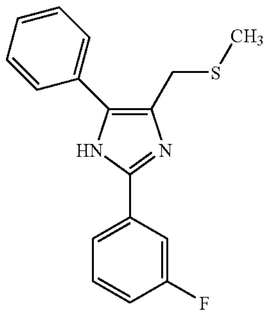 | 1HCl | Crystal<br>Melting point:<br>218-220° C.<br>MS · APCI (m/z):<br>299 (M + H) + |
| 132 | 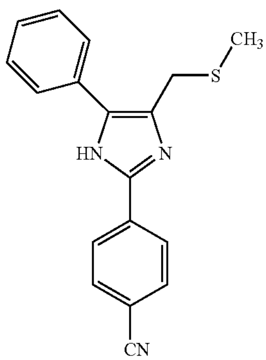 | 1HCl | Crystal<br>Melting point:<br>256-259° C.<br>MS · APCI (m/z):<br>306 (M + H) + |
| 133 | 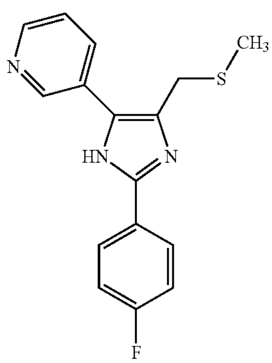 | Free material | Crystal<br>Melting point:<br>172-174° C.<br>MS · APCI (m/z):<br>300 (M + H) + |
| 134 | 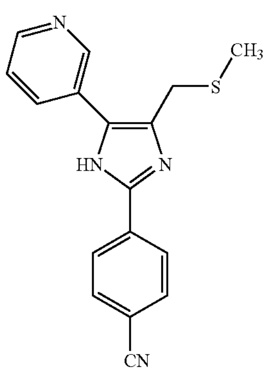 | Free material | Crystal<br>Melting point:<br>209-211° C.<br>MS · APCI (m/z):<br>307 (M + H) + |

Preparation Example 135

To a solution of 2-(3-fluorophenyl)-5-methylthiomethyl-4-(3-pyridyl)imidazole (152 mg) in tetrahydrofuran (10 ml) was added metachloroperbenzoic acid (97 mg, 70% purity) under ice-cooling, and the mixture was stirred at room temperature for 5 hours. To the reaction mixture was added a saturated aqueous sodium hydrogen carbonate solution, and the mixture was extracted with ethyl acetate. The organic layer was washed with brine and dried over anhydrous sodium sulfate, and the solvent was removed under reduced pressure. The resulting residue was purified by silica gel column chromatography (solvent: chloroform:methanol=19:1), and then, treated with hydrogen chloride-dioxane solution to obtain 2-(3-fluorophenyl)-5-methylsulfinylmethyl-4-(3-pyridyl)imidazole hydrochloride (140 mg) as colorless powder.

MS•APCI (m/z): 316 (MH+)

Preparation Examples 136 to 140

The following compounds shown in Table 13 were prepared in a manner similar to Preparation example 135 by using corresponding starting materials.

TABLE 13

| Preparation example No. | Chemical structure | Salt | Physical constant, etc. |
|---|---|---|---|
| 136 | 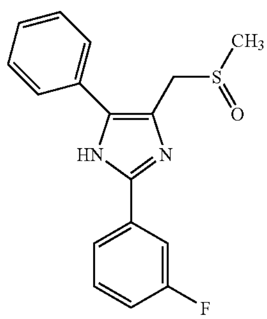 | 1HCl | Crystal Melting point: 198-200° C. MS · APCI (m/z): 315 (M + H) + |
| 137 | 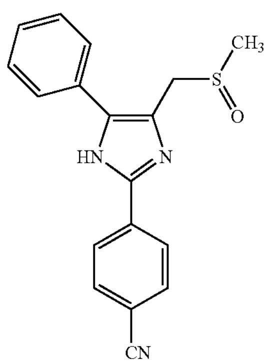 | 1HCl | Powder MS · APCI (m/z): 322 (M + H) + |
| 138 | 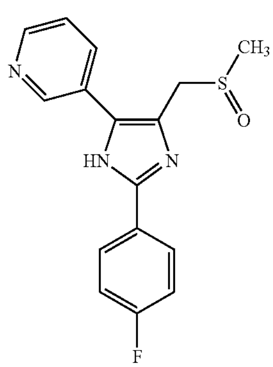 | 2HCl | Powder MS · APCI (m/z): 316 (M + H) + |
| 139 | | 2HCl | Powder MS · APCI (m/z): 323 (M + H) + |
| 140 | | 1HCl | Crystal Melting point: 278-280° C. MS · APCI (m/z): 351 (M + H) + |

Preparation Example 141

A mixture of ethyl 2-(5-chlorothiophen-2-yl)-5-(3-pyridyl)-oxazole-4-yl acetate (68 mg), lithium hydroxide (9 mg), ethanol (4 ml) and water (4 ml) was stirred at room temperature for 2.5 hours. The reaction mixture was concentrated under reduced pressure, acidified to pH 4 with 10% hydrochloric acid, and precipitated solid was collected by filtration. This solid was treated with hydrogen chloride-dioxane solution to obtain 2-(5-chlorothiophen-2-yl)-5-(3-pyridyl)oxazole-4-yl acetic acid hydrochloride (50 mg) as pale yellowish powder.

Melting point: 234 to 238° C. (decomposed)

MS•APCI (m/z): 321/323 (MH+)

Preparation Example 142

The following compounds shown in Table 14 were prepared in a manner similar to Preparation example 141 by using corresponding starting materials.

TABLE 14

| Preparation example No. | Chemical structure | Salt | Physical constant, etc. |
|---|---|---|---|
| 142 | [Structure: 2-(4-chlorophenyl)-5-(3-pyridyl)oxazole with -CH2-C(=O)-OH at position 4] | 1HCl | Powder<br>MS · APCI (m/z): 313 (M − H) |

Preparation Examples 143 and 144

A mixture of 2-(5-chlorothiophen-3-yl)-5-ethyl-4-(3-pyridyl)-imidazole (2.00 g) in chlorosulfonic acid (15 ml) was stirred at room temperature for one week. The mixture was slowly added dropwise to 28% aqueous ammonia (500 ml), and the resulting mixture was stirred for 30 minutes and then concentrated under reduced pressure. The resulting residue was dissolved in methanol-tetrahydrofuran (5:1), dried over anhydrous sodium sulfate and the solvent was removed under reduced pressure. The residue was purified by silica gel flush column chromatography (solvent: chloroform:methanol=10:1→2.5:1), and then, by NH silica gel flush column chromatography (solvent: chloroform:methanol=10:1→4:1) to obtain 2-(5-chloro-2-sulfothiophen-3-yl)-5-ethyl-4-(3-pyridyl)imidazole and 2-(5-chloro-2-sulfamoylthiophen-3-yl)-5-ethyl-4-(3-pyridyl)imidazole. Each product was treated with hydrogen chloride-dioxane solution to obtain 2-(5-chloro-2-sulfothiophen-3-yl)-5-ethyl-4-(3-pyridyl)imidazole dihydrochloride (741 mg) and 2-(5-chloro-2-sulfamoylthiophen-3-yl)-5-ethyl-4-(3-pyridyl)imidazole dihydrochloride (105 mg) each as colorless powder.

2-(5-Chloro-2-sulfothiophen-3-yl)-5-ethyl-4-(3-pyridyl)-imidazole dihydrochloride (Preparation example 143)

ESI•MS (m/z): 368 (M-H)

2-(5-Chloro-2-sulfamoylthiophen-3-yl)-5-ethyl-4-(3-pyridyl) imidazole dihydrochloride (Preparation example 144)

MS•APCI (m/z): 369 (MH+)

Preparation Example 145

To a solution of 2-(2-ethoxycarbonylthiophen-3-yl)-5-ethyl-4-(3-pyridyl)imidazole (879 mg) in tetrahydrofuran (20 ml) was added lithium aluminumhydride (204 mg) under ice-cooling, and the mixture was stirred under argon atmosphere at the same temperature for 1.5 hours. Under ice-cooling, an aqueous potassium sodium tartarate solution and ethyl acetate were added to the mixture and the organic layer was collected. The organic layer was washed with water and brine, dried over anhydrous magnesium sulfate, and the solvent was removed under reduced pressure. The resulting residue was purified by silica gel column chromatography (solvent: chloroform:methanol=19:1), and then, treated with hydrogen chloride-ethanol solution to obtain 2-(2-hydroxymethylthiophen-3-yl)-5-ethyl-4-(3-pyridyl)imidazole dihydrochloride (788 mg) as colorless powder.

MS•APCI (m/z): 286 (MH+)

Preparation Example 146

To a solution of ethyl 2-(5-chlorothiophen-2-yl)-4-(3-pyridyl)imidazol-5-yl acetate (122 mg) in tetrahydrofuran (3.5 ml) was added lithium aluminum hydride (15 mg) under ice-cooling, and the mixture was stirred under ice-cooling for 2.5 hours. Under ice-cooling, an aqueous sodium hydroxide solution and ethyl acetate were added to the mixture, and the organic layer was collected. The organic layer was washed with water and brine, dried over anhydrous sodium sulfate, and the solvent was removed under reduced pressure. The resulting residue was purified by preparative thin-layer chromatography (TLC) (silica gel; solvent: chloroform:methanol=20:1) to obtain 2-(5-chloro-thiophen-2-yl)-5-hydroxyethyl-4-(3-pyridyl)imidazole (109 mg) as colorless crystalline powder. 27 mg of the product was treated with hydrogen chloride-dioxane solution to obtain the dihydrochloride salt (26 mg) as colorless powder.

Melting point: 179 to 180° C. (free material)

MS•APCI (m/z): 306 (MH+) (hydrochloride)

Preparation Example 147

A mixture of ethyl 4-(4-fluorobenzoylamino)-4-(2-thienyl)-3-ketobutyrate (349 mg), and phosphorus oxychloride (0.12 ml) in N,N-dimethylformamide (5 ml) was stirred at room temperature for 2.5 hours. The reaction mixture was poured into water, neutralized with a saturated aqueous sodium hydrogen carbonate solution and extracted with ethyl acetate. The organic layer was washed with water and brine, dried over anhydrous sodium sulfate and the solvent was removed under reduced pressure. The resulting residue was purified by silica gel flush column chromatography (solvent: hexane:ethyl acetate=20:1) to obtain ethyl 2-(4-fluorophenyl)-4-(2-thienyl)oxazol-5-ylacetate (95 mg) as pale yellowish powder.

MS•APCI (m/z): 332 (MH+)

Preparation Example 148

To a solution of ethyl 2-(4-fluorophenyl)-4-(2-thienyl)-oxazol-5-ylacetate (94 mg) in tetrahydrofuran (3 ml) and ethanol (3 ml) was added 1N aqueous sodium hydroxide solution (1 ml) and the mixture was stirred at room temperature for one hour. To the reaction mixture was added 10% hydrochloric acid, and the mixture was extracted with ethyl acetate. The organic layer was washed with brine, dried over anhydrous sodium sulfate and the solvent was removed under reduced pressure. The resulting residue was dissolved in methanol (5 ml), 0.5M sodium methoxide (556 µl, methanol solution) was added to the solution and the solvent was removed under reduced pressure to obtain sodium 2-(4-fluorophenyl)-4-(2-thienyl)oxazol-5-ylacetate (90 mg) as pale brownish powder.

ESI•MS (m/z): 302 (M-H)

Preparation Example 149

To a solution of ethyl 2-(4-fluorophenyl)oxazol-4-yl acetate (11.10 g) in chloroform (110 ml) was added bromine (2.47 ml) at room temperature and the mixture was stirred at room temperature for one hour. To the reaction mixture was added a saturated aqueous sodium hydrogen carbonate solution and a saturated aqueous sodium thiosulfate solution, and the organic layer was collected. The organic layer was washed with brine and dried over anhydrous sodium sulfate, and the solvent was removed under reduced pressure. The resulting residue was crystallized from hexane-diethyl ether to obtain ethyl 5-bromo-2-(4-fluorophenyl)oxazol-4-yl acetate (7.47 g) as colorless crystal. Further, the filtrate was purified by silica gel flush column chromatography (solvent: n-hexane: ethyl acetate=10:1) to obtain ethyl 5-bromo-2-(4-fluorophenyl)-oxazol-4-yl acetate (3.57 g) as pale yellowish crystal.
Melting point: 84 to 85° C.
MS•APCI (m/z): 323/330 (MH+)

Preparation Example 150

A mixture of ethyl 2-(4-fluorophenyl)oxazol-4-yl acetate (249 mg), iodine (127 mg) and [bis(trifluoroacetoxy)]iodo]benzene (244 mg) in chloroform (3 ml) was stirred at room temperature for 4 hours. To the reaction mixture were added a saturated aqueous sodium hydrogen carbonate solution and a saturated aqueous sodium thiosulfate solution, and the organic layer was collected. The organic layer was washed with brine and dried over anhydrous sodium sulfate, and the solvent was removed under reduced pressure. The resulting residue was purified by silica gel flush column chromatography (solvent: n-hexane:ethyl acetate=8:1) to obtain ethyl 2-(4-fluorophenyl)-5-iodoxazol-4-yl acetate (300 mg) as colorless crystal.
Melting point: 120 to 122° C.
MS•APCI (m/z): 376 (MH+)

Preparation Example 151

A mixture of ethyl 5-bromo-2-(4-fluorophenyl)oxazol-4-yl acetate (328 mg), 5-chlorothiophen-2-boric acid (244 mg), bis(triphenylphosphine)palladium (II) dichloride (35 mg) in 2M aqueous sodium carbonate solution (1.5 ml) and dimethoxyethane (5 ml) was refluxed for one hour. After cooling, to the reaction mixture were added water and ethyl acetate, the organic layer was collected, dried over anhydrous sodium sulfate, and the solvent was removed under reduced pressure. The resulting residue was purified by silica gel flush column chromatography (solvent: n-hexane:ethyl acetate=6:1) to obtain ethyl 5-(5-chlorothiophen-2-yl)-2-(4-fluorophenyl)oxazol-4-yl acetate (181 mg) as pale yellowish crystal.
Melting point: 129 to 130° C.
MS•APCI (m/z): 366/368 (MH+)

Preparation Example 152

To a solution of ethyl 5-(5-chlorothiophen-2-yl)-2-(4-fluorophenyl)oxazol-4-yl acetate (115 mg) in methanol (5 ml) was added 4N aqueous sodium hydroxide solution (1 ml), and the mixture was refluxed for 30 minutes. After cooling, ethyl acetate and 10% hydrochloric acid were added to the reaction mixture, and the organic layer was collected. The organic layer was washed with brine, dried over anhydrous sodium sulfate, and the solvent was removed under reduced pressure. The resulting residue was dissolved in methanol (5 ml), 0.5M sodium methoxide (605 µl, methanol solution) was added to the solution and the solvent was removed under reduced pressure. The resulting residue was triturated with acetone to obtain 5-(5-chloro-thiophen-2-yl)-2-(4-fluorophenyl)oxazol-4-yl acetic acid sodium salt (100 mg) as pale yellowish powder.
ESI•MS (m/z): 336 (M-H)

Preparation Examples 153 to 166

The following compounds shown in Table 15 were prepared in a manner similar to Preparation example 63, 151 or 152 by using corresponding starting materials.

TABLE 15

| Preparation example No. | Chemical structure | Salt | Physical property, etc. |
|---|---|---|---|
| 153 | 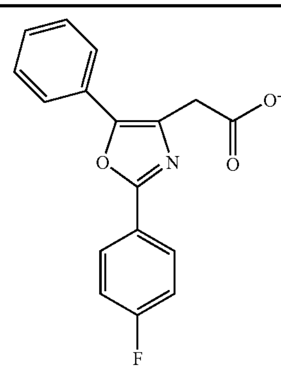 | Na | Crystal Melting point: >300° C. MS · APCI (m/z): 296 (M − Na) |
| 154 | 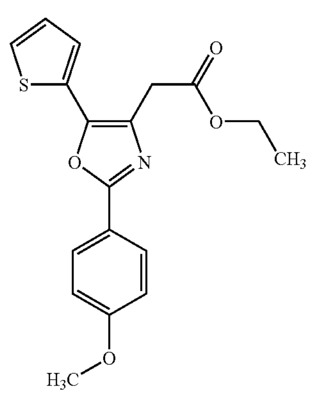 | Free material | Crystal Melting point: 105-107° C. MS · APCI (m/z): 344 (M + H) + |

TABLE 15-continued
| Preparation example No. | Chemical structure | Salt | Physical property, etc. |
|---|---|---|---|
| 155 | 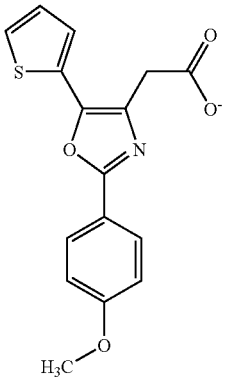 | Na | Powder<br>ESI · MS (m/z):<br>314 (M − Na) |
| 156 | 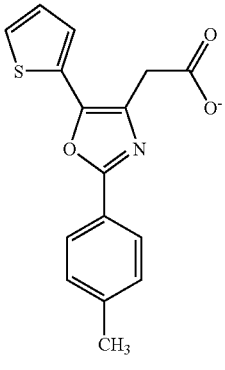 | Na | Powder<br>ESI · MS (m/z):<br>298 (M − Na) |
| 157 | 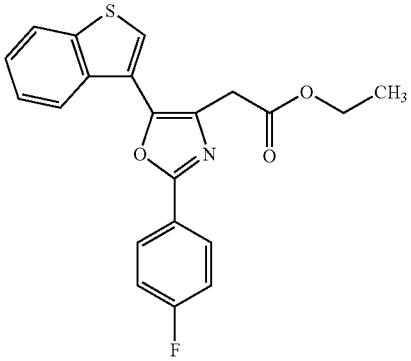 | Free material | Powder<br>MS · APCI (m/z):<br>382 (M + H) + |
| 158 | 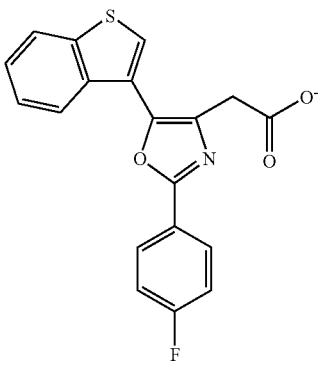 | Na | Powder<br>MS · APCI (m/z):<br>352 (M − Na) |

TABLE 15-continued

| Preparation example No. | Chemical structure | Salt | Physical property, etc. |
|---|---|---|---|
| 159 | 5-(3,4-dimethoxyphenyl)-2-(4-fluorophenyl)oxazol-4-yl acetic acid ethyl ester | Free material | Powder<br>MS·APCI (m/z): 386 (M + H) + |
| 160 | 5-(3,4-dimethoxyphenyl)-2-(4-fluorophenyl)oxazol-4-yl acetate | Na | Powder<br>MS·APCI (m/z): 356 (M − Na) |
| 161 | 5-(2-fluorophenyl)-2-(4-fluorophenyl)oxazol-4-yl acetic acid ethyl ester | Free material | Crystal<br>Melting point: 88-89° C.<br>MS·APCI (m/z): 344 (M + H) + |

TABLE 15-continued

| Preparation example No. | Chemical structure | Salt | Physical property, etc. |
|---|---|---|---|
| 162 | 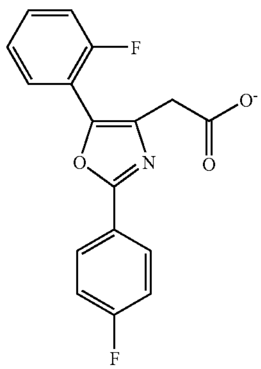 | Na | Powder<br>MS · APCI (m/z):<br>314 (M − Na) |
| 163 | 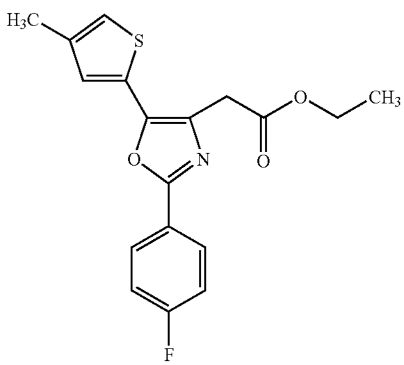 | Free material | Crystal<br>Melting point: 138-139° C.<br>MS · APCI (m/z):<br>346 (M + H) + |
| 164 | 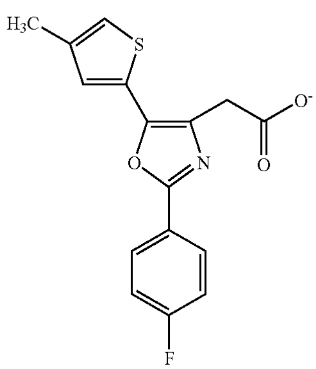 | Na | Powder<br>MS · APCI (m/z):<br>316 (M − Na) |
| 165 | 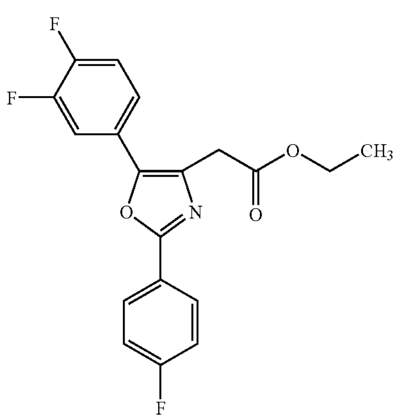 | Free material | Powder<br>MS · APCI (m/z):<br>362 (M + H) + |

TABLE 15-continued

| Preparation example No. | Chemical structure | Salt | Physical property, etc. |
|---|---|---|---|
| 166 | [structure: 2-(4-fluorophenyl)-5-(3,4-difluorophenyl)oxazol-4-yl acetate] | Na | Powder<br>MS · APCI (m/z):<br>332 (M − Na) |

Preparation Examples 167 to 202

The following compounds shown in Table 16 were prepared in a manner similar to one of the above-mentioned Preparation examples, or conventionally known preparation processes as described in Japanese Provisional Patent Publications No. 5832/1972, No. 29771/1973 and the like.

TABLE 16

| Preparation example No. | Chemical structure | Salt | Physical property, etc. |
|---|---|---|---|
| 167 | [structure: 2-(4-fluorophenyl)-4-(4-methoxyphenyl)-1H-imidazole] | Free material | MS · EI (m/z):<br>268 (M+) |
| 168 | [structure: 2-(4-fluorophenyl)-5-methyl-4-(thiophen-3-yl)-1H-imidazole] | Free material | MS · EI (m/z):<br>258 (M+) |

TABLE 16-continued
| Preparation example No. | Chemical structure | Salt | Physical property, etc. |
|---|---|---|---|
| 169 | 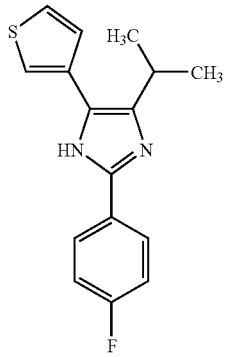 | Free material | MS · EI (m/z): 286 (M+) |
| 170 | 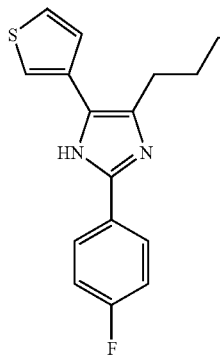 | Free material | |
| 171 | 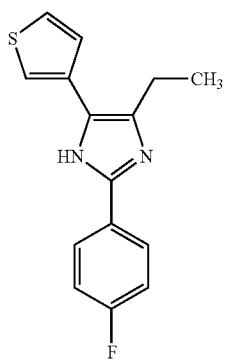 | Free material | MS · EI (m/z): 272 (M+) |
| 172 | 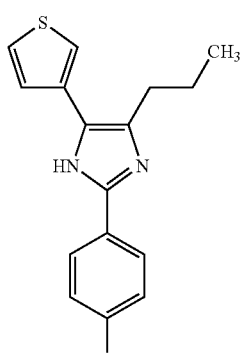 | Free material | MS · EI (m/z): 286 (M+) |

TABLE 16-continued

| Preparation example No. | Chemical structure | Salt | Physical property, etc. |
|---|---|---|---|
| 173 | 4-(4-fluorophenyl)-5-(thiophen-3-yl)-2-(trifluoromethyl-CH2)-1H-imidazole structure | Free material | MS · EI (m/z): 326 (M+) |
| 174 | 2-(4-fluorophenyl)-4-methyl-5-phenyl-1H-imidazole structure | Free material | MS · EI (m/z): 252 (M+) |
| 175 | 2-(4-fluorophenyl)-5-phenyl-4-(trifluoromethyl-CH2)-1H-imidazole structure | Free material | MS · EI (m/z): 320 (M+) |
| 176 | 2-(4-chlorophenyl)-4-(hydroxymethyl)-5-phenyl-1H-imidazole structure | Free material | |

TABLE 16-continued

| Preparation example No. | Chemical structure | Salt | Physical property, etc. |
|---|---|---|---|
| 177 | 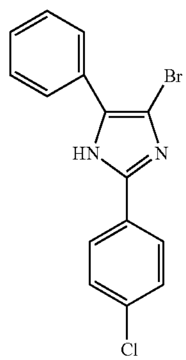 | Free material | MS·EI (m/z): 332/334/336 (M+) |
| 178 | 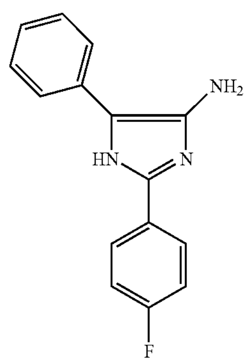 | 2HCl | Powder MS APCI (m/z): 254 (M + H) + |
| 179 | 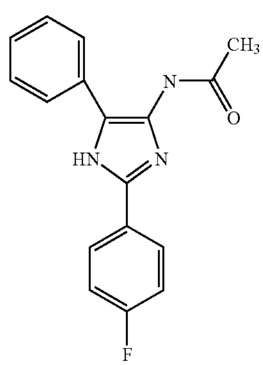 | 1HCl | Powder MS APCI (m/z): 296 (M + H) + |
| 180 | 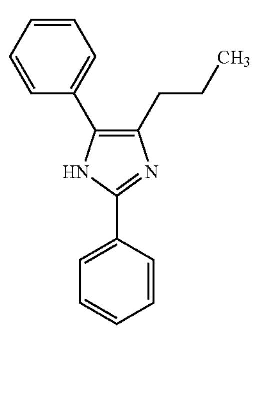 | 1HCl | Powder MS APCI (m/z): 263 (M + H) + |

TABLE 16-continued

| Preparation example No. | Chemical structure | Salt | Physical property, etc. |
|---|---|---|---|
| 181 | 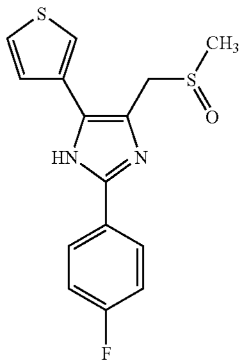 | 1HCl | Powder<br>MS APCI (m/z):<br>321 (M + H) + |
| 182 | 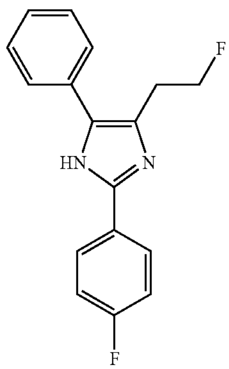 | 1HCl | Powder<br>MS APCI (m/z):<br>285 (M + H) + |
| 183 | 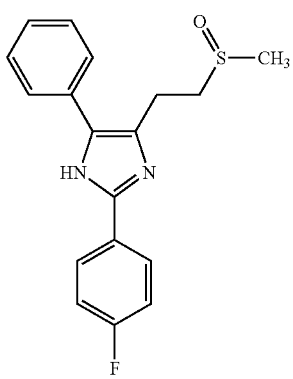 | 1HCl | Powder<br>MS APCI (m/z):<br>329 (M + H) + |
| 184 | 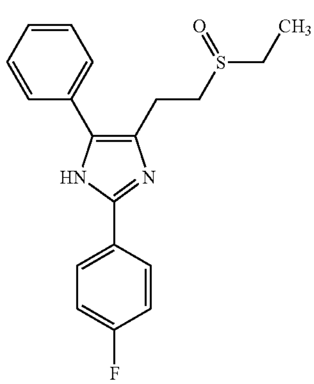 | 1HCl | Powder<br>MS APCI (m/z):<br>343 (M + H) + |

TABLE 16-continued

| Preparation example No. | Chemical structure | Salt | Physical property, etc. |
|---|---|---|---|
| 185 | 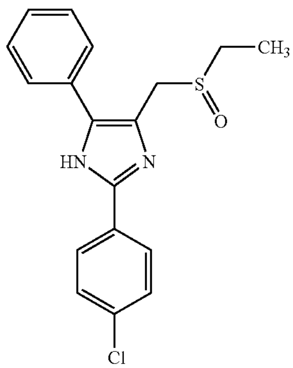 | 1HCl | Powder<br>MS APCI (m/z):<br>345 (M + H) + |
| 186 | 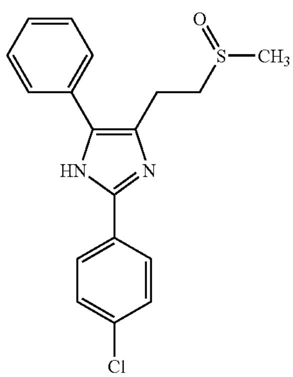 | 1HCl | Powder<br>MS APCI (m/z):<br>345 (M + H) + |
| 187 | 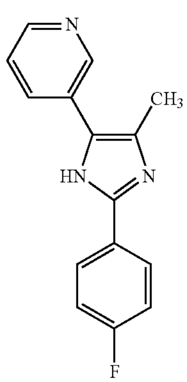 | 2HCl | Powder<br>MS APCI (m/z):<br>254 (M + H) + |
| 188 | 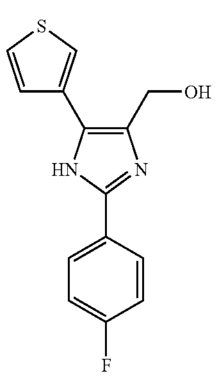 | Free material | |

TABLE 16-continued

| Preparation example No. | Chemical structure | Salt | Physical property, etc. |
|---|---|---|---|
| 189 | 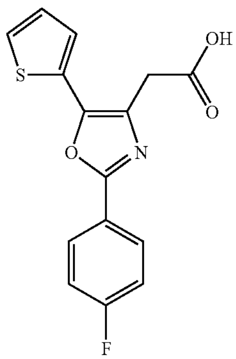 | Free material | Crystal Melting point: 208-209° C. |
| 190 | 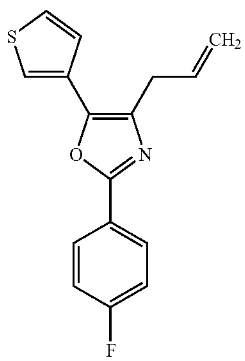 | Free material | Powder MS EI (m/z): 285 (M+) |
| 191 | 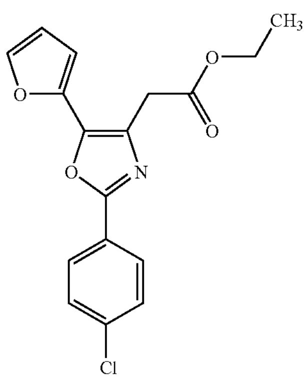 | Free material | Crystal Melting point: 109-111° C. MS · APCI (m/z): 332 (M + H) + |
| 192 | 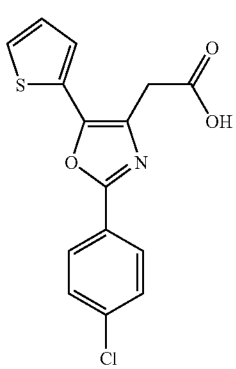 | Free material | Crystal Melting point: 214-215° C. |

TABLE 16-continued

| Preparation example No. | Chemical structure | Salt | Physical property, etc. |
|---|---|---|---|
| 193 | 2-(4-chlorophenyl)-5-phenyl-thiazole-4-acetic acid | Free material | |
| 194 | 2-(4-chlorophenyl)-5-(furan-2-yl)-thiazole-4-acetic acid | Free material | Powder<br>MS EI (m/z): 319/321 (M+) |
| 195 | 2-(4-chlorophenyl)-5-(thiophen-3-yl)-thiazole-4-acetamide | Free material | MS EI (m/z): 334/336 (M+) |
| 196 | ethyl 2-(4-methylphenyl)-5-(thiophen-2-yl)-oxazole-4-acetate | Free material | Crystal<br>Melting point: 125-127° C.<br>MS · APCI (m/z): 328 (M + H) + |

TABLE 16-continued

| Preparation example No. | Chemical structure | Salt | Physical property, etc. |
|---|---|---|---|
| 197 | (structure) | Na | Powder<br>MS · ESI (m/z):<br>302 (M − Na) |
| 198 | (structure) | Na | Powder<br>MS · ESI (m/z):<br>298 (M − Na) |
| 199 | (structure) | Na | Powder<br>MS · ESI (m/z):<br>314 (M − Na) |

TABLE 16-continued

| Preparation example No. | Chemical structure | Salt | Physical property, etc. |
|---|---|---|---|
| 200 | (structure: 2-(4-methoxyphenyl)-5-(thiophen-3-yl)oxazole-4-acetic acid) | Free material | Crystal Melting point: 198-199° C. |
| 201 | (structure: sodium 2-(4-chlorophenyl)-5-(furan-2-yl)oxazole-4-acetate) | Na | Powder MS · APCI (m/z): 302 (M − Na) |
| 202 | (structure: ethyl 2-(4-fluorophenyl)-5-(thiophen-2-yl)oxazole-4-acetate) | Free material | Crystal Melting point: 123-125° C. MS · APCI (m/z): 327 (M + H) + |

Preparation Example 203

A mixture of ethyl 3-amino-4-(5-chlorothiophen-2-yl)-4-oxobutyrate hydrochloride (300 mg), benzo[b]furan-5-carboxylic acid (245 mg), 3-ethyl-1-(3-dimethylamino-propyl) carbodiimide hydrochloride (289 mg), 1-hydroxybenzotriazole (204 mg) and triethylamine (0.35 ml) in methylene chloride (4.5 ml) was stirred at room temperature for overnight. A saturated aqueous sodium hydrogen carbonate solution was added to the reaction mixture, and the mixture was extracted with chloroform. The organic layer was dried over anhydrous sodium sulfate and the solvent was removed under reduced pressure. The resulting residue was purified by silica gel column chromatography (solvent: hexane:ethyl acetate=4:1), and then, triturated with diisopropyl ether to obtain ethyl 3-[(5-benzo[b]furoyl)amino-4-(5-chlorothiophen-2-yl)-4-oxo-butyrate (352 mg) as colorless powder.

To a solution of the resulting ethyl 3-[(5-benzo[b]furoyl)-amino-4-(5-chlorothiophen-2-yl)-4-oxobutyrate (331 mg) in N,N-dimethylformamide (4.08 ml) was added phosphoryl chloride (0.23 ml) under ice-cooling, and the mixture was stirred at 60° C. overnight. To the reaction mixture was added a saturated aqueous sodium hydrogen carbonate solution, the mixture was extracted with ethyl acetate, dried over anhydrous sodium sulfate and the solvent was removed under reduced pressure. The resulting residue was purified by silica gel column chromatography (solvent: chloroform:ethyl acetate=20:1), and then, triturated with diisopropyl ether to obtain ethyl 2-(5-benzo[b]furyl)-5-(5-chlorothiophen-2-yl) oxazol-4-yl acetate (257 mg) as colorless powder.

MS•APCI (m/z): 388/390 (MH+)

Preparation Examples 204 to 226

The following compounds shown in Table 17 were prepared in a manner similar to Preparation example 203 by using corresponding starting materials.

TABLE 17

| Preparation example No. | Chemical structure | Salt | Physical property, etc. |
|---|---|---|---|
| 204 | 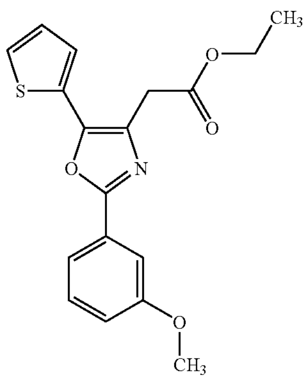 | Free material | Powder MS · APCI (m/z): 344 (M + H) + |
| 205 | 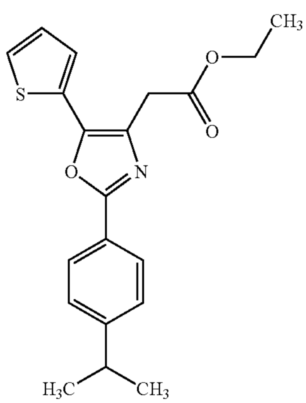 | Free material | Powder MS · APCI (m/z): 356 (M + H) + |
| 206 | 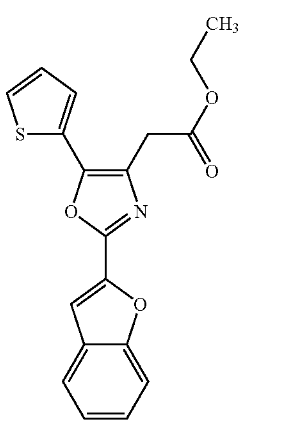 | Free material | Powder MS · APCI (m/z): 354 (M + H) + |

TABLE 17-continued

| Preparation example No. | Chemical structure | Salt | Physical property, etc. |
|---|---|---|---|
| 207 | 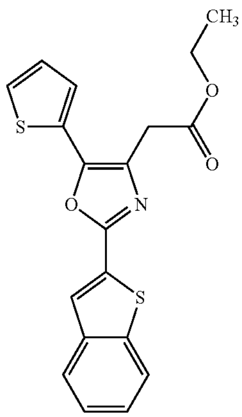 | Free material | Powder MS · APCI (m/z): 370 (M + H) + |
| 208 | 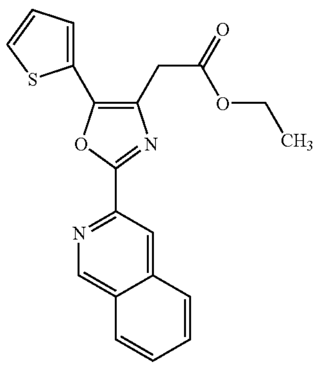 | Free material | Powder MS · APCI (m/z): 365 (M + H) + |
| 209 | 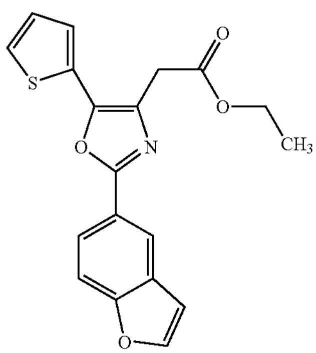 | Free material | Powder MS · APCI (m/z): 354 (M + H) + |
| 210 | 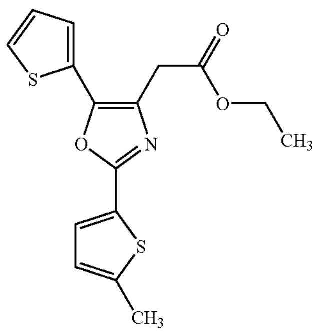 | Free material | Powder MS · APCI (m/z): 334 (M + H) + |

TABLE 17-continued

| Preparation example No. | Chemical structure | Salt | Physical property, etc. |
|---|---|---|---|
| 211 | 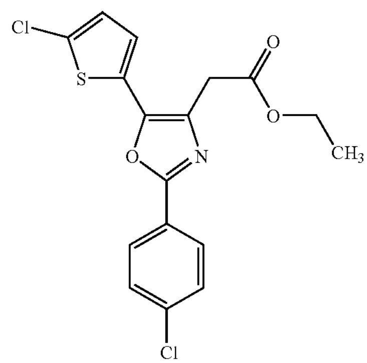 | Free material | Powder MS · APCI (m/z): 382/384 (M + H) + |
| 212 | 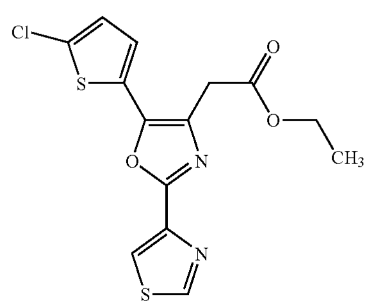 | Free material | Powder MS · APCI (m/z): 355/357 (M + H) + |
| 213 | 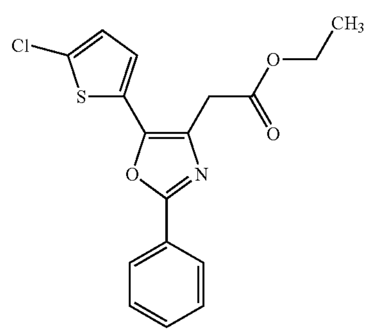 | Free material | Powder MS · APCI (m/z): 348 (M + H) + |
| 214 | 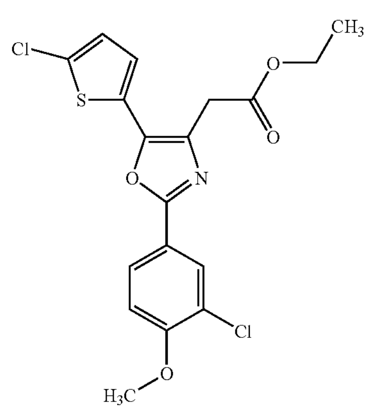 | Free material | Powder MS · APCI (m/z): 412 (M + H) + |

TABLE 17-continued

| Preparation example No. | Chemical structure | Salt | Physical property, etc. |
|---|---|---|---|
| 215 | 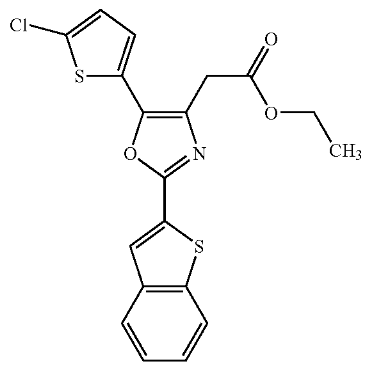 | Free material | Powder MS · APCI (m/z): 404/406 (M + H) + |
| 216 | 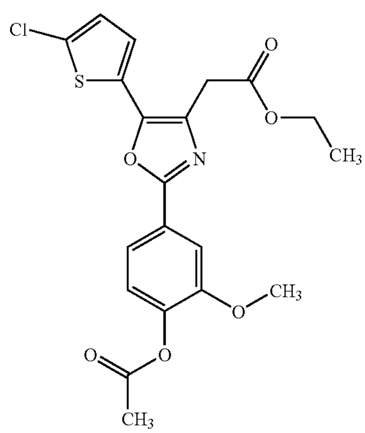 | Free material | Powder MS · APCI (m/z): 436/438 (M + H) + |
| 217 | 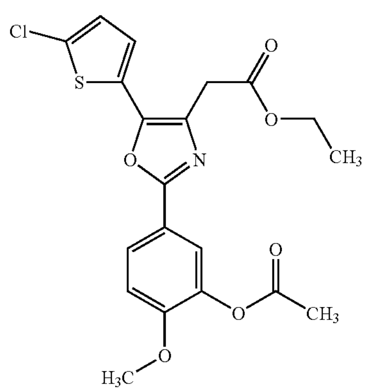 | Free material | Powder MS · APCI (m/z): 436/438 (M + H) + |
| 218 | 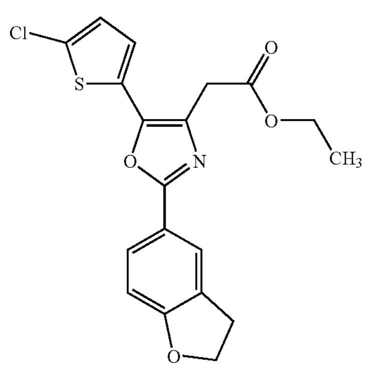 | Free material | Powder MS · APCI (m/z): 390/392 (M + H) + |

TABLE 17-continued
| Preparation example No. | Chemical structure | Salt | Physical property, etc. |
|---|---|---|---|
| 219 | 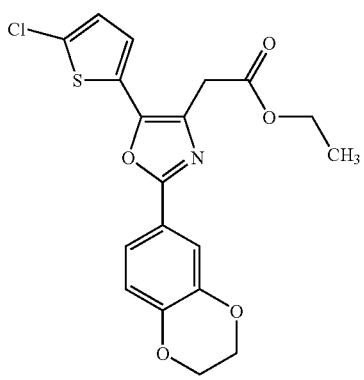 | Free material | Powder MS · APCI (m/z): 406/408 (M + H) + |
| 220 | 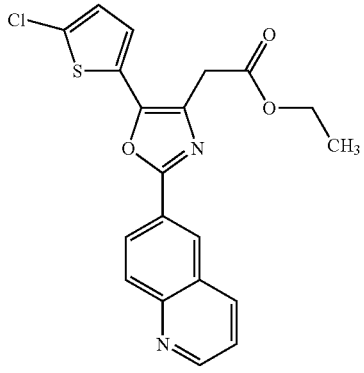 | Free material | Powder MS · APCI (m/z): 399/401 (M + H) + |
| 221 | 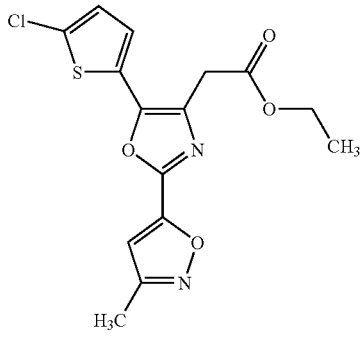 | Free material | Powder MS · APCI (m/z): 353/355 (M + H) + |
| 222 | 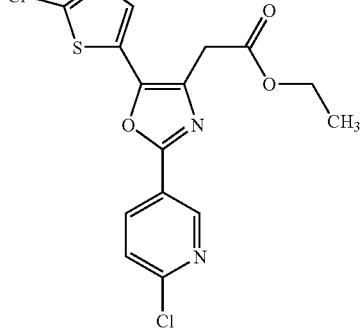 | Free material | Powder MS · APCI (m/z): 383/385 (M + H) + |

TABLE 17-continued

| Preparation example No. | Chemical structure | Salt | Physical property, etc. |
|---|---|---|---|
| 223 | 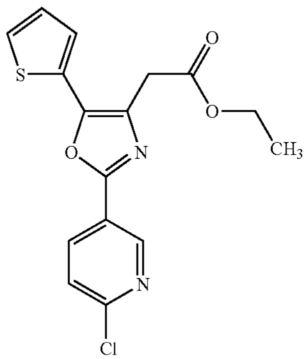 | Free material | Powder MS·APCI (m/z): 349/351 (M + H) + |
| 224 | 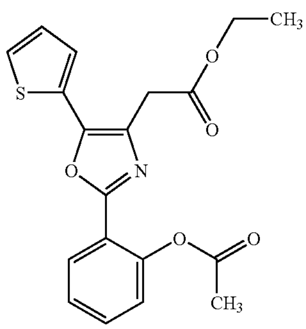 | Free material | Powder MS·APCI (m/z): 372 (M + H) + |
| 225 | 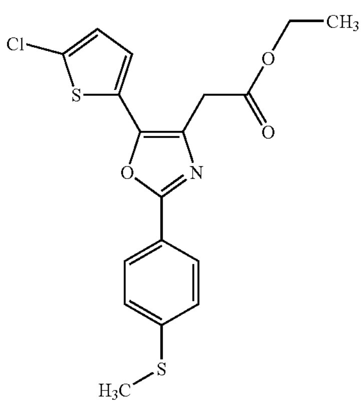 | Free material | Powder MS·APCI (m/z): 394 (M + H) + |
| 226 | 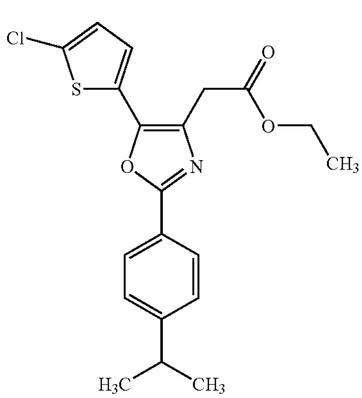 | Free material | Powder MS·APCI (m/z): 392/394 (M + H) + |

Preparation Example 227

To a solution of 4-[(5-benzo[b]furoyl)aminoacetyl]-2-chlorothiophene (543 mg) in N,N-dimethylformamide (10 ml) was added sodium hydride (71.3 mg, 60% mineral oil) under ice-cooling, and the mixture was stirred at room temperature for 20 minutes. After ice-cooling, ethyl bromoacetate (0.21 ml) was added dropwise to the mixture, and the resulting mixture was stirred at room temperature for 40 minutes. After cooling, 5% aqueous citric acid solution was added to the reaction mixture and the mixture was extracted with ethyl acetate. The organic layer was washed with water and brine, dried over anhydrous sodium sulfate and the solvent was removed under reduced pressure to obtain a crude product of ethyl 3-[(5-benzo[b]furoyl)amino]-4-(5-chlorothiophen-3-yl)-4-oxobutyrate (896 mg).

To a solution of the resulting crude product of ethyl 3-[(5-benzo[b]furoyl)amino]-4-(5-chlorothiophen-3-yl)-4-oxobutyrate (896 mg) in N,N-dimethylformamide (7 ml) was added phosphoryl chloride (0.48 ml) at room temperature, and the mixture was stirred at the same temperature overnight. To the reaction mixture was added water, the mixture was extracted with ethyl acetate, dried over anhydrous sodium sulfate and the solvent was removed under reduced pressure. The resulting residue was purified by silica gel column chromatography (solvent: hexane:acetone=7:1), and then, triturated with diethyl ether to obtain ethyl 2-(5-benzo[b]furyl)-5-(5-chlorothiophen-3-yl)oxazol-4-ylacetate (349 mg) as colorless powder.

MS·APCI (m/z): 388 (MH+)

Preparation Examples 228 to 232

The following compounds shown in Table 18 were prepared in a manner similar to Preparation example 227 by using corresponding starting materials.

TABLE 18

| Preparation example No. | Chemical structure | Salt | Physical constant, etc. |
|---|---|---|---|
| 228 | 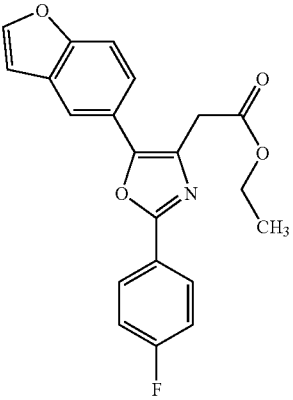 | Free material | Powder<br>MS · APCI (m/z): 366 (M + H) + |
| 229 | 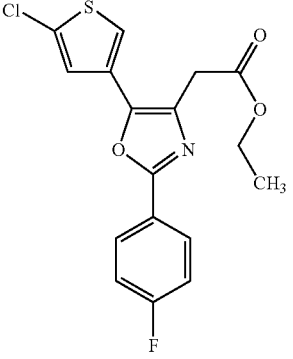 | Free material | Powder<br>MS · APCI (m/z): 366 (M + H) + |

TABLE 18-continued

| Preparation example No. | Chemical structure | Salt | Physical constant, etc. |
|---|---|---|---|
| 230 | 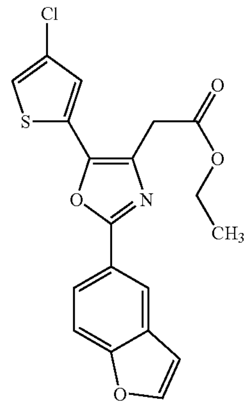 | Free material | Powder MS · APCI (m/z): 388 (M + H) + |
| 231 | 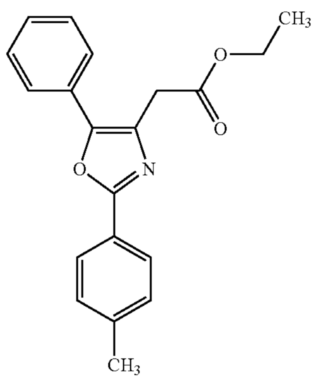 | Free material | |
| 232 | 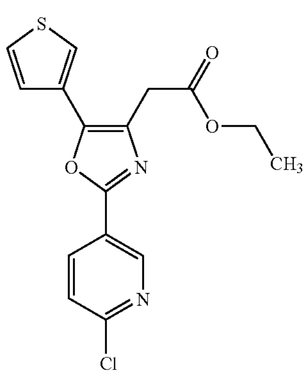 | Free material | Powder MS · APCI (m/z): 349/351 (M + H) + |

Preparation Examples 233 to 293
The following compounds shown in Table 19 were prepared in a manner similar to Preparation example 148 or 152 by using corresponding starting materials.
TABLE 19
| Preparation example No. | Chemical structure | Salt | Physical property, etc. |
|---|---|---|---|
| 233 | 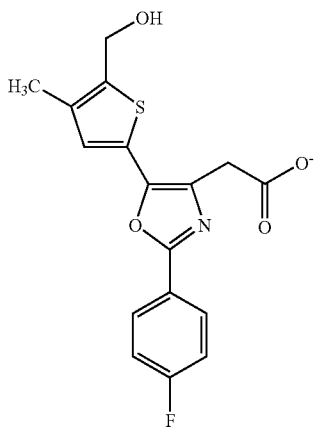 | Na | Powder ESI·MS (m/z): 346 (M − Na) |
| 234 | 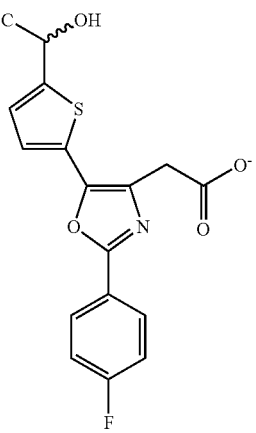 | Na | Powder ESI·MS (m/z): 346 (M − Na) |
| 235 | 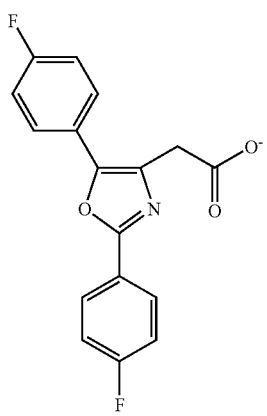 | Na | Powder ESI·MS (m/z): 314 (M − Na) |

TABLE 19-continued

| Preparation example No. | Chemical structure | Salt | Physical property, etc. |
|---|---|---|---|
| 236 | 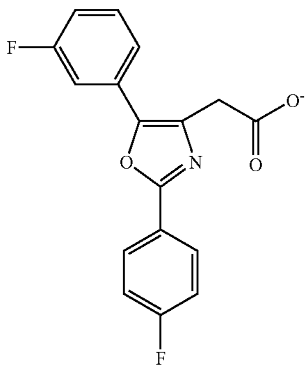 | Na | Powder<br>ESI · MS (m/z):<br>314 (M − Na) |
| 237 | 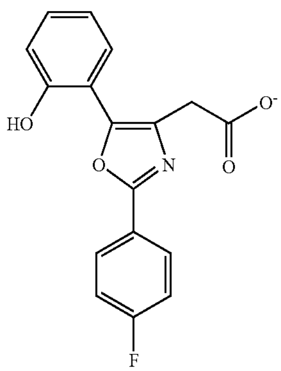 | Na | Powder<br>ESI · MS (m/z):<br>312 (M − Na) |
| 238 | 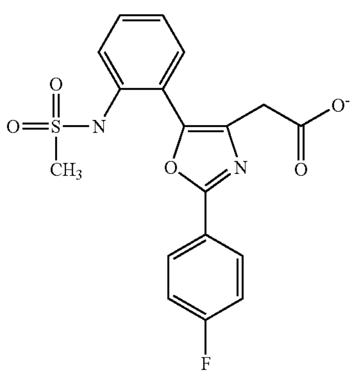 | Na | Powder<br>ESI · MS (m/z):<br>389 (M − Na) |
| 239 | 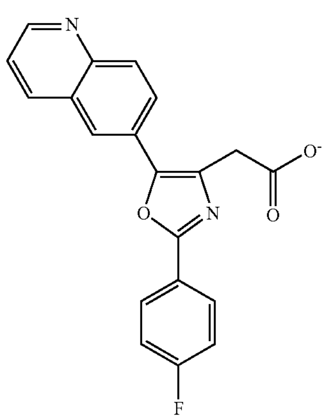 | Na | Powder<br>ESI · MS (m/z):<br>347 (M − Na) |

TABLE 19-continued
| Preparation example No. | Chemical structure | Salt | Physical property, etc. |
|---|---|---|---|
| 240 | 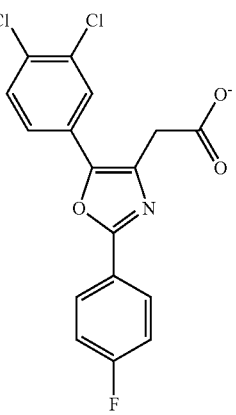 | Na | Powder ESI·MS (m/z): 364 (M − Na) |
| 241 | 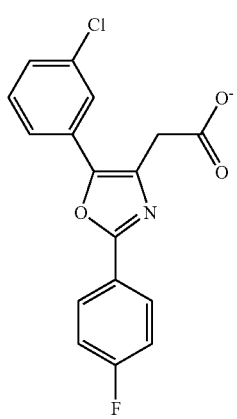 | Na | Powder ESI·MS (m/z): 330 (M − Na) |
| 242 | 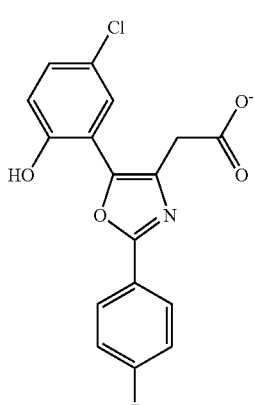 | Na | Powder ESI·MS (m/z): 346 (M − Na) |

TABLE 19-continued
| Preparation example No. | Chemical structure | Salt | Physical property, etc. |
|---|---|---|---|
| 243 | 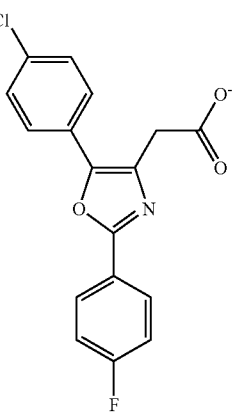 | Na | Powder<br>ESI·MS (m/z):<br>330 (M − Na) |
| 244 | 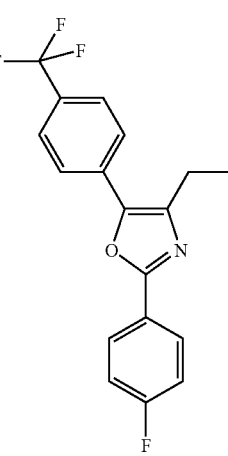 | Na | Powder<br>ESI·MS (m/z):<br>364 (M − Na) |
| 245 | 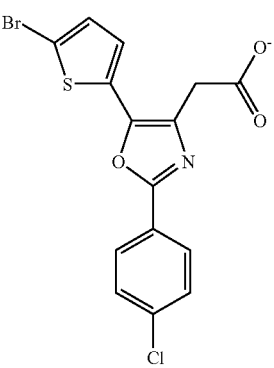 | Na | Powder<br>ESI·MS (m/z):<br>396 (M − Na) |

TABLE 19-continued
| Preparation example No. | Chemical structure | Salt | Physical property, etc. |
|---|---|---|---|
| 246 | 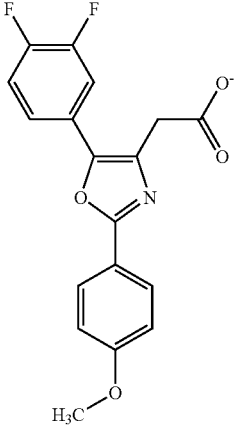 | Na | Powder<br>ESI · MS (m/z):<br>344 (M − Na) |
| 247 | 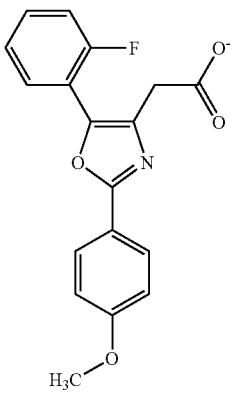 | Na | Powder<br>ESI · MS (m/z):<br>326 (M − Na) |
| 248 | 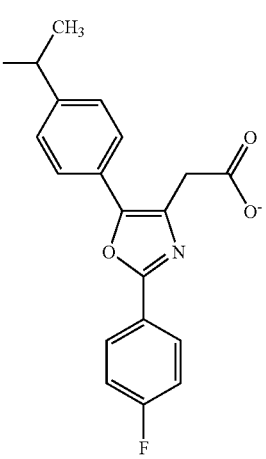 | Na | Powder<br>ESI · MS (m/z):<br>338 (M − Na) |

TABLE 19-continued

| Preparation example No. | Chemical structure | Salt | Physical property, etc. |
|---|---|---|---|
| 249 | 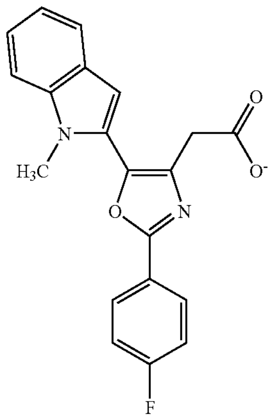 | Na | Powder ESI·MS (m/z): 349 (M − Na) |
| 250 | 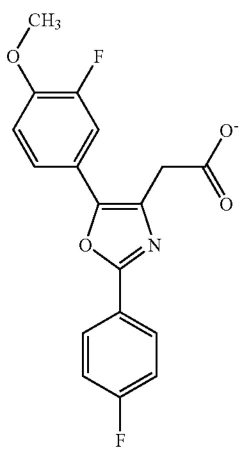 | Na | Powder ESI·MS (m/z): 344 (M − Na) |
| 251 | 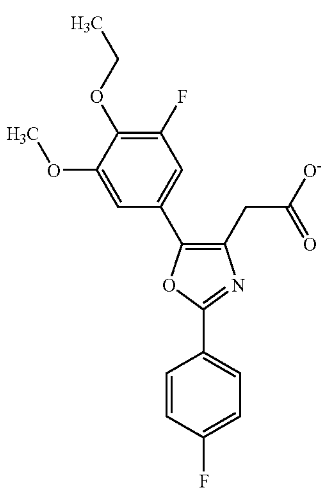 | Na | Powder ESI·MS (m/z): 388 (M − Na) |

TABLE 19-continued

| Preparation example No. | Chemical structure | Salt | Physical property, etc. |
|---|---|---|---|
| 252 | 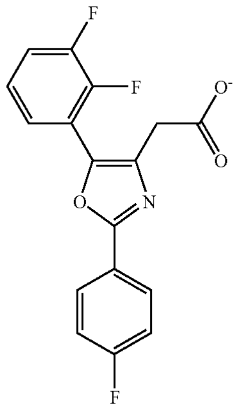 | Na | Powder<br>ESI · MS (m/z):<br>322 (M − Na) |
| 253 | 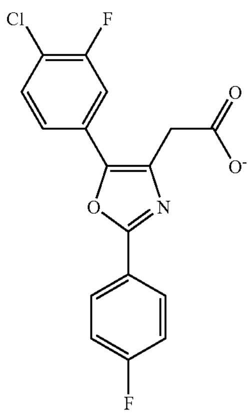 | Na | Powder<br>ESI · MS (m/z):<br>348 (M − Na) |
| 254 | 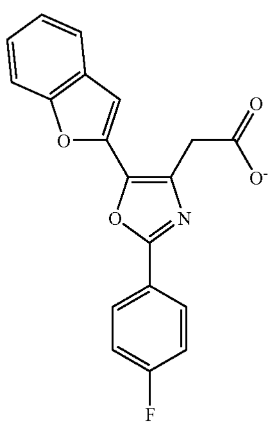 | Na | Powder<br>ESI · MS (m/z):<br>336 (M − Na) |

TABLE 19-continued

| Preparation example No. | Chemical structure | Salt | Physical property, etc. |
|---|---|---|---|
| 255 | 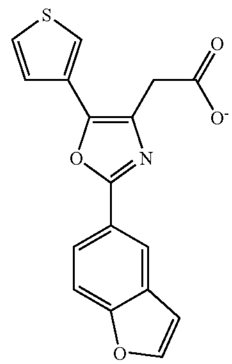 | Na | Powder ESI · MS (m/z): 324 (M − Na) |
| 256 | 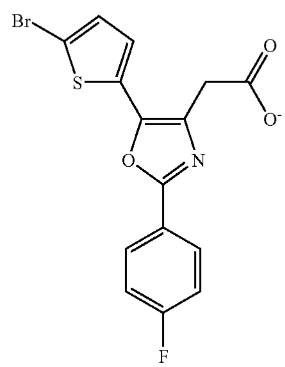 | Na | Powder ESI · MS (m/z): 382 (M − Na) |
| 257 | 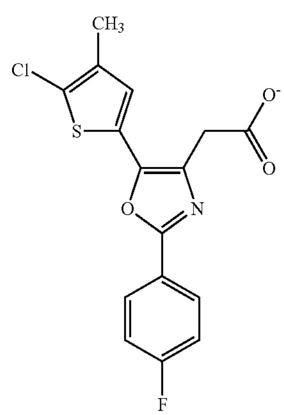 | Na | Powder ESI · MS (m/z): 350 (M − Na) |
| 258 | 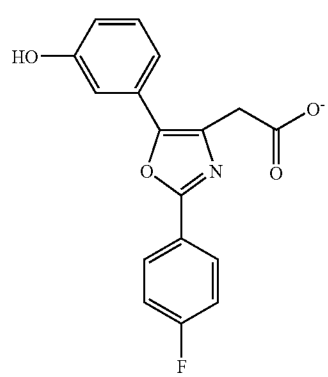 | Na | Powder ESI · MS (m/z): 312 (M − Na) |

TABLE 19-continued

| Preparation example No. | Chemical structure | Salt | Physical property, etc. |
|---|---|---|---|
| 259 | 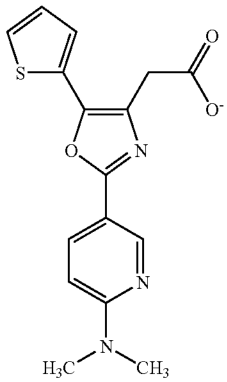 | Na | Powder<br>ESI·MS (m/z):<br>328 (M − Na) |
| 260 | 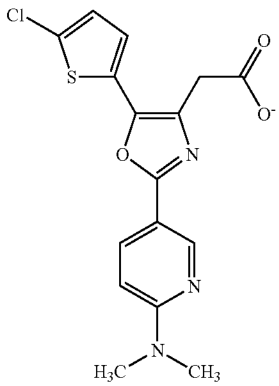 | Na | Powder<br>ESI·MS (m/z):<br>362/364 (M − Na) |
| 261 | 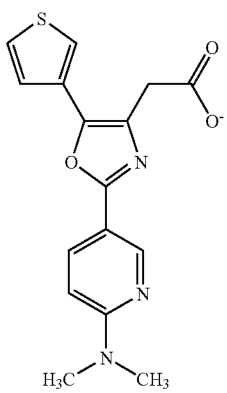 | Na | Powder<br>ESI·MS (m/z):<br>328 (M − Na) |
| 262 | 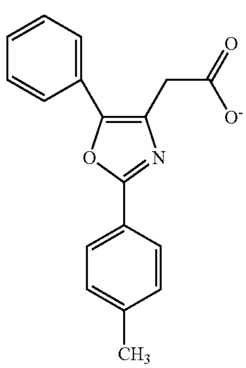 | Na | Powder<br>ESI·MS (m/z):<br>292 (M − Na) |

TABLE 19-continued

| Preparation example No. | Chemical structure | Salt | Physical property, etc. |
|---|---|---|---|
| 263 | 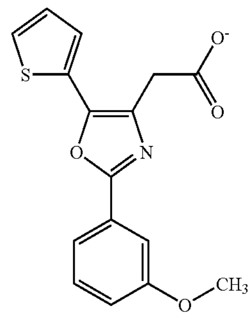 | Na | Powder ESI·MS (m/z): 314 (M − Na) |
| 264 | 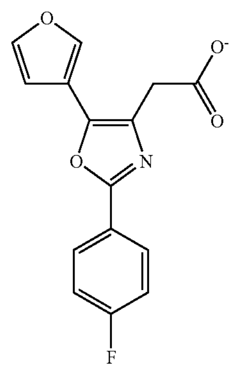 | Na | Powder ESI·MS (m/z): 286 (M − Na) |
| 265 | 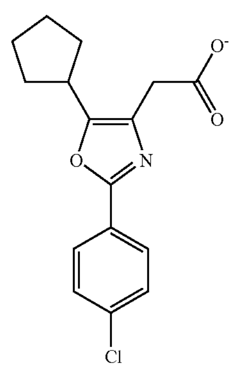 | Na | Powder ESI·MS (m/z): 304 (M − Na) |
| 266 | 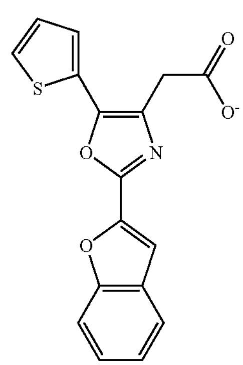 | Na | Powder ESI·MS (m/z): 324 (M − Na) |

TABLE 19-continued
| Preparation example No. | Chemical structure | Salt | Physical property, etc. |
|---|---|---|---|
| 267 | 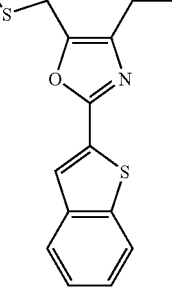 | Na | Powder<br>ESI · MS (m/z):<br>340 (M − Na) |
| 268 | 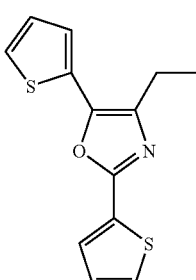 | Na | Powder<br>ESI · MS (m/z):<br>304 (M − Na) |
| 269 | 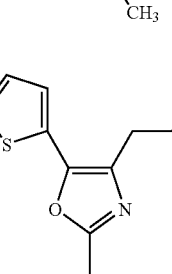 | Na | Powder<br>ESI · MS (m/z):<br>324 (M − Na) |
| 270 | 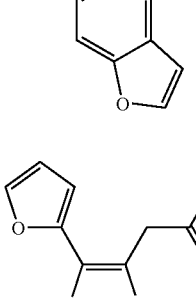 | Na | Powder<br>ESI · MS (m/z):<br>286 (M − Na) |

TABLE 19-continued

| Preparation example No. | Chemical structure | Salt | Physical property, etc. |
|---|---|---|---|
| 271 | 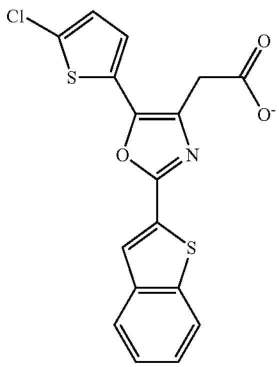 | Na | Powder<br>ESI · MS (m/z):<br>374/376 (M − Na) |
| 272 | 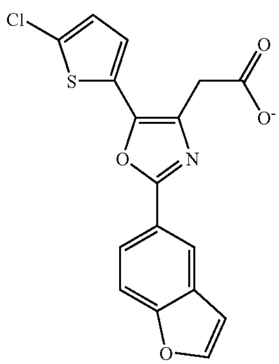 | Na | Powder<br>ESI · MS (m/z):<br>358/360 (M − Na) |
| 273 | 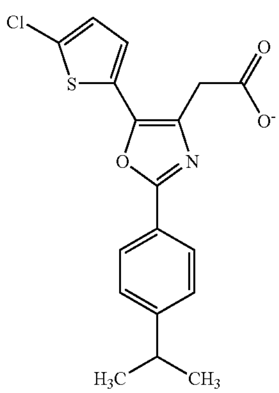 | Na | Powder<br>ESI · MS (m/z):<br>360 (M − Na) |
| 274 | 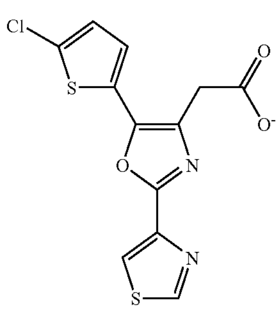 | Na | Powder<br>ESI · MS (m/z):<br>325 (M − Na) |

TABLE 19-continued

| Preparation example No. | Chemical structure | Salt | Physical property, etc. |
| --- | --- | --- | --- |
| 275 | 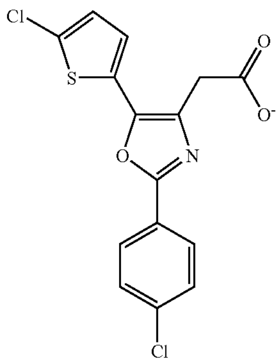 | Na | Powder<br>ESI·MS (m/z):<br>352/354 (M− Na) |
| 276 | 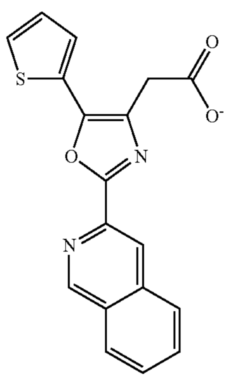 | Na | Powder<br>ESI·MS (m/z):<br>335 (M − Na) |
| 277 | 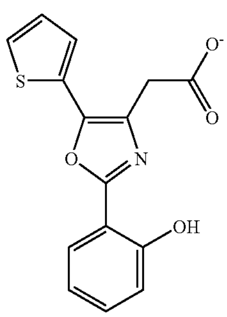 | Na | Powder<br>ESI·MS (m/z):<br>300 (M − Na) |
| 278 | 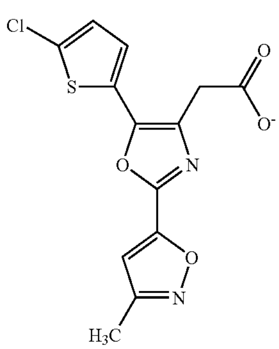 | Na | Powder<br>ESI·MS (m/z):<br>323/325 (M − Na) |

TABLE 19-continued

| Preparation example No. | Chemical structure | Salt | Physical property, etc. |
|---|---|---|---|
| 279 | 5-(5-chlorothiophen-2-yl)-2-phenyloxazol-4-yl acetate | Na | Powder ESI·MS (m/z): 318 (M − Na) |
| 280 | 5-(5-chlorothiophen-2-yl)-2-(3-chloro-4-methoxyphenyl)oxazol-4-yl acetate | Na | Powder ESI·MS (m/z): 382 (M − Na) |
| 281 | 5-(5-chlorothiophen-2-yl)-2-(4-methylthiophenyl)oxazol-4-yl acetate | Na | Powder ESI·MS (m/z): 364 (M − Na) |
| 282 | 5-(5-chlorothiophen-2-yl)-2-(2,3-dihydrobenzofuran-5-yl)oxazol-4-yl acetate | Na | Powder ESI·MS (m/z): 360/362 (M − Na) |

TABLE 19-continued
| Preparation example No. | Chemical structure | Salt | Physical property, etc. |
|---|---|---|---|
| 283 | 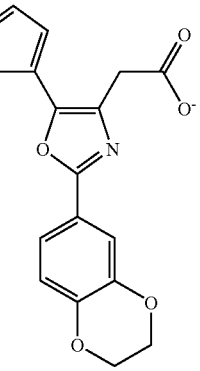 | Na | Powder<br>ESI · MS (m/z):<br>376/378 (M − Na) |
| 284 | 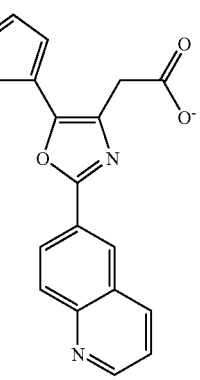 | Na | Powder<br>ESI · MS (m/z):<br>369/371 (M − Na) |
| 285 | 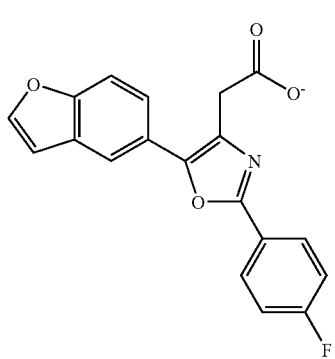 | Na | Powder<br>ESI · MS (m/z):<br>336 (M − Na) |
| 286 | 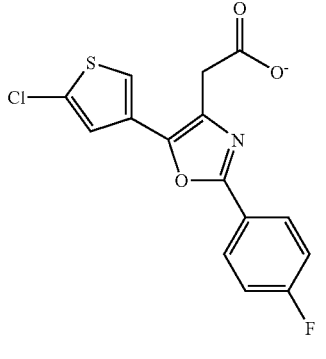 | Na | Powder<br>ESI · MS (m/z):<br>336/338 (M − Na) |

TABLE 19-continued

| Preparation example No. | Chemical structure | Salt | Physical property, etc. |
|---|---|---|---|
| 287 | 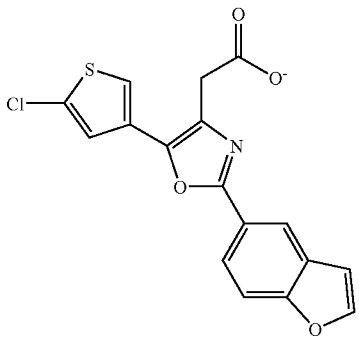 | Na | Powder ESI·MS (m/z): 358 (M − Na) |
| 288 | 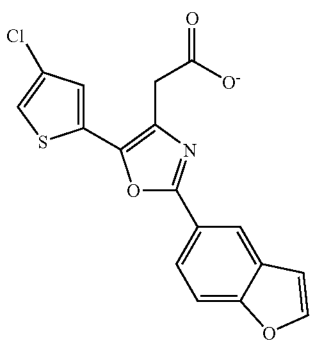 | Na | Powder ESI·MS (m/z): 358 (M − Na) |
| 289 | 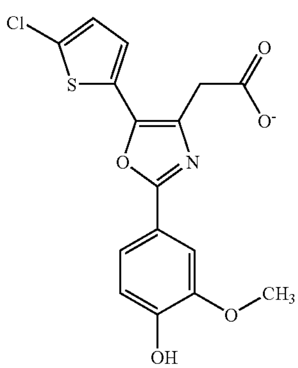 | Na | Powder ESI·MS (m/z): 364/366 (M − Na) |
| 290 | 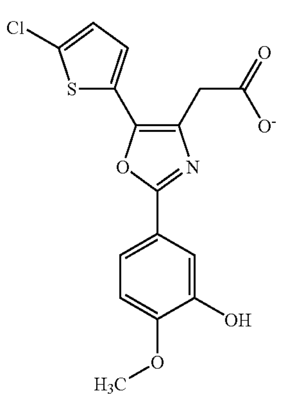 | Na | Powder ESI·MS (m/z): 364/366 (M − Na) |

TABLE 19-continued
| Preparation example No. | Chemical structure | Salt | Physical property, etc. |
|---|---|---|---|
| 291 | 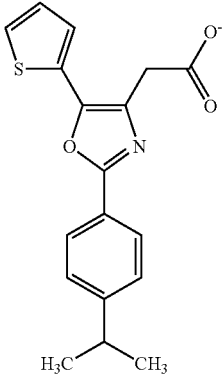 | Na | Powder<br>ESI · MS (m/z):<br>326 (M − Na) |
| 292 | 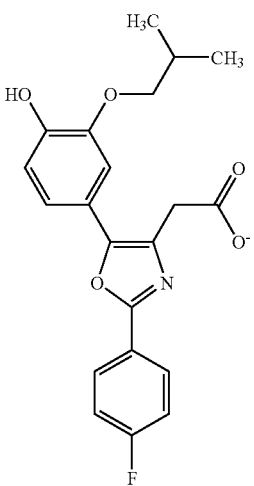 | Na | Powder<br>ESI · MS (m/z):<br>384 (M − Na) |
| 293 | 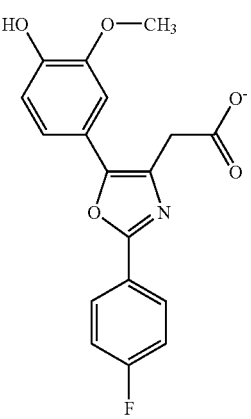 | Na | Powder<br>ESI · MS (m/z):<br>342 (M − Na) |

Preparation Examples 294 and 295

The following compounds shown in Table 20 were prepared in a manner similar to Preparation example 149 by using corresponding starting materials.

TABLE 20

| Preparation example No. | Chemical structure | Salt | Physical property, etc. |
|---|---|---|---|
| 294 | (structure shown) | Free material | Powder<br>MS·APCI (m/z): 340/342 (M + H) + |
| 295 | (structure shown) | Free material | Crystal<br>Melting point: 120-122° C.<br>MS·APCI (m/z): 376 (MH) + |

Preparation Example 296

A mixture of ethyl 5-bromo-2-(4-fluorophenyl)oxazol-4-yl acetate (164 mg), phenylboric acid (91 mg) and bis(triphenylphosphine) palladium (II) chloride (18 mg) in 2M aqueous sodium carbonate solution (0.75 ml) and dimethoxyethane (3 ml) was stirred under argon atmosphere at 100° C. for one hour. After cooling, to the reaction mixture were added water and ethyl acetate, the organic layer was collected, washed with brine and dried over anhydrous sodium sulfate, and the solvent was removed under reduced pressure. The resulting residue was purified by silica gel column chromatography (solvent: hexane:ethyl acetate=6:1) to obtain ethyl 2-(4-fluoro-phenyl)-5-phenyloxazol-4-yl acetate (144 mg) as colorless powder.

Melting point: 118 to 120° C.
MS•APCI (m/z): 326 (MH+)

Preparation Examples 297 to 320

The following compounds shown in Table 21 were prepared in a manner similar to Preparation example 296 by using corresponding starting materials.

TABLE 21

| Preparation example No. | Chemical structure | Salt | Physical constant, etc. |
|---|---|---|---|
| 297 | 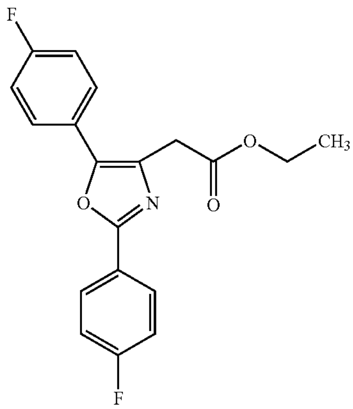 | Free material | Powder MS·APCI (m/z): 344 (M + H) + |
| 298 | 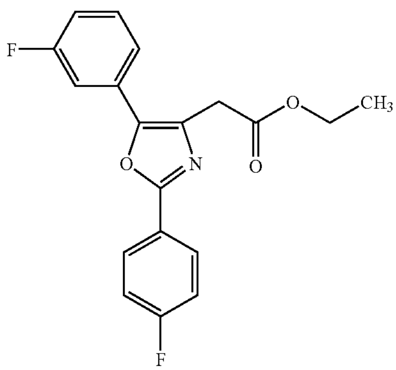 | Free material | Powder MS·APCI (m/z): 344 (M + H) + |
| 299 | 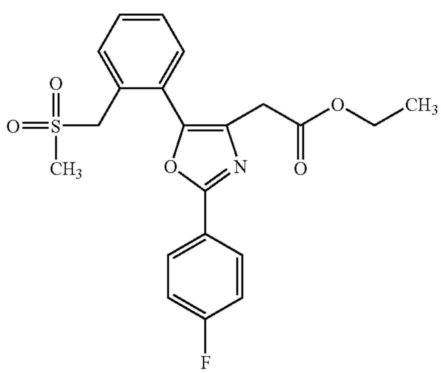 | Free material | Powder MS·APCI (m/z): 419 (M + H) + |
| 300 | 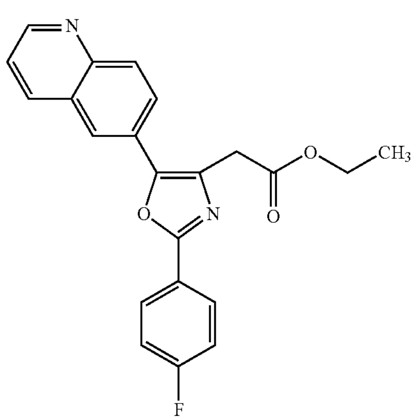 | Free material | Powder MS·APCI (m/z): 377 (M + H) + |

TABLE 21-continued

| Preparation example No. | Chemical structure | Salt | Physical constant, etc. |
|---|---|---|---|
| 301 | 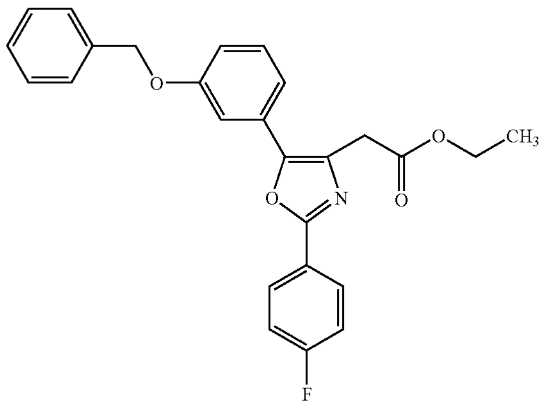 | Free material | Powder MS · APCI (m/z): 432 (M + H) + |
| 302 | 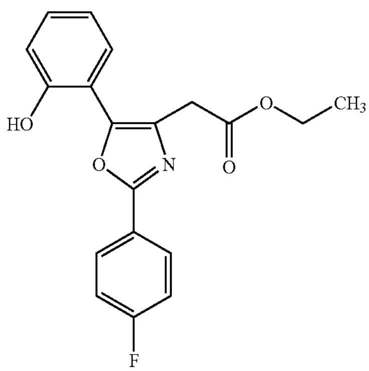 | Free material | Powder MS · APCI (m/z): 342 (M + H) + |
| 303 | 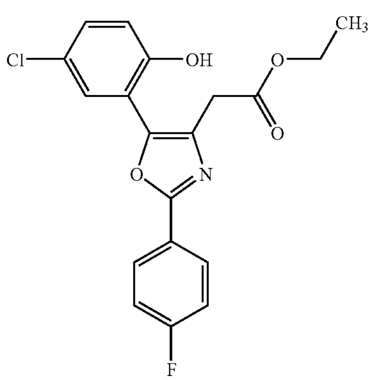 | Free material | Powder MS · APCI (m/z): 376 (M + H) + |
| 304 | 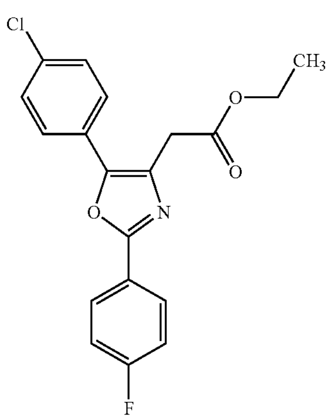 | Free material | Powder MS · APCI (m/z): 360 (M + H) + |

TABLE 21-continued

| Preparation example No. | Chemical structure | Salt | Physical constant, etc. |
|---|---|---|---|
| 305 | (structure) | Free material | Powder MS·APCI (m/z): 394 (M + H) + |
| 306 | (structure) | Free material | Powder MS·APCI (m/z): 394/396 (M + H) + |
| 307 | (structure) | Free material | Powder MS·APCI (m/z): 360/362 (M + H) + |

TABLE 21-continued
| Preparation example No. | Chemical structure | Salt | Physical constant, etc. |
|---|---|---|---|
| 308 | 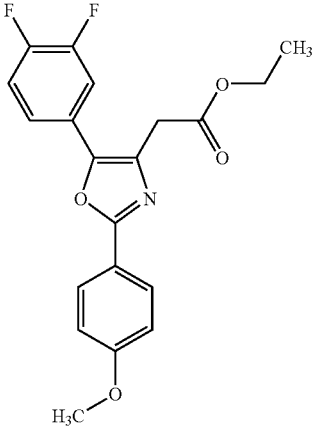 | Free material | Powder MS · APCI (m/z): 374 (M + H) + |
| 309 | 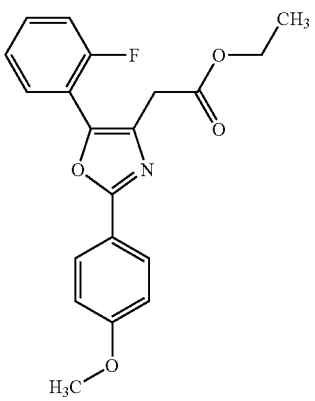 | Free material | Powder MS · APCI (m/z): 356 (M + H) + |
| 310 | 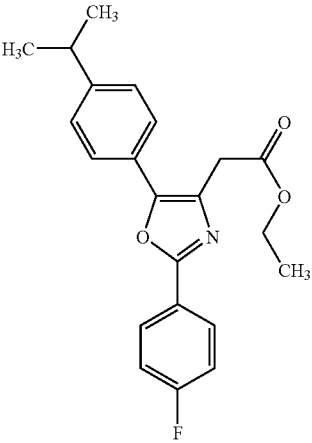 | Free material | Powder MS · APCI (m/z): 368 (M + H) + |

TABLE 21-continued
| Preparation example No. | Chemical structure | Salt | Physical constant, etc. |
|---|---|---|---|
| 311 | 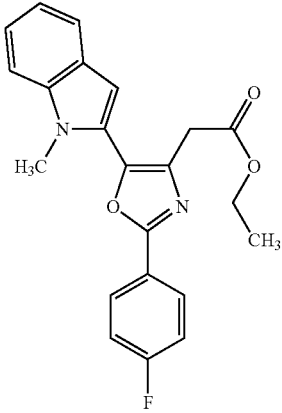 | Free material | Powder MS · APCI (m/z): 379 (M + H) + |
| 312 | 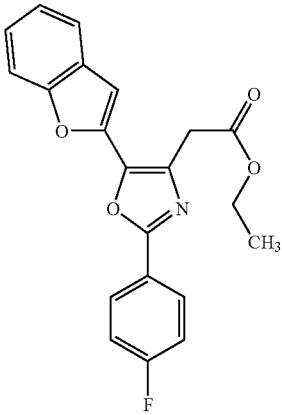 | Free material | Powder MS · APCI (m/z): 366 (M + H) + |
| 313 | 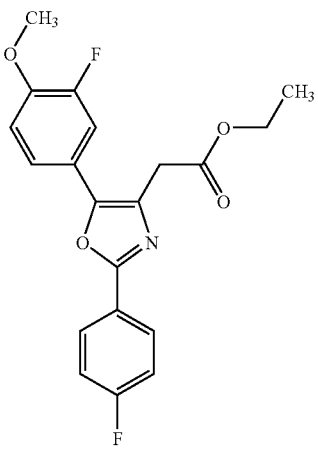 | Free material | Powder MS · APCI (m/z): 374 (M + H) + |

TABLE 21-continued
| Preparation example No. | Chemical structure | Salt | Physical constant, etc. |
|---|---|---|---|
| 314 | 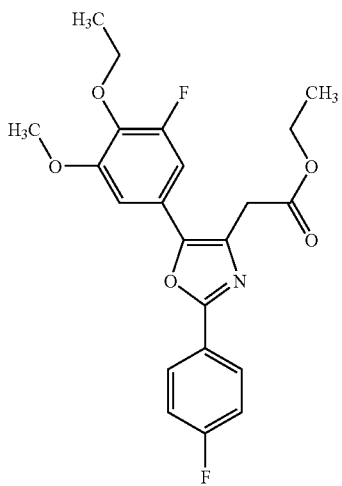 | Free material | Powder MS · APCI (m/z): 418 (M + H) + |
| 315 | 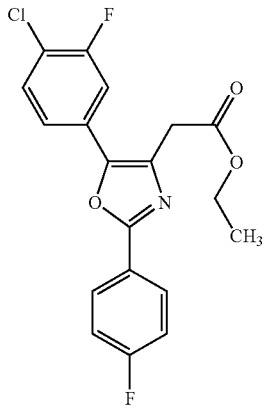 | Free material | Powder MS · APCI (m/z): 378 (M + H) + |
| 316 | 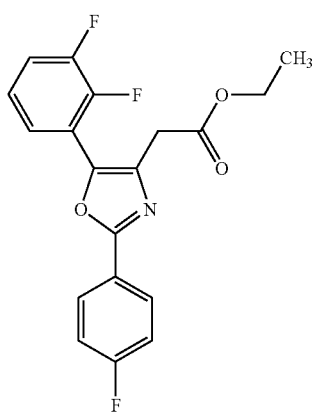 | Free material | Powder MS · APCI (m/z): 362 (M + H) + |

TABLE 21-continued

| Preparation example No. | Chemical structure | Salt | Physical constant, etc. |
|---|---|---|---|
| 317 | 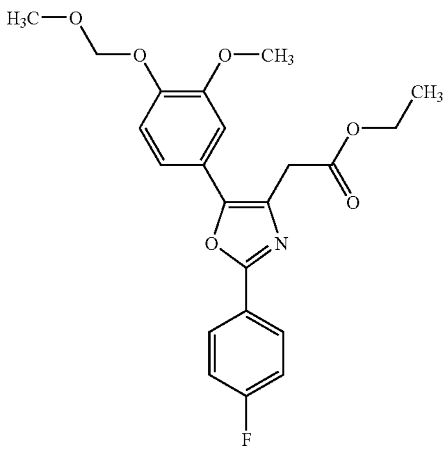 | Free material | Powder MS · APCI (m/z): 416 (M + H) + |
| 318 | 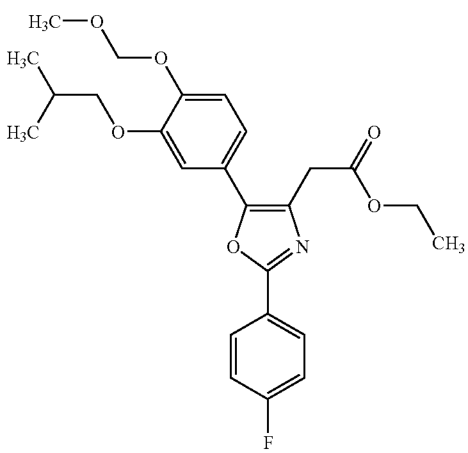 | Free material | Powder MS · APCI (m/z): 468 (M + H) + |
| 319 | 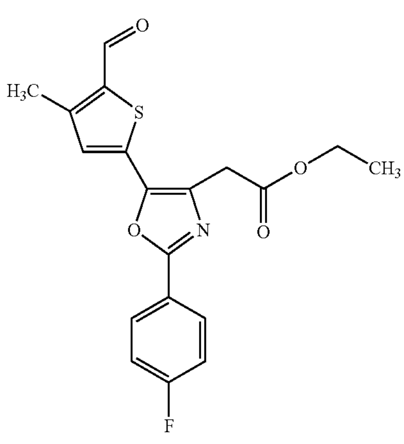 | Free material | Powder MS · APCI (m/z): 374 (M + H) + |

TABLE 21-continued

| Preparation example No. | Chemical structure | Salt | Physical constant, etc. |
|---|---|---|---|
| 320 | (structure) | Free material | Powder MS · APCI (m/z): 374 (M + H) + |

Preparation Example 321

To a suspension of ethyl 2-(4-fluorophenyl)5-(2-thienyl)-oxazol-4-yl acetate (166 mg) in chloroform (1.5 ml) and acetic acid (1.5 ml) was added N-bromosuccinimide (94 mg), and the mixture was stirred at room temperature overnight. To the reaction mixture were added a saturated aqueous sodium hydrogen carbonate solution and ethyl acetate, and the organic layer was collected. The organic layer was washed with water and brine, dried over anhydrous sodium sulfate, and the solvent was removed under reduced pressure. The resulting residue was crystallized from diethylether-n-hexane to obtain ethyl 2-(4-fluorophenyl)-5-(5-bromothiophen-2-yl)oxazol-4-yl acetate (147 mg).

MS•APCI (m/z): 410/412 (MH+)

Preparation Example 322

The following compound shown in Table 22 was prepared in a manner similar to Preparation example 321 by using corresponding starting materials.

Preparation Example 323

A mixed solution of ethyl 2-(4-fluorophenyl)-5-[3-(2-methylpropyloxy)-4-methoxymethoxyphenyl]oxazol-4-yl acetate (300 mg), 4N hydrogen chloride-dioxane solution (5 ml) and ethanol (5 ml) was stirred at room temperature overnight. After the solvent was removed under reduced pressure, the residue was triturated with diethyl ether and washed with n-hexane to obtain ethyl 2-(4-fluorophenyl)-5-[3-(2-methylpropyloxy)-4-hydroxyphenyl]oxazol-4-yl acetate (269 mg).

MS•APCI (m/z): 414 (MH+)

Preparation Example 324

The following compound shown in Table 23 was prepared in a manner similar to Preparation example 323 by using corresponding starting materials.

TABLE 22

| Preparation example No. | Chemical structure | Salt | Physical constant, etc. |
|---|---|---|---|
| 322 | (structure) | Free material | Powder MS · APCI (m/z): 380/382 (M + H)+ |

TABLE 23

| Preparation example No. | Chemical structure | Salt | Physical constant, etc. |
|---|---|---|---|
| 324 | HO, O—CH₃ (structure with oxazole, ethyl acetate group, 4-fluorophenyl) | Free material | Powder<br>MS · APCI (m/z):<br>372 (M + H)+ |

Preparation Example 325

To a mixed solution of ethyl 2-(4-fluorophenyl)-5-(5-formyl-4-methylthiophen-2-yl)oxazol-4-yl acetate (175 mg) in ethanol (5 ml) and tetrahydrofuran (5 ml) was added sodium borohydride (54 mg), and the mixture was stirred at room temperature for 30 minutes. To the reaction mixture were added water and ethyl acetate, the organic layer was collected, washed with brine and dried over anhydrous magnesium sulfate, and the solvent was removed under reduced pressure. The resulting residue was purified by silica gel column chromatography (solvent: hexane:ethyl acetate=2:1) to obtain ethyl 2-(4-fluorophenyl)-5-(5-hydroxymethyl-4-methylthiophen-2-yl)oxazol-4-yl acetate (125 mg) as pale yellowish powder.
MS•APCI (m/z): 376 (MH+)

Preparation Example 326

The following compound shown in Table 24 was prepared in a manner similar to Preparation example 325 by using corresponding starting materials.

Preparation Example 327

To a solution of ethyl 5-(3-benzyloxyphenyl)-2-(4-fluorophenyl)oxazol-4-yl acetate (349 mg) in methanol (20 ml) was added 10% palladium-carbon (350 mg), and the mixture was stirred under hydrogen atmosphere at room temperature for 2 hours. After the reaction, palladium-carbon was removed by filtration, the residue was washed with methanol and the filtrate was concentrated under reduced pressure. The resulting residue was crystallized from diisopropyl ether to obtain ethyl 2-(4-fluorophenyl)-5-(3-hydroxyphenyl) oxazol-4-yl acetate (195 mg) as colorless crystal.
Melting point: 175 to 177° C.
MS•APCI (m/z): 342 (MH+)

Preparation Example 328

To a solution of ethyl 2-[2-(4-fluorophenyl)-5-(3-thienyl)-oxazol-4-yl]-2-methylpropionate (54 mg) in methylene chloride (3 ml) was added boron tribromide (0.45 ml, 1.0M methylene chloride solution) under ice-cooling, and the mixture

TABLE 24

| Preparation example No. | Chemical structure | Salt | Physical constant, etc. |
|---|---|---|---|
| 326 | H₃C, OH (structure with thiophene, oxazole, ethyl acetate group, 4-fluorophenyl) | Free material | Powder<br>MS · APCI (m/z):<br>376 (M + H)+ | was allowed to warm to room temperature. To the mixture, another portion of boron tribromide (1.05 ml, 1.0M methylene chloride solution) was added to the mixture, and the resulting mixture was stirred at room temperature for 18 hours. To the reaction mixture were added water and ethyl acetate, the organic layer was collected, washed with brine and dried over anhydrous sodium sulfate, and the solvent was removed under reduced pressure. The resulting residue was purified by silica gel column chromatography (solvent: chloroform:methanol=15:1) to obtain 2-[2-(4-fluorophenyl)-5-(3-thienyl)oxazol-4-yl]-2-methylpropionic acid (32 mg). The product was dissolved in methanol, sodium methoxide (0.19 ml, 0.5M methanol solution) was added to the solution and after the mixture was stirred for 10 minutes, the solvent was removed under reduced pressure. The resulting residue was triturated with acetone to obtain sodium 2-[2-(4-fluorophenyl)-5-(3-thienyl)oxazol-4-yl]-2-methyl-propionate (30 mg) as pale brownish powder.

MS•ESI (m/z): 330 (M-Na)

Preparation Example 329

To a solution of ethyl 2-(4-fluorophenyl)-5-(3-thienyl)-oxazol-4-yl acetate (130 mg) in N,N-dimethylformamide (5 ml) was added sodium hydride (47 mg, 60% mineral oil) under ice-cooling, and the mixture was stirred at room temperature under argon atmosphere for 20 minutes. To the mixture was added methyl iodide (0.06 ml) in an ice bath, and the resulting mixture was stirred at room temperature for 14 hours. To the reaction mixture were added a saturated aqueous ammonium chloride solution and ethyl acetate, the organic layer was collected. The organic layer was washed with water and brine, dried over anhydrous sodium sulfate, and the solvent was removed under reduced pressure. The resulting residue was purified by silica gel column chromatography (solvent: n-hexane:diisopropyl ether=5:1) to obtain ethyl 2-[2-(4-fluorophenyl)-5-(3-thienyl)oxazol-4-yl]-2-methylpropionate (62 mg) as colorless oil.

MS•APCI (m/z): 360 (MH+)

Preparation Example 330

A solution of ethyl 2-(6-chloropyridin-3-yl)-5-(5-chlorothiophen-2-yl)oxazol-4-yl acetate (150 mg) in 50% aqueous dimethylamine solution (656 mg) and ethanol (3 ml) was refluxed for 16 hours. After cooling, water and ethyl acetate were added to the reaction mixture, and the organic layer was collected, dried over anhydrous sodium sulfate, and the solvent was removed under reduced pressure. The resulting residue was purified by silica gel column chromatography (solvent: chloroform:ethyl acetate=7:1) to obtain ethyl 2-(6-dimethylaminopyridin-3-yl)-5-(5-chlorothiophen-2-yl) oxazol-4-yl acetate (54 mg) as pale yellowish solid.

MS•APCI (m/z): 392/394 (MH+)

Preparation Examples 331 and 332

The following compounds shown in Table 25 were prepared in a manner similar to Preparation example 330 by using corresponding starting materials.

TABLE 25

| Preparation example No. | Chemical structure | Salt | Physical constant, etc. |
|---|---|---|---|
| 331 | 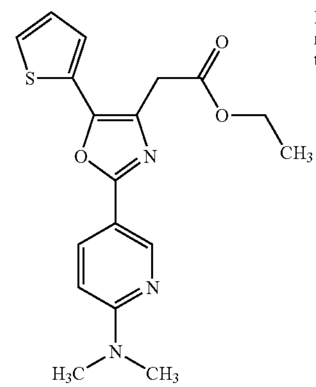 | Free material | Powder MS · APCI (m/z): 358 (M + H)+ |
| 332 | 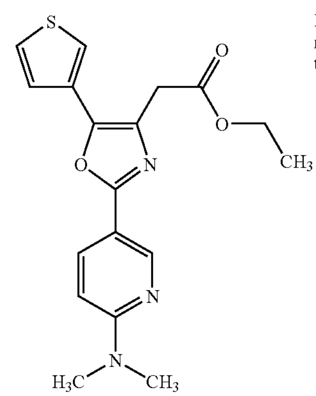 | Free material | Powder MS · APCI (m/z): 358 (M + H)+ |

Preparation Example 333

A mixture of methyl 3-(5-benzo[b]furoylamino)-4-(3-thienyl)-4-oxobutyrate (240 mg) and phosphorus oxychloride (0.19 ml) in N,N-dimethylformamide (4.8 ml) was stirred at room temperature for 2 hours. The reaction mixture was poured into water, neutralized by a saturated aqueous sodium hydrogen carbonate solution and extracted with ethyl acetate. The organic layer was washed with water and brine, dried over anhydrous sodium sulfate and the solvent was removed under reduced pressure. The resulting residue was purified by silica gel column chromatography (solvent: hexane:ethyl acetate=20:1) to obtain methyl 2-(5-benzo[b]furyl)-5-(3-thienyl)oxazole-4-yl acetate (121 mg) as colorless powder.

MS•APCI (m/z): 340 (MH+)

Preparation Examples 334 to 336

The following compounds shown in Table 26 were prepared in a manner similar to one of the above-mentioned Preparation examples, or conventionally known preparation processes as described in U.S. Pat. No. 3,470,195 and the like.

TABLE 26

| Preparation example No. | Chemical structure | Salt | Physical constant, etc. |
|---|---|---|---|
| 334 | (5-bromothien-2-yl / 4-chlorophenyl oxazole ethyl acetate structure) | Free material | |
| 335 | (2-(4-methoxyphenyl)oxazole ethyl acetate structure) | Free material | |
| 336 | (2-(4-fluorophenyl)oxazole ethyl acetate structure) | Free material | Powder MS · APCI (m/z): 250 (M + H)+ |

Preparation Example 337

To a solution of 2-[(4-fluorobenzoylamino)acetyl]thiophene (527 mg) in N,N-dimethylformamide (10 ml) was added sodium hydride (88 mg, 60% mineral oil) under ice-cooling, and the mixture was stirred under argon atmosphere at room temperature for one hour. After ice-cooling, acrylonitrile (127 ml) was added to the mixture and the mixture was stirred at room temperature for 3 hours. After addition of ice-water, the mixture was extracted with ethyl acetate. The organic layer was washed with water and brine, dried over anhydrous sodium sulfate and the solvent was removed under reduced pressure. The resulting residue was dissolved in N,N-dimethylformamide (10 ml), and phosphoryl chloride (240 µl) was added to the solution under ice-cooling. The mixture was stirred under argon atmosphere at room temperature for 3 hours. To the reaction mixture was added a saturated aqueous sodium hydrogen carbonate solution, the mixture was extracted with ethyl acetate and dried over anhydrous sodium sulfate, and the solvent was removed under reduced pressure. The resulting residue was purified by silica gel column chromatography (solvent: hexane:ethyl acetate=9:1→7:1), and triturated with hexane and ethyl acetate to obtain 4-(2-cyanoethyl)-2-(4-fluorophenyl)-5-(2-thienyl)oxazole (132 mg) as colorless powder.

MS•APCI (m/z): 299 (MH+)

Preparation Example 338

A mixture of 4-(2-cyanoethyl)-2-(4-fluorophenyl)-5-(2-thienyl)oxazole (95 mg), conc. hydrochloric acid (3 ml) and formic acid (4 ml) was stirred at 60° C. overnight. After addition of conc. hydrochloric acid (1 ml), the mixture was stirred at 70° C. for 6 hours. After cooling, water was added to the reaction mixture, and the mixture was extracted with ethyl acetate. The organic layer was washed with water and brine, dried over anhydrous sodium sulfate and the solvent was removed under reduced pressure. The resulting residue was purified by silica gel column chromatography (solvent: chloroform:methanol=19:1) The resulting colorless powder was dissolved in methanol (5 ml), 0.5M sodium methoxide (600 μl, methanol solution) was added to the solution and the solvent was removed under reduced pressure. The resulting residue was triturated with acetone to obtain 2-(4-fluorophenyl)-5-(2-thienyl)oxazole-4-yl propionic acid sodium salt (103 mg) as pale brownish powder.

MS•ESI (m/z): 316 (M-Na)

Preparation Example 339

(1) To a suspension of tellurium powder (153 mg) in ethanol (3 ml) was added sodium borohydride (108 mg), and the mixture was refluxed under argon atmosphere for 15 minutes. Under ice-cooling, acetic acid (160 μl) and a solution of ethyl 5-(5-chlorothiophen-2-yl)-2-(4-fluorophenyl)oxazole-4-yl acrylate (302 mg) in tetrahydrofuran (4 ml) were added to the mixture, and the resulting mixture was stirred at room temperature for one hour. The reaction mixture was filtered through Cellite and the residue was washed with ethyl acetate. The filtrate was washed with water and brine, dried over anhydrous sodium sulfate and the solvent was removed under reduced pressure. The resulting reside was purified by silica gel column chromatography (solvent: hexane:ethyl acetate=30:1), and triturated with hexane to obtain a crude product of ethyl 5-(5-chlorothiophen-2-yl)-2-(4-fluorophenyl)oxazole-4-yl propionate (263 mg) as colorless powder.

(2) To a solution of the product obtained in the above-mentioned (1) (63 mg) in tetrahydrofuran (1 ml) and ethanol (2 ml) was added 1N aqueous sodium hydroxide solution (170 μl) and the resulting mixture was refluxed for 1.5 hours. After cooling, the reaction mixture was concentrated under reduced pressure. The resulting residue was triturated with acetone to obtain 5-(5-chlorothiophen-2-yl)-2-(4-fluorophenyl)oxazole-4-yl propionic acid sodium salt (60 mg) as colorless powder.

MS•ESI (m/z): 350/352 (M-Na)

Preparation Example 340

(1) A mixture of 5-(5-chlorothiophen-2-yl)-2-(4-fluorophenyl)-4-hydroxymethyloxazole (1.44 g) and manganese dioxide (4.76 g) in tetrahydrofuran (20 ml) was refluxed for 3 hours. The reaction mixture was filtered through Cellite and the filtrate was concentrated under reduced pressure. The resulting reside was triturated with diethyl ether to obtain 5-(5-chlorothiophen-2-yl)-2-(4-fluorophenyl)-4-formyl-oxazole (943 mg) as colorless powder.

MS•APCI (m/z): 308 (MH+)

(2) To a solution of ethyl diethylphosphonoacetate (740 μl) in tetrahydrofuran (12 ml) was added sodium hydride (153 mg, 60% mineral oil) in an ice-acetone bath, and the resulting mixture was stirred at the same temperature for 15 minutes. 5-(5-chlorothiophen-2-yl)-2-(4-fluorophenyl)-4-formyloxazole (400 mg) was added to the mixture and the mixture was allowed to warm to room temperature for one hour. After cooling, the reaction mixture was neutralized by a saturated aqueous ammonium chloride solution and extracted with ethyl acetate. The organic layer was washed with water and brine, dried over anhydrous sodium sulfate and the solvent was removed under reduced pressure. The resulting residue was purified by silica gel column chromatography (solvent: hexane:ethyl acetate=30:1), and then, triturated with diethyl ether and hexane to obtain 404 mg of ethyl 5-(5-chlorothiophen-2-yl)-2-(4-fluorophenyl)oxazole-4-yl acrylate as colorless powder.

MS•APCI (m/z): 378 (MH+)

Preparation Example 341

A mixture of 5-(5-chlorothiophen-2-yl)-2-(4-fluorophenyl)-4-methoxycarbonyloxazole (1.8 g) and lithium borohydride (580 mg) in tetrahydrofuran (40 ml) was stirred at room temperature for one hour, and then, refluxed for 1.5 hours. After cooling, water and 10% hydrochloric acid were added to the reaction mixture, and the mixture was extracted with ethyl acetate. The organic layer was washed with water and brine, dried over anhydrous sodium sulfate and the solvent was removed under reduced pressure. The resulting residue was triturated with diethyl ether-ethyl acetate to obtain 5-(5-chlorothiophen-2-yl)-2-(4-fluoro-phenyl)-4-hydroxymethyloxazole (1.48 g) as colorless powder.

MS•APCI (m/z): 310/312 (MH+)

Preparation Example 342

In a manner similar to Preparation example 341 by using the corresponding starting materials, 5-(4-chloro-3-fluorophenyl)-2-(4-fluorophenyl)-4-hydroxymethyloxazole was obtained.

MS•APCI (m/z): 322/324 (MH+)

Preparation Example 343

To a solution of ethyl 2-(4-fluorophenyl)oxazole-4-carboxylate (7.44 g) in chloroform (100 ml) was added dropwise bromine (8.1 ml) at room temperature, and the resulting mixture was stirred at room temperature for 30 minutes and then refluxed for 8 hours. After cooling the reaction mixture, 10% aqueous sodium thiosulfate solution was added to the mixture and the mixture was extracted with chloroform. The organic layer was washed with a saturated aqueous sodium hydrogen carbonate solution and brine, dried over anhydrous sodium sulfate and the solvent was removed under reduced pressure. The residue was purified by silica gel column chromatography (solvent: ethyl acetate:n-hexane=1:9) to obtain ethyl 5-bromo-2-(4-fluorophenyl)-oxazol-4-carboxylate (9.21 g) as pale yellowish powder.

MS•APCI (m/z): 314/316 (MH+)

Preparation Example 344

To a solution of methyl 3-(5-chlorothiophen-2-yl)-2-(4-fluorobenzoylamino)-3-oxopropionate (7.25 g) in N,N-dimethyl-formamide (80 ml) was added dropwise phosphorus oxychloride (5.7 ml) under ice-cooling, and the mixture was then stirred at room temperature for 3 days. After cooling, water was added to the reaction mixture and the mixture was extracted with ethyl acetate. The organic layer was washed with water and brine, dried over anhydrous sodium sulfate and the solvent was removed under reduced pressure. The resulting residue was purified by silica gel column chromatography (solvent: hexane:ethyl acetate=100:1), and then, triturated with diethyl ether-hexane to obtain methyl 5-(5-chloro-thiophen-2-yl)-2-(4-fluorophenyl)oxazol-4-carboxylate (2.8 g) as colorless powder.

MS•APCI (m/z): 338/340 (MH+)

Preparation Example 345

In a manner similar to Preparation example 344 by using the corresponding starting materials, methyl 5-(3-thienyl)-2-(4-fluorophenyl)oxazol-4-carboxylate was obtained.

Preparation Example 346

A mixture of ethyl 5-bromo-2-(4-fluorophenyl)oxazol-4-carboxylate (600 mg), 0.05M (4-chloro-3-fluorophenyl) zinc bromide (6 ml, tetrahydrofuran solution), and tetrakis-(triphenylphosphine) palladium (231 mg) in tetrahydrofuran (5 ml) was stirred under argon atmosphere at room temperature for 2 hours, followed by refluxing for 40 minutes. The reaction mixture was cooled and concentrated under reduced pressure, and water was added to the residue and the mixture was extracted with ethyl acetate. The organic layer was successively washed with 10% hydrochloric acid, a saturated aqueous sodium hydrogen carbonate solution and brine, dried over anhydrous sodium sulfate and the solvent was removed under reduced pressure. The residue was purified by silica gel column chromatography (solvent: ethyl acetate:n-hexane=1:8) to obtain ethyl 5-(4-chloro-3-fluoro-phenyl)-2-(4-fluorophenyl)oxazol-4-carboxylate (580 mg) as pale reddish solid.

MS•APCI (m/z): 364/366 (MH+)

Preparation Example 347

A mixture of p-fluorobenzamide (5 g), ethyl bromopyruvate (9.92 ml), and sodium hydrogen carbonate (15 g) in tetrahydrofuran (150 ml) was refluxed for 20 hours. After cooling the reaction mixture, insoluble material was removed by filtration through Cellite and the filtrate was concentrated under reduced pressure. The residue was dissolved in tetrahydrofuran (30 ml) and trifluoroacetic anhydride (30 ml) was added to the mixture in an ice bath. After stirring at room temperature for one hour, a saturated aqueous sodium hydrogen carbonate solution was added to the mixture in an ice bath, and the mixture was extracted with ethyl acetate. The organic layer was washed with brine, dried over anhydrous sodium sulfate and the solvent was removed under reduced pressure. The resulting residue was purified by silica gel column chromatography (solvent: ethyl acetate n-hexane=1:9) to obtain ethyl 2-(4-fluorophenyl)oxazol-4-carboxylate (7.44 g) as colorless solid.

MS•APCI (m/z): 236 (MH+)

Preparation Example 348

(1) Chlorine gas was bubbled through a suspension of 2-[5-(4-chloro-3-fluorophenyl)-2-(4-fluorophenyl)oxazol-4-yl]methylthiourea (200 mg) in water (15 ml) under ice-cooling for 5 minutes. The mixture was stirred at the same temperature for 30 minutes followed by stirring at room temperature for 30 minutes. Water was added to the reaction mixture, and the mixture was extracted with chloroform. The organic layer was washed with water and brine, dried over anhydrous sodium sulfate and the solvent was removed under reduced pressure to obtain a crude product of 5-(4-chloro-3-fluorophenyl)-2-(4-fluorophenyl)-oxazol-4-yl methanesulfonyl chloride.

(2) The product obtained in (1) was dissolved in tetrahydrofuran (3 ml), 28% aqueous ammonia (2 ml) was added to the solution, and the mixture was stirred at room temperature for 3 hours. The reaction mixture was concentrated under reduced pressure and the residue was purified by silica gel column chromatography (solvent: chloroform:methanol=20:1) to obtain 5-(4-chloro-3-fluorophenyl)-2-(4-fluorophenyl)oxazol-4-ylmethanesulfonamide (164 mg) as pale yellowish solid.

MS•APCI (m/z): 385/387 (MH+)

(3) To a solution of 5-(4-chloro-3-fluorophenyl)-2-(4-fluoro-phenyl)oxazol-4-ylmethanesulfonamide obtained in (2) (125 mg) in methanol was added 0.5M sodium methoxide (0.64 ml, methanol solution). The solvent was removed under reduced pressure, and the resulting residue was triturated with acetone to obtain 5-(4-chloro-3-fluorophenyl)-2-(4-fluorophenyl)oxazol-4-yl methanesulfonamide sodium salt (80 mg).

MS•APCI (m/z): 383/385 (MH+)

Preparation Example 349

(1) A solution of 5-(4-chloro-3-fluorophenyl)-2-(4-fluorophenyl)-4-hydroxymethyloxazole (965 mg) and thionyl chloride (1.1 ml) in tetrahydrofuran (30 ml) was stirred at 0° C. for 30 minutes, followed by stirring at room temperature for 2 hours. Additional thionyl chloride (1.1 ml) was added to the mixture and the mixture was refluxed for one hour. The reaction mixture was concentrated under reduced pressure. The remaining volatiles were removed by evaporation with toluene, and further dried under reduced pressure to obtain a crude product of 5-(4-chloro-3-fluorophenyl)-4-chloromethyl-2-(4-fluoro-phenyl)oxazole (925 mg).

(2) A solution of the crude product obtained in (1) (925 mg) and thiourea (269 mg) in tetrahydrofuran (50 ml) was refluxed for 15 hours. The reaction mixture was concentrated under reduced pressure to one-third volume, and the residue was triturated with adding diethyl ether to obtain 2-[5-(4-chloro-3-fluorophenyl)-2-(4-fluorophenyl)-oxazol-4-yl]-methylthiourea hydrochloride (954 mg).

MS•APCI (m/z): 380/382 (MH+)

Preparation Example 350

To a solution of 5-(2-cyanoethyl)-2-(4-fluorophenyl)-4-(2-methoxyphenyl)imidazole (40 mg) in dichloromethane (10 ml) was added dropwise boron tribromide (94 mg) under ice-cooling, and the mixture was stirred at room temperature overnight. To the reaction mixture was added dropwise a saturated aqueous sodium hydrogen carbonate solution under ice-cooling, and then, the mixture was extracted with chloroform. The organic layer was dried over anhydrous sodium sulfate, and the solvent was removed under reduced pressure. The residue was purified by preparative TLC (solvent: hexane:ethyl acetate=1:1), and further purified by NH silica gel column chromatography (solvent: hexane:ethyl acetate=1:1). To the product was added hydrogen chloride-ethanol solution and the mixture was concentrated to obtain 5-(2-cyanoethyl)-2-(4-fluorophenyl)-4-(2-hydroxyphenyl)-imidazole hydrochloride (6 mg) as colorless solid.

MS•APCI (m/z): 308 (MH+)

Preparation Examples 351 to 355

The following compounds shown in Table 27 were prepared in a manner similar to Preparation examples 43 and Preparation example 152 by using the corresponding starting materials.

TABLE 27

| Preparation example No. | Chemical structure | Salt | Physical constant, etc. |
|---|---|---|---|
| 351 | Cl-thiophene-imidazole-benzothiophene with acetate | Na | Powder ESI·MS (m/z): 373/375 (M − Na)− |
| 352 | Cl-thiophene-imidazole-pyridine-N(CH3)2 with acetate | Na | Powder ESI·MS (m/z): 361/363 (M − H) |
| 353 | Cl-thiophene-imidazole-phenyl-OCH3 with acetate | Na | Powder ESI·MS (m/z): 347/349 (M − Na) |
| 354 | Cl-thiophene-imidazole-pyrimidine-N(CH3)2 with acetate | Na | Powder ESI·MS (m/z): 362/364 (M − Na) |
| 355 | Cl-phenyl-imidazole-benzothiophene with acetate | Na | Powder ESI·MS (m/z): 367/369 (M − H) |

Preparation Example 356

A mixture of ethyl 2-(6-aminopyridin-3-yl)-5-(5-chlorothiophen-2-yl)oxazol-4-yl acetate (70 mg) and 40% aqueous chloroacetoaldehyde solution (47 μl) in ethanol (2.1 ml) was refluxed for 3 hours, and 40% aqueous chloroacetoaldehyde solution (16 μl) was added to the mixture and the resulting mixture was refluxed for one hour. After cooling, a saturated aqueous sodium hydrogen carbonate solution was added to the reaction mixture, the mixture was extracted with ethyl acetate, dried over anhydrous sodium sulfate and the solvent was removed under reduced pressure. The resulting residue was purified by silica gel column chromatography (solvent: chloroform:methanol=49:1→97:3) to obtain ethyl 2-(imidazo[a,1]pyridin-5-yl)-5-(5-chlorothiophen-2-yl)oxazol-4-yl acetate (65 mg).

MS·APCI (m/z): 388/390 (MH+)

Preparation Example 357

(1) To a solution of ethyl 2-(6-chloropyridin-3-yl)-5-(5-chlorothiophen-2-yl)oxazol-4-yl acetate (1 g) in N,N-di-methylformaldehyde (10 ml) was added sodium azide (1.7 g), and the mixture was refluxed overnight. After cooling, water was added to the reaction mixture and the mixture was extracted with ethyl acetate, the organic layer was dried over anhydrous sodium sulfate and the solvent was removed under reduced pressure. The resulting residue was purified by silica gel column chromatography (solvent: chloroform:ethyl acetate=8:1) to obtain ethyl 2-(6-azidopyridin-3-yl)-5-(5-chlorothiophen-2-yl)oxazol-4-yl acetate (401 mg) as yellowish powder.

(2) A mixture of ethyl 2-(6-azidopyridin-3-yl)-5-(5-chlorothiophen-2-yl)oxazol-4-yl acetate (401 mg) and 540 mg of triphenylphosphine (540 mg) in water (2 ml) and acetic acid (8 ml) was refluxed for 2 hours. After cooling, water was added to the reaction mixture and the mixture was extracted with ethyl acetate. The organic layer was washed with water and brine, dried over anhydrous sodium sulfate and the solvent was removed under reduced pressure. The resulting residue was purified by silica gel column chromatography (solvent: chloroform:ethyl acetate=5:1→2:3→1:2), and then, triturated with diethyl ether to obtain ethyl 2-(6-aminopyridin-3-yl)-5-(5-chlorothiophen-2-yl)oxazol-4-yl acetate (177 mg) as yellowish powder.

MS•APCI (m/z): 364/366 (MH+)

Preparation Example 358

A mixture of ethyl 5-(5-chlorothiophen-2-yl)-2-(1-formylindolin-5-yl)oxazol-4-yl acetate (160 mg) and 6N hydrochloric acid (2 ml) in ethanol (4 ml) was stirred at 60° C. for 4 days. Water was added to the reaction mixture and the mixture was extracted with ethyl acetate. The organic layer was washed with brine, dried over anhydrous sodium sulfate, and the solvent was removed under reduced pressure. The residue was purified by preparative TLC (solvent: chloroform:methanol=20:1) to obtain ethyl 5-(5-chlorothiophen-2-yl)-2-(5-indolinyl)oxazol-4-yl acetate (53 mg) as colorless powder.

MS•APCI (m/z): 389/391 (MH+)

Preparation Example 359

To a suspension of ethyl 2-(2-methylthiopyrimidin-5-yl)-5-(5-chlorothiophen-2-yl)oxazol-4-yl acetate (156 mg) in tetrahydrofuran (3.12 ml) was added metachloroperbenzoic acid (88 mg, 70% purity) under ice-cooling, and the mixture was stirred at room temperature for one hour. After ice-cooling again, 70% metachloroperbenzoic acid (40 mg) was added to the mixture and the resulting mixture was stirred at room temperature for one hour. To the mixture was added 50% aqueous dimethylamine solution (1 ml) and the mixture was stirred at room temperature for 30 minutes. Water was added to the reaction mixture and the mixture was extracted with chloroform. The organic layer was washed with brine, dried over anhydrous sodium sulfate and the solvent was removed under reduced pressure. The resulting residue was purified by silica gel column chromatography (solvent: chloroform:ethyl acetate=8:1) to obtain ethyl 2-(2-dimethylaminopyrimidin-5-yl)-5-(5-chlorothiophen-2-yl) oxazol-4-yl acetate (139 mg) as colorless powder.

MS•APCI (m/z): 393/395 (MH+)

Preparation Examples 360 and 361

The following compounds shown in Table 28 were prepared in a manner similar to Preparation examples 359 by using the corresponding starting materials.

TABLE 28

| Preparation example No. | Chemical structure | Salt | Physical constant, etc. |
|---|---|---|---|
| 360 | (structure shown) | Free material | Powder MS · APCI (m/z): 407/409 (M + H)+ |

TABLE 28-continued

| Preparation example No. | Chemical structure | Salt | Physical constant, etc. |
|---|---|---|---|
| 361 | (structure) | Free material | Powder MS·APCI (m/z): 405/407 (M + H)+ |

Preparation Examples 362 to 364

The compounds obtained in Preparation examples 359 to 361 were subjected to hydrolysis according to the conventional manner to obtain the compounds shown in Table 29.

TABLE 29

| Preparation example No. | Chemical structure | Salt | Physical constant, etc. |
|---|---|---|---|
| 362 | (structure) | Na | Powder ESI·MS (m/z): 363/365 (M − Na)− |
| 363 | (structure) | Na | Powder ESI·MS (m/z): 377/379 (M − Na)− |
| 364 | (structure) | Na | Powder ESI·MS (m/z): 375/377 (M − Na)− |

Preparation Example 365

To a suspension of ethyl 2-(6-chloropyridin-3-yl)-5-(3-thienyl)oxazol-4-yl acetate (150 mg) in ethanol (3 ml) was added 15% aqueous sodium methyl sulfide solution (2 ml), and the mixture was refluxed for 3 days. After cooling, the reaction mixture was neutralized by 10% hydrochloric acid, and extracted with ethyl acetate. The organic layer was dried over anhydrous sodium sulfate and the solvent was removed under reduced pressure. The resulting residue was washed with diethyl ether and dissolved in methanol (5 ml), and 0.5M sodium methoxide (495 μl, methanol solution) was added to the solution and the solvent was removed under reduced pressure. The resulting residue was triturated with acetone to obtain 2-(6-methylthiopyridin-3-yl)-5-(3-thienyl)oxazol-4-yl acetic acid sodium salt (74 mg) as pale yellowish powder.

MS•ESI (m/z): 331 (M-Na)

Preparation Example 366

In a manner similar to Preparation example 365 and using corresponding starting materials, 2-(6-methylthiopyridin-3-yl)-5-(2-thienyl)oxazol-4-yl acetic acid sodium salt was obtained.

MS•ESI (m/z): 331 (M-Na)

Preparation Example 367

To a suspension of ethyl 2-(6-chloropyridin-3-yl)-5-(5-chlorothiophen-2-yl)oxazol-4-yl acetate (192 mg) in ethanol (5 ml) was added sodium hydride (100 mg, 60% mineral oil), and the mixture was refluxed for 6 hours, and then, water (1 ml) was added to the mixture and the mixture was further refluxed for 30 minutes. After cooling, the reaction mixture was neutralized by 10% hydrochloric acid, and extracted with ethyl acetate. The organic layer was dried over anhydrous sodium sulfate and the solvent was removed under reduced pressure. The resulting residue was washed with hexane and dissolved in methanol (5 ml), and 0.5M sodium methoxide (867 µl, methanol solution) was added to the solution and the solvent was removed under reduced pressure. The resulting residue was triturated with acetone to obtain 2-(6-ethoxypyridin-3-yl)-5-(5-chlorothiophen-2-yl)oxazol-4-yl acetic acid sodium salt (169 mg) as pale yellowish powder.

MS•ESI (m/z): 363/365 (M-Na)

Preparation Examples 368 and 369

The following compounds shown in Table 30 were prepared in a manner similar to Preparation examples 367 by using the corresponding starting materials.

TABLE 30

| Preparation example No. | Chemical structure | Salt | Physical constant, etc. |
|---|---|---|---|
| 368 | [structure] | Na | Powder ESI · MS (m/z): 349/351 (M − Na)− |
| 369 | [structure] | Na | Powder ESI · MS (m/z): 315 (M − Na)− |

Preparation Example 370

To a mixture of 2-(4-fluorophenyl)-5-(3-thienyl)oxazol-4-yl acetic acid (130 mg) in N,N-dimethylformamide (5 ml) was added N,N-carbonyldiimidazole (347 mg), and the mixture was stirred at room temperature for 2 hours. Methanesulfonamide (204 mg) and 1,8-diazabicyclo[5.4.0]undecene (0.32 ml) were added to the mixture and the resulting mixture was stirred at 100° C. overnight. The reaction mixture was poured into 10% hydrochloric acid, and extracted with ethyl acetate. The organic layer was washed with water and brine, and dried over anhydrous sodium sulfate, and the solvent was removed under the reduced pressure. The resulting residue was purified by silica gel column chromatography (solvent: hexane:ethyl acetate=1:1), and then, the resulting product was dissolved in methanol (10 ml), and 0.5M sodium methoxide (68 µl, methanol solution) was added to the solution and the solvent was removed under reduced pressure to obtain N-[2-(4-fluorophenyl)-5-(3-thienyl)oxazol-4-yl acetyl] methanesulfonamide sodium salt (42 mg) as colorless powder.

MS•ESI (m/z): 379 (M-Na)

Preparation Example 371

Corresponding starting compounds are treated in a manner similar to Preparation example 370 to obtain the compound shown in Table 31.

TABLE 31

| Preparation example No. | Chemical structure | Salt | Physical constant, etc. |
|---|---|---|---|
| 371 | [structure] | Na | Powder ESI · MS (m/z): 442 (M − H) |

Preparation Example 372

To a mixture of ethyl 2-(4-fluorophenyl)-5-(5-chlorothiophen-2-yl)oxazol-4-yl acetate (1.01 g) in ethanol (5 ml), diethyl ether (5 ml) and tetrahydrofuran (6 ml) was added sodium hydride (110 mg, 60% mineral oil) under argon atmosphere, and the mixture was stirred for 10 minutes under ice-cooling. After addition of isoamyl nitrite (647 mg), the mixture was stirred at room temperature for 1.5 hours. 10% Hydrochloric acid was added to the mixture and the resulting mixture was extracted with ethyl acetate. The organic layer was washed with water and brine, dried over anhydrous sodium sulfate and the solvent was removed under reduced pressure. The resulting crude product (395 mg) was taken up into formic acid (4 ml) and ethanol (3 ml). To the mixture zinc powder (291 mg) was added at room temperature, and the mixture was stirred for 10 minutes followed by stirring at 70° C. for 20 minutes. After cooling, the reaction mixture was filtered through glass filter, the residue was washed with ethanol and the filtrate was concentrated under reduced pressure. To the resulting residue was added a saturated aqueous sodium hydrogen carbonate solution, the mixture was extracted with ethyl acetate and the organic layer was washed with water and brine, dried over anhydrous sodium sulfate, and the solvent was removed under reduced pressure. The resulting residue was triturated with diethyl ether-hexane to obtain ethyl 2-amino-2-[5-(5-chlorothiophen-2-yl)-2-(4-fluorophenyl)-oxazol-4-yl]acetate (307 mg) as colorless powder.

MS•APCI (m/z): 381/383 (MH+)

Preparation Example 373

A mixture of 2-(4-fluorophenyl)-5-(3-thienyl)oxazol-4-yl acetic acid (100 mg), methoxyamine hydrochloride (37.6 mg), 3-ethyl-1-(3-dimethylaminopropyl)carbodiimide hydrochloride (95 mg), 1-hydroxybenzotriazole (67 mg) and triethylamine (0.14 ml) in N,N-dimethylformamide (3 ml) was stirred at room temperature overnight. Water was added to the reaction mixture, the mixture was extracted with chloroform. The organic layer was washed with water and brine, dried over anhydrous sodium sulfate and the solvent was removed under reduced pressure. The resulting residue was purified by silica gel column chromatography (solvent: chloroform:methanol=20:1), and triturated with diethyl ether-hexane to obtain N-methoxy-[2-(4-fluorophenyl)-5-(3-thienyl)oxazol-4-yl]acetamide (75 mg) as colorless powder.

MS•APCI (m/z): 333 (MH+)

Preparation Examples 374 to 377

The corresponding starting materials were treated in a manner similar to Preparation example 373 to obtain the compounds shown in Table 32 below.

TABLE 32

| Preparation example No. | Chemical structure | Salt | Physical constant, etc. |
|---|---|---|---|
| 374 | 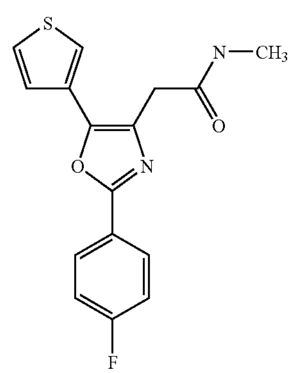 | Free material | Powder MS · APCI(m/z): 317(M + H) |
| 375 | 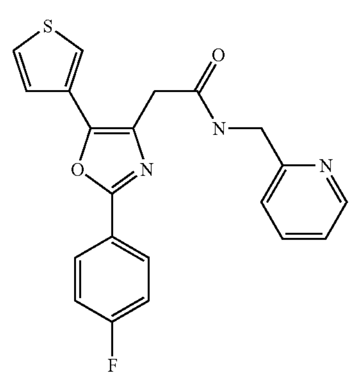 | HCl | Powder MS · APCI(m/z): 394(M + H) |

TABLE 32-continued

| Preparation example No. | Chemical structure | Salt | Physical constant, etc. |
|---|---|---|---|
| 376 | 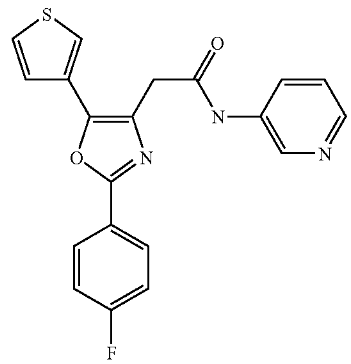 | HCl | Powder<br>MS · APCI(m/z):<br>380(M + H) |
| 377 | 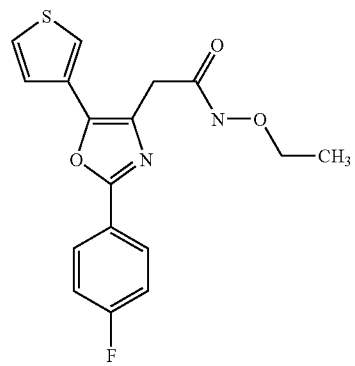 | Free material | Crystal<br>Melting point:<br>183-184° C.<br>MS · APCI(m/z):<br>347(M + H) |

Preparation Example 378

(1) Under argon atmosphere, to a solution of 2-(4-fluorophenyl)-4-(2-hydroxyethyl)-5-(3-thienyl)oxazole (300 mg) in methylene chloride (10 ml) were successively added methane-sulfonyl chloride (96 μl) and triethylamine (188 μl) under ice-cooling, and the mixture was stirred at room temperature for 3 hours. The reaction mixture was poured into water and extracted with methylene chloride. The organic layer was washed with water and brine, dried over anhydrous sodium sulfate and the solvent was removed under reduced pressure to obtain a crude product of 2-(4-fluorophenyl)-4-(2-methanesulfonyloxyethyl)-5-(3-thienyl)oxazole.

(2) To a solution of methanesulfonamide (136 mg) in N,N-di-methylformamide (10 ml) was added sodium hydride (57 mg, 60% mineral oil) under ice-cooling, and the mixture was stirred at room temperature for one hour. After the mixture was ice-cooled again, an N,N-dimethylformamide solution of the crude product obtained in (1) was added to the mixture and the resulting mixture was stirred at room temperature for one hour and then stirred at 60° C. overnight. The reaction mixture was ice-cooled, and then, poured into an aqueous ammonium chloride solution and extracted with ethyl acetate. The organic layer was washed with water and brine, dried over anhydrous sodium sulfate and the solvent was removed under reduced pressure. After the resulting residue was purified by silica gel column chromatography (solvent: hexane:ethyl acetate=4:1), the obtained product was dissolved in methanol (5 ml), and 0.5M sodium methoxide (562 μl, methanol solution) was added to the solution and the solvent was removed under reduced pressure to obtain 2-(4-fluoro-phenyl)-4-methanesulfonylaminoethyl-5-(3-thienyl)oxazole sodium salt (143 mg) as colorless powder.

MS•ESI (m/z): 365 (M-Na)

Preparation Example 379

(1) A mixture of 2-(4-fluorophenyl)-5-(3-thienyl)oxazol-4-yl acetic acid (1.5 g), diphenylphosphoryl azide (1.28 ml) and triethylamine (0.83 ml) in t-butanol (30 ml) was refluxed for one day. After cooling the reaction mixture, the solvent was removed under reduced pressure. Water was added to the residue and the mixture was extracted with chloroform. The organic layer was washed with a saturated aqueous sodium hydrogen carbonate solution and brine, dried over anhydrous sodium sulfate, and the solvent was removed under reduced pressure. Chloroform was added to the residue, the mixture was heated and insoluble material was removed by filtration, and the filtrate was concentrated under reduced pressure. The residue was purified by silica gel column chromatography (solvent: ethyl acetate:n-hexane=1:9→1:7) to obtain 4-(t-butoxycarbonylamino)methyl-2-(4-fluorophenyl-5-(3-thienyl) oxazole (501 mg).

MS•APCI (m/z): 375 (MH+)

(2) A solution of 4-(t-butoxycarbonylamino)methyl-2-(4-florophenyl)-5-(3-thienyl)oxazole (455 mg) in 4N hydrogen chloride-dioxane solution was stirred at room temperature for 13 hours. The reaction mixture was concentrated under reduced pressure and the remaining volatiles were removed by evaporation with toluene, and the resulting residue was triturated with diethyl ether to obtain 4-aminomethyl-2-(4-fluorophenyl)-5-(3-thienyl)oxazole hydrochloride (288 mg) as colorless powder.

MS•APCI (m/z): 2.75 (MH+)

Preparation Example 380

(1) To a suspension of 4-aminomethyl-2-(4-fluorophenyl)-5-(3-thienyl)oxazole (110 mg) in dichloromethane (5 ml) were successively added dropwise under acetone-ice cooling methanesulfonyl chloride (0.036 ml) and triethylamine (0.15 ml) The reaction mixture was stirred at 0° C. for one hour, and further stirred at room temperature for 2 hours. To the reaction mixture was added a saturated aqueous ammonium chloride solution and extracted with chloroform. The organic layer was washed with water and brine, dried over anhydrous sodium sulfate, and the solvent was removed under reduced pressure. The residue was purified by silica gel column chromatography (solvent: chloroform:methanol=100:0→95:5) to obtain a crude product of N-[2-(4-fluorophenyl)-5-(3-thienyl)oxazol-4-yl]-methanesulfonamide (140 mg).

(2) Crude N-[2-(4-fluorophenyl)-5-(3-thienyl)oxazol-4-yl]-methanesulfonamide (133 mg) was dissolved in methanol (5 ml) and tetrahydrofuran (5 ml), and 0.5M sodium methoxide (0.72 ml, methanol solution) was added to the solution and the mixture was stirred at room temperature for 10 minutes. The reaction mixture was concentrated under reduced pressure and the resulting residue was triturated with acetone to obtain N-[2-(4-fluorophenyl)-5-(3-thienyl)oxazol-4-yl] methanesulfonamide sodium salt (112 mg).

MS•APCI (m/z): 353 (MH+)

Preparation Examples 381 to 429

The following compounds shown in Table 33 were prepared in a manner similar to Preparation example 63 by using corresponding starting materials.

TABLE 33

| Preparation example No. | Chemical structure | Salt | Physical constant, etc. |
|---|---|---|---|
| 381 | 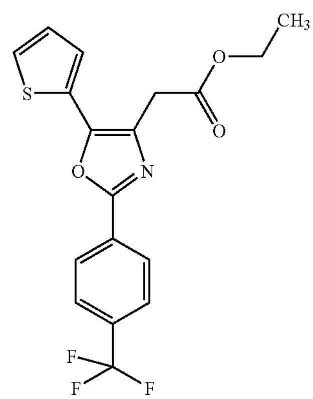 | Free material | Crystal Melting point: 108.5-109° C. MS · APCI(m/z): 381(M + H) |
| 382 | 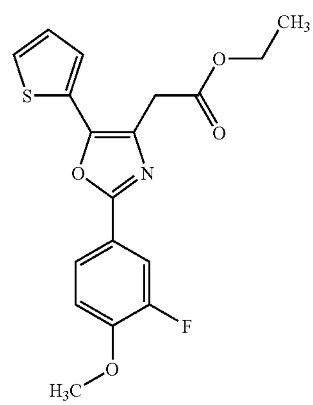 | Free material | Crystal Melting point: 117-117.5° C. MS · APCI(m/z): 362(M + H) |

TABLE 33-continued
| Preparation example No. | Chemical structure | Salt | Physical constant, etc. |
|---|---|---|---|
| 383 | 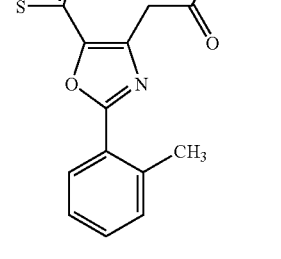 | Free material | Crystal Melting point: 67-68° C. MS · APCI(m/z): 382(M + H) |
| 384 | 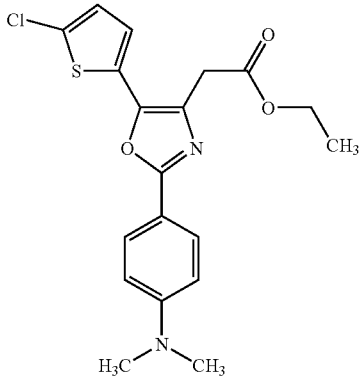 | Free material | Crystal Melting point: 118-119° C. MS · APCI(m/z): 391(M + H) |
| 385 | 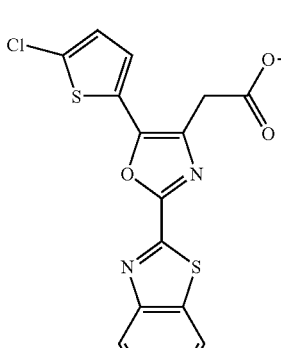 | Free material | Powder MS · APCI(m/z): 405/407(M + H)+ |
| 386 | 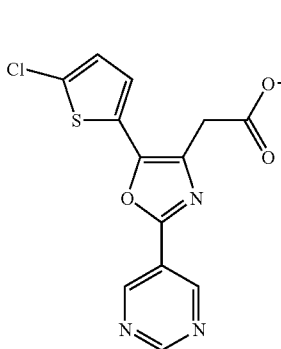 | Free material | Powder MS · APCI(m/z): 396/398(M + H)+ |

TABLE 33-continued

| Preparation example No. | Chemical structure | Salt | Physical constant, etc. |
|---|---|---|---|
| 387 | 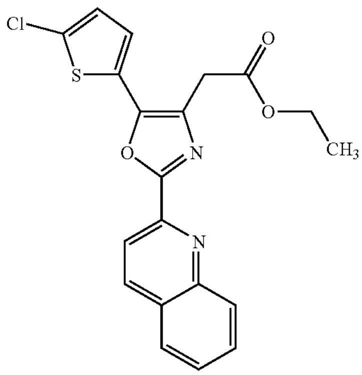 | Free material | Powder MS·APCI(m/z): 399/401(M + H) |
| 388 | 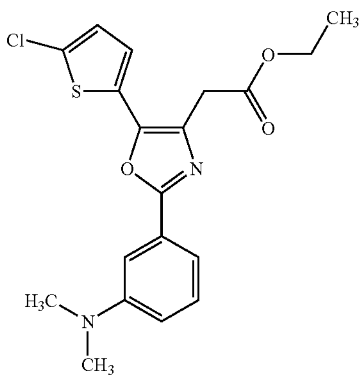 | Free material | Powder MS·APCI(m/z): 391/393(M + H)+ |
| 389 | 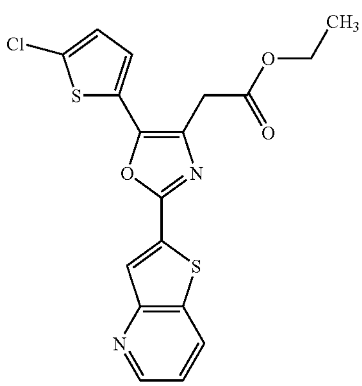 | Free material | Powder MS·APCI(m/z): 405/407(M + H)+ |
| 390 | 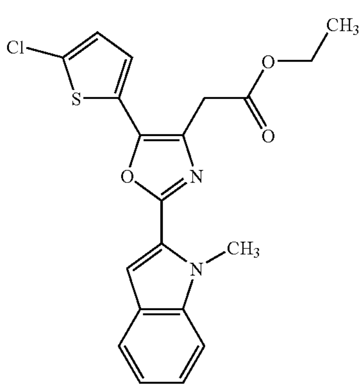 | Free material | Powder MS·APCI(m/z): 401/403(M + H)+ |

TABLE 33-continued

| Preparation example No. | Chemical structure | Salt | Physical constant, etc. |
|---|---|---|---|
| 391 | 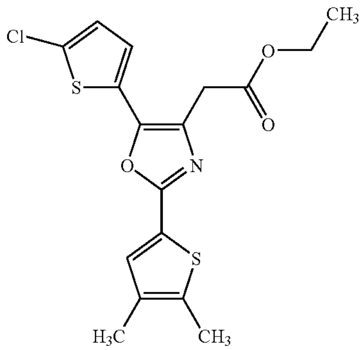 | Free material | Powder MS · APCI(m/z): 382/384(M + H)+ |
| 392 | 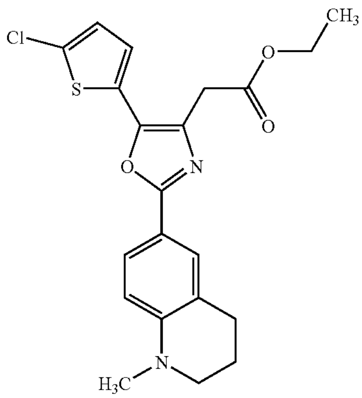 | Free material | Powder MS · APCI(m/z): 417/419(M + H)+ |
| 393 | 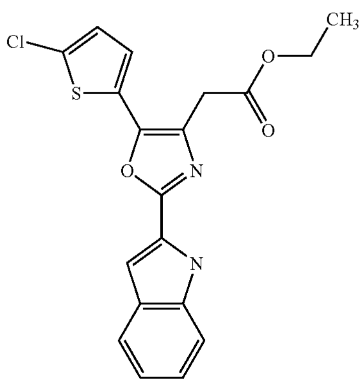 | Free material | Powder MS · APCI(m/z): 387/389(M + H)+ |
| 394 | 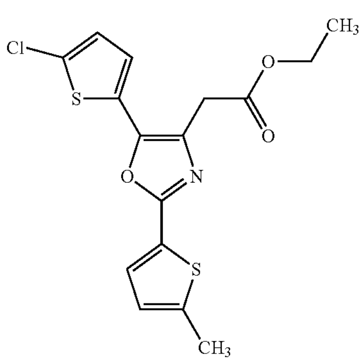 | Free material | Powder MS · APCI(m/z): 368/370(M + H)+ |

TABLE 33-continued
| Preparation example No. | Chemical structure | Salt | Physical constant, etc. |
|---|---|---|---|
| 395 | 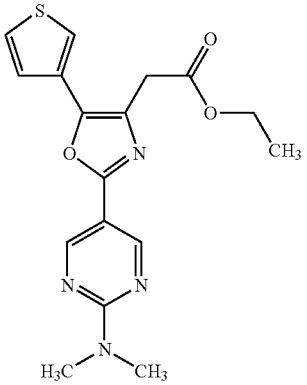 | Free material | Powder MS·APCI(m/z): 359(M + H)+ |
| 396 | 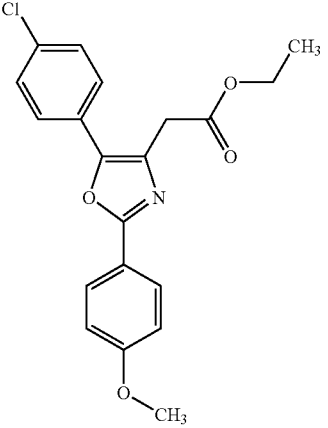 | Free material | Powder MS·APCI(m/z): 372/374(M + H)+ |
| 397 | 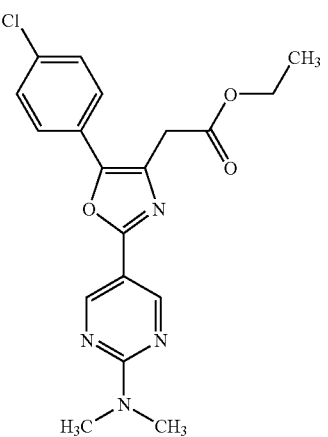 | Free material | Powder MS·APCI(m/z): 387/389(M + H)+ |

TABLE 33-continued

| Preparation example No. | Chemical structure | Salt | Physical constant, etc. |
|---|---|---|---|
| 398 | 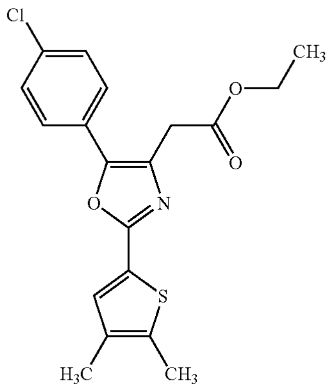 | Free material | Powder MS · APCI(m/z): 376/378(M + H)+ |
| 399 | 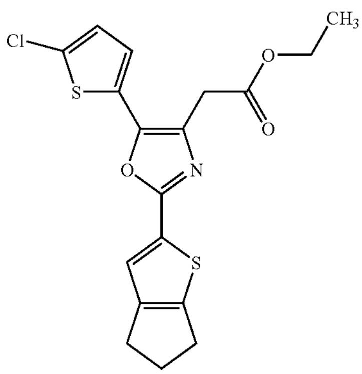 | Free material | Powder MS · APCI(m/z): 394/396(M + H)+ |
| 400 | 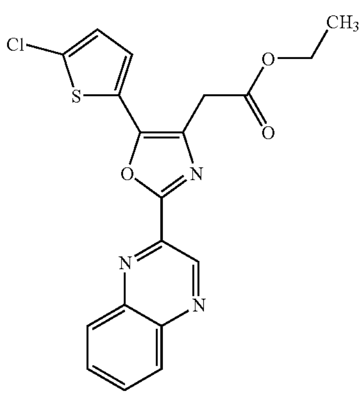 | Free material | Powder MS · APCI(m/z): 400/402(M + H)+ |
| 401 | 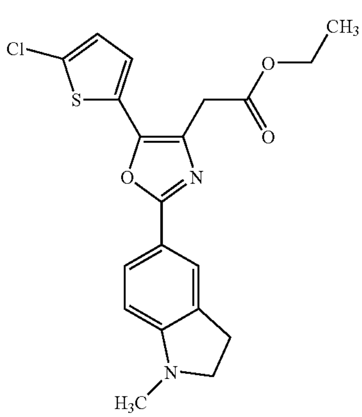 | Free material | Powder MS · APCI(m/z): 403/405(M + H)+ |

TABLE 33-continued

| Preparation example No. | Chemical structure | Salt | Physical constant, etc. |
|---|---|---|---|
| 402 | 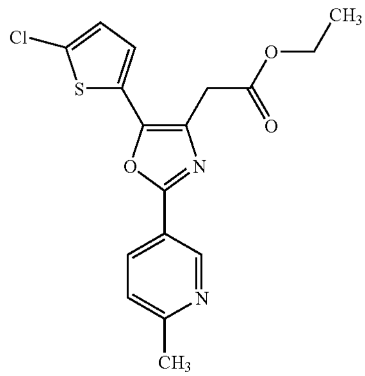 | Free material | Powder MS · APCI(m/z): 333/335(M − Na)− |
| 403 | 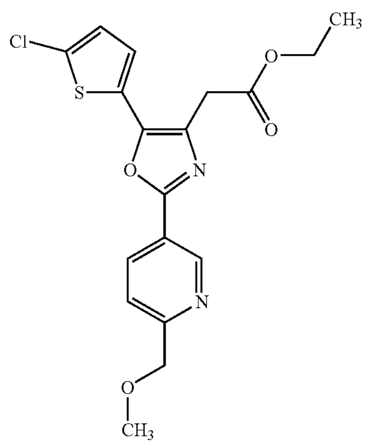 | Free material | Powder MS · APCI(m/z): 393/395(M + H)+ |
| 404 | 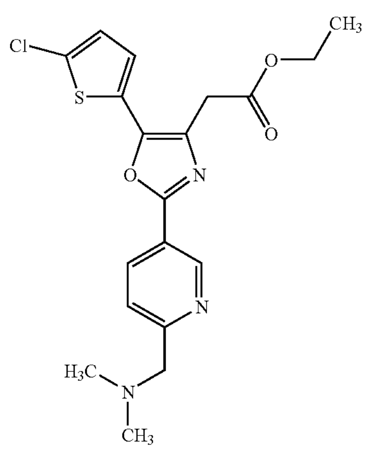 | Free material | Powder MS · APCI(m/z): 406/408(M + H)+ |

TABLE 33-continued

| Preparation example No. | Chemical structure | Salt | Physical constant, etc. |
|---|---|---|---|
| 405 | 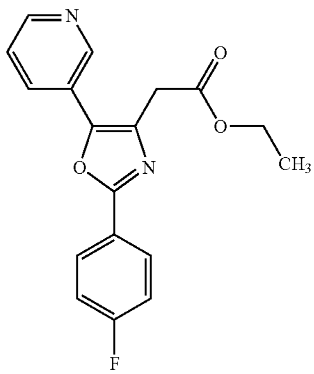 | Free material | Powder<br>MS · APCI(m/z):<br>327(M + H) |
| 406 | 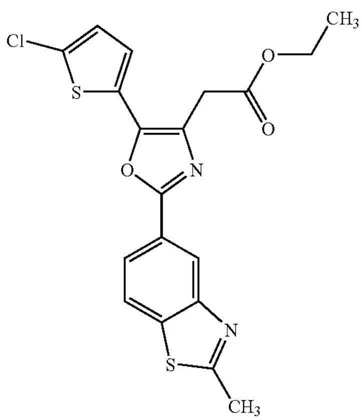 | Free material | Powder<br>MS · APCI(m/z):<br>418/420(M + H)+ |
| 407 | 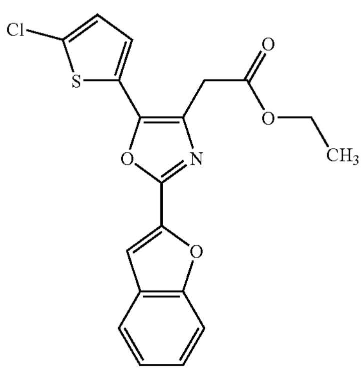 | Free material | Powder<br>MS · APCI(m/z):<br>388/390(M + H) |
| 408 | 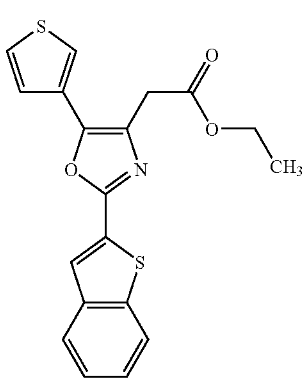 | Free material | Crystal<br>Melting point:<br>155-156.5° C.<br>MS · APCI(m/z):<br>370(M + H)+ |

TABLE 33-continued

| Preparation example No. | Chemical structure | Salt | Physical constant, etc. |
|---|---|---|---|
| 409 | 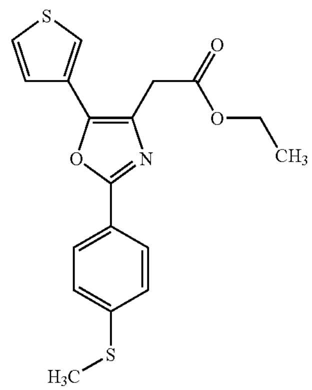 | Free material | Crystal<br>Melting point:<br>77-78° C.<br>MS · APCI(m/z):<br>360(M + H)+ |
| 410 | 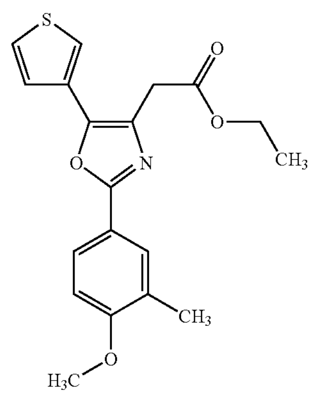 | Free material | Crystal<br>Melting point:<br>84-86° C.<br>MS · APCI(m/z):<br>358(M + H)+ |
| 411 | 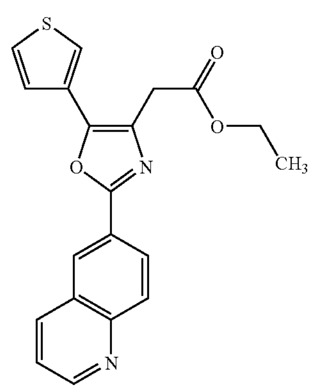 | Free material | Crystal<br>Melting point:<br>130-133° C.<br>MS · APCI(m/z):<br>365(M + H)+ |
| 412 | 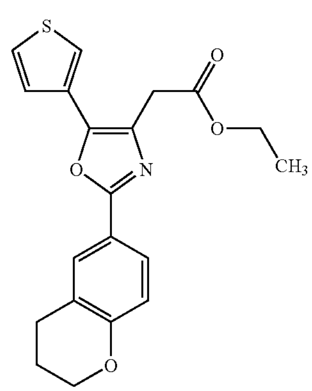 | Free material | Oil<br>MS · APCI(m/z):<br>370(M + H)+ |

TABLE 33-continued

| Preparation example No. | Chemical structure | Salt | Physical constant, etc. |
|---|---|---|---|
| 413 | 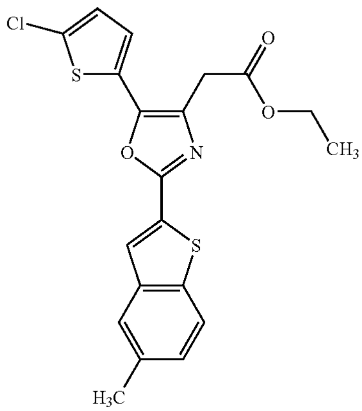 | Free material | Powder MS·APCI(m/z): 418/420(M + H)+ |
| 414 | 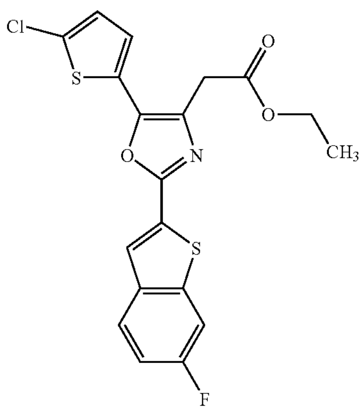 | Free material | Powder MS·APCI(m/z): 422/424(M + H)+ |
| 415 | 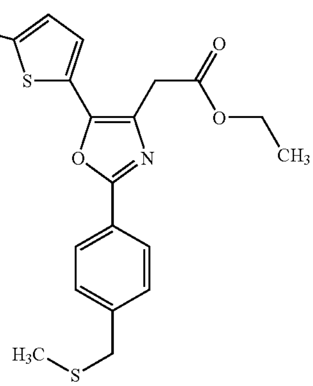 | Free material | Powder MS·APCI(m/z): 408/410(M + H)+ |

TABLE 33-continued

| Preparation example No. | Chemical structure | Salt | Physical constant, etc. |
|---|---|---|---|
| 416 | 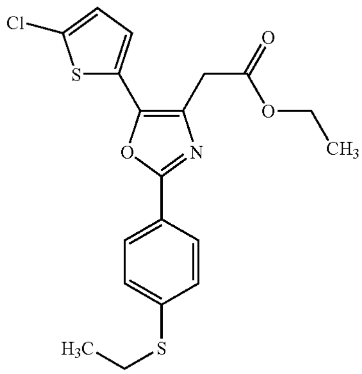 | Free material | Powder MS·APCI(m/z): 408/410(M + H)+ |
| 417 | 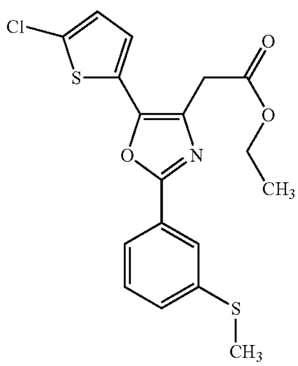 | Free material | Powder MS·APCI(m/z): 394/396(M + H)+ |
| 418 | 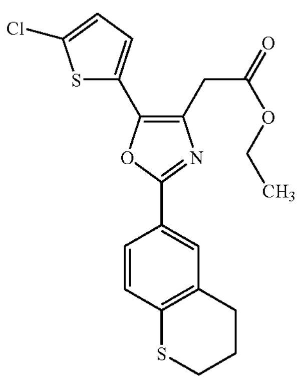 | Free material | Powder MS·APCI(m/z): 420/422(M + H)+ |
| 419 | 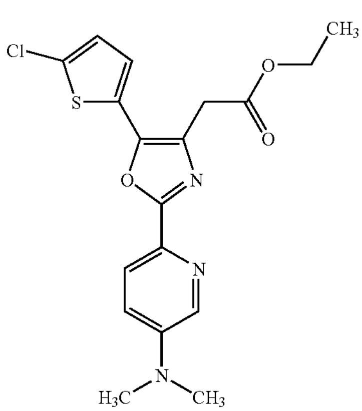 | Free material | Powder MS·APCI(m/z): 392/394(M + H)+ |

TABLE 33-continued

| Preparation example No. | Chemical structure | Salt | Physical constant, etc. |
|---|---|---|---|
| 420 | 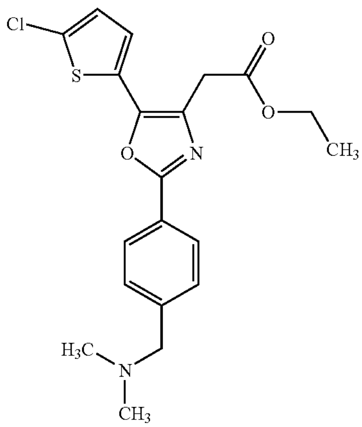 | Free material | Powder MS · APCI(m/z): 405/407(M + H)+ |
| 421 | 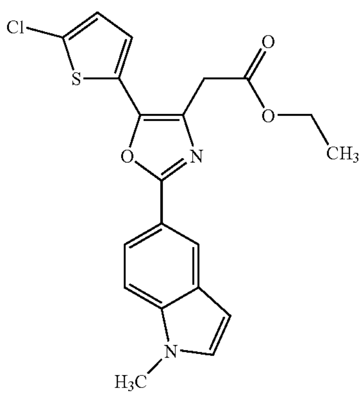 | Free material | Powder MS · APCI(m/z): 401/403(M + H)+ |
| 422 | 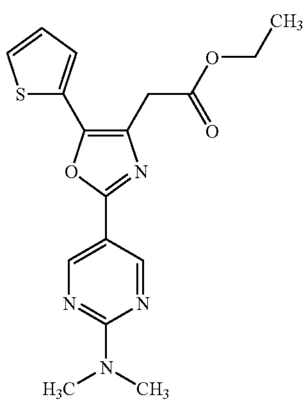 | Free material | Powder MS · APCI(m/z): 359(M + H)+ |
| 423 | 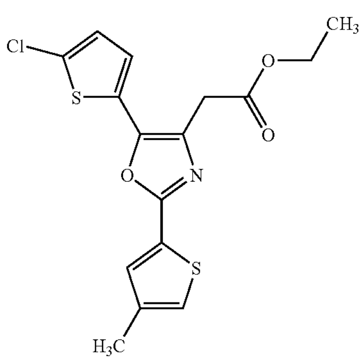 | Free material | Powder MS · APCI(m/z): 368/370(M + H)+ |

TABLE 33-continued

| Preparation example No. | Chemical structure | Salt | Physical constant, etc. |
|---|---|---|---|
| 424 | 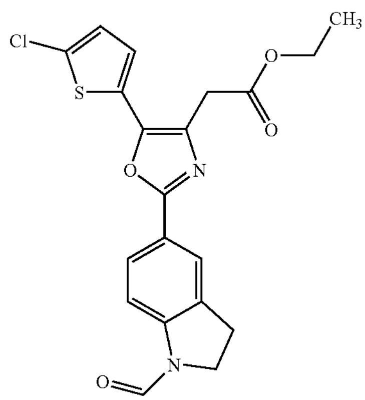 | Free material | Powder<br>MS · APCI(m/z):<br>417/419(M + H)+ |
| 425 | 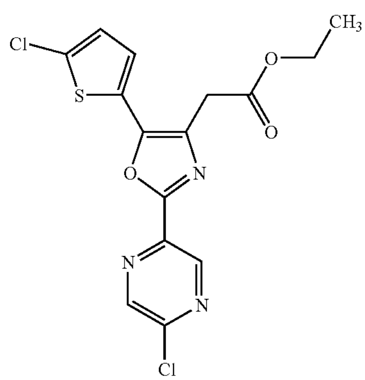 | Free material | Powder<br>MS · APCI(m/z):<br>384/386(M + H)+ |
| 426 | 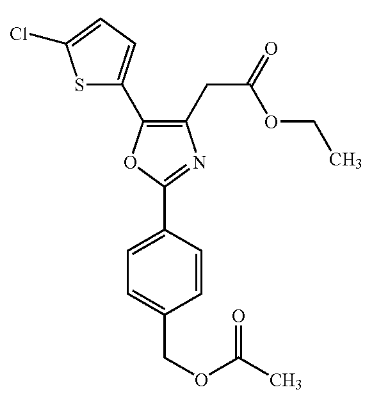 | Free material | Crystal<br>Melting point:<br>112-113° C.<br>MS · APCI(m/z):<br>420(M + H)+ |
| 427 | 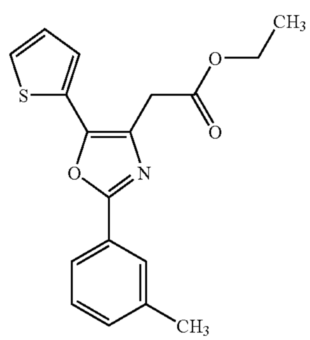 | Free material | Crystal<br>Melting point:<br>80-81° C.<br>MS · APCI(m/z):<br>328(M + H)+ |

TABLE 33-continued

| Preparation example No. | Chemical structure | Salt | Physical constant, etc. |
|---|---|---|---|
| 428 | (structure) | Free material | Crystal Melting point: 168.5-169.5° C. MS · APCI(m/z): 365(M + H)+ |
| 429 | (structure) | Free material | Crystal Melting point: 145-146° C. MS · APCI(m/z): 389/391(M + H)+ |

Preparation Examples 430 to 479

The following compounds shown in Table 34 were prepared in a manner similar to Preparation example 148 or 152 by using corresponding starting materials.

TABLE 34

| Preparation example No. | Chemical structure | Salt | Physical constant, etc. |
|---|---|---|---|
| 430 | (structure) | Na | Powder ESI · MS(m/z): 352(M − Na) |

TABLE 34-continued

| Preparation example No. | Chemical structure | Salt | Physical constant, etc. |
|---|---|---|---|
| 431 | 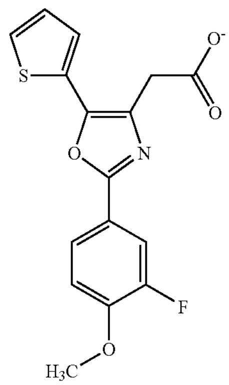 | Na | Powder<br>ESI · MS(m/z): 332(M − Na) |
| 432 | 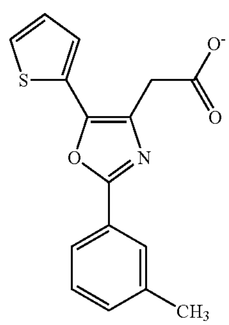 | Na | Powder<br>ESI · MS(m/z): 298(M − Na) |
| 433 | 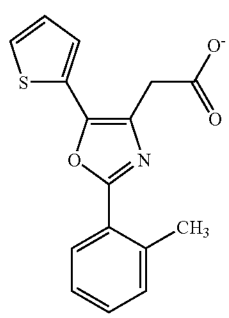 | Na | Powder<br>ESI · MS(m/z): 298(M − Na) |
| 434 | 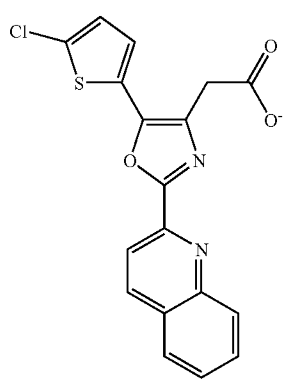 | Na | Powder<br>ESI · MS(m/z): 369(M − Na) |

TABLE 34-continued

| Preparation example No. | Chemical structure | Salt | Physical constant, etc. |
|---|---|---|---|
| 435 | 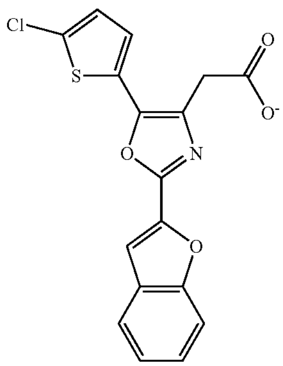 | Na | Powder<br>ESI · MS(m/z): 358/360(M − Na) |
| 436 | 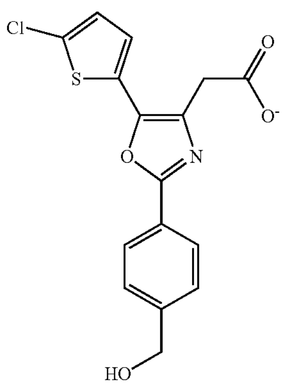 | Na | Powder<br>ESI · MS(m/z): 348(M − Na) |
| 437 | 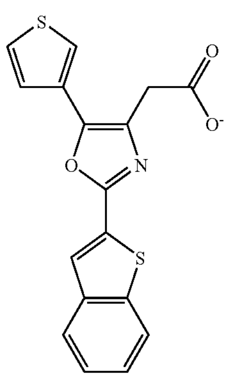 | Na | Powder<br>ESI · MS(m/z): 340(M − Na)− |
| 438 | 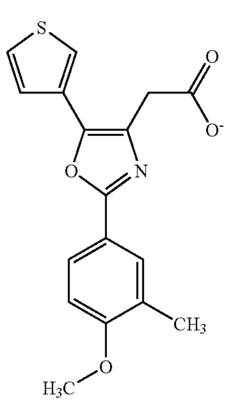 | Na | Powder<br>ESI · MS(m/z): 328(M − Na)− |

TABLE 34-continued

| Preparation example No. | Chemical structure | Salt | Physical constant, etc. |
|---|---|---|---|
| 439 | 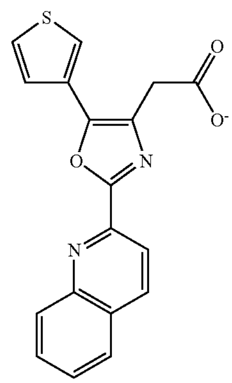 | Na | Powder<br>ESI · MS(m/z): 335(M − Na)− |
| 440 | 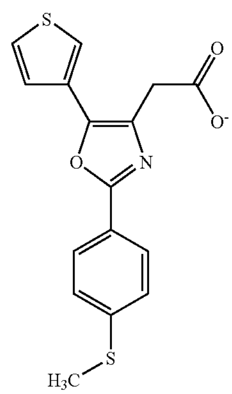 | Na | Powder<br>ESI · MS(m/z): 330(M − Na)− |
| 441 | 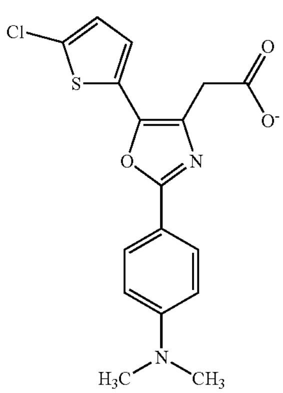 | Na | Powder<br>ESI · MS(m/z): 361/363(M − Na)− |
| 442 | 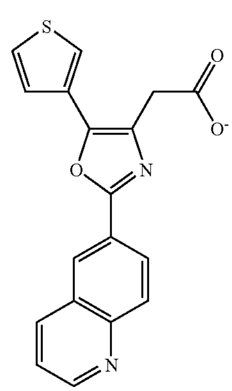 | Na | Powder<br>ESI · MS(m/z): 335(M − Na)− |

TABLE 34-continued

| Preparation example No. | Chemical structure | Salt | Physical constant, etc. |
|---|---|---|---|
| 443 | 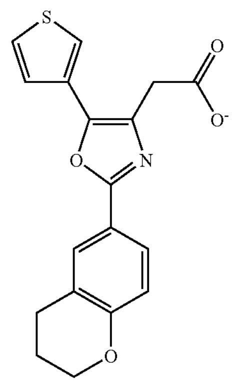 | Na | Powder<br>ESI·MS(m/z): 340(M − Na)− |
| 444 | 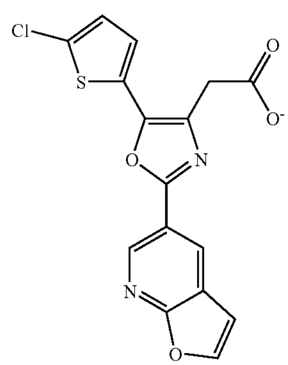 | Na | Powder<br>ESI·MS(m/z): 359/361(M − Na)− |
| 445 | 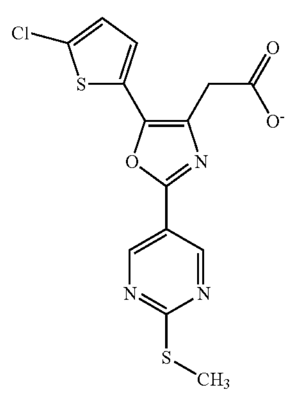 | Na | Powder<br>ESI·MS(m/z): 366/368(M − Na)− |
| 446 | 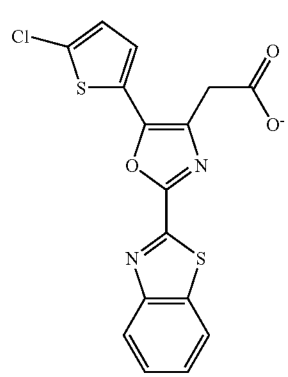 | Na | Powder<br>ESI·MS(m/z): 375/377(M − Na)− |

TABLE 34-continued

| Preparation example No. | Chemical structure | Salt | Physical constant, etc. |
| --- | --- | --- | --- |
| 447 | 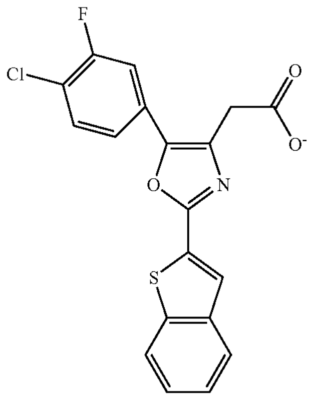 | Na | Powder<br>ESI · MS(m/z): 386/388(M − Na)− |
| 448 | 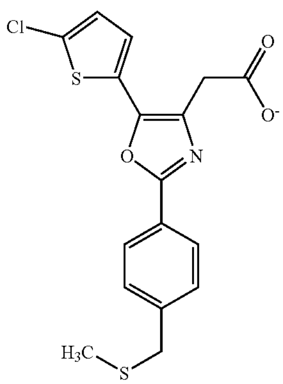 | Na | Powder<br>ESI · MS(m/z): 378/380(M − Na)− |
| 449 | 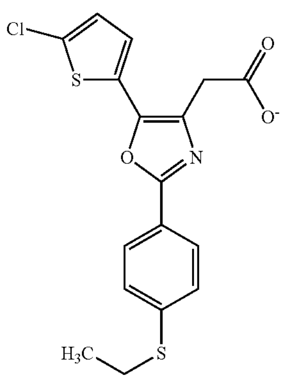 | Na | Powder<br>ESI · MS(m/z): 378/380(M − Na)− |
| 450 | 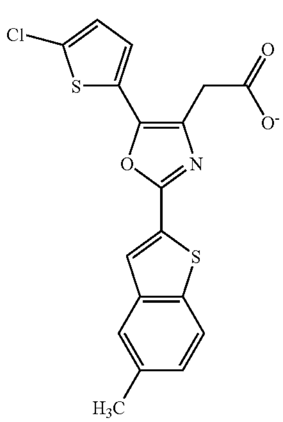 | Na | Powder<br>ESI · MS(m/z): 388/390(M − Na)− |

TABLE 34-continued

| Preparation example No. | Chemical structure | Salt | Physical constant, etc. |
|---|---|---|---|
| 451 | 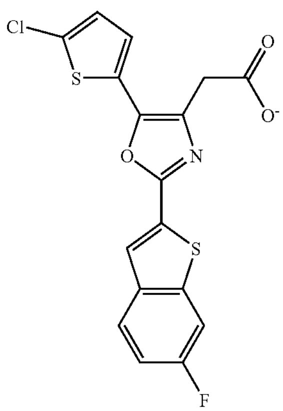 | Na | Powder<br>ESI · MS(m/z): 392/394(M − Na)− |
| 452 | 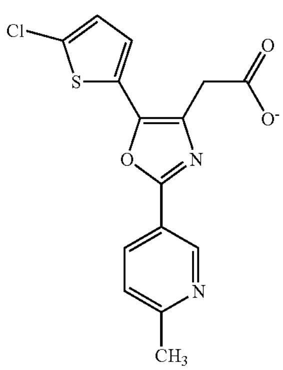 | Na | Powder<br>ESI · MS(m/z): 333/335(M − Na)− |
| 453 | 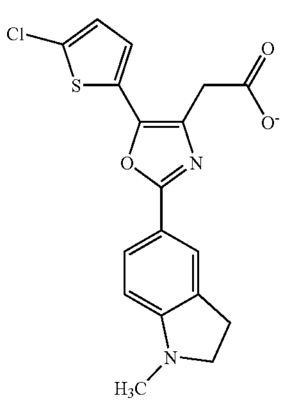 | Na | Powder<br>ESI · MS(m/z): 373/375(M − Na)− |

TABLE 34-continued

| Preparation example No. | Chemical structure | Salt | Physical constant, etc. |
|---|---|---|---|
| 454 | 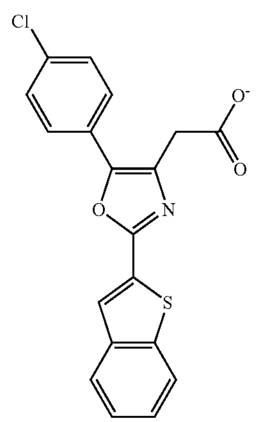 | Na | Powder<br>ESI·MS(m/z): 368/370(M − Na)− |
| 455 | 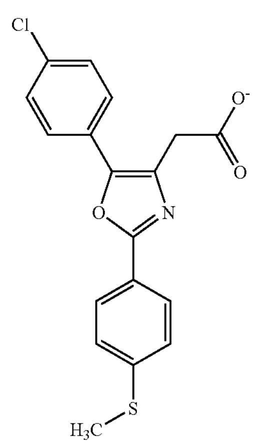 | Na | Powder<br>ESI·MS(m/z): 358/360(M − Na)− |
| 456 | 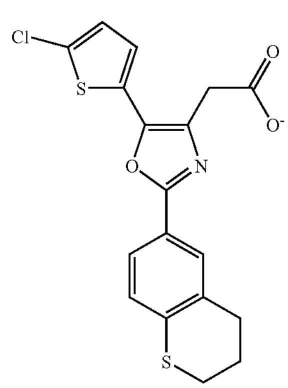 | Na | Powder<br>ESI·MS(m/z): 390/392(M − Na)− |

TABLE 34-continued

| Preparation example No. | Chemical structure | Salt | Physical constant, etc. |
|---|---|---|---|
| 457 | 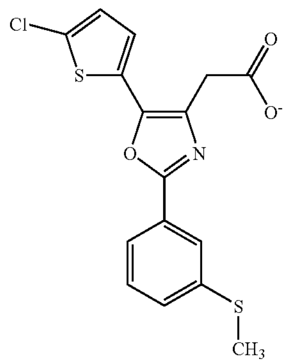 | Na | Powder<br>ESI·MS(m/z): 364/366(M − Na)− |
| 458 | 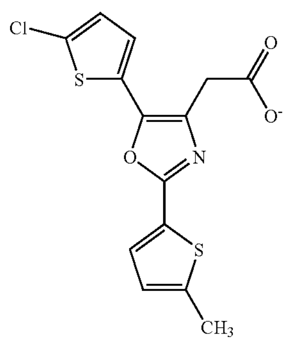 | Na | Powder<br>ESI·MS(m/z): 338/340(M − Na)− |
| 459 | 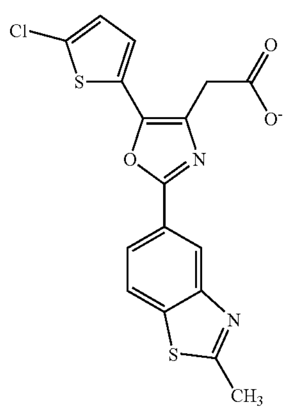 | Na | Powder<br>ESI·MS(m/z): 389/391(M − Na)− |
| 460 | 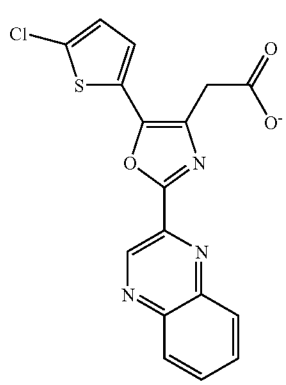 | Na | Powder<br>ESI·MS(m/z): 370/372(M − Na)− |

TABLE 34-continued

| Preparation example No. | Chemical structure | Salt | Physical constant, etc. |
|---|---|---|---|
| 461 | 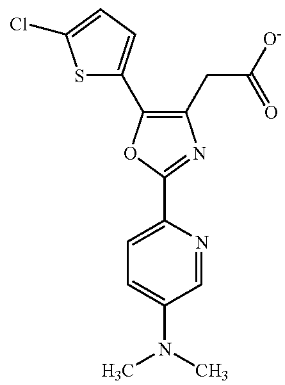 | Na | Powder<br>ESI · MS(m/z): 362/364(M − Na)− |
| 462 | 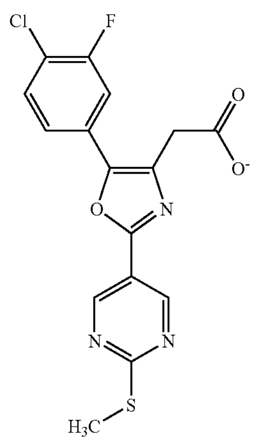 | Na | Powder<br>ESI · MS(m/z): 378/380(M − Na)− |
| 463 | 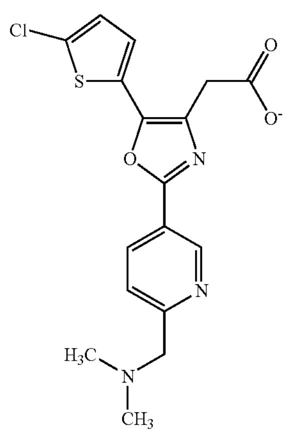 | Na | Powder<br>ESI · MS(m/z): 376/378(M − Na)− |

TABLE 34-continued

| Preparation example No. | Chemical structure | Salt | Physical constant, etc. |
|---|---|---|---|
| 464 | 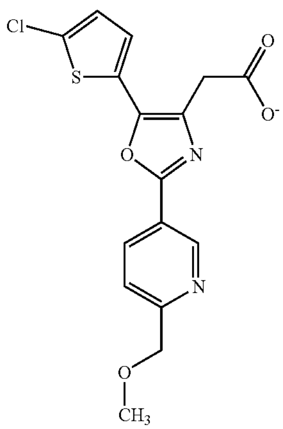 | Na | Powder<br>ESI · MS(m/z): 363/365(M − Na)− |
| 465 | 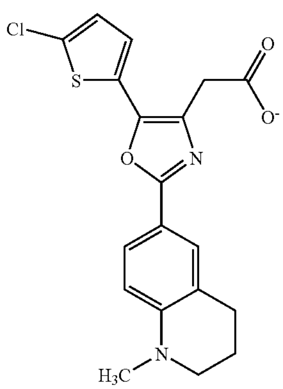 | Na | Powder<br>ESI · MS(m/z): 387/389(M − Na)− |
| 466 | 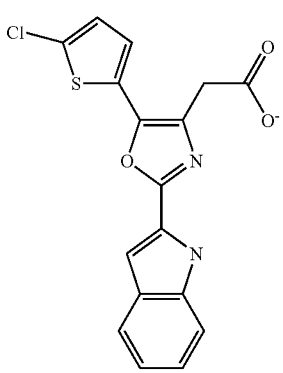 | Na | Powder<br>ESI · MS(m/z): 357/359(M − Na)− |
| 467 | 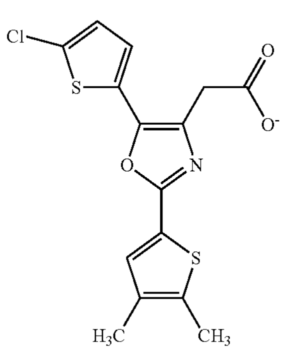 | Na | Powder<br>ESI · MS(m/z): 352/354(M − Na)− |

TABLE 34-continued

| Preparation example No. | Chemical structure | Salt | Physical constant, etc. |
|---|---|---|---|
| 468 | 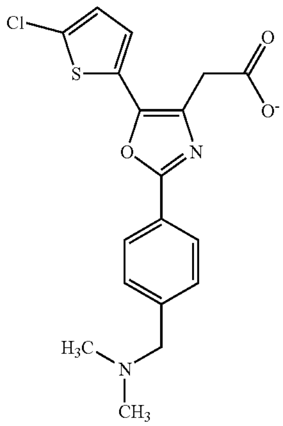 | Na | Powder<br>ESI·MS(m/z): 375/377(M − Na)− |
| 469 | 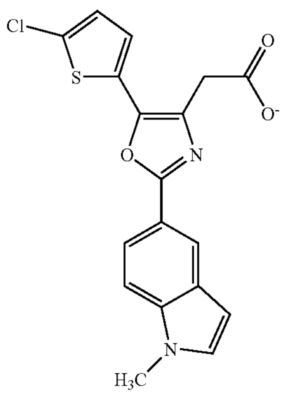 | Na | Powder<br>ESI·MS(m/z): 371/373(M − Na)− |
| 470 | 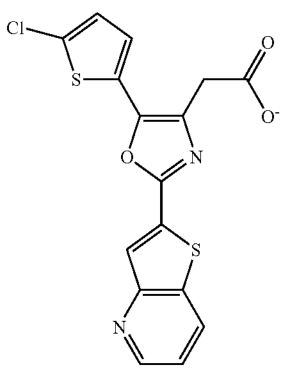 | Na | Powder<br>ESI·MS(m/z): 375/377(M − Na)− |
| 471 | 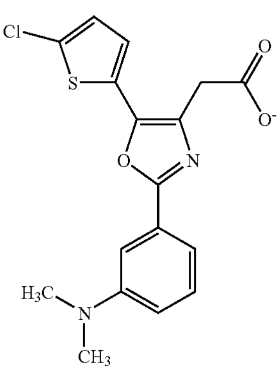 | Na | Powder<br>ESI·MS(m/z): 361/363(M − Na)− |

TABLE 34-continued

| Preparation example No. | Chemical structure | Salt | Physical constant, etc. |
|---|---|---|---|
| 472 | (5-chlorothiophen-2-yl / 1-methylindol-2-yl oxazole acetate structure) | Na | Powder<br>ESI · MS(m/z): 371/373(M − Na)− |
| 473 | (4-chlorophenyl / 2-(dimethylamino)pyrimidin-5-yl oxazole acetate structure) | Na | Powder<br>ESI · MS(m/z): 357/359(M − Na)− |
| 474 | (4-chlorophenyl / 4,5-dimethylthiophen-2-yl oxazole acetate structure) | Na | Powder<br>ESI · MS(m/z): 346/348(M − Na)− |

TABLE 34-continued

| Preparation example No. | Chemical structure | Salt | Physical constant, etc. |
|---|---|---|---|
| 475 | (4-chlorophenyl)-(4-methoxyphenyl)-oxazole acetate | Na | Powder<br>ESI·MS(m/z): 342/344(M − Na)− |
| 476 | (thiophen-3-yl)-(2-isopropylpyrimidin-5-yl)-oxazole acetate | Na | Powder<br>ESI·MS(m/z): 329(M − Na)− |
| 477 | (thiophen-2-yl)-(2-isopropylpyrimidin-5-yl)-oxazole acetate | Na | Powder<br>ESI·MS(m/z): 329(M − Na)− |
| 478 | (5-chlorothiophen-2-yl)-(4-methylthiophen-2-yl)-oxazole acetate | Na | Powder<br>ESI·MS(m/z): 338/340(M − Na)− |

TABLE 34-continued

| Preparation example No. | Chemical structure | Salt | Physical constant, etc. |
|---|---|---|---|
| 479 | (structure) | Na | Powder ESI·MS(m/z): 364/366(M − Na)− |

Preparation Example 480

A mixture of ethyl 3-(4-chlorobenzoylamino)-4-phenyl-4-oxobutyrate (25 g) in acetic acid (150 ml) was heated to 130° C., and a largely excessive amount of ammonium acetate was added to the mixture. After confirming completion of the reaction by TLC, the reaction mixture was cooled. Ice-water was added to the mixture and the mixture was extracted with ethyl acetate. The organic layer was washed with an aqueous sodium hydrogen carbonate solution and brine, and dried over anhydrous sodium sulfate, and the solvent was removed under reduced pressure. The residue was crystallized from diisopropyl ether to obtain 2-(4-chlorophenyl)-4-phenylimidazol-5-ylacetamide (10.42 g).

MS•EI (m/z): 311 (M+)

Preparation Example 481

To a solution of 2-(4-chlorophenyl)-4-phenylimidazol-5-yl acetamide (10.00 g) in N,N-dimethylformamide (50 ml) was added dropwise 8.9 ml of phosphorus oxychloride (8.9 ml) below 20° C., and the mixture was stirred at room temperature for one hour. To the reaction mixture were added ice-water and ethyl acetate, and the mixture was neutralized by sodium hydrogen carbonate. The organic layer was collected, washed with brine, and dried over anhydrous sodium sulfate and the solvent was removed under reduced pressure. The residue was crystallized from diisopropyl ether to obtain 2-(4-chlorophenyl)-5-cyano-methyl-4-phenylimidazole (6.85 g).

MS•EI (m/z): 293 (M+)

Preparation Example 482

The corresponding starting materials were treated in a manner similar to Preparation example 112 to obtain 2-(5-chloro-thiophen-3-yl)-5-hydroxymethyl-4-(3-pyridyl)imidazole.

MS•APCI (m/z): 292 (MH+)

Preparation Example 483

The corresponding starting materials were treated in a manner similar to Preparation example 130 to obtain 2-(4-fluoro-phenyl)-5-methylthiomethyl-4-phenylimidazole hydrochloride.

MS•APCI (m/z): 298 (M+)

Preparation Example 484

The corresponding starting materials were treated in a manner similar to Preparation example 141 to obtain 2-(4-fluoro-phenyl)-5-(3-pyridyl)oxazol-4-yl acetic acid hydrochloride.

MS•APCI (m/z): 299 (M+)

Preparation Example 485

A mixture of 2-(2-hydroxymethylthiophen-3-yl)-5-ethyl-4-(3-pyridyl)imidazole dihydrochloride (212 mg) and manganese oxide (2 g) in tetrahydrofuran (15 ml) was refluxed for one hour. The reaction mixture was filtered and washed with tetrahydrofuran, and the filtrate was concentrated under reduced pressure. The residue was purified by silica gel column chromatography (solvent: chloroform:methanol=30:1→20:1) to obtain 2-(2-formylthiophen-3-yl)-5-ethyl-4-(3-pyridyl)imidazole (93 mg) as orange crystal.

MS•APCI (m/z): 284 (MH+)

Preparation Example 486

To a solution of 2-(2-formylthiophen-3-yl)-5-ethyl-4-(3-pyridyl)imidazole (68 mg) in tetrahydrofuran (5 ml) was added dropwise 3M methyl magnesium bromide (0.24 ml, diethyl ether solution) under argon atmosphere in an ice bath, and the mixture was stirred at the same temperature for 30 minutes. To the reaction mixture was added a saturated aqueous ammonium chloride solution, and the mixture was extracted with ethyl acetate. The organic layer was washed with brine, dried over anhydrous magnesium sulfate and the solvent was removed under reduced pressure. The residue was purified by silica gel column chromatography (solvent: chloroform:methanol=20:1) to obtain 2-[2-(1-hydroxyethyl)thiophen-3-yl]-5-ethyl-4-(3-pyridyl)-imidazole dihydrochloride (60 mg) as orange brownish powder.

MS•APCI (m/z): 300 (MH+)

Preparation Example 487

(1) A mixture of ethyl 4-(2-thienyl)-2-(4-fluorophenyl)oxazol-5-yl acetate (140 mg), N-chlorosuccinic imide (62 mg) and a catalytic amount of 70% aqueous perchloric acid solution in carbon tetrachloride (7 ml) was stirred at room temperature overnight. The reaction mixture was poured into water, neutralized by a saturated aqueous sodium hydrogen carbonate solution and extracted with ethyl acetate. The organic layer was washed with water and brine and dried over anhydrous sodium sulfate, and the solvent was removed under reduced pressure. The resulting residue was purified by silica gel column chromatography (solvent: hexane:ethyl acetate=95:5) to obtain ethyl 4-(5-chlorothiophen-2-yl)-2-(4-fluorophenyl)oxazol-5-yl acetate (39.6 mg) as colorless powder.

MS•APCI (m/z): 366/368 (MH+)

(2) The compound obtained in the above (1) was hydrolyzed according to the conventional manner to obtain 4-(5-chloro-thiophen-2-yl)-2-(4-fluorophenyl)oxazol-5-yl acetic acid sodium salt.

ESI•MS (m/z): 336/338 (M-Na)—

Preparation Examples 488 to 502

The corresponding starting materials were treated in a manner similar to Preparation example 147 to obtain the compounds shown in Table 35 below.

TABLE 35

| Preparation example No. | Chemical structure | Salt | Physical constant, etc. |
|---|---|---|---|
| 488 | 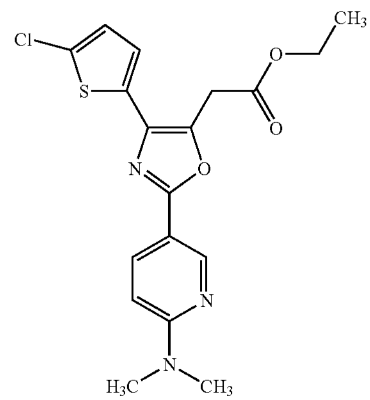 | Free material | Powder MS · APCI (m/z): 392/394 (M + H) + |
| 489 | 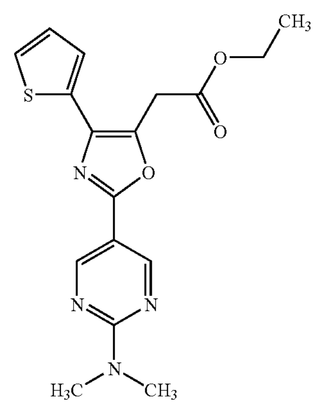 | Free material | Powder MS · APCI (m/z): 359 (M + H) + |
| 490 | 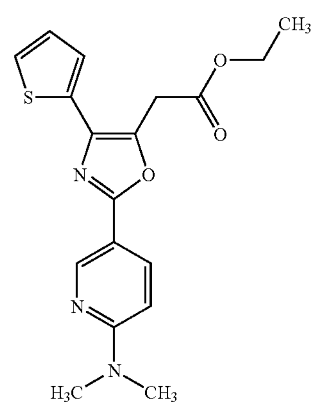 | Free material | Oil MS · APCI (m/z): 358 (M + H) + |

TABLE 35-continued
| Preparation example No. | Chemical structure | Salt | Physical constant, etc. |
|---|---|---|---|
| 491 | 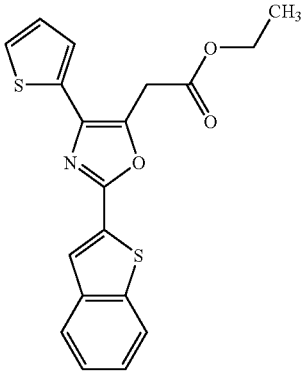 | Free material | Powder MS · APCI (m/z): 370 (M + H) + |
| 492 | 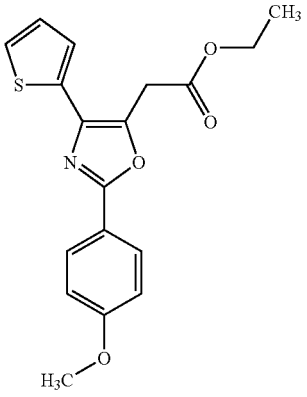 | Free material | Oil MS · APCI (m/z): 344 (M + H) + |
| 493 | 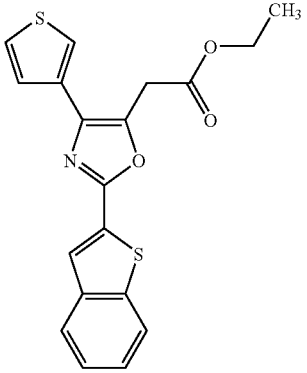 | Free material | Powder MS · APCI (m/z): 370 (M + H) + |

TABLE 35-continued

| Preparation example No. | Chemical structure | Salt | Physical constant, etc. |
|---|---|---|---|
| 494 | 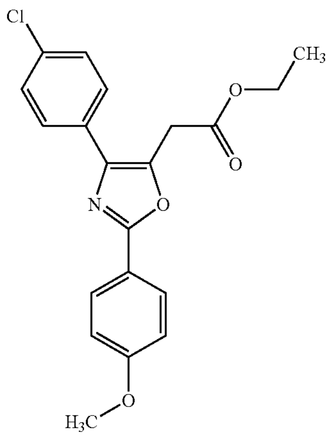 | Free material | Oil MS·APCI (m/z): 372/374 (M + H)+ |
| 495 | 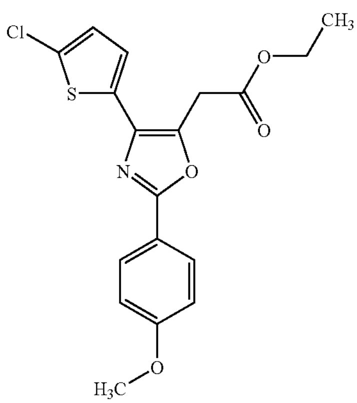 | Free material | Oil MS·APCI (m/z): 378/380 (M + H)+ |
| 496 | 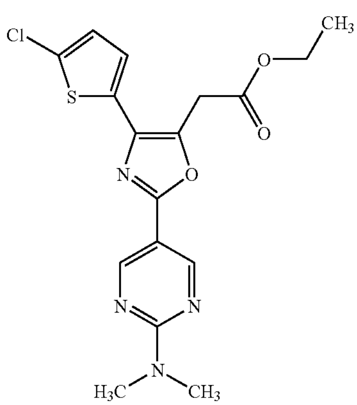 | Free material | Powder MS·APCI (m/z): 393/395 (M + H)+ |

TABLE 35-continued
| Preparation example No. | Chemical structure | Salt | Physical constant, etc. |
|---|---|---|---|
| 497 | 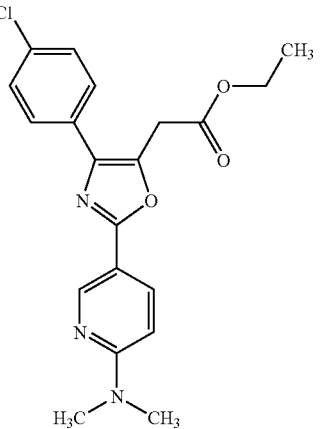 | Free material | Powder MS · APCI (m/z): 386/388 (M + H) + |
| 498 | 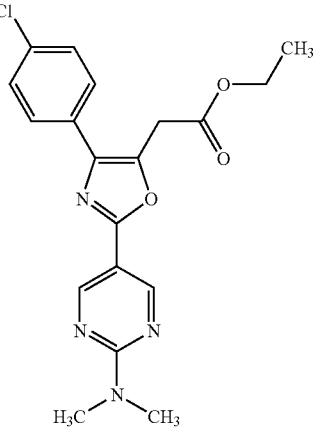 | Free material | Powder MS · APCI (m/z): 387/389 (M + H) + |
| 499 | 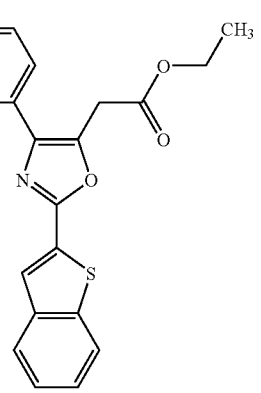 | Free material | Powder MS · APCI (m/z): 398/400 (M + H) + |

TABLE 35-continued

| Preparation example No. | Chemical structure | Salt | Physical constant, etc. |
|---|---|---|---|
| 500 | 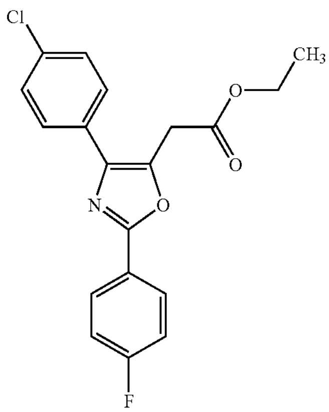 | Free material | Powder MS · APCI (m/z): 360/362 (M + H) + |
| 501 | 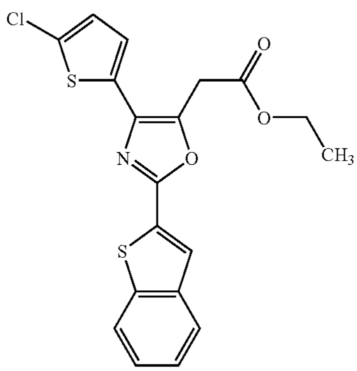 | Free material | Powder MS · APCI (m/z): 404/406 (M + H) + |
| 502 | 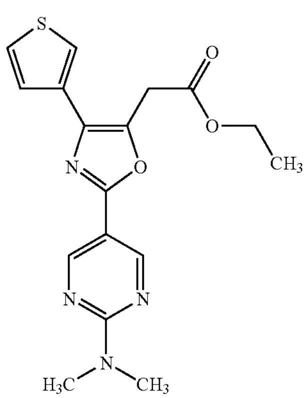 | Free material | Powder MS · APCI (m/z): 359 (M + H) + |

Preparation Examples 503 to 517
The corresponding starting materials were treated in a manner similar to Preparation example 148 to obtain the compounds shown in Table 36 below.
TABLE 36
| Preparation example No. | Chemical structure | Salt | Physical constant, etc. |
|---|---|---|---|
| 503 | 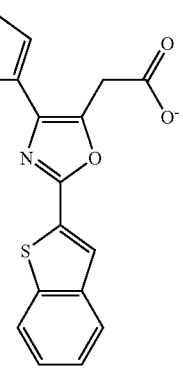 | Na | Powder<br>ESI · MS (m/z):<br>374/376 (M + Na) + |
| 504 | 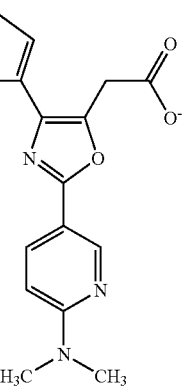 | Na | Powder<br>ESI · MS (m/z):<br>362/364 (M − Na) − |
| 505 | 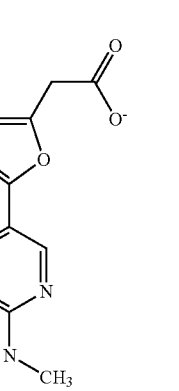 | Na | Powder<br>ESI · MS (m/z):<br>329 (M − Na) − |

TABLE 36-continued
| Preparation example No. | Chemical structure | Salt | Physical constant, etc. |
|---|---|---|---|
| 506 | 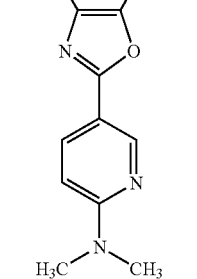 | Na | Powder<br>ESI · MS (m/z):<br>328 (M − Na) − |
| 507 | 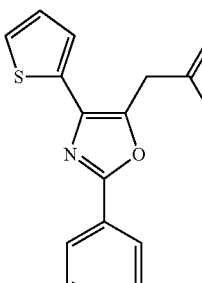 | Na | Powder<br>ESI · MS (m/z):<br>314 (M − Na) − |
| 508 | 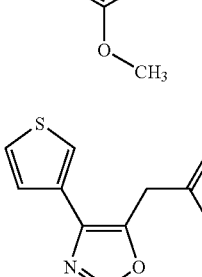 | Na | Powder<br>ESI · MS (m/z):<br>329 (M − Na) − |
| 509 | 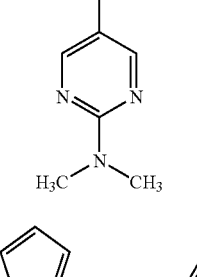 | Na | Powder<br>ESI · MS (m/z):<br>681 (2M − Na + H) − |

TABLE 36-continued

| Preparation example No. | Chemical structure | Salt | Physical constant, etc. |
| --- | --- | --- | --- |
| 510 | 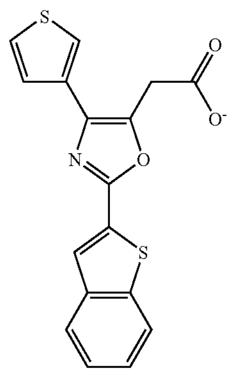 | Na | Powder<br>ESI · MS (m/z):<br>340 (M − H) − |
| 511 | 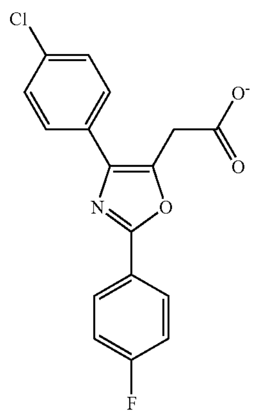 | Na | Powder<br>ESI · MS (m/z):<br>330/332 (N − Na) − |
| 512 | 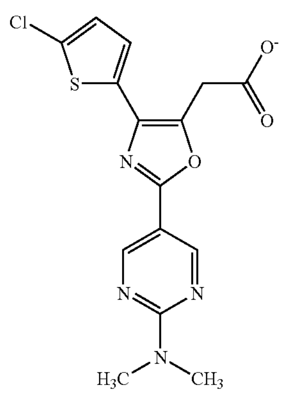 | Na | Powder<br>ESI · MS (m/z):<br>363/365 (M − Na) − |

TABLE 36-continued

| Preparation example No. | Chemical structure | Salt | Physical constant, etc. |
|---|---|---|---|
| 513 | 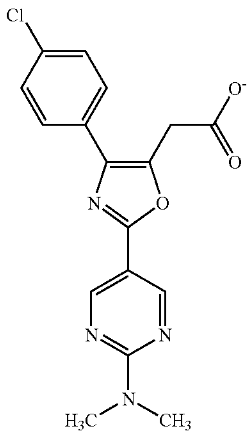 | Na | Powder<br>ESI·MS (m/z):<br>357/359 (N − Na) − |
| 514 | 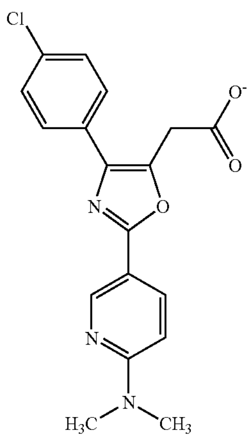 | Na | Powder<br>ESI·MS (m/z):<br>356/358 (M − Na) − |
| 515 | 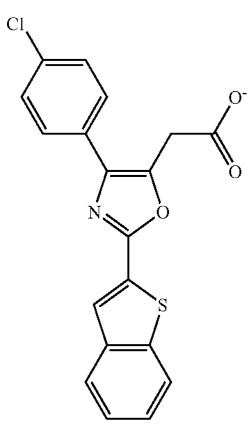 | Na | Powder<br>ESI·MS (m/z):<br>368/370 (M − Na) − |

TABLE 36-continued

| Preparation example No. | Chemical structure | Salt | Physical constant, etc. |
|---|---|---|---|
| 516 | (5-chlorothiophen-2-yl)-oxazole-(4-methoxyphenyl) acetate structure | Na | Powder ESI · MS (m/z): 348/350 (M − Na) − |
| 517 | (4-chlorophenyl)-oxazole-(4-methoxyphenyl) acetate structure | Na | Powder ESI · MS (m/z): 342/344 (M − Na) − |

Preparation Examples 518 to 521

The corresponding starting materials were treated in a manner similar to Preparation example 151 or 296 to obtain the compounds shown in Table 37 below.

TABLE 37

| Preparation example No. | Chemical structure | Salt | Physical constant, etc. |
|---|---|---|---|
| 518 | (3-cyanophenyl)-oxazole-(4-fluorophenyl) ethyl acetate structure | Free material | Powder MS · APCI (m/z): 351 (M + H) |

TABLE 37-continued
| Preparation example No. | Chemical structure | Salt | Physical constant, etc. |
|---|---|---|---|
| 519 | 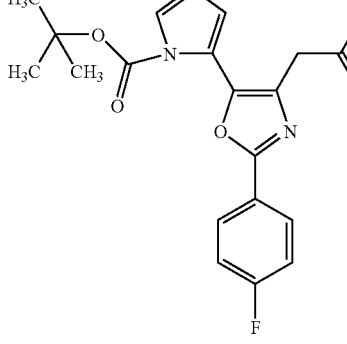 | Free material | Powder MS · APCI (m/z): 415 (M + H) |
| 520 | 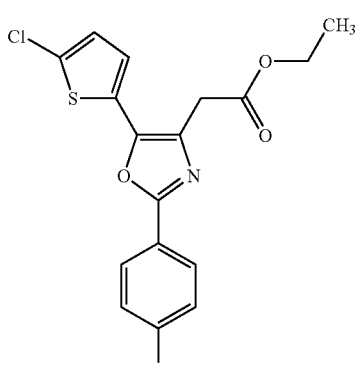 | Free material | Powder MS · APCI (m/z): 378 (M + H) |
| 521 | 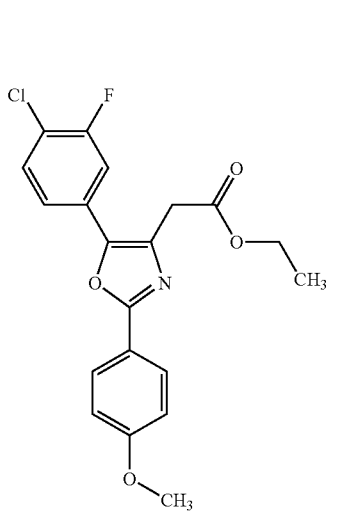 | Free material | Powder MS · APCI (m/z): 390/392 (M + H) + |

Preparation Examples 522 to 525

The corresponding starting materials were treated in a manner similar to Preparation example 152 to obtain the compounds shown in Table 38 below.

TABLE 38

| Preparation example No. | Chemical structure | Salt | Physical constant, etc. |
|---|---|---|---|
| 522 | 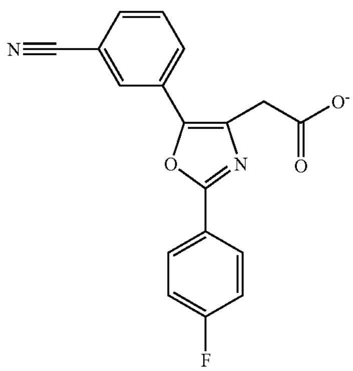 | Na | Powder<br>ESI · MS (m/z):<br>321 (M − Na) |
| 523 | 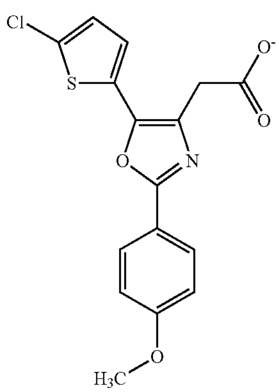 | Na | Powder<br>ESI · MS (m/z):<br>348 (M − Na) |
| 524 | 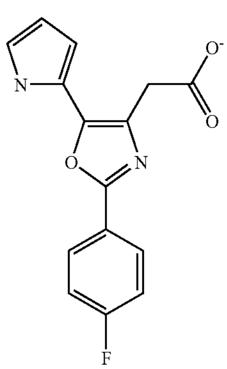 | Na | Powder<br>ESI · MS (m/z):<br>285 (M − Na) |

TABLE 38-continued

| Preparation example No. | Chemical structure | Salt | Physical constant, etc. |
|---|---|---|---|
| 525 | 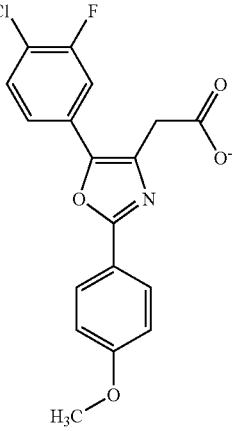 | Na | Powder ESI · MS (m/z): 360/362 (M − Na) − |

Preparation Examples 526 to 528

The corresponding starting materials were treated in a manner similar to Preparation example 330 to obtain the compounds shown in Table 39 below.

TABLE 39

| Preparation example No. | Chemical structure | Salt | Physical constant, etc. |
|---|---|---|---|
| 526 | 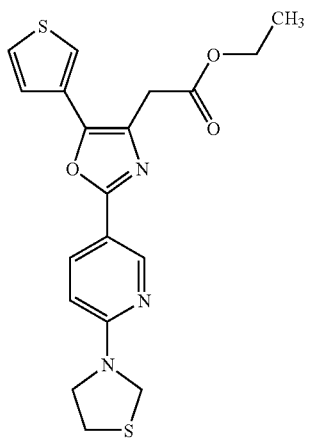 | Free material | Powder MS · APCI (m/z): 402 (M + H) + |

TABLE 39-continued

| Preparation example No. | Chemical structure | Salt | Physical constant, etc. |
|---|---|---|---|
| 527 | (thiophen-3-yl at 5-position, ethyl ester at 4-position of oxazole; 2-position linked to pyridine bearing N(CH₂CH₃)₂) | Free material | Powder MS · APCI (m/z): 386 (M + H) + |
| 527 | (5-chlorothiophen-2-yl at 5-position, ethyl ester at 4-position of oxazole; 2-position linked to pyridine bearing N(cyclopropyl)(CH₃)) | Free material | Powder MS · APCI (m/z): 418/420 (M + H) + |

Preparation Examples 529 to 531

The corresponding starting materials were hydrolyzed in the conventional method to obtain the compounds shown in Table 40 below.

TABLE 40

| Preparation example No. | Chemical structure | Salt | Physical constant, etc. |
|---|---|---|---|
| 529 | (thiophen-3-yl at 5-position, carboxylate at 4-position of oxazole; 2-position linked to pyridine bearing thiazolidin-3-yl) | Na | Powder ESI · MS (m/z): 372 (M − 2Na + H) − |

TABLE 40-continued

| Preparation example No. | Chemical structure | Salt | Physical constant, etc. |
|---|---|---|---|
| 530 | (structure) | Na | Powder<br>ESI · MS (m/z):<br>356 (M − Na) − |
| 531 | (structure) | Na | Powder<br>ESI · MS (m/z):<br>388/390 (M − Na) − |

Preparation Examples 532 to 536

The corresponding starting materials were treated in a manner similar to Preparation example 227 to obtain the compounds shown in Table 41 below.

TABLE 41

| Preparation example No. | Chemical structure | Salt | Physical constant, etc. |
|---|---|---|---|
| 532 | (structure) | HCl | Powder<br>MS · APCI (m/z):<br>269 (M + H) |

TABLE 41-continued
| Preparation example No. | Chemical structure | Salt | Physical constant, etc. |
|---|---|---|---|
| 533 | 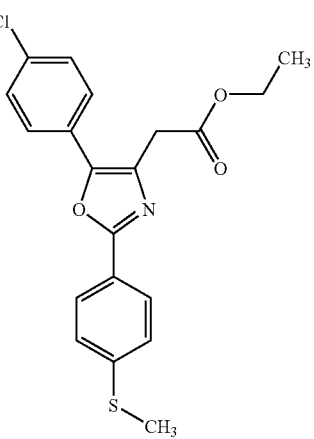 | Free material | Powder MS · APCI (m/z): 388/390 (M + H) + |
| 534 | 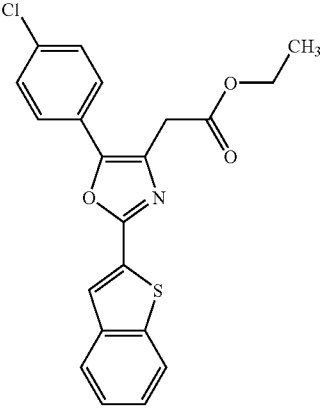 | Free material | Powder MS · APCI (m/z): 398/400 (M + H) + |
| 535 | 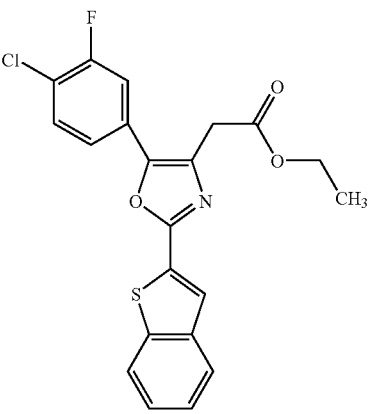 | Free material | Powder MS · APCI (m/z): 416/418 (M + H) |

TABLE 41-continued

| Preparation example No. | Chemical structure | Salt | Physical constant, etc. |
|---|---|---|---|
| 536 | [structure: 4-chloro-3-fluorophenyl substituted oxazole with ethyl acetate group and 2-(methylthio)pyrimidin-5-yl] | Free material | Powder MS · APCI (m/z): 408/410 (M + H) + |

Preparation Example 537

A mixture of ethyl 3-bromo-4-(5-chlorothiophen-2-yl)-4-oxo-butyrate (651 mg) and 4-fluorothiobenzamide (310 mg) in N,N-dimethylformamide (10 ml) was stirred at 70° C. for 2 hours. After cooling, water was added to the reaction mixture, and extracted with ethyl acetate. The organic layer was washed with water and brine, dried over anhydrous sodium sulfate, and the solvent was removed under reduced pressure. The resulting residue was purified by NH silica gel column chromatography (solvent: hexane:ethyl acetate=10:1) to obtain ethyl 4-(5-chlorothiophen-2-yl)-2-(4-fluorophenyl)thiazol-5-yl acetate (471 mg).

MS•APCI (m/z): 382/284 (MH+)

Preparation Examples 538 to 567

The corresponding starting materials were treated in a manner similar to Preparation example 537 to obtain the compounds shown in Table 42 below.

TABLE 42

| Preparation example No. | Chemical structure | Salt | Physical constant, etc. |
|---|---|---|---|
| 538 | [structure: 4-chlorophenyl substituted thiazole with methyl acetate group and 6-(dimethylamino)pyridin-3-yl] | Free material | Powder $^1$H-NMR 300 MHz (DMSO-$d_6$) δ 3.11 (6H, s), 3.70 (3H, s), 4.05 (2H, s), 6.74 (1H, dd), 7.52-7.58 (2H, m), 7.64-7.77 (2H, m), 8.00 (1H, dd), 8.63-8.65 (2H, m) |

TABLE 42-continued

| Preparation example No. | Chemical structure | Salt | Physical constant, etc. |
|---|---|---|---|
| 539 | (4-chlorophenyl at 4-position, 4-methoxyphenyl at 2-position of thiazole, methyl acetate at 5-position) | Free material | Powder MS·APCI (m/z): 374/376 (M + H) + |
| 540 | (4-chlorophenyl at 4-position, benzothiophen-2-yl at 2-position of thiazole, methyl acetate at 5-position) | Free material | Powder MS·APCI (m/z): 400/402 (M + H) + |
| 541 | (4-chlorophenyl at 4-position, 4-fluorophenyl at 2-position of thiazole, methyl acetate at 5-position) | Free material | Powder MS·APCI (m/z): 362/364 (M + H) + |

TABLE 42-continued

| Preparation example No. | Chemical structure | Salt | Physical constant, etc. |
|---|---|---|---|
| 542 | 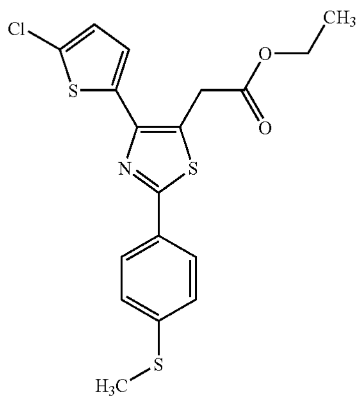 | Free material | Powder MS·APCI (m/z): 410/412 (M + H)+ |
| 543 | 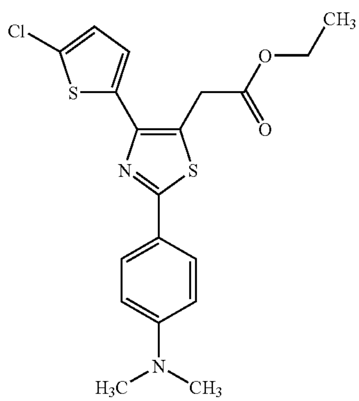 | Free material | Powder MS·APCI (m/z): 407/409 (M + H)+ |
| 544 | 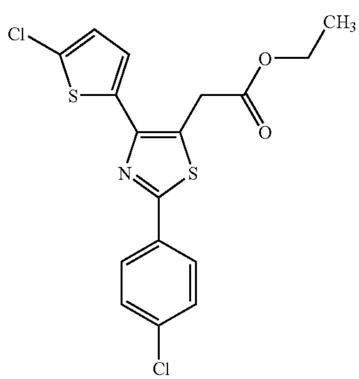 | Free material | Powder MS·APCI (m/z): 398/400 (M + H)+ |
| 545 | 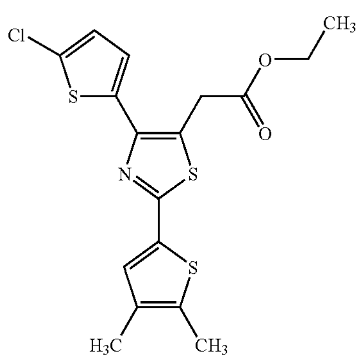 | Free material | Powder MS·APCI (m/z): 398/400 (M + H)+ |

TABLE 42-continued
| Preparation example No. | Chemical structure | Salt | Physical constant, etc. |
|---|---|---|---|
| 546 | 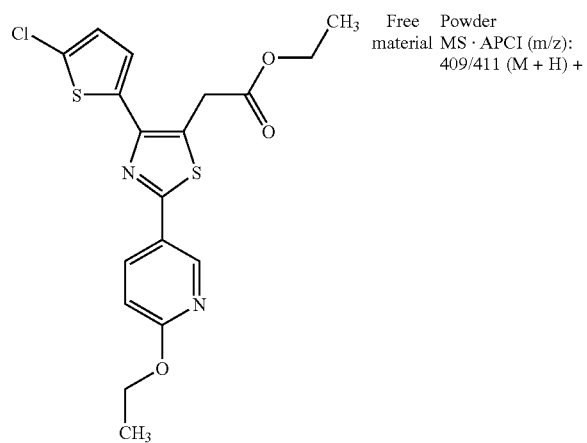 | Free material | Powder MS · APCI (m/z): 409/411 (M + H) + |
| 547 | 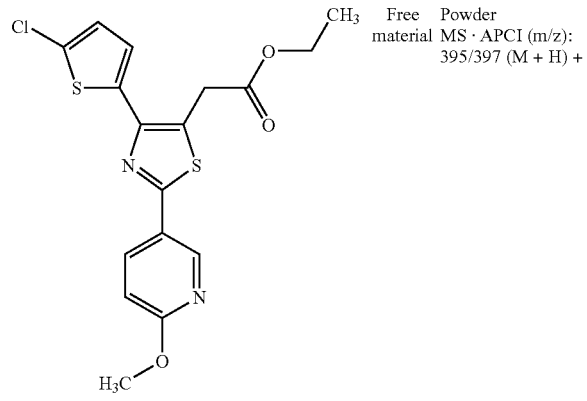 | Free material | Powder MS · APCI (m/z): 395/397 (M + H) + |
| 548 | 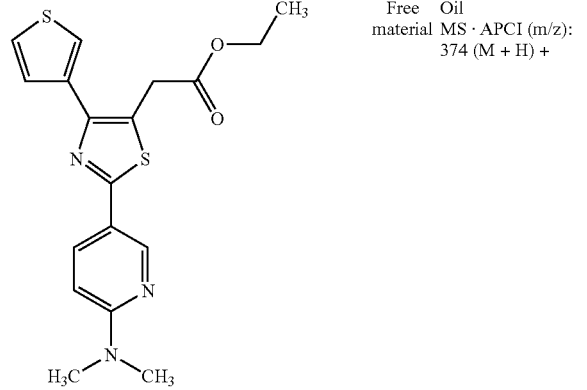 | Free material | Oil MS · APCI (m/z): 374 (M + H) + |

TABLE 42-continued
| Preparation example No. | Chemical structure | Salt | Physical constant, etc. |
|---|---|---|---|
| 549 | 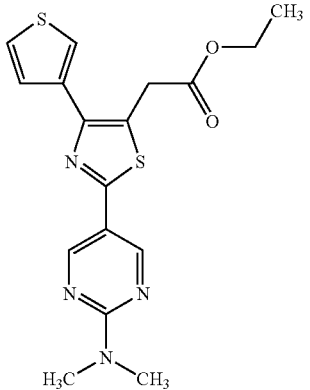 | Free material | Powder MS·APCI (m/z): 375 (M + H) + |
| 550 | 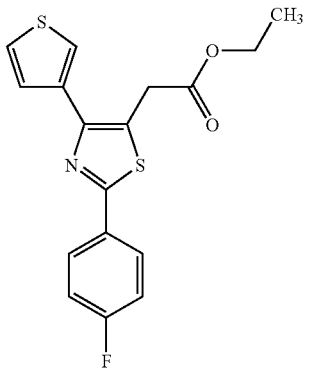 | Free material | Oil MS·APCI (m/z): 348 (M + H) + |
| 551 | 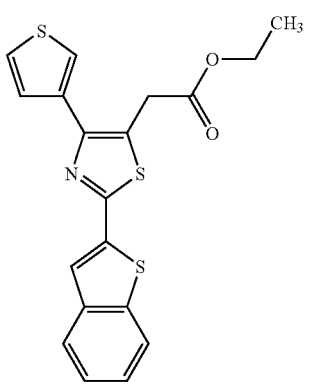 | Free material | Powder MS·APCI (m/z): 386 (M + H) + |

TABLE 42-continued
| Preparation example No. | Chemical structure | Salt | Physical constant, etc. |
|---|---|---|---|
| 552 | 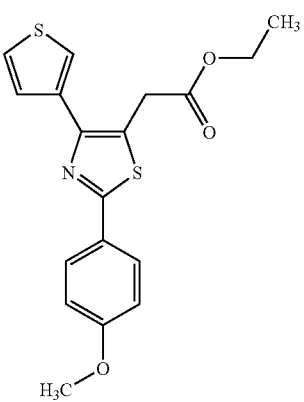 | Free material | Powder MS·APCI (m/z): 360 (M + H) + |
| 553 | 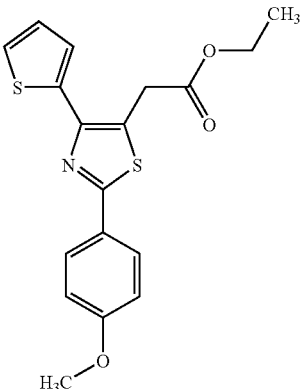 | Free material | Oil MS·APCI (m/z): 360 (M + H) + |
| 554 | 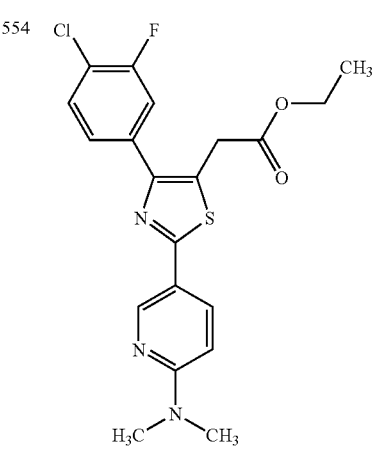 | Free material | Powder MS·APCI (m/z): 420/422 (M + H) + |

TABLE 42-continued
| Preparation example No. | Chemical structure | Salt | Physical constant, etc. |
|---|---|---|---|
| 555 | 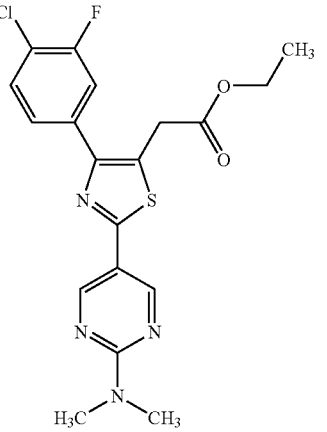 | Free material | Powder MS·APCI (m/z): 421/423 (M + H) |
| 556 | 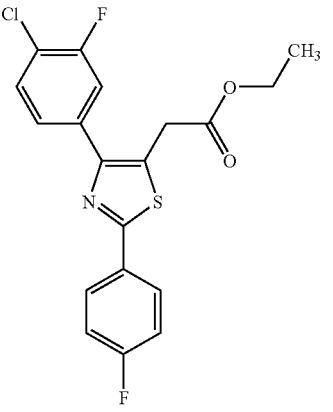 | Free material | Powder MS·APCI (m/z): 394/396 (M + H) + |
| 557 | 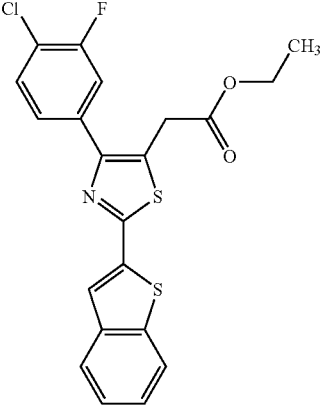 | Free material | Powder MS·APCI (m/z): 432/434 (M + H) + |

TABLE 42-continued

| Preparation example No. | Chemical structure | Salt | Physical constant, etc. |
|---|---|---|---|
| 558 | 2-(4-methoxyphenyl)-4-(4-chloro-3-fluorophenyl)thiazole-5-yl acetic acid ethyl ester | Free material | Powder MS·APCI (m/z): 406/408 (M + H) + |
| 559 | 2-(benzo[b]thiophen-2-yl)-4-(5-chlorothiophen-2-yl)thiazole-5-yl acetic acid ethyl ester | Free material | Powder MS·APCI (m/z): 420/422 (M + H) + |
| 560 | 2-(2-methylthiopyrimidin-5-yl)-4-(5-chlorothiophen-2-yl)thiazole-5-yl acetic acid ethyl ester | Free material | Powder MS·APCI (m/z): 412/414 (M + H) + |

TABLE 42-continued
| Preparation example No. | Chemical structure | Salt | Physical constant, etc. |
|---|---|---|---|
| 561 | 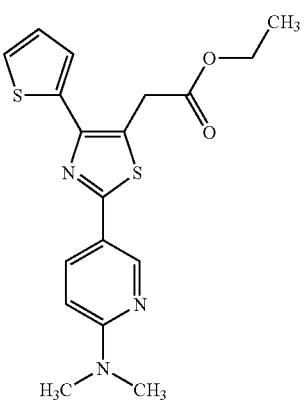 | Free material | Powder MS·APCI (m/z): 374 (M + H) + |
| 562 | 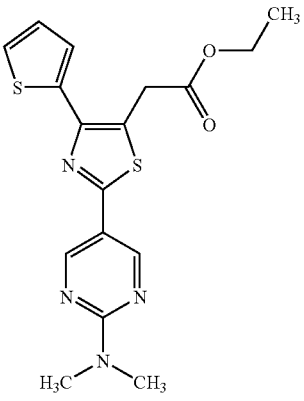 | Free material | Powder MS·APCI (m/z): 375 (M + H) + |
| 563 | 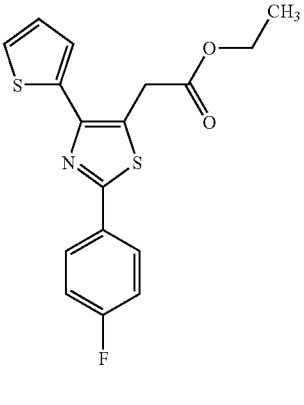 | Free material | Powder MS·APCI (m/z): 348 (M + H) + |

TABLE 42-continued
| Preparation example No. | Chemical structure | Salt | Physical constant, etc. |
|---|---|---|---|
| 564 | 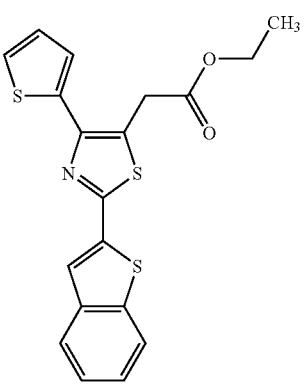 | Free material | Powder MS · APCI (m/z): 386 (M + H) + |
| 565 | 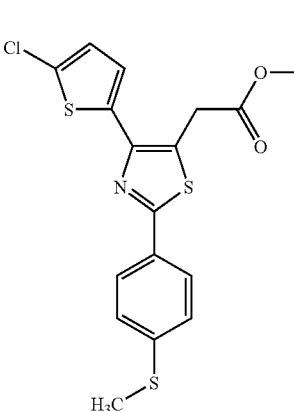 | Free material | Powder MS · APCI (m/z): 392/394 (M + H) + |
| 566 | 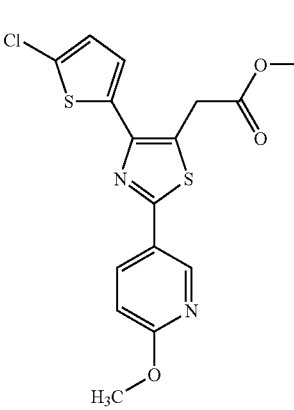 | Free material | Powder MS · APCI (m/z): 394/396 (M + H) + |

TABLE 42-continued

| Preparation example No. | Chemical structure | Salt | Physical constant, etc. |
|---|---|---|---|
| 567 | [Structure: 5-chlorothiophene-thiazole-CH2-C(=O)-O-CH2CH3 with 2-(4-dimethylaminophenyl) substituent] | Free material | Powder MS·APCI (m/z): 408/410 (M + H) + |

Preparation Examples 568 to 597

The corresponding starting materials were hydrolyzed in the conventional manner to obtain the compounds shown in Table 43 below.

TABLE 43

| Preparation example No. | Chemical structure | Salt | Physical constant, etc. |
|---|---|---|---|
| 568 | [Structure: 5-chlorothiophene-thiazole-CH2-COO⁻ with 2-(4-fluorophenyl) substituent] | Na | Powder ESI·MS (m/z): 352/354 (M − Na) − |
| 569 | [Structure: 5-chlorothiophene-thiazole-CH2-COO⁻ with 2-(benzothiophen-2-yl) substituent] | Na | Powder ESI·MS (m/z): 390/392 (M − Na) − |

TABLE 43-continued

| Preparation example No. | Chemical structure | Salt | Physical constant, etc. |
|---|---|---|---|
| 570 | 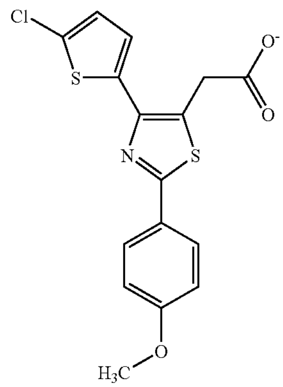 | Na | Powder<br>ESI · MS (m/z):<br>364/366 (M − Na) − |
| 571 | 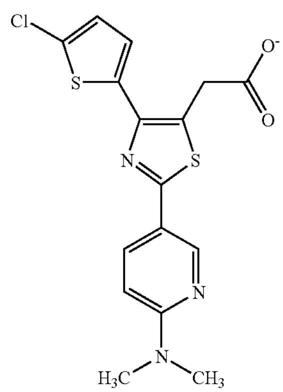 | Na | Powder<br>ESI · MS (m/z):<br>378/380 (M − Na) − |
| 572 | 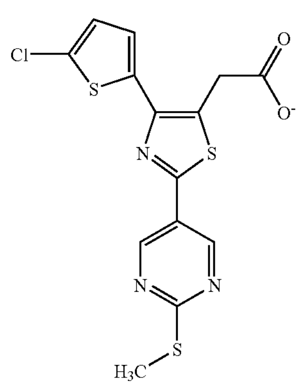 | Na | Powder<br>ESI · MS (m/z):<br>384/386 (M − Na) − |
| 573 | 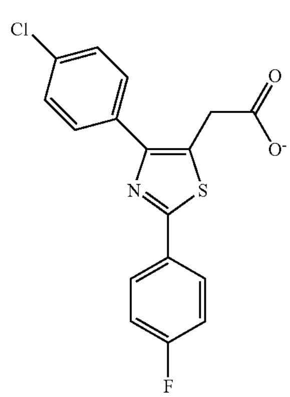 | Na | Powder<br>ESI · MS (m/z):<br>346 (M − Na) − |

TABLE 43-continued
| Preparation example No. | Chemical structure | Salt | Physical constant, etc. |
|---|---|---|---|
| 574 | 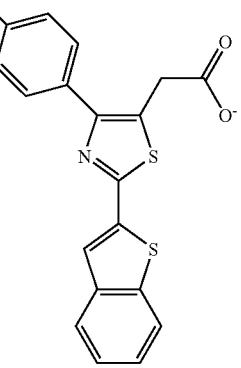 | Na | Powder<br>ESI · MS (m/z):<br>384/386 (M − Na) − |
| 575 | 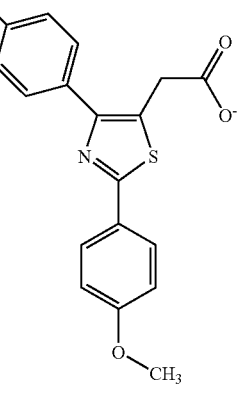 | Na | Powder<br>ESI · MS (m/z):<br>358/360 (M − Na) − |
| 576 | 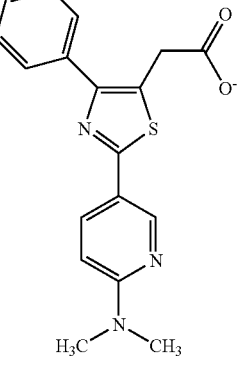 | Na | Powder<br>ESI · MS (m/z):<br>372/374 (M − Na) − |
| 577 | 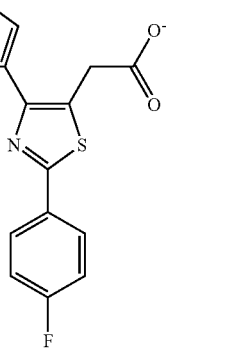 | Na | Powder<br>ESI · MS (m/z):<br>318 (M − Na) − |

TABLE 43-continued
| Preparation example No. | Chemical structure | Salt | Physical constant, etc. |
|---|---|---|---|
| 578 | 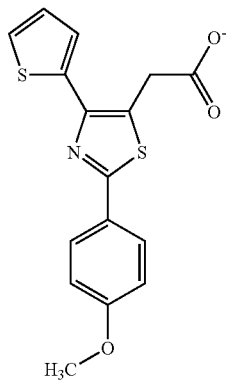 | Na | Powder<br>ESI · MS (m/z):<br>330 (M − Na) − |
| 579 | 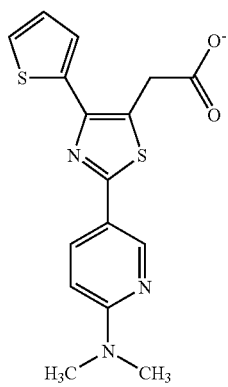 | Na | Powder<br>ESI · MS (m/z):<br>344 (M − Na) − |
| 580 | 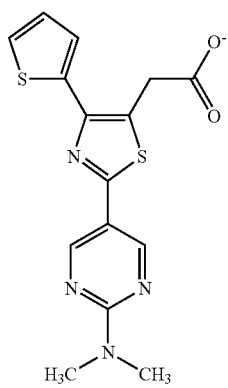 | Na | Powder<br>ESI · MS (m/z):<br>345 (M − Na) − |

TABLE 43-continued
| Preparation example No. | Chemical structure | Salt | Physical constant, etc. |
|---|---|---|---|
| 581 | 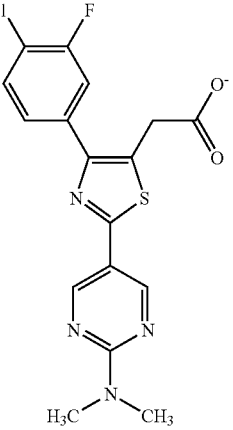 | Na | Powder<br>ESI·MS (m/z):<br>391/393 (M − Na) − |
| 582 | 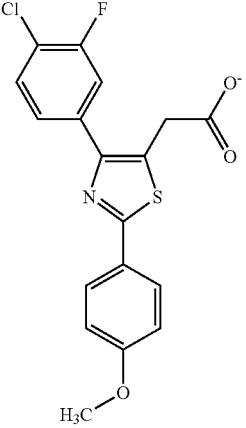 | Na | Powder<br>ESI·MS (m/z):<br>376/378 (M − Na) − |
| 583 | 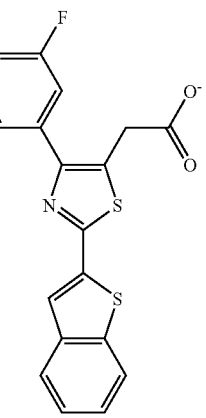 | Na | Powder<br>ESI·MS (m/z):<br>358/360 (M − Na) − |

TABLE 43-continued
| Preparation example No. | Chemical structure | Salt | Physical constant, etc. |
|---|---|---|---|
| 584 | 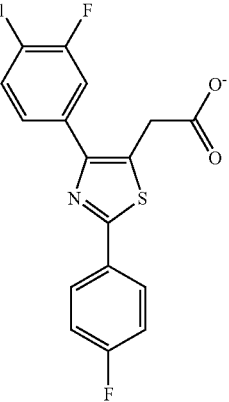 | Na | Powder<br>ESI · MS (m/z):<br>364/366 (M − Na) − |
| 585 | 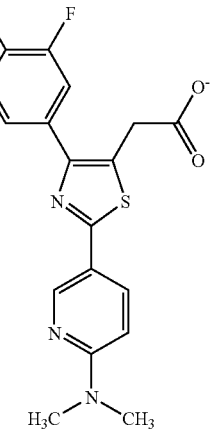 | Na | Powder<br>ESI · MS (m/z):<br>390/392 (M − Na) − |
| 586 | 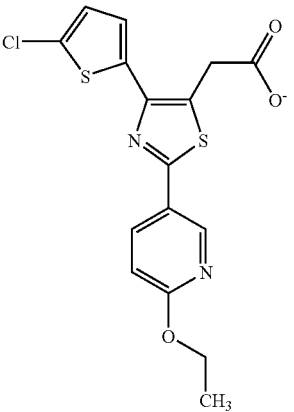 | Na | Powder<br>ESI · MS (m/z):<br>379/381 (M − Na) − |

TABLE 43-continued

| Preparation example No. | Chemical structure | Salt | Physical constant, etc. |
|---|---|---|---|
| 587 | 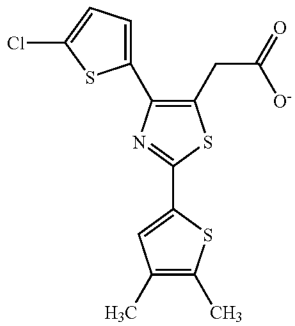 | Na | Powder ESI·MS (m/z): 368/370 (M − Na) − |
| 588 | 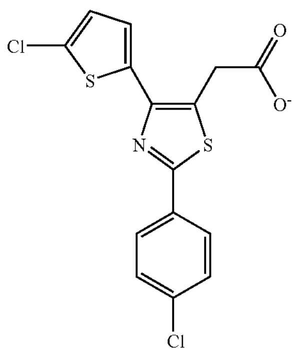 | Na | Powder ESI·MS (m/z): 368/370 (M − Na) − |
| 589 | 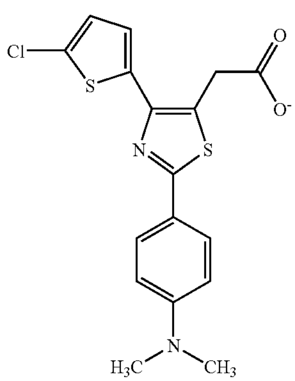 | Na | Powder ESI·MS (m/z): 377/379 (M − Na) − |
| 590 | 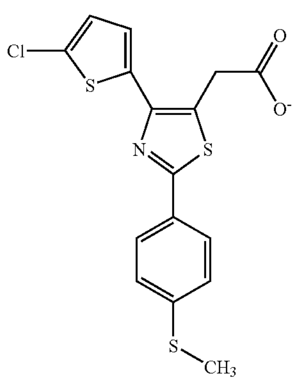 | Na | Powder ESI·MS (m/z): 380/382 (M − Na) − |

TABLE 43-continued

| Preparation example No. | Chemical structure | Salt | Physical constant, etc. |
|---|---|---|---|
| 591 | 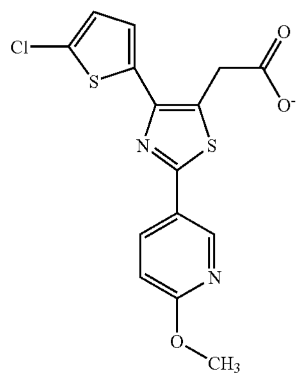 | Na | Powder<br>ESI·MS (m/z):<br>365/367 (M − Na) − |
| 592 | 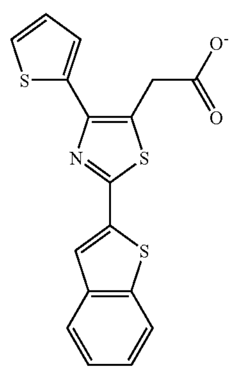 | Na | Powder<br>ESI·MS (m/z):<br>356 (M − Na) − |
| 593 | 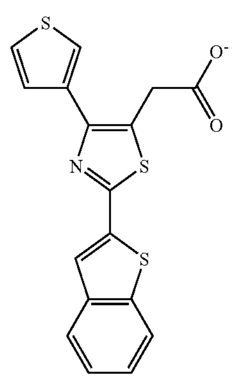 | Na | Powder<br>ESI·MS (m/z):<br>356 (M − Na) − |
| 594 | 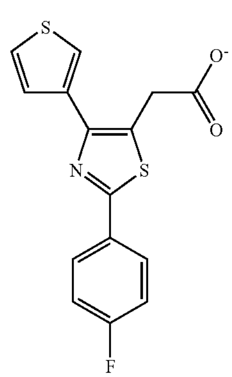 | Na | Powder<br>ESI·MS (m/z):<br>318 (M − Na) − |

TABLE 43-continued
| Preparation example No. | Chemical structure | Salt | Physical constant, etc. |
|---|---|---|---|
| 595 | 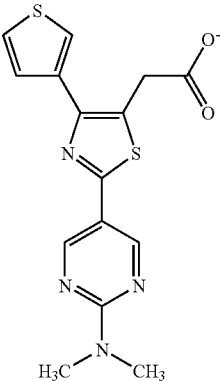 | Na | Powder<br>ESI·MS (m/z):<br>345 (M − Na) − |
| 596 | 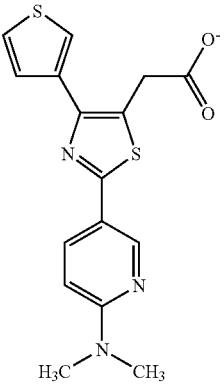 | Na | Powder<br>ESI·MS (m/z):<br>344 (M − Na) − |
| 597 | 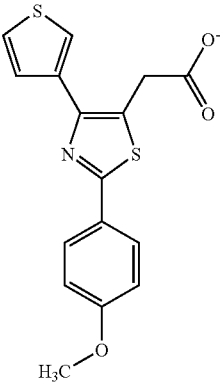 | Na | Powder<br>ESI·MS (m/z):<br>330 (M − Na) − |

Preparation Examples 598 to 599

The corresponding starting materials were treated in a manner similar to Preparation example 359 to obtain the compounds shown in Table 44 below.

TABLE 44

| Preparation example No. | Chemical structure | Salt | Physical constant, etc. |
|---|---|---|---|
| 598 | 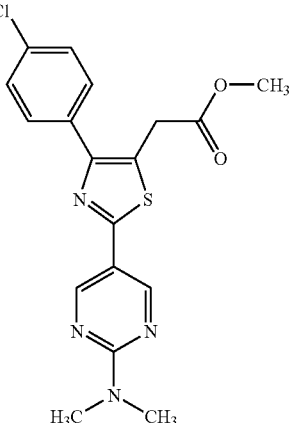 | Free material | Powder<br>MS · APCI (m/z):<br>389/391 (M + H)+ |
| 599 | 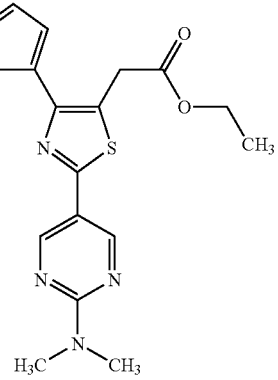 | Free material | Powder<br>MS · APCI (m/z):<br>409/411 (M + H)+ |

Preparation Examples 600 to 601

The corresponding starting materials were hydrolyzed in the conventional manner to obtain the compounds shown in Table 45 below.

TABLE 45

| Preparation example No. | Chemical structure | Salt | Physical constant, etc. |
|---|---|---|---|
| 600 | 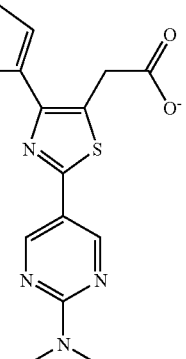 | Na | Powder<br>ESI · MS(m/z):<br>379/381 (M − Na) |

TABLE 45-continued

| Preparation example No. | Chemical structure | Salt | Physical constant, etc. |
|---|---|---|---|
| 601 | [structure: 4-chlorophenyl-thiazole with acetate and 2-(dimethylamino)pyrimidin-5-yl substituent] | Na | Powder
ESI·MS(m/z):
373/375 (M – Na)– |

Preparation Example 602

A mixture of ethyl 3-amino-4-(5-chlorothiophen-2-yl)-4-oxobutyrate hydrochloride (596 mg), 4-fluorobenzoyl chloride (380 mg) and sodium hydrogen carbonate (1.0 g) in ethyl acetate (10 ml) and water (10 ml) was stirred at room temperature for 2 hours. To the reaction mixture were added ethyl acetate (30 ml) and water (30 ml), and the organic layer was collected. The organic layer was washed with water and brine, dried over anhydrous magnesium sulfate and the solvent was removed under reduced pressure. The resulting residue was triturated with hexane to obtain a crude product of ethyl 4-(5-chlorothiophen-2-yl)-3-[(4-fluorobenzoyl)amino]-4-oxobutyrate (732 mg) as colorless powder.

A mixture of ethyl 4-(5-chlorothiophen-2-yl)-3-[(4-fluoro-benzoyl)amino]-4-oxobutyrate (720 mg) and 2,4-bis(4-methoxyphenyl)-1,3-dithia-2,4-diphosphetan-2,4-disulfide (1.14 g) in tetrahydrofuran (20 ml) was refluxed for 2.5 hours. The reaction mixture was cooled and purified by silica gel column chromatography (solvent: hexane:ethyl acetate=20:1), and triturated with hexane to obtain ethyl 5-(5-chlorothiophen-2-yl)-2-(4-fluorophenyl)thiazol-4-yl acetate (667 mg) as yellowish powder.

MS•APCI (m/z): 382/284 (MH+)

Preparation Examples 603 to 607

The corresponding starting materials were treated in a manner similar to Preparation example 602 to obtain the compounds shown in Table 46 below.

TABLE 46

| Preparation example No. | Chemical structure | Salt | Physical constant, etc. |
|---|---|---|---|
| 603 | [structure: 5-chlorothiophene-thiazole-4,5-disubstituted with ethyl acetate and 4,5-dimethylthiophen-2-yl] | Free material | Powder
MS·APCI(m/z):
398/400 (M + H)+ |

TABLE 46-continued

| Preparation example No. | Chemical structure | Salt | Physical constant, etc. |
|---|---|---|---|
| 604 | 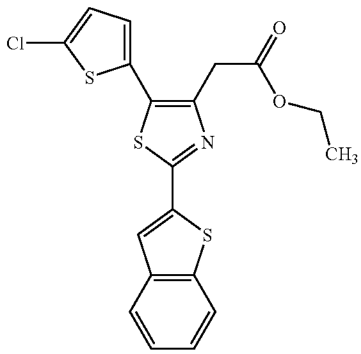 | Free material | Powder MS·APCI(m/z): 420/422 (M + H)+ |
| 605 | 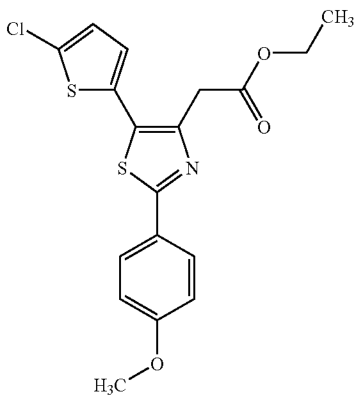 | Free material | Powder MS·APCI(m/z): 394/396 (M + H)+ |
| 606 | 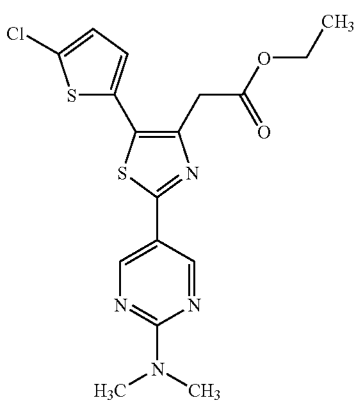 | Free material | Powder MS·APCI(m/z): 409/411 (M + H)+ |
| 607 | 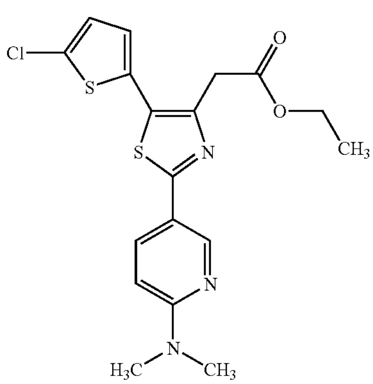 | Free material | Powder MS·APCI(m/z): 408/410 (M + H)+ |

Preparation Examples 608 to 612

The corresponding starting materials were hydrolyzed in the conventional manner to obtain the compounds shown in Table 47 below.

TABLE 47

| Preparation example No. | Chemical structure | Salt | Physical constant, etc. |
|---|---|---|---|
| 608 | 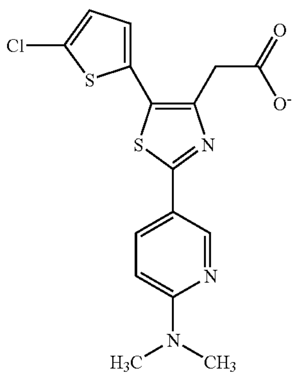 | Na | Powder<br>ESI · MS(m/z):<br>378/380 (M − Na)− |
| 609 | 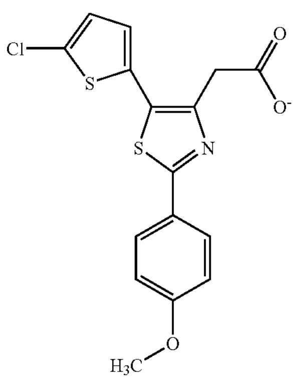 | Na | Powder<br>ESI · MS(m/z):<br>364/366 (M − Na)− |
| 610 | 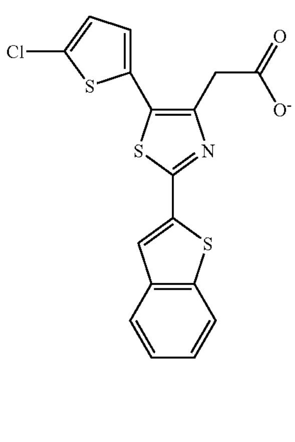 | Na | Powder<br>ESI · MS(m/z):<br>390/392 (M − Na)− |

TABLE 47-continued

| Preparation example No. | Chemical structure | Salt | Physical constant, etc. |
|---|---|---|---|
| 611 | 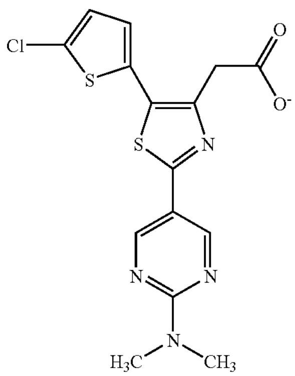 | Na | Powder ESI · MS(m/z): 379/381 (M − Na)− |
| 612 | 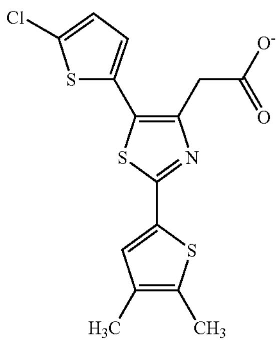 | Na | Powder ESI · MS(m/z): 368/370 (M − Na)− |

Preparation Examples 613 to 622

In accordance with the above-mentioned preparation examples or the conventionally known preparation processes, the compounds shown in Table 48 below were obtained.

TABLE 48

| Preparation example No. | Chemical structure | Salt | Physical constant, etc. |
|---|---|---|---|
| 613 | 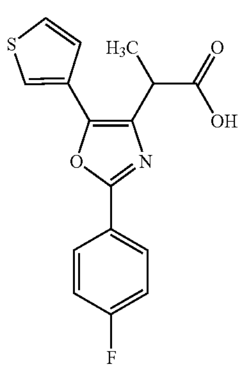 | | Free material |

TABLE 48-continued

| Preparation example No. | Chemical structure | Salt | Physical constant, etc. |
|---|---|---|---|
| 614 | 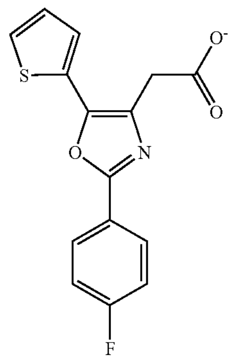 | Na | Powder<br>ESI·MS(m/z):<br>302 (M − Na) |
| 615 | 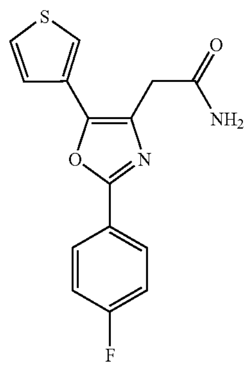 | | Free material |
| 616 | 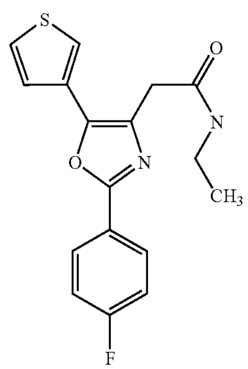 | | Free material |
| 617 | 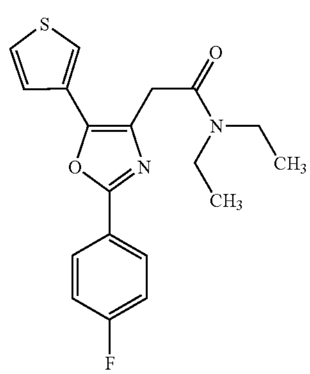 | | Free material |

TABLE 48-continued

| Preparation example No. | Chemical structure | Salt | Physical constant, etc. |
|---|---|---|---|
| 618 | 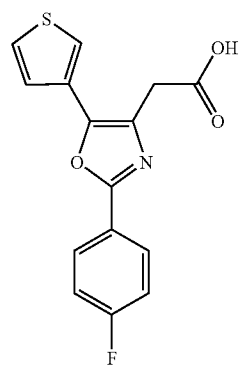 | Free material | Crystal Melting point: 207-209° C. |
| 619 | 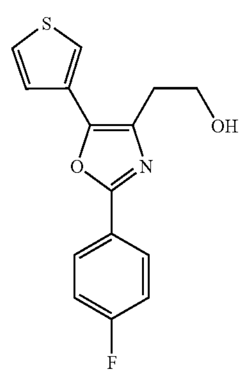 | Free material | Crystal Melting point: 110-111° C. |
| 620 | 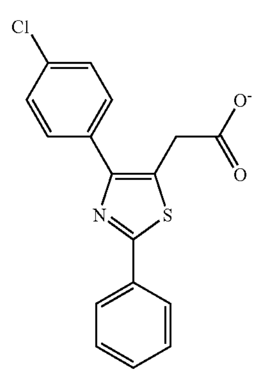 | Na | Powder ESI·MS(m/z): 328/330 (M − Na)− |
| 621 | 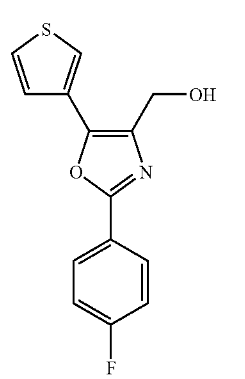 | Free material | Powder |

TABLE 48-continued

| Preparation example No. | Chemical structure | Salt | Physical constant, etc. |
|---|---|---|---|
| 622 | 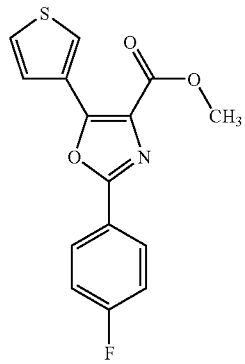 | Free material | Crystal Melting point: 213-214° C. |

Preparation Examples 623 to 631

According to the preparation example 129, 130, 135, 148, 152 or 330 mentioned above, the compounds shown in Table 49 below were obtained.

TABLE 49

| Preparation example No. | Chemical structure | Salt | Physical constant, etc. |
|---|---|---|---|
| 623 | 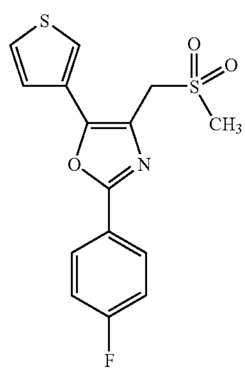 | Free material | Crystal Melting point: 208-210° C. MS · APCI(m/z): 338(M + H) |
| 624 | 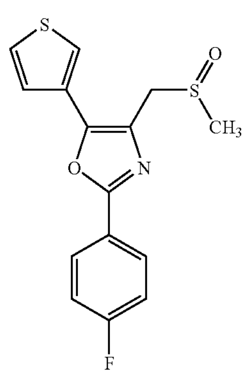 | Free material | Crystal Melting point: 173-174.5° C. MS · APCI(m/z): 322(M + H) |

TABLE 49-continued

| Preparation example No. | Chemical structure | Salt | Physical constant, etc. |
|---|---|---|---|
| 625 | 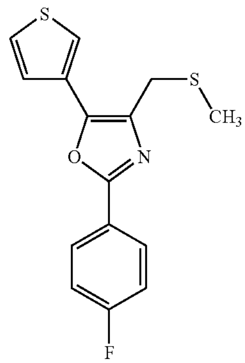 | Free material | Crystal Melting point: 111-112° C. MS·APCI(m/z): 486 (M + H) |
| 626 | 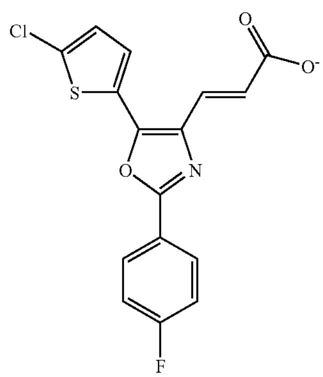 | Na | Powder ESI·MS(m/z): 348/350 (M − Na)− |
| 627 | 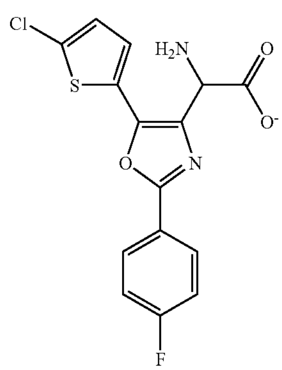 | Na | Powder ESI·MS(m/z): 351/353 (M − Na)− |
| 628 | 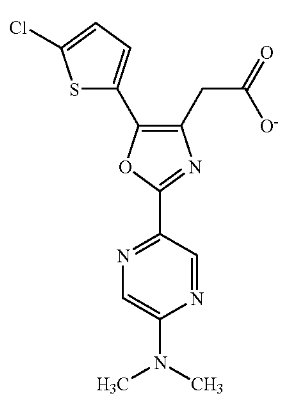 | Na | Powder MS·APCI(m/z): 363/365 (M − Na)− |

TABLE 49-continued

| Preparation example No. | Chemical structure | Salt | Physical constant, etc. |
|---|---|---|---|
| 629 | 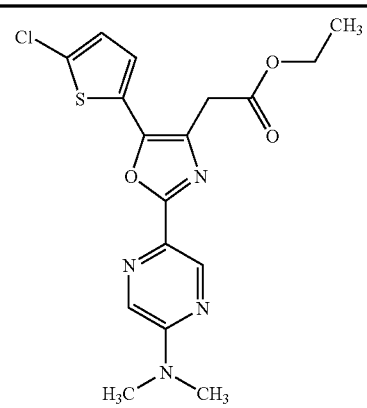 | Free material | Solid<br>MS · APCI(m/z):<br>393/395 (M + H) |
| 630 | 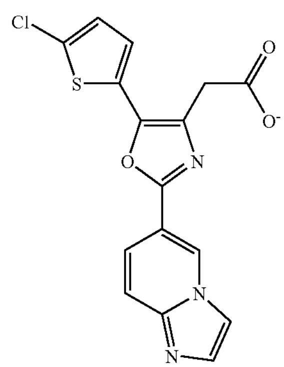 | Na | Powder<br>ESI · MS(m/z):<br>358/360 (M − Na)− |
| 631 | 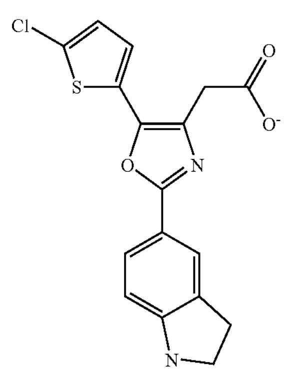 | Na | Powder<br>ESI · MS(m/z):<br>359/361 (M − Na)− |

Preparation Example 632

(1) Ethyl 2-(4-chlorophenyl)-5-phenylthiazol-4-ylacetate (4.5 g) was dissolved in methanol (50 ml), and ammonia was saturated in the solution at 0° C. and the resulting mixture was allowed to stand at room temperature for 3 days. After removing the solvent, methanol was added to the residue. The resulting precipitate was collected and dried to obtain 2-(4-chloro-phenyl)-5-phenylthiazol-4-yl acetamide (4.2 g).

Melting point: 202-203° C.

MS•EI (m/z): 328 (M+)

(2) To a solution of 2-(4-chlorophenyl)-5-phenylthiazol-4-yl acetamide (3.4 g) and phosphorus oxychloride (3 ml) in chloroform (50 ml) was added one drop of pyridine, and the mixture was refluxed for 8 hours. Cold diluted aqueous ammonia was poured into the mixture and the organic layer was collected. After removing the solvent under reduced pressure, ethanol was added to the residue and crystal was collected by filtration to obtain 2-(4-chlorophenyl)-5-phenylthiazol-4-yl acetonitrile (3.1 g).

Melting point: 118-120° C.

MS•EI (m/z): 310 (M+)

(3) To a solution of 2-(4-chlorophenyl)-5-phenylthiazol-4-yl acetonitrile (2.33 g) in N,N-dimethylformamide (30 ml) were added sodium azide (1.40 g) and ammonium chloride (1.3 g), and the mixture was stirred at 90° C. for 12 hours. After removing the solvent under reduced pressure, ethyl acetate and water were added to the residue. The organic layer was collected, dried and the solvent was removed under reduced pressure. The residue was recrystallized from chloroform and methanol to obtain 5-[2-(4-chlorophenyl)-5-phenyl-thiazol-4-ylmethyl]tetrazole (1.75 g).

Melting point: 213-214° C.

MS•EI (m/z): 353 (M+)

Preparation Examples 633 to 641

The corresponding starting materials were treated in a manner similar to Preparation example 43, 135, 608 or the conventionally known processes to obtain the compounds shown in Table 50 below.

TABLE 50

| Preparation example No. | Chemical structure | Salt | Physical constant, etc. |
|---|---|---|---|
| 633 | 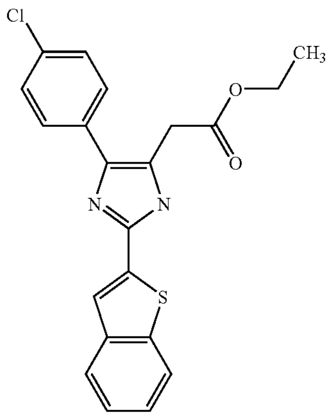 | Free material | Solid<br>MS · APCI(m/z):<br>397/399 (M + H)+ |
| 634 | 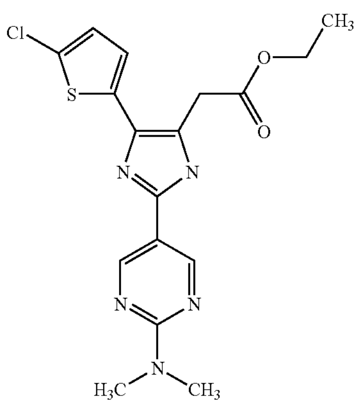 | Free material | Powder<br>MS · APCI(m/z):<br>392/394 (M + H)+ |
| 635 | 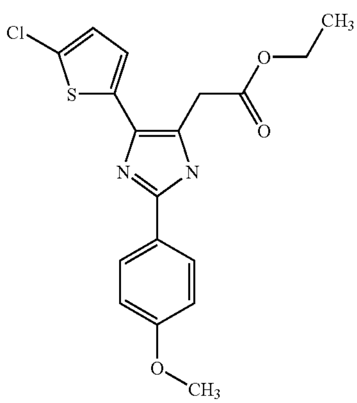 | Free material | Powder<br>MS · APCI(m/z):<br>377/379 (M + H)+ |

TABLE 50-continued

| Preparation example No. | Chemical structure | Salt | Physical constant, etc. |
|---|---|---|---|
| 636 | 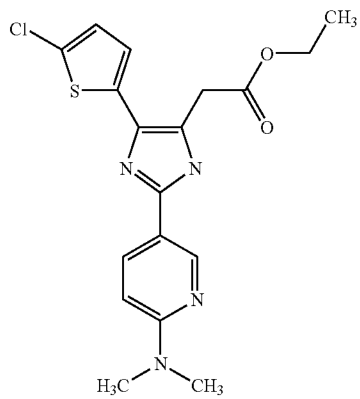 | Free material | Powder MS·APCI(m/z): 391/393 (M + H)+ |
| 637 | 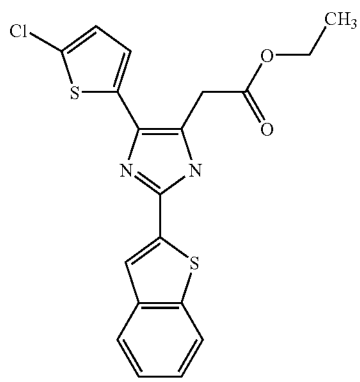 | Free material | Powder MS·APCI(m/z): 402/404 (M + H)+ |
| 638 | 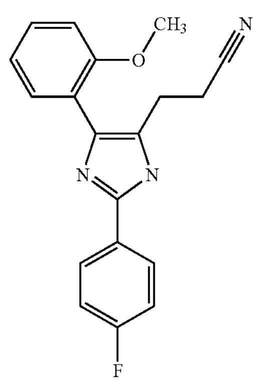 | Free material | Powder MS·APCI(m/z): 308 (MH+) |
| 639 | 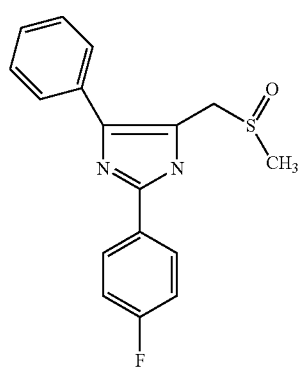 | 1HCl | Crystal Melting point: 203-204° C. EI·MS(m/z): 298 (M⁺ − 16)+ |

TABLE 50-continued

| Preparation example No. | Chemical structure | Salt | Physical constant, etc. |
|---|---|---|---|
| 640 | (5-chlorothiophen-2-yl / 4-fluorophenyl thiazole acetate structure) | Na | Powder<br>ESI · MS (m/z):<br>352 (M − Na) |
| 641 | (5-phenyl-2-(4-methylphenyl)oxazole ethyl acetate structure) | Free material | |

Reference Examples 642 to 644

The following compounds listed in Table 50a were prepared in a manner similar to Example 608 or 632, or similar to that described in Japanese Provisional Patent Publication No. 167685/1986.

TABLE 50a

| Preparation example No. | Chemical structure | Salt | Physical constant, etc. |
|---|---|---|---|
| 642 | (5-(5-chlorothiophen-2-yl)-2-(benzothiophen-2-yl)thiazole tetrazolylmethyl structure) | Free | Powder<br>ESI · MS(m/z):<br>414/416 (M − H)− |

TABLE 50a-continued

| Preparation example No. | Chemical structure | Salt | Physical constant, etc. |
|---|---|---|---|
| 643 | (structure) | Na | Powder<br>ESI · MS(m/z):<br>334 (M − Na)− |
| 644 | (structure) | Free | |

Reference Example 1

(1) A mixture of 2-acetylpyrimidine (2.90 g), hydroxylamine hydrochloride (2.48 g) and triethylamine (5.3 ml) in ethanol (40 ml) was stirred at room temperature overnight. The reaction mixture was poured into water, and extracted with methylene chloride. The organic layer was washed with a saturated aqueous ammonium sulfate solution and brine, dried over anhydrous sodium sulfate, and the solvent was removed under reduced pressure to obtain 2-acetylpyrimidine oxime (4.44 g) as colorless powder.

MS•APCI (m/z): 138 (MH+)

(2) A mixture of 2-acetylpyrimidine oxime (4.40 g) and p-toluenesulfonyl chloride (6.79 g) in pyridine (40 ml) was stirred at room temperature overnight. The reaction mixture was poured into ice-water and precipitated crude product was collected by filtration. The filtrate was neutralized by 10% hydrochloric acid and extracted with ethyl acetate. The organic layer was washed with water and brine, dried over anhydrous sodium sulfate and the solvent was removed under reduced pressure. The resulting residue and the crude product previously obtained were combined and triturated with diethyl ether to obtain O-p-toluenesulfonyl-2-acetylpyrimidine oxime (4.53 g) as colorless powder.

(3) To ice-cooled ethanol (19 ml) was added sodium hydride (681 mg, 60% mineral oil) and the mixture was stirred at room temperature for 30 minutes. To the solution was added dropwise a solution of O-p-toluenesulfonyl-2-acetylpyrimidine oxime (4.51 g) in ethanol (16 ml) and of tetrahydrofuran (10 ml) under ice-cooling, and the resulting mixture was stirred at room temperature for 1.5 hours. To the reaction mixture was added diethyl ether (150 ml) and precipitated insoluble material was removed by filtration. The filtrate was extracted with 2N hydrochloric acid and the aqueous layer was concentrated under reduced pressure. The resulting residue was triturated with acetone-ethanol to obtain 2-(2-aminoacetyl)pyrimidine hydrochloride (2.87 g) as pale brownish powder.

MS•APCI (m/z): 138 (MH+)

Reference Examples 2 to 4

Corresponding starting compounds were treated in a manner similar to Reference example 1 to obtain the compounds shown in Table 51 below.

TABLE 51

| Reference example No. | Chemical structure | Salt | Physical constant, etc. |
|---|---|---|---|
| 2 | (structure) | 1HCl | Powder<br>MS · APCI(m/z):<br>143 (M + H)+ |
| 3 | (structure) | 1HCl | Powder<br>MS · APCI(m/z):<br>143 (M + H)+ |

TABLE 51-continued

| Reference example No. | Chemical structure | Salt | Physical constant, etc. |
|---|---|---|---|
| 4 | (pyrazinyl-C(=O)-CH$_2$-NH$_2$) | 1HCl | Powder<br>MS · APCI(m/z):<br>138 (M + H)+ |

Reference Example 5

(1) To a solution of 1-(3-pyridyl)-1-butanone (20.0 g) in 47% aqueous hydrobromic acid (40 ml) and acetic acid (40 ml) was added bromine (15.2 ml), and the mixture was stirred at 60° C. for 30 minutes. The reaction mixture was poured into ice-water, and after adding a saturated aqueous sodium thiosulfate solution, potassium carbonate was added to the mixture to adjust pH to 4. The reaction mixture was extracted with ethyl acetate, washed successively with a saturated aqueous sodium hydrogen carbonate solution and brine, and dried over anhydrous sodium sulfate. The solvent was removed under reduced pressure to obtain a crude product of 2-bromo-1-(3-pyridyl)-1-butanone (30.15 g) as brownish oil.

(2) The crude product obtained in the above (1) was dissolved in N,N-dimethylformamide (100 ml), and sodium azide (9.50 g) was added to the solution under ice-cooling and the resulting mixture was stirred at room temperature for one hour. Water was added to the reaction mixture, the mixture was extracted with ethyl acetate three times, and combined organic layers was washed with brine, and dried over anhydrous sodium sulfate. The solvent was removed under reduced pressure and the residue was purified by silica gel flush column chromatography (solvent: n-hexane:ethyl acetate=2:1) to obtain 2-azido-1-(3-pyridyl)-1-butanone (18.65 g) as yellowish oil.

MS•APCI (m/z): 191 (MH+)

(3) A mixture of 2-azido-1-(3-pyridyl)-1-butanone (18.60 g), di-t-butyldicarbonate (23.50 g) and 10% palladium-carbon (2.70 g) in methanol (200 ml) was stirred under hydrogen atmosphere at room temperature for one hour. After removing the palladium-carbon by filtration, the solvent was removed under reduced pressure and the residue was purified by silica gel flush column chromatography (solvent: hexane:ethyl acetate=2:14→1:1) to obtain 2-(t-butoxycarbonylamino)-1-(3-pyridyl)-1-butanone (20.53 g) as yellowish red oil.

(4) A mixture of 2-(t-butoxycarbonylamino)-1-(3-pyridyl)-1-butanone (20.50 g) and 6N hydrochloric acid (38.8 ml) in ethanol (100 ml) was refluxed for one hour. After cooling, the reaction mixture was concentrated under reduced pressure and the resulting residue was triturated with ethanol-ethylacetate (1:1) to obtain 2-amino-1-(3-pyridyl)-1-butanone dihydrochloride (13.40 g) as pale reddish purple crystalline powder.

Melting point: 199 to 201° C. (decomposed)

Reference Examples 6 to 8

Corresponding starting compounds were treated in a manner similar to Reference example 5 to obtain the compounds shown in Table 52 below.

TABLE 52

| Reference example | Chemical structure | Salt | Physical |
|---|---|---|---|
| 6 | (thiophenyl-C(=O)-CH(NH$_2$)-CH$_2$CH$_2$-CH$_3$) | 1HCl | Powder<br>MS · APCI(m/z):<br>184 (M + H)+ |
| 7 | (phenyl-C(=O)-CH(NH$_2$)-CH$_2$CH$_2$-CH$_3$) | 1HCl | Crystal<br>Melting point:<br>156-158° C.<br>MS · APCI(m/z):<br>178 (M + H)+ |
| 8 | (phenyl-C(=O)-CH(NH$_2$)-CH$_2$-CH$_3$) | 1HCl | Powder<br>MS · APCI(m/z):<br>164 (M + H)+ |

Reference Example 9

To a solution of an acid chloride product prepared from 6-methyl nicotinic acid (245 mg) in chloroform (10 ml) were added 2-amino-1-(3-pyridyl)-1-butanone dihydrochloride (356 mg) and triethylamine (1.05 ml), and the mixture was stirred for 30 minutes. The mixture was poured into water and extracted with ethyl acetate. The organic layer was collected, washed with brine and dried over anhydrous sodium sulfate. The solvent was removed under reduced pressure to obtain a crude product of 2-(6-methylnicotynoylamino)-1-(3-pyridyl)-1-butanone (425 mg).

Reference Example 10

(1) A mixture of 3-(2-aminoacetyl)pyridine dihydrochloride (50.00 g), 4-fluorobenzoylchloride (41.71 g) and sodium hydrogen carbonate (100.44 g) in ethyl acetate (1 liter) and water (0.6 liter) was stirred at room temperature for 2 hours. To the reaction mixture were added tetrahydrofuran (0.5 liter) and water (1 liter), and the organic layer was collected. The organic layer was washed with water and brine, dried over anhydrous magnesium sulfate and the solvent was removed under reduced pressure. The resulting residue was triturated with ethyl acetate to obtain 3-[2-(4-fluorobenzoyl)aminoacetyl]pyridine (40.87 g) as pale yellowish powder.

Melting point: 164.5 to 165.5° C.

MS•APCI (m/z): 259 (MH+)

(2) To a solution of 3-[2-(4-fluorobenzoyl)aminoacetyl]-pyridine (500 mg) in N,N-dimethylformamide (10 ml) were added sodium hydride (81.3 mg, 60% mineral oil) and acrylonitrile (113 mg) under dry ice-acetone cooling, and the mixture was stirred at the same temperature under argon atmosphere for 10 minutes. The mixture was warmed slowly to 0° C. and stirred at the same temperature for 30 minutes. To the reaction mixture was added a saturated aqueous ammonium chloride solution and the mixture was extracted with ethyl acetate. The organic layer was washed with brine, dried over anhydrous sodium sulfate and the solvent was removed under reduced pressure to obtain a crude product of 4-cyano-2-(4-fluorobenzoylamino)-1-(3-pyridyl)-1-butanone (500 mg).

Reference Example 11

(1) To acetic anhydride (2.39 ml) was added dropwise formic acid (0.97 ml) under ice-cooling, and the mixture was stirred at 50° C. for 30 minutes. The mixture was ice-cooled again, and diluted with tetrahydrofuran (9 ml). To the mixture were added 2-amino-1-(3-pyridyl)-1-butanone dihydrochloride (600 mg) and triethylamine (1.41 ml), and the mixture was stirred under ice-cooling for 1.5 hours. To the reaction mixture was added a saturated aqueous sodium hydrogen carbonate solution, and the mixture was extracted with ethyl acetate. The organic layer was washed with brine, dried over anhydrous sodium sulfate and the solvent was removed under reduced pressure. The resulting residue was triturated with ethyl acetate-diethyl ether to obtain 2-formylamino-1-(3-pyridyl)-1-butanone (440 mg) as colorless powder.

MS•APCI (m/z): 193 (MH+)

(2) A mixture of 2-formylamino-1-(3-pyridyl)-1-butanone (640 mg) and ammonium acetate (5.13 g) in acetic acid (5 ml) was stirred at 100° C. for 1.5 hours. After cooling, 28% aqueous ammonia was added to the reaction mixture and the mixture was extracted with chloroform. The organic layer was washed with brine, dried over anhydrous sodium sulfate and the solvent was removed under reduced pressure. The resulting residue was triturated with ethyl acetate-diethyl ether to obtain 5-ethyl-4-(3-pyridyl)imidazole (520 mg) as colorless powder.

MS•APCI (m/z): 174 (MH+)

(3) To a solution of 5-ethyl-4-(3-pyridyl)imidazole (1.50 g) and potassium acetate (2.55 g) in methanol (40 ml) was added iodine (2.86 g), and the mixture was stirred at room temperature overnight. To the reaction mixture were added water and ethyl acetate, and the organic layer was collected, washed with a saturated aqueous sodium thiosulfate solution and brine and dried over anhydrous sodium sulfate, and the solvent was removed under reduced pressure. The resulting residue was purified by NH silica gel flush column chromatography (solvent: ethyl acetate) to obtain 5-ethyl-2-iodo-4-(3-pyridyl)imidazole (1.75 g).

MS•APCI (m/z): 300 (MH+)

Reference Example 12

(1) A mixture of methyl α-amino-2-thiophene acetate (1.48 g), 4-fluorobenzoyl chloride (1.64 g) and sodium hydrogen carbonate (2.89 g) in methylene chloride (20 ml) and water (20 ml) was stirred at room temperature overnight. The organic layer was collected, washed with water and brine, and the solvent was removed under reduced pressure. The resulting residue was triturated with ethyl acetate-hexane to obtain methyl α-(4-fluorobenzoylamino)-2-thiophene acetate (2.40 g) as colorless powder.

MS•APCI (m/z): 294 (MH+)

(2) To a solution of diisopropylamine (2.48 g) in tetrahydrofuran (45 ml) was added dropwise 1.6M n-butyl lithium (15.71 ml, n-hexane solution) under argon atmosphere at −78° C., and after stirring for 30 minutes, a solution of ethyl acetate (2.16 g) in tetrahydrofuran (5 ml) was added dropwise to the mixture and the resulting mixture was further stirred for 30 minutes. To the mixture was slowly added a solution of methyl α-(4-fluorobenzoylamino)-2-thiophene acetate (2.40 g) in tetrahydrofuran (15 ml), and the mixture was stirred for one hour. To the reaction mixture were added a saturated aqueous ammonium chloride solution and the mixture was extracted with ethylacetate. The organic layer was washed with water and brine, dried over anhydrous sodium sulfate and the solvent was removed under reduced pressure. The resulting residue was purified by silica gel flush column chromatography (solvent: chloroform:ethanol=100:1) to obtain ethyl 4-(4-fluorobenzoylamino)-4-(2-thienyl)acetacetate (2.53 g) as yellowish oil.

MS•APCI (m/z): 350 (MH+)

Reference Example 13

(1) To a solution of benzo[b]furan-5-carboxylic acid (1.30 g) and of methyl isocyanoacetate (834 mg) in N,N-dimethylformamide (10 ml) were added diethyl cyanophosphate (1.33 ml) and triethylamine (3.6 ml) at room temperature, and the mixture was stirred overnight. After removing the solvent under reduced pressure, an aqueous citric acid solution and ethyl acetate were added to the residue, the organic layer was collected, washed successively with an aqueous citric acid solution, water, a saturated aqueous sodium hydrogen carbonate solution and brine, dried over anhydrous sodium sulfate, and the solvent was removed under reduced pressure. The resulting residue was purified by silica gel column chromatography (solvent: n-hexane:ethyl acetate=1:1) to obtain a crude product of methyl 5-(5-benzo[b]furyl)oxazol-4-carboxylate (1.14 g).

(2) To a solution of the crude product of methyl 5-(5-benzo[b]furyl)oxazol-4-carboxylate (1.14 g) in methanol (20 ml) and tetrahydrofuran (5 ml) was added conc. hydrochloric acid (8 ml), and the mixture was stirred overnight. The reaction mixture was concentrated under reduced pressure and the resulting residue was triturated with methanol-diethyl ether-acetone to obtain 5-(aminoacetyl)benzo[b]furan hydrochloride (600 mg).

MS•APCI (m/z): 176 (MH+)

Reference Example 14

Corresponding starting compounds were treated in a manner similar to Reference example 13(1) and (2) to obtain the compounds shown in Table 53 below.

TABLE 53

| Reference example No. | Chemical structure | Salt | Physical constant, etc. |
|---|---|---|---|
| 14 (1) | [structure] | Free material | Solid MS · APCI (m/z): 244 (M + H)+ |
| 14 (2) | [structure] | 1 HCl | Powder MS · APCI (m/z): 176 (M + H)+ |

Reference Examples 15 to 19

Corresponding starting compounds were treated in a manner similar to Reference example 10(1) to obtain the compounds shown in Table 54 below.

TABLE 54

| Reference example No. | Chemical structure | Salt | Physical constant, etc. |
|---|---|---|---|
| 15 | (benzofuran-5-yl)-C(O)-CH2-NH-C(O)-(4-fluorophenyl) | Free material | Powder MS·APCI (m/z): 298 (M + H)+ |
| 16 | (5-chlorothiophen-3-yl)-C(O)-CH2-NH-C(O)-(4-fluorophenyl) | Free material | Powder MS·APCI (m/z): 298 (M + H)+ |
| 17 | (4-chlorothiophen-2-yl)-C(O)-CH2-NH-C(O)-(benzofuran-5-yl) | Free material | Powder MS·APCI (m/z): 320 (M + H)+ |
| 18 | (5-chlorothiophen-3-yl)-C(O)-CH2-NH-C(O)-(benzofuran-5-yl) | Free material | Powder MS·APCI (m/z): 320 (M + H)+ |
| 19 | (thiophen-3-yl)-C(O)-CH2-NH-C(O)-(6-chloropyridin-3-yl) | Free material | Powder MS·APCI (m/z): 281/283 (M + H)+ |

Reference Example 20

(1) To a solution of 2-chloro-5-(bromoacetyl)thiophene (28.04 g) in acetonitrile (150 ml) was added sodium diformylimide (13.35 g), and the mixture was stirred at room temperature for 45 minutes followed by stirring at 50° C. for 2.5 hours. The reaction mixture was filtered through Celite, insoluble material was washed with tetrahydrofuran, the filtrate and the washed solution were combined and the solvent was removed under reduced pressure. The residue was crystallized from diisopropyl ether to obtain a crude crystal of 2-chloro-5-(diformylaminoacetyl)thiophene (20.63 g).

(2) To the crude crystal of 2-chloro-5-(diformylaminoacetyl)-thiophene were added potassium hydroxide (0.60 g), ethanol (70 ml) and tetrahydrofuran (40 ml), and the mixture was stirred at room temperature for one hour. After removing the solvent under reduced pressure, tetrahydrofuran (150 ml) and anhydrous magnesium sulfate were added to the residue, and insoluble material was removed by filtration and washed with tetra-hydrofuran. The filtrate and the washed solution were combined and the solvent was removed under reduced pressure. The residue was crystallized from diisopropyl ether-ethyl acetate to obtain 2-chloro-5-(formylaminoacetyl)thiophene (14.81 g) as pale brownish crystal.

Melting point: 111 to 113° C.

MS·APCI (m/z): 204 (MH+)

(3) To a solution of 2-chloro-5-(formylaminoacetyl) thiophene (20.1 g) in N,N-dimethylformamide (400 ml) was added sodium hydride (4.44 g, 60% mineral oil) under ice-cooling, and the mixture was stirred under argon atmosphere at room temperature for one hour. After ice-cooling, to the mixture was added dropwise ethyl bromoacetate (20.8 g), and the mixture was stirred at room temperature for 2 hours. After cooling, ice was added to the reaction mixture, and then water and ethyl acetate were also added to the mixture. The organic layer was collected washed with water and brine, dried over anhydrous sodium sulfate and the solvent was removed under reduced pressure. The resulting residue was purified by silica gel column chromatography (solvent: n-hexane:ethyl acetate=6:1) to obtain ethyl 4-(5-chlorothiophen-2-yl)-3-formylamino-4-oxobutyrate (17.8 g) as yellowish oil.

MS•APCI (m/z): 290/292 (MH+)

(4) To a solution of 4-(5-chlorothiophen-2-yl)-3-formyl-amino-4-oxobutyrate (17.8 g) in ethanol (178 ml) was added 4N hydrogen chloride-dioxane solution (178 ml) under ice-cooling, and the mixture was stirred at room temperature for 18 hours. After completion of the reaction, the solvent was removed under reduced pressure, and the resulting residue was triturated with ethyl acetate to obtain ethyl 4-(5-chlorothiophen-2-yl)-3-amino-4-oxobutyrate hydrochloride (14.2 g) as colorless powder.

MS•APCI (m/z): 262/264 (MH+)

Reference Example 21

Corresponding starting compounds were treated in a manner similar to Reference example 20(1) to (4) to obtain the compounds shown in Table 55 below.

TABLE 55

| Reference example No. | Chemical structure | Salt | Physical constant, etc. |
|---|---|---|---|
| 21 (1) | 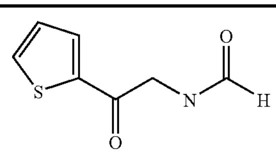 | Free material | Powder MS · APCI (m/z): 170 (M + H)+ |
| 21 (2) | 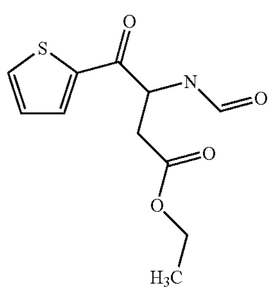 | Free material | Powder MS · APCI (m/z): 256 (M + H)+ |
| 21 (3) | 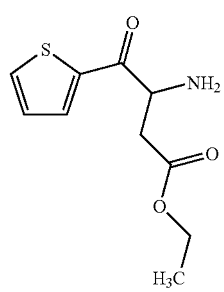 | 1 HCl | Powder MS · APCI (m/z): 228 (M + H)+ |

Reference Example 22

(1) A mixed solution of β-methyl N-(5-benzo[b]furoyl) aspartate (1.0 g) and acetic anhydride (10 ml) was stirred at 85° C. for one hour. The reaction mixture was cooled to room temperature and the solvent was removed under reduced pressure. The resulting residue was crystallized from n-hexane-diethyl ether to obtain 2-(5-benzo[b]furyl)-4-methoxycarbonylmethyl-5-oxo-2-oxazoline (751 mg) as colorless powder.

(2) To a mixture of 2-(5-benzo[b]furyl)-4-methoxycarbonyl-methyl-5-oxo-2-oxazoline (410 mg) and 3-thenoyl chloride (242 mg) in ethyl acetate (8 ml) was added triethyl amine (0.23 ml) under ice-cooling, and the mixture was stirred at room temperature for 0.5 hour. Ethyl acetate was added to the mixture, the mixture was filtered and the resulting filtrate was concentrated under reduced pressure. A mixture of the resulting residue and pyridine (3.6 ml) was stirred at room temperature for 10 minutes followed by stirring at 60° C. for 2 hours. Then, acetic acid (1.35 ml) was added to the mixture and the resulting mixture was stirred at 80° C. for 1.5 hours. After cooling, to the reaction mixture were added water and ethyl acetate, the organic layer was collected, washed successively with a 10% aqueous hydrochloric acid solution, a saturated aqueous sodium hydrogen carbonate solution and brine, dried over anhydrous sodium sulfate, and the solvent was removed under reduced pressure. The resulting residue was purified by silica gel column chromatography (solvent: hexane:ethyl acetate=5:1) to obtain methyl 3-(5-benzo[b]furoylamino)-4-(3-thienyl)-4-oxobutyrate (253 mg) as colorless powder.

MS•APCI (m/z): 358 (MH+)

Reference Example 23

Corresponding starting compounds were treated in a manner similar to Reference example 10(1) to obtain 2-[2-(4-fluorobenzoyl-amino) acetyl]thiophene.

Reference Example 24

(1) To a solution of methyl 5-(5-chlorothiophen-2-yl)oxazol-4-carboxylate (12.6 g) in methanol (150 ml) was added 4N hydrogen chloride-dioxane solution (100 ml) under argon atmosphere, and the mixture was stirred at 70° C. for overnight. The reaction mixture was cooled and the solvent was removed under reduced pressure, and the resulting residue was triturated with acetone to obtain methyl 2-amino-3-(5-chlorothiophen-2-yl)-3-oxo-propionate hydrochloride (13.9 g) as colorless powder.

MS•APCI (m/z): 234 (MH+)

(2) A mixture of methyl 2-amino-3-(5-chlorothiophen-2-yl)-3-oxopropionate hydrochloride (6.0 g), 4-fluorobenzoyl chloride (4.23 g) and sodium hydrogen carbonate (11.2 g) in ethyl acetate (100 ml) and water (10 ml) was stirred at room temperature for 2 hours. The organic layer was collected, washed with water and brine, dried over anhydrous magnesium sulfate and the solvent was removed under reduced pressure. The resulting residue was triturated with diethyl ether to obtain methyl 3-(5-chlorothiophen-2-yl)-2-(4-fluorobenzoylamino)-3-oxopropionate (7.3 g) as colorless powder.

MS•APCI (m/z): 356/358 (MH+)

Reference Example 25

A mixture of 1,2,3,4-tetrahydroquinolin-6-carboxylic acid (2 g), 32% aqueous formalin solution (2 ml) and 10% palladium-carbon (400 mg) in N,N-dimethylformamide (10 ml) was stirred under hydrogen atmosphere at room temperature for one hour. After removing the palladium-carbon by filtration, the solvent was removed under reduced pressure and the resulting residue was triturated with diethyl ether to obtain 1-methyl-1,2,3,4-tetrahydroquinolin-6-carboxylic acid (1.98 g) as yellowish powder.

ESI•MS (m/z): 190 (M-H)–

Reference Example 26

Corresponding starting compounds were treated in a manner similar to Reference example 25 to obtain 1-methylindolin-5-carboxylic acid.
ESI•MS (m/z): 176 (M-H)–

Reference Example 27

A mixture of methyl 6-methoxymethylnicotinate (737 mg) in a 2N aqueous sodium hydroxide solution (2 ml) and methanol (15 ml) was refluxed overnight. After cooling, the reaction mixture was concentrated under reduced pressure, and the resulting residue was triturated with diethyl ether to obtain 6-methoxymethylnicotinic acid sodium salt (754 mg) as colorless powder.
ESI•MS (m/z): 166 (M-Na)

Reference Example 28

(1) To a solution of methyl 6-bromomethylnicotinate (350 mg) in tetrahydrofuran (5 ml) was added a 50% aqueous dimethylamine solution (3 ml), and the mixture was vigorously stirred at room temperature for 10 minutes. To the reaction mixture was added water and the mixture was extracted with ethyl acetate. The organic layer was washed with water and brine, dried over anhydrous sodium sulfate, and the solvent was removed under reduced pressure. The resulting residue was purified by silica gel column chromatography (solvent: chloroform:methanol=100:1) to obtain methyl 6-(dimethylamino)methylnicotinate (276 mg) as brownish powder.
MS•APCI (m/z): 195 (MH+)

(2) A mixture of methyl 6-(dimethylamino)methylnicotinate (256 mg) and 10N hydrochloric acid was refluxed overnight. After cooling, the reaction mixture was concentrated under reduced pressure to obtain 6-(dimethylamino)methylnicotinic acid hydrochloride (329 mg) as colorless powder.
MS•APCI (m/z): 181 (MH+)

Reference Example 29

To a suspension of 3-(2-aminoacetyl)pyridine dihydrochloride (5.23 g) in chloroform (50 ml) were added di-t-butyl dicarbonate (5.73 g) and triethylamine (10.5 ml), and the mixture was stirred for one hour. Water was added to the reaction mixture and the mixture was extracted with chloroform. The organic layer was washed with water and brine, dried over anhydrous sodium sulfate, and active charcoal was added thereto and insoluble material was removed by filtration. The filtrate was concentrated under reduced pressure, and the residue was purified by medium pressure column chromatography (solvent: chloroform:methanol=30:1→20:1), and triturated with diisopropyl ether to obtain 3-(2-t-butoxycarbonylaminoacetyl)pyridine (3.20 g).
Melting point: 98 to 99° C.
MS•APCI (m/z): 237 (MH+)

Reference Example 30

(1) A mixture of (2-methoxy)phenacyl bromide (550 mg) and sodium diformylimide (274 mg) in acetonitrile (2.5 ml) was stirred at room temperature for 30 minutes, and then, stirred at 70° C. for 24 hours. Insoluble material was removed by filtration, washed with acetonitrile and the filtrate was concentrated under reduced pressure. The residue was purified by silica gel column chromatography (solvent: hexane:ethyl acetate=2:1), and triturated with hexane-ethyl acetate to obtain 2-(diformyl-amino)-2'-methoxyacetophenone (4.40 g) as colorless powder.

(2) A mixture of 2-(diformyl-amino)-2'-methoxyacetophenone (3.28 g) and 5% hydrogen chloride-ethanol solution (37 ml) was stirred at room temperature for 17 hours. The reaction mixture was concentrated under reduced pressure and the residue was triturated with diethyl ether. To the powder was again added 5% hydrogen chloride-ethanol solution and the mixture was stirred at room temperature for one day, and the mixture was concentrated under reduced pressure. The residue was washed with diethyl ether and ethyl acetate to obtain 2-amino-2'-methoxyacetophenone hydrochloride (2.91 g) as colorless solid.
MS•APCI (m/z): 166 (MH+)

Reference Example 31

A mixture of methyl dl-α-amino-2-thiophene acetate (5.59 g), N-chlorosuccinimide (4.67 g) and acetic acid (60 ml) was stirred at room temperature overnight. The reaction mixture was concentrated under reduced pressure, to the residue obtained was added water, and the mixture was extracted with ethylacetate. The organic layer was washed with water and brine, dried over anhydrous sodium sulfate, and the solvent was removed under reduced pressure. To the resulting residue were added methanol (40 ml) and 4N hydrogen chloride-dioxane solution (30 ml), the solvent was removed under reduced pressure and the residue was triturated with using diethyl ether and methanol to obtain methyl dl-α-amino-2-(5-chlorothiophene)acetate hydrochloride (4.24 g) as pale brownish powder.
MS•APCI (m/z): 206/208 (MH+)

Reference Examples 32 to 46

Corresponding starting compounds were treated in a manner similar to Reference example 12(1) to obtain the compounds shown in Table 56 below.

TABLE 56

| Reference example No. | Chemical structure | Salt | Physical constant, etc. |
|---|---|---|---|
| 32 | [structure: methyl 2-(4-chlorophenyl)-2-(4-fluorobenzoylamino)acetate with OCH$_3$ ester] | Free material | Powder MS · APCI (m/z): 360/362 (M + H)+ |

TABLE 56-continued

| Reference example No. | Chemical structure | Salt | Physical constant, etc. |
|---|---|---|---|
| 33 | 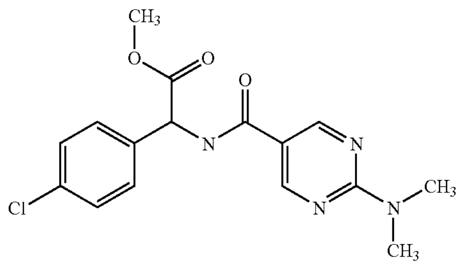 | Free material | Powder MS·APCI (m/z): 349/351 (M + H)+ |
| 34 | 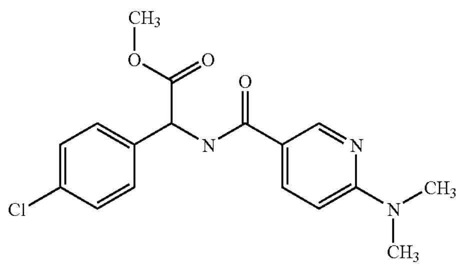 | Free material | Powder MS·APCI (m/z): 348/350 (M + H)+ |
| 35 | 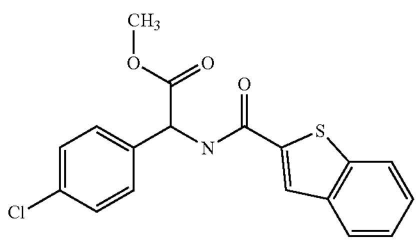 | Free material | Powder MS·APCI (m/z): 360/362 (M + H)+ |
| 36 | 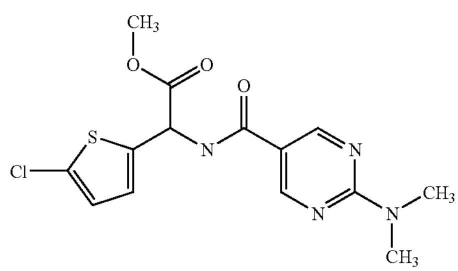 | Free material | Powder MS·APCI (m/z): 355/357 (M + H)+ |
| 37 | 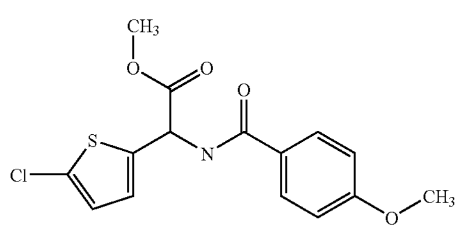 | Free material | Powder MS·APCI (m/z): 340/342 (M + H)+ |
| 38 | 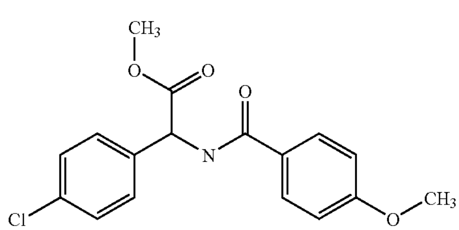 | Free material | Powder MS·APCI (m/z): 335/336 (M + H)+ |

TABLE 56-continued

| Reference example No. | Chemical structure | Salt | Physical constant, etc. |
|---|---|---|---|
| 39 | 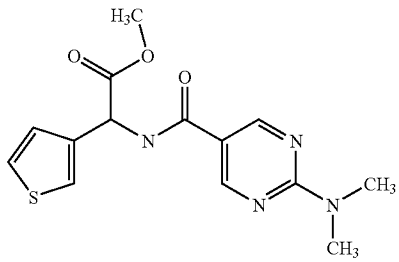 | Free material | Powder MS·APCI (m/z): 321 (M + H)+ |
| 40 | 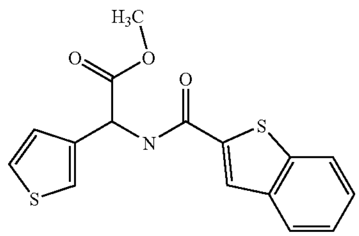 | Free material | Powder MS·APCI (m/z): 332 (M + H)+ |
| 41 | 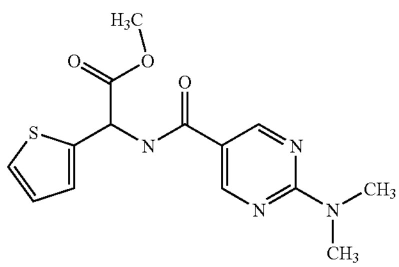 | Free material | Powder MS·APCI (m/z): 321 (M + H)+ |
| 42 | 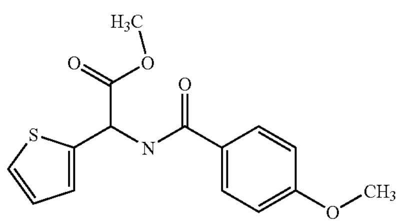 | Free material | Powder MS·APCI (m/z): 306 (M + H)+ |
| 43 | 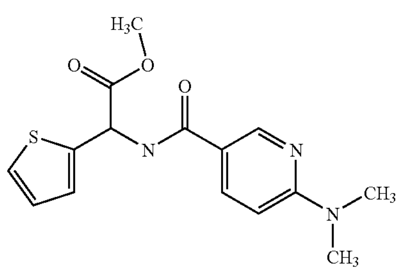 | Free material | Powder MS·APCI (m/z): 320 (M + H)+ |
| 44 | 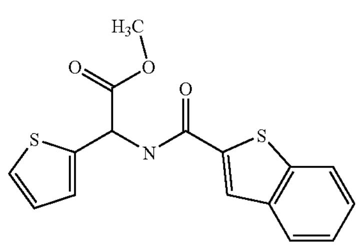 | Free material | Powder MS·APCI (m/z): 332 (M + H)+ |

TABLE 56-continued

| Reference example No. | Chemical structure | Salt | Physical constant, etc. |
|---|---|---|---|
| 45 | 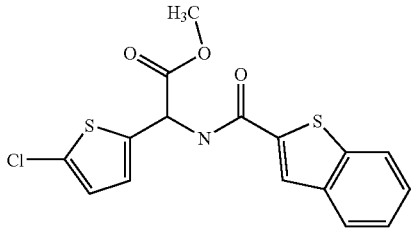 | Free material | Powder MS · APCI (m/z): 366/368 (M + H)+ |
| 46 | 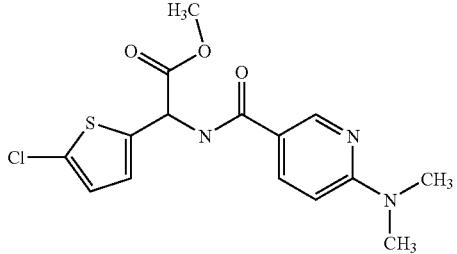 | Free material | Powder MS · APCI (m/z): 354/356 (M + H)+ |

Reference Examples 47 to 61

Corresponding starting compounds were treated in a manner similar to Reference example 12(2) to obtain the compounds shown in Table 57 below.

TABLE 57

| Reference example No. | Chemical structure | Salt | Physical constant, etc. |
|---|---|---|---|
| 47 | 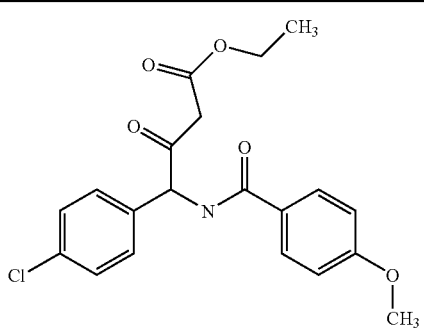 | Free material | Powder MS · APCI (m/z): 390/392 (M + H)+ |
| 48 | 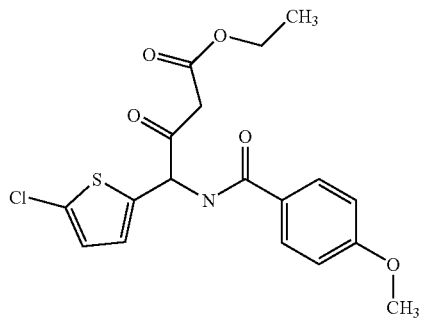 | Free material | Powder MS · APCI (m/z): 396/398 (M + H)+ |

TABLE 57-continued
| Reference example No. | Chemical structure | Salt | Physical constant, etc. |
|---|---|---|---|
| 49 | 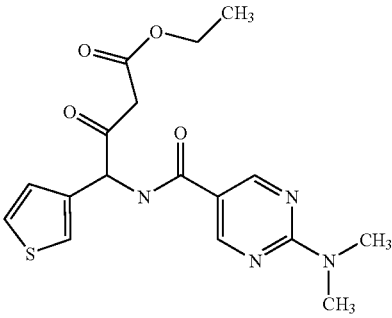 | Free material | Powder MS · APCI (m/z): 377 (M + H)+ |
| 50 | 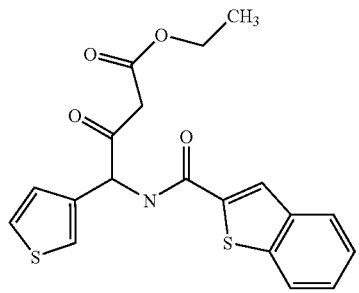 | Free material | Powder MS · APCI (m/z): 388 (M + H)+ |
| 51 | 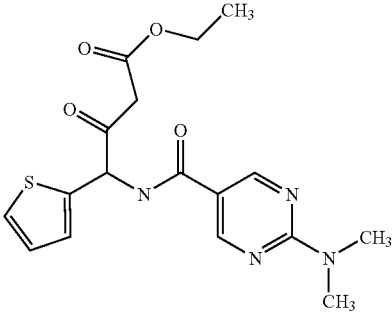 | Free material | Powder MS · APCI (m/z): 377 (M + H)+ |
| 52 | 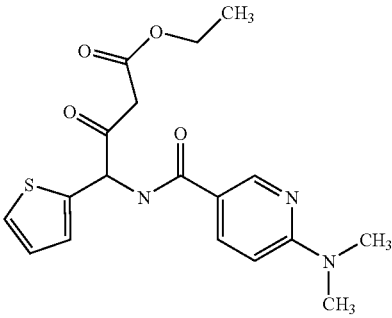 | Free material | Powder MS · APCI (m/z): 376 (M + H)+ |

TABLE 57-continued

| Reference example No. | Chemical structure | Salt | Physical constant, etc. |
|---|---|---|---|
| 53 | 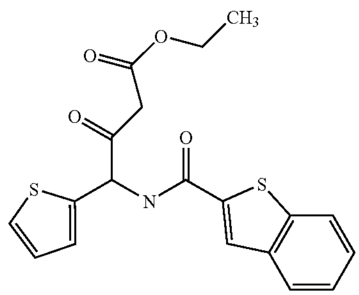 | Free material | Powder MS · APCI (m/z): 388 (M + H)+ |
| 54 | 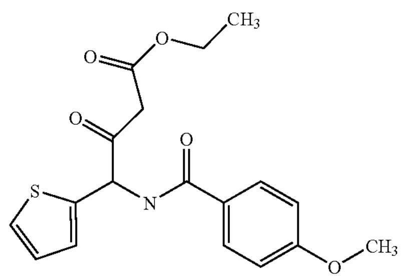 | Free material | Oil MS · APCI (m/z): 362 (M + H)+ |
| 55 | 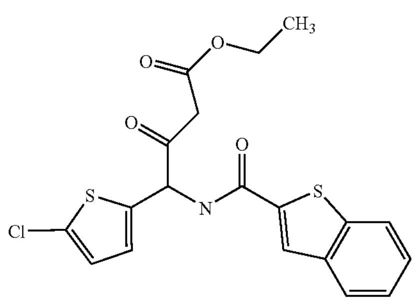 | Free material | Powder MS · APCI (m/z): 422/424 (M + H)+ |
| 56 | 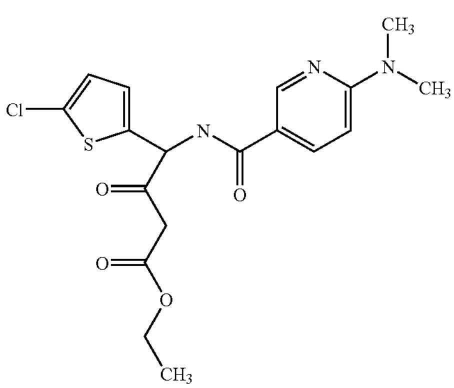 | Free material | Crystal Melting point: 126-128° C. MS · APCI (m/z): 410/412 (M + H)+ |

TABLE 57-continued

| Reference example No. | Chemical structure | Salt | Physical constant, etc. |
|---|---|---|---|
| 57 | (ethyl 4-(4-chlorophenyl)-4-(benzothiophene-2-carboxamido)-3-oxobutanoate) | Free material | Powder MS · APCI (m/z): 416/418 (M + H)+ |
| 58 | (ethyl 4-(5-chlorothiophen-2-yl)-4-{[2-(dimethylamino)pyrimidin-5-yl]carboxamido}-3-oxobutanoate) | Free material | Powder MS · APCI (m/z): 411/413 (M + H)+ |
| 59 | (ethyl 4-(4-chlorophenyl)-4-{[2-(dimethylamino)pyrimidin-5-yl]carboxamido}-3-oxobutanoate) | Free material | Powder MS · APCI (m/z): 405/407 (M + H)+ |
| 60 | (ethyl 4-(4-chlorophenyl)-4-{[6-(dimethylamino)pyridin-3-yl]carboxamido}-3-oxobutanoate) | Free material | Powder MS · APCI (m/z): 404/406 (M + H)+ |

TABLE 57-continued

| Reference example No. | Chemical structure | Salt | Physical constant, etc. |
|---|---|---|---|
| 61 | (structure) | Free material | Powder MS · APCI (m/z): 378/380 (M + H)+ |

Reference Examples 62 to 66

Corresponding starting compounds were treated in a manner similar to Reference example 10(1) to obtain the compounds shown in Table 58 below.

TABLE 58

| Reference example No. | Chemical structure | Salt | Physical constant, etc. |
|---|---|---|---|
| 62 | (structure) | Free material | Powder MS · APCI (m/z): 259 (M + H) |
| 63 | (structure) | Free material | Powder MS · APCI (m/z): 340/342 (M + H)+ |
| 64 | (structure) | Free material | Powder MS · APCI (m/z): 348/350 (M + H)+ |
| 65 | (structure) | Free material | Powder MS · APCI (m/z): 320/322 (M + H)+ |

TABLE 58-continued

| Reference example No. | Chemical structure | Salt | Physical constant, etc. |
|---|---|---|---|
| 66 | (4-chlorophenyl)-C(=O)-CH2-NH-C(=O)-benzothiophen-2-yl | Free material | Powder MS · APCI (m/z): 330/332 (M + H)+ |

Reference Example 67

Under argon atmosphere, to a solution of 4-chloro-3-fluoro-benzaldehyde (10 g) in N,N-dimethylformamide (50 ml) was added sodium cyanide (620 mg) at room temperature, and the mixture was stirred at the same temperature for 3 hours. Then, to the mixture was added dropwise a solution of ethyl acrylate (5.2 ml) in N,N-dimethylformamide (25 ml), and the resulting mixture was stirred at the room temperature for 3 hours. The reaction mixture was poured into water and extracted with diethyl ether. The organic layer was washed with water and brine, dried over anhydrous sodium sulfate and the solvent was removed under reduced pressure. The resulting residue was purified by silica gel column chromatography (solvent: hexane:ethyl acetate=20:1) to obtain ethyl 4-(4-chloro-3-fluorophenyl)-4-oxobutyrate (9.4 g) as pale yellowish powder.

MS•APCI (m/z): 259/261 (MH+)

Reference Example 68

Under argon atmosphere, a mixture of succinic acid mono-ethyl ester monochloride (2.0 g), tributyl(3-thienyl) tin (5.44 g) and bis (triphenylphosphine) palladium chloride (853 mg) in dioxane (40 ml) was refluxed for 3 hours. After cooling, to the residue was added a saturated aqueous sodium hydrogen carbonate solution, and the mixture was extracted with ethyl acetate. The organic layer was washed with brine, dried over anhydrous sodium sulfate and the solvent was removed under reduced pressure. The resulting residue was purified by silica gel column chromatography (solvent: hexane:ethyl acetate=6:1), and recrystallized from ethyl acetate-hexane to obtain ethyl 4-(3-thienyl)-4-oxobutyrate (1.4 g) as pale yellowish powder.

MS•APCI (m/z): 213 (MH+)

Reference Example 69

To a solution of ethyl 4-(5-chlorothiophen-2-yl)-4-oxobutyrate (900 mg) in dichloromethane (9 ml) was added bromine (200 µl) under ice-cooling, and after stirring at the same temperature for 30 minutes, the reaction mixture was warmed to room temperature and the mixture was stirred for one hour. The reaction mixture was poured into ice-water, and ethyl acetate and diethyl ether were added thereto. The organic layer was collected, washed with water and brine, dried over anhydrous sodium sulfate and the solvent was removed under reduced pressure to obtain ethyl 3-bromo-4-(5-chlorothiophen-2-yl)-4-oxo-butyrate (1.22 g) as pale brownish liquid.

MS•APCI (m/z): 326/328 (MH+)

Reference Examples 70 and 71

Corresponding starting compounds were treated in a manner similar to Reference example 69 to obtain the compounds shown in Table 59 below.

TABLE 59

| Reference example No. | Chemical structure | Salt | Physical constant, etc. |
|---|---|---|---|
| 70 | F, Cl-phenyl-C(=O)-CH(Br)-CH2-C(=O)-O-CH3 | Free material | Oil MS · APCI (m/z): 337/339 (M + H)+ |
| 71 | 3-thienyl-C(=O)-CH(Br)-CH2-C(=O)-O-CH3 | Free material | Oil MS · APCI (m/z): 291/293 (M + H)+ |

Reference Example 72 to a mixture of (2-methylthio)pyrimidin-5-carboxylic acid sodium salt (1.50 g), ammonium chloride (2.09 g) and 1-hydroxybenzotriazole (1.27 g) in N,N-dimethylformamide (20 ml) were successively added 3-ethyl-1-(3-dimethylaminopropyl)carbodiimide hydrochloride (1.80 g) and triethylamine (6.5 ml) under ice-cooling, and the mixture was stirred at room temperature overnight. To the reaction mixture was added an aqueous ammonium chloride solution and the mixture was extracted with ethyl acetate, washed with water and brine, dried over anhydrous sodium sulfate and the solvent was removed under reduced pressure. The resulting residue was digested with diethyl ether-ethyl acetate. Then, the suspension was cooled and the precipitate was filtered, and washed with diethyl ether-n-hexane to obtain (2-methylthio) pyrimidin-5-carboxamide (927 mg).

MS•APCI (m/z): 170 (MH+)

Reference Example 73

Corresponding starting compounds were treated in a manner similar to Reference example 72 to obtain 4,5-dimethylthiophen-2-carboxamide.

MS•APCI (m/z): 156 (MH+)

Reference Example 74

To a suspension of 6-chloronicotinamide (1.50 g) in ethanol (30 ml) was added sodium hydride (1.88 g, 60% mineral oil), and the mixture was stirred at room temperature for 24 hours. Another portion of sodium hydride (940 mg, 60% mineral oil) was added to the mixture, and the resulting mixture was stirred at room temperature for 24 hours followed by refluxing for 4.5 hours. Then, the reaction mixture was cooled, a saturated aqueous ammonium chloride solution was added thereto and the mixture was extracted with ethyl acetate. The organic layer was washed with brine, dried over anhydrous sodium sulfate and the solvent was removed under reduced pressure. The residue was triturated with diethyl ether to obtain 6-ethoxynicotinamide (1.05 g) as colorless powder.

MS•APCI (m/z): 167 (MH+)

Reference Example 75

A mixture of (2-methylthio)pyrimidin-5-carboxamide (569 mg) and Lawesson's reagent (2.72 g) in chloroform (20 ml) was refluxed overnight. After cooling the reaction mixture, it was purified by NH silica gel column chromatography (solvent: ethyl acetate). The residue was triturated with diethyl ether and washed with n-hexane to obtain (2-methylthio)pyrimidin-5-carbothioamide (247 mg) as yellowish powder.

MS•APCI (m/z): 186 (MH+)

Reference Examples 76 to 80

Corresponding starting compounds were treated in a manner similar to Reference example 75 to obtain the compounds shown in Table 60 below.

TABLE 60

| Reference example No. | Chemical structure | Salt | Physical constant, etc. |
|---|---|---|---|
| 76 | (structure) | Free material | Crystal Melting point: 227.5-228.5° C. MS · APCI (m/z): 183 (M + H)+ |

TABLE 60-continued

| Reference example No. | Chemical structure | Salt | Physical constant, etc. |
|---|---|---|---|
| 77 | (structure) | Free material | Powder MS · APCI (m/z): 182 (M + H)+ |
| 78 | (structure) | Free material | Powder MS · APCI (m/z): 183 (M + H)+ |
| 79 | (structure) | Free material | Powder MS · APCI (m/z): 194 (M + H)+ |
| 80 | (structure) | Free material | Powder ESI · MS (m/z): 170 (M − H) |

Reference Example 81

Corresponding starting compounds were treated in a manner similar to Reference example 13(1) to obtain methyl 5-(3-chloro-4-fluorphenyl)oxazol-4-yl carboxylate.

MS•APCI (m/z): 256/258 (MH+)

Reference Examples 82 and 83

Corresponding starting compounds were treated in a manner similar to Reference example 13(2) to obtain the compounds shown in Table 61 below.

TABLE 61

| Reference example No. | Chemical structure | Salt | Physical constant, etc. |
|---|---|---|---|
| 82 | (structure) | HCl | Powder MS · APCI (m/z): 136 (M + H)+ |
| 83 | (structure) | HCl | Powder MS · APCI (m/z): 188/190 (M + H)+ |

Reference Examples 84 to 87

Corresponding starting compounds were treated in a manner similar to Reference example 10(1) or Reference example 20(4) to obtain the compounds shown in Table 62 below.

TABLE 62

| Reference example No. | Chemical structure | Salt | Physical constant, etc. |
|---|---|---|---|
| 84 | 4-Cl-C6H4-CO-CH(NH2)-CH2-COO-CH2CH3 | HCl | Powder<br>MS · APCI (m/z):<br>256/258 (M + H)+ |
| 85 | 3-thienyl-CO-CH(NH2)-CH2-COO-CH2CH3 | HCl | Powder<br>MS · APCI (m/z):<br>228 (M + H)+ |
| 86 | 3-pyridyl-CO-CH(NH2)-CH2-COO-CH2CH3 | HCl | Powder<br>MS · APCI (m/z):<br>223 (M + H) |
| 87 | 2-thienyl-CO-CH2-NH-CO-C6H4-4-F | Free | Crystal<br>Melting point:<br>158-159° C. |

Reference Examples 88 to 90

Corresponding starting compounds were treated in a manner similar to Reference example 20(3) to obtain the compounds shown in Table 63 below.

TABLE 63

| Reference example No. | Chemical structure | Salt | Physical constant, etc. |
|---|---|---|---|
| 88 | 4-Cl-C6H4-CO-CH(NHCHO)-CH2-COO-CH2CH3 | Free material | Oily state<br>MS · APCI(m/z):<br>284/286(M + H)+ |

TABLE 63-continued

| Reference example No. | Chemical structure | Salt | Physical constant, etc. |
|---|---|---|---|
| 89 | (3-thienyl-C(=O)-CH(NH-CHO)-CH2-C(=O)-O-CH2CH3) | Free material | Oily state MS·APCI(m/z): 256(M + H)+ |
| 90 | (3-pyridyl-C(=O)-CH(NH-C(=O)-O-C(CH3)3)-CH2-C(=O)-O-CH2CH3) | Free material | Oily state MS·APCI(m/z): 323(M + H) |

Experimental Example 1

Relaxation effect on potassium-induced contraction of isolated rabbit urinary bladder Urinary bladder was isolated from Male NZW rabbits (2.0-3.5 kg) and immersed in ice-cold Krebs-bicarbonate solution (in mM: 118 NaCl, 4.7 KCl, 1.2, 2.5 $CaCl_2$, $MgSO_4$, 1.2 $KH_2PO_4$, 11 glucose, 25 $NaHCO_3$). The urinary bladder was cut into longitudinal strips (5 mm length, 3-4 mm width) after mucosal layer was removed. Preparations were mounted in organ baths containing 10 ml of Krebs solution maintained at 37° C. and gassed with 95% $O_2$/5% $CO_2$. Accordingly, preparations were stretched with an initial tension of 2.0±1.0 g, and changes in isometric tension were measured by force-displacement transducer. The preparations were pre-contracted by changing organ-bath solution into high-$K^+$ (30 mM) Krebs solution (in mM: 92.7 NaCl, 30 KCl, 1.2, 2.5 $CaCl_2$, $MgSO_4$, 1.2 $KH_2PO_4$, 11 glucose, 25 $NaHCO_3$).

After stable tension was obtained, compounds were added into organ baths cumulatively ($10^{-8}$M-$10^{-4}$M). The effects of compounds were expressed as a percentage of the maximum relaxation produced by 0.1 mM papaverine. 50% relaxation concentration ($EC_{50}$) was calculated and $EC_{50}$ value range (μM) of the compounds of the present invention was shown in the following Table 64 with a rank of A, B or C. These ranges are as mentioned below.

$3 \geq C \geq 1 \geq B \geq 0.5 \geq A$

TABLE 64

| Preparation example No. | $EC_{50}$ value range |
|---|---|
| 5 | C |
| 10 | C |
| 13 | A |
| 14 | C |
| 16 | C |
| 19 | A |
| 25 | A |
| 30 | C |
| 33 | A |
| 34 | C |
| 35 | C |
| 36 | C |
| 38 | C |
| 39 | C |
| 49 | B |
| 50 | C |
| 51 | A |
| 52 | A |
| 53 | B |
| 54 | C |
| 55 | C |
| 56 | B |
| 57 | C |
| 59 | C |
| 60 | C |
| 61 | C |
| 81 | C |
| 84 | A |
| 86 | B |
| 87 | C |
| 88 | C |
| 90 | C |
| 95 | C |
| 96 | C |
| 97 | B |
| 99 | B |
| 104 | B |
| 108 | C |
| 120 | A |
| 121 | C |
| 131 | C |
| 132 | B |
| 136 | B |
| 140 | C |
| 152 | C |
| 155 | C |
| 158 | C |
| 168 | B |
| 169 | C |

TABLE 64-continued

| Preparation example No. | EC$_{50}$ value range |
|---|---|
| 170 | C |
| 171 | C |
| 172 | C |
| 173 | C |
| 180 | C |
| 181 | B |
| 182 | A |
| 187 | B |
| 197 | C |
| 235 | B |
| 240 | B |
| 243 | A |
| 244 | C |
| 245 | C |
| 246 | B |
| 247 | C |
| 248 | C |
| 249 | C |
| 252 | B |
| 253 | B |
| 255 | C |
| 256 | A |
| 257 | A |
| 262 | C |
| 265 | C |
| 267 | A |
| 268 | A |
| 269 | A |
| 271 | B |
| 272 | A |
| 273 | C |
| 275 | A |
| 277 | B |
| 278 | B |
| 279 | A |
| 280 | A |
| 281 | A |
| 282 | B |
| 283 | A |
| 284 | C |
| 285 | C |
| 286 | A |
| 287 | A |
| 288 | A |
| 339 | C |
| 350 | C |
| 355 | A |
| 362 | C |
| 363 | C |
| 364 | C |
| 365 | C |
| 366 | A |
| 367 | B |
| 372 | C |
| 373 | C |
| 374 | C |
| 377 | C |
| 378 | C |
| 431 | B |
| 432 | A |
| 434 | B |
| 435 | B |
| 437 | A |
| 438 | C |
| 441 | C |
| 444 | C |
| 445 | C |
| 446 | A |
| 451 | C |
| 452 | A |
| 453 | B |
| 454 | C |
| 455 | C |
| 458 | A |
| 459 | C |
| 462 | B |

TABLE 64-continued

| Preparation example No. | EC$_{50}$ value range |
|---|---|
| 464 | C |
| 469 | C |
| 473 | B |
| 478 | A |
| 479 | A |
| 486 | C |
| 487 | B |
| 503 | C |
| 504 | C |
| 506 | B |
| 507 | A |
| 511 | A |
| 512 | B |
| 514 | B |
| 517 | A |
| 524 | C |
| 531 | C |
| 572 | C |
| 574 | C |
| 575 | A |
| 576 | B |
| 578 | B |
| 579 | B |
| 584 | C |
| 586 | A |
| 587 | B |
| 590 | A |
| 594 | A |
| 596 | C |
| 597 | A |
| 600 | A |
| 601 | B |
| 609 | B |
| 610 | A |
| 612 | A |
| 616 | C |
| 623 | C |
| 626 | C |
| 639 | C |

Experimental Example 2

Inhibitory effect on the rhythmic bladder contractions induced by substance P in anesthetized rats For the experiments, Sprague-Dawley female rats (9 to 12 weeks old) weighing between 200 to 300 g were used. After urethane anesthetization (subcutaneously administered with a dose of 1.2 g/kg), cannulae were placed in both right and left femoral veins. One intravenous catheter was used for administration of compounds, and the other was for the substance P (0.33 µg/kg/min) infusion. We also cannulated into ureter to pass urine. Polyethylene catheters were inserted into carotid artery for continuous monitoring of arterial blood pressure and heart rate. For continuous infusion, transurethral bladder catheter was inserted into the bladder through the urethra and tied in place by a ligature around the urethral orifice. One end of the catheter was attached to a pressure transducer in order to measure intravesical pressure. The other end of the catheter was used for infusion of saline into the bladder. After stabilization of blood pressure and heart rate and after the bladder was emptied, cystometry was performed by filling the bladder slowly with about 0.6 ml of saline. After about 10 minutes, intravenous infusion of substance P (0.33 µg/kg/min) was started for stabilization of the micturition reflex. Compounds were administered after stable rhythmic bladder contraction was obtained over 15 minutes. All compounds were dissolved or suspended in saline containing 0.5% Tween 80 for intravenous administration (0.1 ml/kg). The rhythmic contraction frequency and the intravesical pressure were observed for 35 minutes after administration of the test compound.

As a result, the compounds of the present invention decreased the frequency of bladder rhythmic contraction without changing the amplitude of contraction. Also, we determined a time (minute) during which the frequency of the rhythmic contraction had been completely inhibited by administering 0.25 mg/kg of the compound. A 100% inhibition time (minute) of the selected compounds of the present invention is shown in the following Table 65 with a rank of A, B or C. These ranges are as mentioned below.

$A \geqq 20 > B \geqq 10 > C$ (minute)

TABLE 65

| Preparation example No. | 100% inhibition time range |
|---|---|
| 13 | C |
| 14 | A |
| 16 | B |
| 24 | C |
| 25 | B |
| 27 | B |
| 28 | B |
| 30 | B |
| 31 | A |
| 34 | A |
| 43 | C |
| 46 | B |
| 47 | B |
| 48 | C |
| 50 | C |
| 53 | C |
| 54 | B |
| 55 | B |
| 56 | B |
| 59 | B |
| 61 | A |
| 62 | C |
| 63 | C |
| 67 | B |
| 72 | C |
| 80 | B |
| 83 | B |
| 85 | C |
| 86 | B |
| 87 | B |
| 88 | B |
| 90 | B |
| 93 | B |
| 99 | B |
| 102 | C |
| 104 | A |
| 107 | B |
| 108 | B |
| 120 | C |
| 122 | B |
| 123 | C |
| 124 | B |
| 125 | C |
| 132 | B |
| 133 | C |
| 136 | C |
| 137 | C |
| 142 | C |
| 143 | C |
| 144 | C |
| 152 | B |
| 153 | B |
| 155 | B |
| 156 | B |
| 158 | C |
| 160 | C |
| 162 | C |
| 164 | B |
| 166 | B |

TABLE 65-continued

| Preparation example No. | 100% inhibition time range |
|---|---|
| 168 | B |
| 171 | B |
| 172 | C |
| 176 | C |
| 181 | B |
| 182 | B |
| 187 | B |
| 189 | C |
| 197 | C |
| 198 | C |
| 201 | C |
| 233 | C |
| 234 | C |
| 235 | B |
| 236 | C |
| 237 | C |
| 238 | C |
| 239 | C |
| 240 | C |
| 241 | C |
| 242 | C |
| 243 | A |
| 244 | B |
| 245 | C |
| 246 | B |
| 247 | C |
| 248 | B |
| 249 | B |
| 250 | B |
| 251 | C |
| 252 | C |
| 253 | A |
| 254 | C |
| 255 | B |
| 256 | C |
| 257 | B |
| 258 | C |
| 259 | B |
| 260 | A |
| 262 | C |
| 263 | C |
| 267 | C |
| 268 | C |
| 269 | B |
| 270 | B |
| 271 | C |
| 272 | B |
| 273 | C |
| 274 | B |
| 275 | A |
| 276 | C |
| 277 | C |
| 278 | B |
| 279 | C |
| 280 | C |
| 281 | C |
| 282 | B |
| 283 | C |
| 284 | B |
| 285 | B |
| 286 | C |
| 287 | B |
| 288 | C |
| 289 | B |
| 290 | B |
| 291 | C |
| 292 | C |
| 293 | C |
| 295 | B |
| 296 | C |
| 331 | A |
| 337 | C |
| 338 | C |
| 348 | C |
| 350 | B |

TABLE 65-continued

| Preparation example No. | 100% inhibition time range |
|---|---|
| 351 | C |
| 362 | A |
| 363 | C |
| 364 | B |
| 365 | B |
| 366 | C |
| 367 | A |
| 368 | B |
| 369 | B |
| 370 | C |
| 371 | C |
| 373 | C |
| 374 | C |
| 375 | C |
| 376 | C |
| 377 | C |
| 378 | C |
| 380 | C |
| 430 | B |
| 431 | B |
| 432 | C |
| 433 | C |
| 434 | B |
| 435 | B |
| 436 | C |
| 437 | B |
| 438 | C |
| 439 | C |
| 440 | C |
| 441 | B |
| 442 | C |
| 443 | C |
| 444 | B |
| 445 | A |
| 446 | C |
| 447 | B |
| 448 | C |
| 449 | B |
| 450 | B |
| 451 | B |
| 452 | B |
| 453 | C |
| 454 | A |
| 455 | B |
| 456 | C |
| 457 | B |
| 458 | B |
| 459 | C |
| 462 | C |
| 464 | C |
| 466 | B |
| 467 | A |
| 469 | B |
| 470 | B |
| 472 | A |
| 473 | A |
| 474 | C |
| 475 | B |
| 476 | B |
| 478 | B |
| 479 | C |
| 482 | C |
| 484 | B |
| 486 | B |
| 487 | C |
| 503 | A |
| 504 | C |
| 505 | B |
| 511 | C |
| 512 | B |
| 513 | C |
| 514 | B |
| 516 | B |
| 517 | C |
| 522 | B |
| 523 | B |
| 524 | B |
| 525 | A |
| 529 | B |
| 530 | C |
| 531 | C |
| 532 | C |
| 568 | A |
| 569 | A |
| 570 | A |
| 571 | A |
| 572 | C |
| 573 | B |
| 574 | B |
| 575 | B |
| 576 | A |
| 577 | B |
| 578 | B |
| 579 | C |
| 580 | C |
| 582 | A |
| 583 | B |
| 584 | A |
| 585 | C |
| 586 | B |
| 587 | A |
| 588 | C |
| 589 | A |
| 590 | B |
| 591 | B |
| 594 | C |
| 596 | B |
| 600 | A |
| 601 | A |
| 608 | B |
| 609 | B |
| 610 | B |
| 611 | B |
| 612 | A |
| 613 | C |
| 614 | C |
| 615 | B |
| 616 | B |
| 617 | B |
| 622 | B |
| 623 | C |
| 624 | C |
| 626 | C |
| 627 | C |
| 628 | C |
| 630 | C |
| 639 | C |

Experimental Example 3

Large conductance calcium-activated K channel opening action in isolated rabbit bladder The urinary bladder strips were prepared according to the same manner as described in Experimental example 1. Briefly, the isolated urinary bladder was cut into longitudinal strips in ice-cold Krebs-bicarbonate solution, and mounted in organ baths. The initial tension was 2.0+/−1.0 g. The preparations were contracted by high-$K^+$ (20 mM or 60 mM) Krebs solution.

Active ingredients of the present invention showed relaxation effect on 20 mM $K^+$-contracted preparation and the effect was blocked by iberiotoxin, a selective large conductance calcium-activated K channel blocker.

Also in in vivo animal study, pre-administration of iberiotoxin (0.15 mg/kg, intravenous administration) reduced inhibitory effect of active ingredients in the present invention on the rhythmic bladder contraction.

It is suggested from the results that the active ingredients of the present invention have a detrusor relaxing activity through the large conductance calcium-activated K channel.

Thus, it was shown that the compounds which are active ingredients of the present invention were effective for prophylaxis and treatment of diseases such as pollakiuria, urinary incontinence and the like through the large conductance calcium-activated K channel opening activity.

The nitrogen-containing 5-membered heterocyclic compound (I) or a pharmaceutically acceptable salt which is an active ingredient of the present invention has an excellent large conductance calcium-activated K channel opening activity and hyperpolarizes a membrane electric potential of cells, so that it is useful for a prophylactic, relief and/or treatment agent of, for example, hypertension, asthma, premature birth, irritable bowel syndrome, chronic heart failure, angina, cardiac infarction, cerebral infarction, subarachnoid hemorrhage, cerebral vasospasm, cerebral hypoxia, peripheral blood vessel disorder, anxiety, male-pattern baldness, erectile dysfunction, diabetes, diabetic peripheral nerve disorder, other diabetic complication, sterility, urolithiasis and pain accompanied thereby, pollakiuria, urinary incontinence, nocturnal enuresis, and the like.

Also, the nitrogen-containing 5-membered heterocyclic compound (I) or a pharmaceutically acceptable salt has a low toxicity, so that it has high safety as a medicine.

The invention claimed is:

1. A nitrogen-containing 5-membered heterocyclic compound represented by the formula (I), or a pharmaceutically acceptable salt thereof,

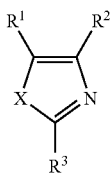

(I)

wherein X represents S, $R^1$ represents a lower alkyl group substituted by a lower alkoxycarbonyl group, $R^2$ represents a phenyl group substituted by two halogen atoms, and $R^3$ represents a 4-lower alkoxyphenyl group.

2. A nitrogen-containing 5-membered heterocyclic compound represented by the formula (I), or a pharmaceutically acceptable salt thereof,

(I)

wherein X represents S, $R^1$ represents a lower alkyl group containing 1 carbon atom and being substituted by a carboxyl group or lower alkoxycarbonyl group, $R^2$ represents a 4-chloro-3-fluoro-phenyl group, and $R^3$ is a 4-lower alkoxyphenyl group.

3. A method of treating pollakiuria or urinary incontinence, comprising:

administering an effective amount of a nitrogen-containing 5-membered heterocyclic compound or a pharmaceutically acceptable salt thereof according to claim 1 or claim 2 to a patient in need thereof.

4. A pharmaceutical composition comprising a therapeutically effective amount of a compound according to claim 1 or claim 2 or a pharmaceutically acceptable salt thereof in admixture with a therapeutically acceptable carrier or diluent.

* * * * *